(12) United States Patent
Chun et al.

(10) Patent No.: US 9,340,787 B2
(45) Date of Patent: May 17, 2016

(54) COMPOSITIONS AND METHODS OF USING MICRO RNAS

(71) Applicant: YALE UNIVERSITY, New Haven, CT (US)

(72) Inventors: Hyung J. Chun, Guilford, CT (US); Jongmin Kim, Gyeonggi-do (KR)

(73) Assignee: Yale University, New Haven, CT (US)

( * ) Notice: Subject to any disclaimer, the term of this patent is extended or adjusted under 35 U.S.C. 154(b) by 12 days.

(21) Appl. No.: 14/080,412

(22) Filed: Nov. 14, 2013

(65) Prior Publication Data

US 2014/0155459 A1     Jun. 5, 2014

Related U.S. Application Data

(60) Provisional application No. 61/726,792, filed on Nov. 15, 2012.

(51) Int. Cl.

| | |
|---|---|
| *C07H 21/02* | (2006.01) |
| *C07H 21/04* | (2006.01) |
| *A61K 48/00* | (2006.01) |
| *C12N 15/11* | (2006.01) |
| *C12N 15/113* | (2010.01) |
| *G01N 33/68* | (2006.01) |
| *C12Q 1/68* | (2006.01) |

(52) U.S. Cl.
CPC .......... *C12N 15/1136* (2013.01); *C12Q 1/6886* (2013.01); *G01N 33/6893* (2013.01); *C12Q 2600/112* (2013.01); *C12Q 2600/178* (2013.01); *G01N 2800/12* (2013.01); *G01N 2800/321* (2013.01)

(58) Field of Classification Search
USPC .......................... 514/44; 536/23.1, 24.3, 24.5
See application file for complete search history.

(56) References Cited

U.S. PATENT DOCUMENTS

| 5,328,470 A | 7/1994 | Nabel et al. |
| 5,837,832 A | 11/1998 | Chee et al. |

FOREIGN PATENT DOCUMENTS

WO    WO2006/137941 A2 * 12/2006

OTHER PUBLICATIONS

Anderson, Science 226:401-409, 1984.
Bloomer et al., Journal of Virology 71:6641-6649, 1997.
Cayouette et al., Human Gene Therapy 8:423-430, 1997.
Chen, et al. PNAS 91: 3054-3057, 1994.

(Continued)

*Primary Examiner* — Terra C Gibbs
(74) *Attorney, Agent, or Firm* — Saul Ewing LLP; Kathryn Doyle; Kelly J. Morgan

(57) ABSTRACT

The present invention provides compositions and methods of using microRNAs to treat pulmonary arterial hypertension. In one aspect, methods are disclosed that are useful for identifying a subject in need of therapeutic intervention to reduce or improve a symptom of pulmonary arterial hypertension, reducing proliferation of pulmonary vascular cells in a subject, or treating pulmonary arterial hypertension in a subject. In another aspect, compositions include an inhibitor of fibroblast growth factor 2 (FGF2) expression comprising at least one of: a mature sequence of miR-424 or miR-503; a pri-miRNA of miR-424 or miR-503; a pre-miRNA of miR-424 or miR-503; and the complement thereof. Pharmaceutical compositions for reducing proliferation of pulmonary vascular cells in a subject in need thereof and biomarker panels are also disclosed.

9 Claims, 78 Drawing Sheets

(56) References Cited

OTHER PUBLICATIONS

Cornetta et al., Nucleic Acid Research and Molecular Biology 36:311-322, 1987.
French et al., Circulation. Nov. 1994;90(5):2402-13.
Friedman, Science 244:1275-1281, 1989.
Guzman et al, Circ. Res. Dec. 1993;73(6):1202-7.
Johnson, Chest 107:77 S-83S, 1995.
Kido et al., Current Eye Research 15:833-844, 1996.
Le Gal La Salle et al., Science 259:988-990, 1993.
Lockhart, et al., Nat. Biotech. 14:1675-1680, 1996.
Miller et al., Biotechniques 7:980-990, 1989.
Miller, Human Gene Therapy 1:5-14, 1990.
Miyoshi et al., Proc. Natl. Acad. Sci. U.S.A. 94:10319, 1997.
Moen, Blood Cells 17:407-416, 1991.
Naldini et al., Science 272:263-267, 1996.
Schena, et al., Proc. Natl. Acad. Sci. 93:10614-10619, 1996.
Sharp, The Lancet 337:1277-1278, 1991.
Tolstoshev et al., Current Opinion in Biotechnology 1:55-61, 1990.

* cited by examiner

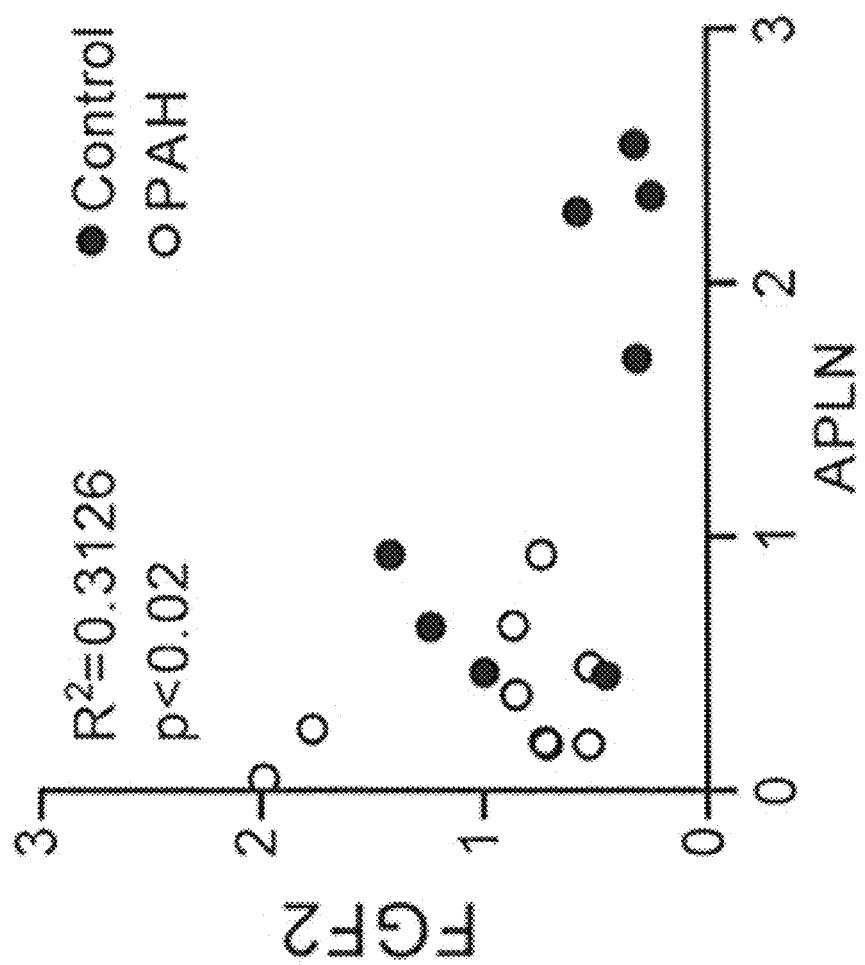

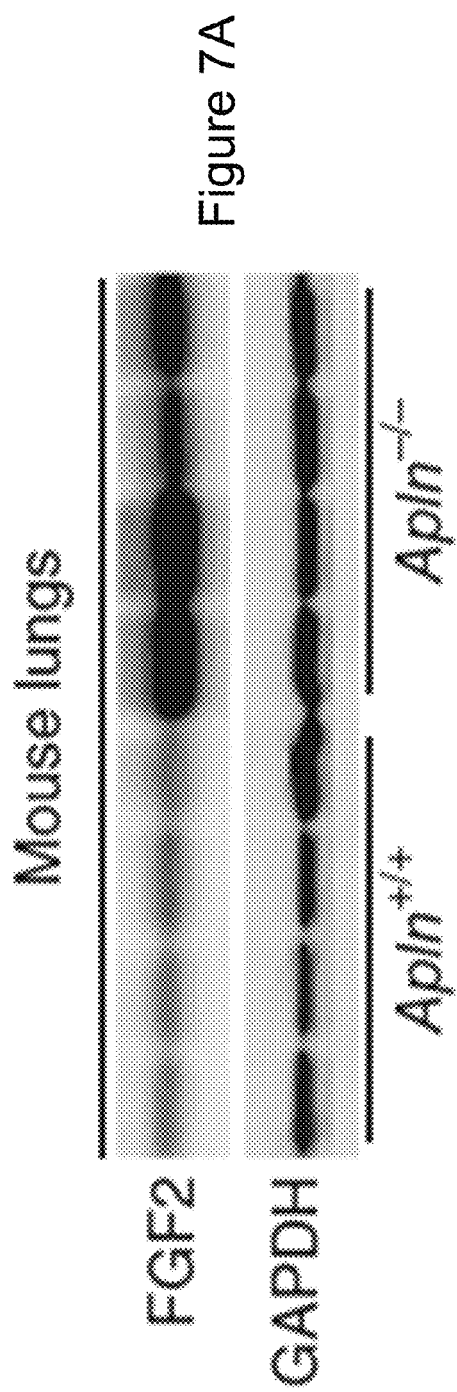
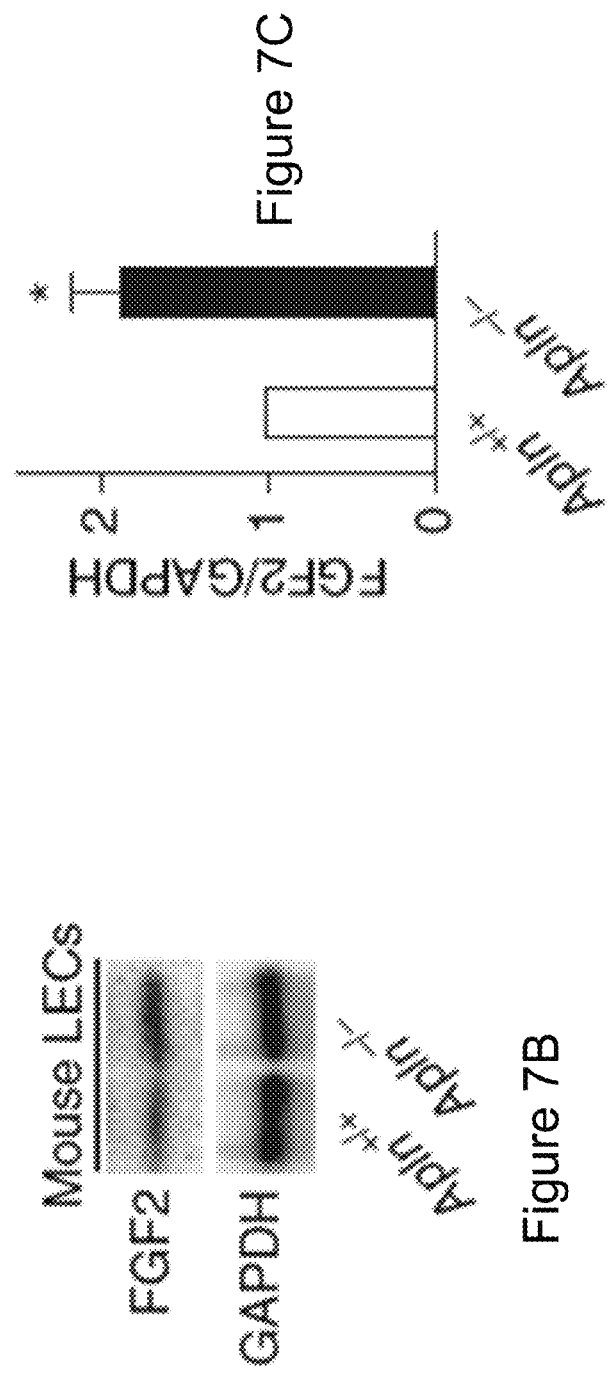
Figure 7A
Figure 7B
Figure 7C

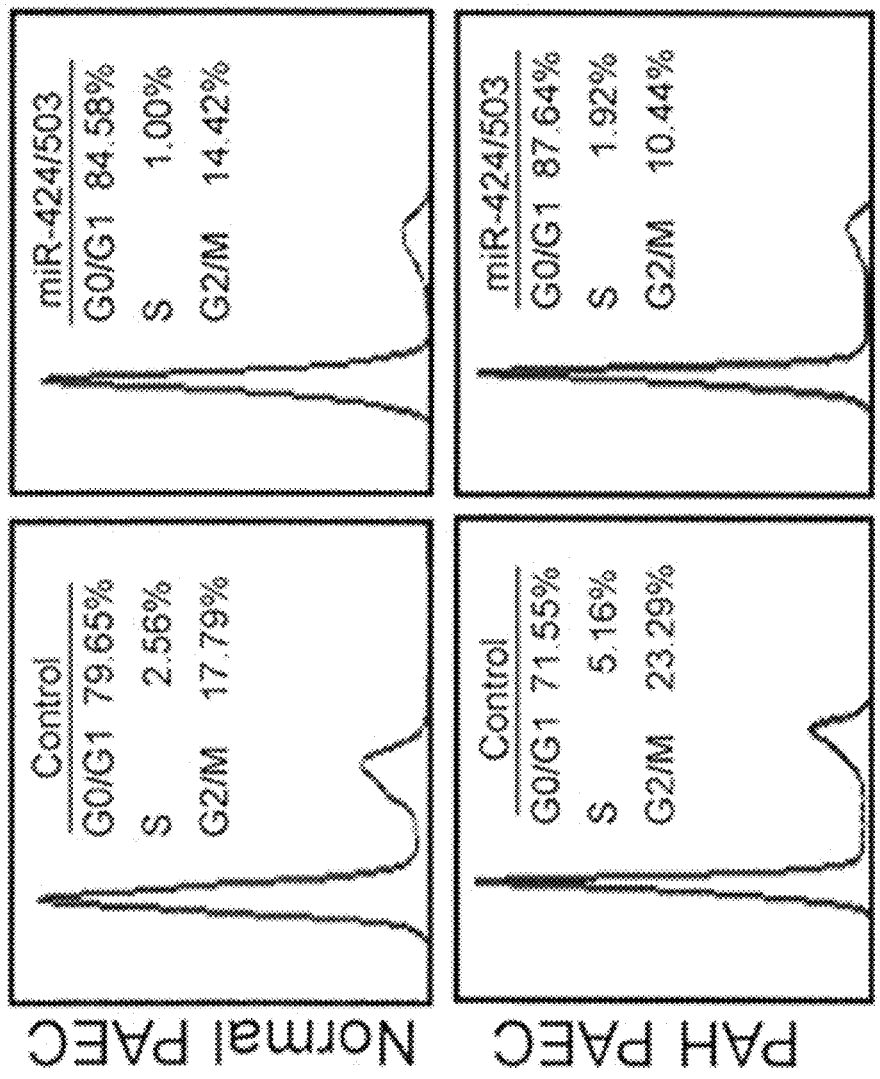

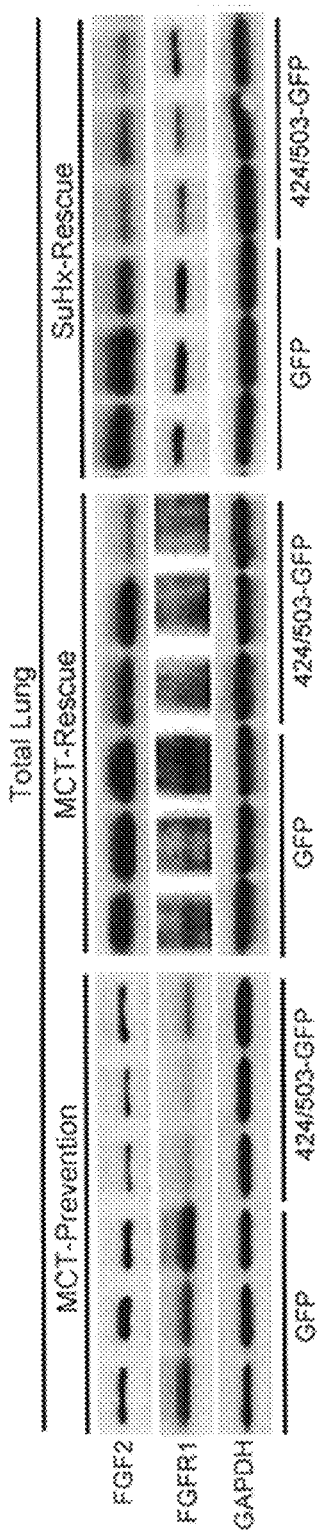
Figure 43A
Figure 43B
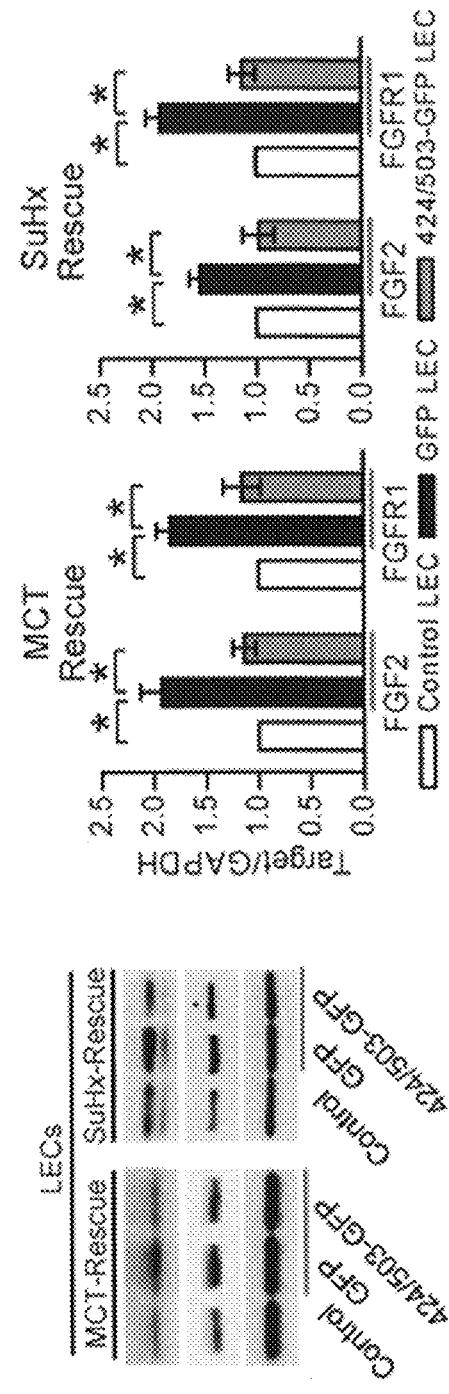
Figure 43C

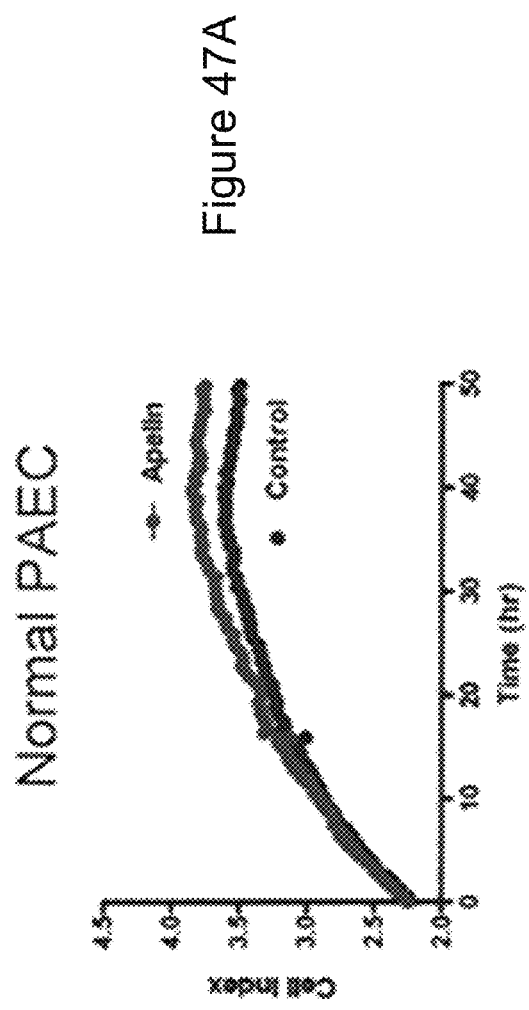
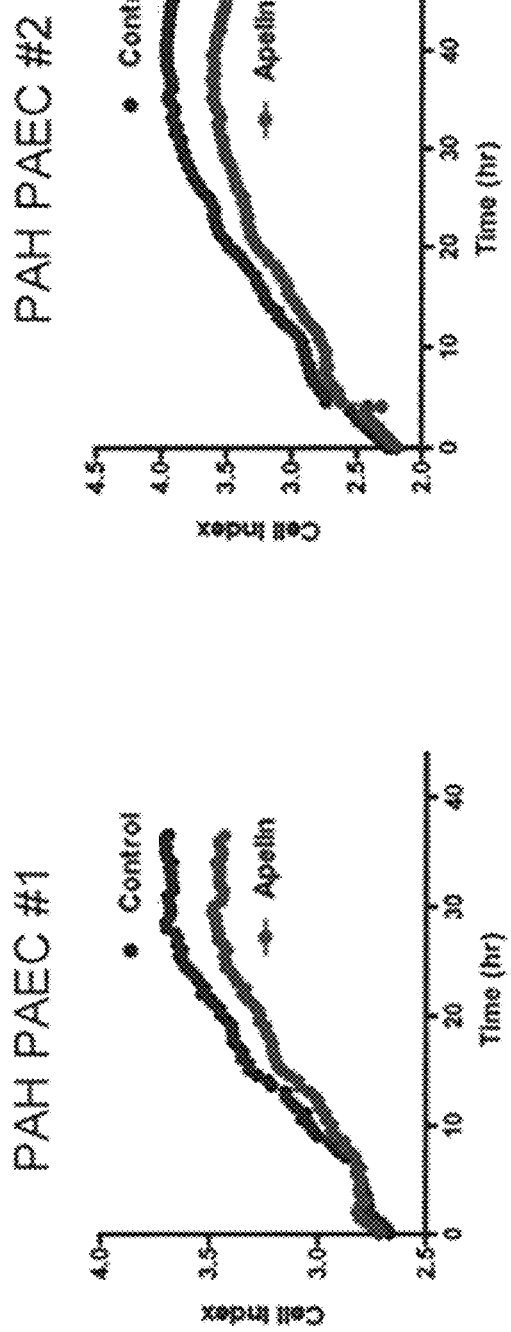
Figure 47A
Figure 47B
Figure 47C

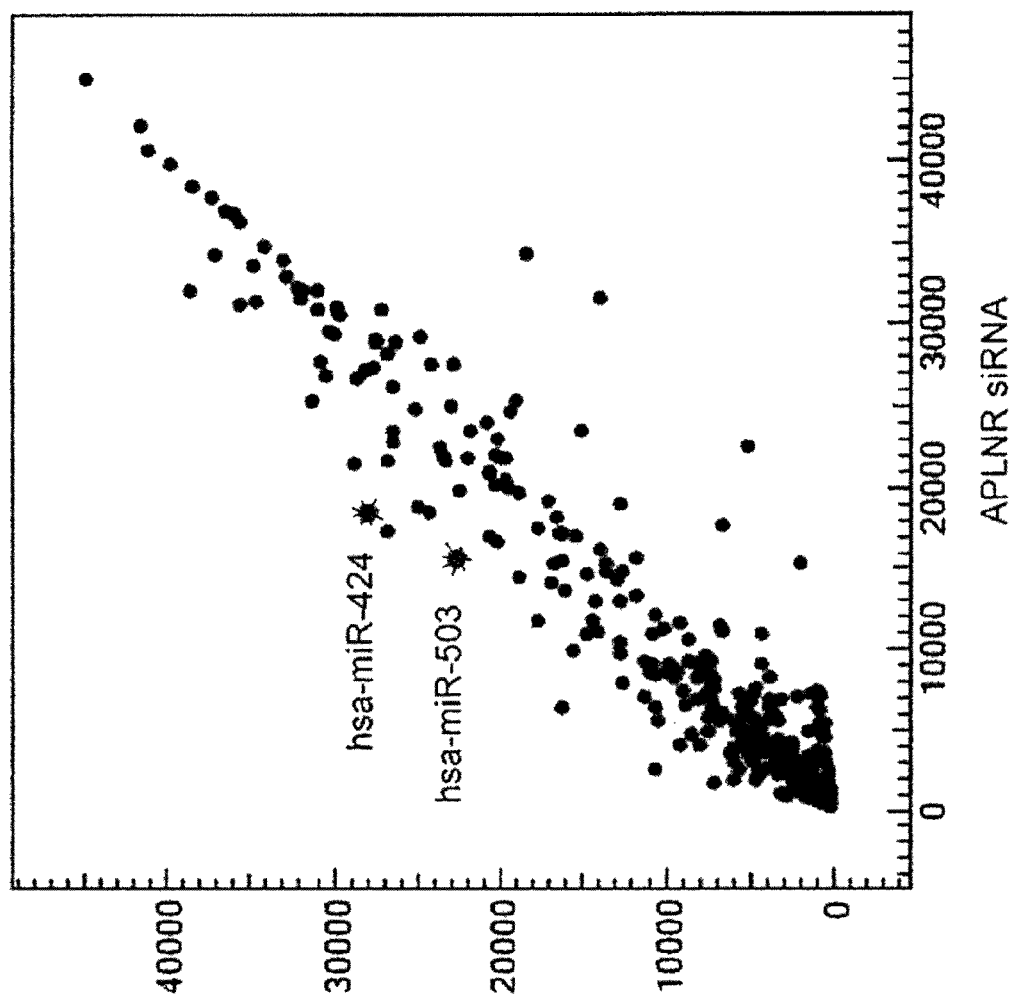

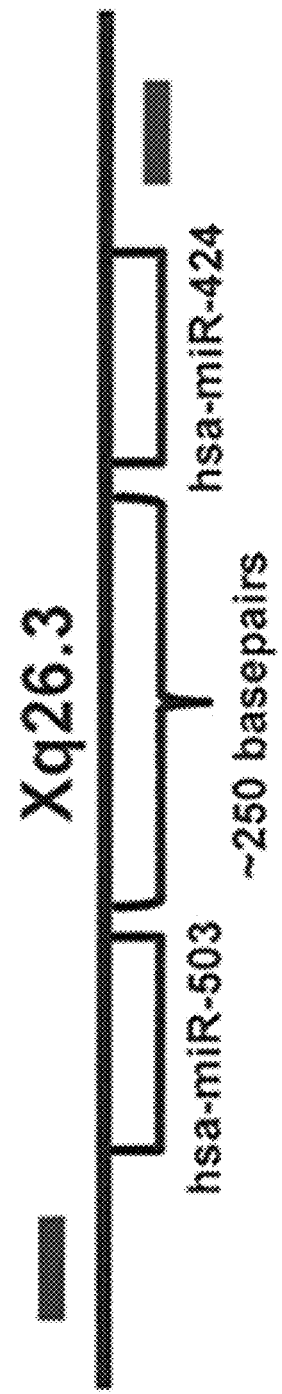
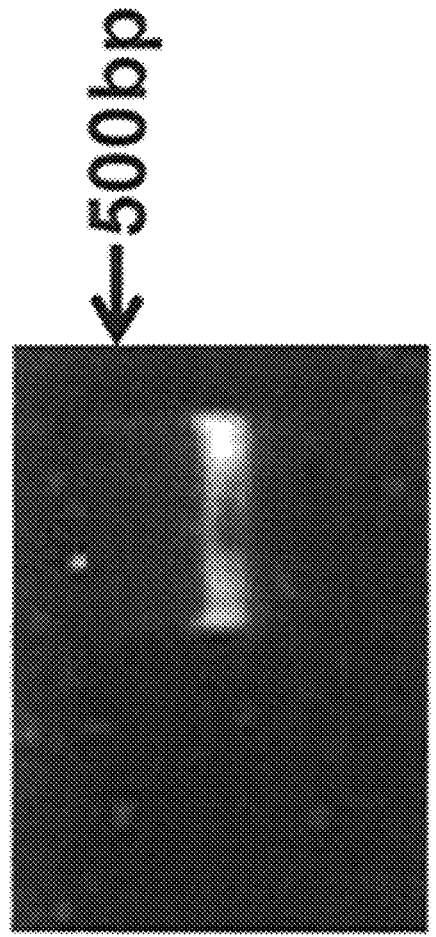
Figure 51A
Figure 51B

FGF2

```
               aaguUUGUACUUAACGAGAc  5'  hsa-miR-424    SEQ ID NO:23
               :|:||| |||  |||||||
SEQ ID  5054:5' uauuAGAAAUUA--UGCUGCUa  3'  FGF2        SEQ ID NO:25
NO:25          ||||  |  :  |||||||
               UCUUGACAAGGGCACGGAU  5'  hsa-miR-503    SEQ ID NO:24 aaGUUUGUACUUAACGACGAc  5'  hsa-miR-424   SEQ ID NO:23
               :|||:||   ||   |||||
SEQ ID  5587:5' uuuAAAAAUAU--UUUGCUGCUa  3'  FGF2       SEQ ID NO:26
NO:26          ||  |  :  :  |||||||
               UCUUGACAA--GGGCGACGAU  5'  hsa-miR-503   SEQ ID NO:24 aaguUUUGUA-CUUAACGACUGCUGAc  5'  hsa-miR-424  SEQ ID NO:23
               :||| ||  |:  |||||||
SEQ ID  5625:5' gaaGAAAUCUACAGAUGCUGCUa  3'  FGF2        SEQ ID NO:27
NO:27          ||  :  :  |||||||
               UCUUGACAAGGGCGACGAU  5'  hsa-miR-503    SEQ ID NO:24
```

Figure 53A

FGFR1

```
3'  aaguuUUGUACUUAACGACGAc 5'  hsa-miR-424  SEQ ID NO:23
         ||:|  ||||||||||
SEQ ID  5' ccucAAUAAAAUUGCUGCUg 3'  FGFR1
NO:28  872:
         ||:    ::|||||||
3'  UCUUGACAAGGGCGACGAU 5'  hsa-miR-503  SEQ ID NO:23

3'  aaguUUUGUACUUAACGACGAc 5'  hsa-miR-424  SEQ ID NO:23
         |||||::  |:|||||||||
SEQ ID  5' gggAAAAUG-GGAUUGCUGCUu 3'  FGFR1
NO:29  2039:
         ||  ||    ::|||||||
3'  UCUUGAC-AAGGGCGACGAU 5'  hsa-miR-503  SEQ ID NO:24
```

Figure 53B

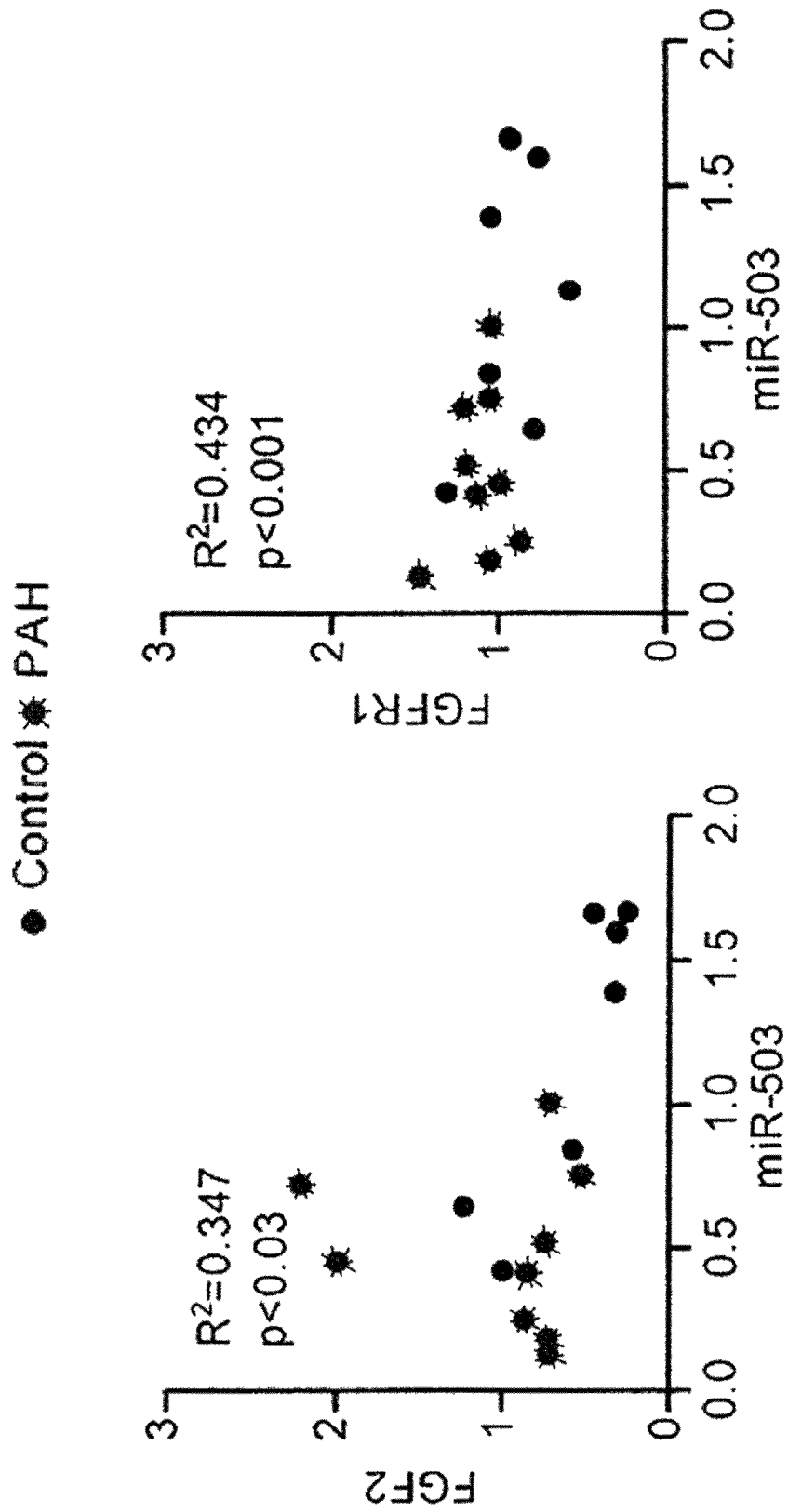

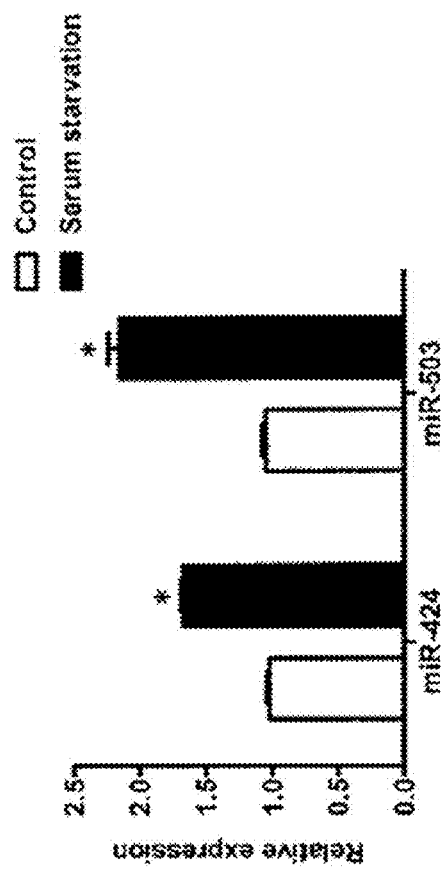
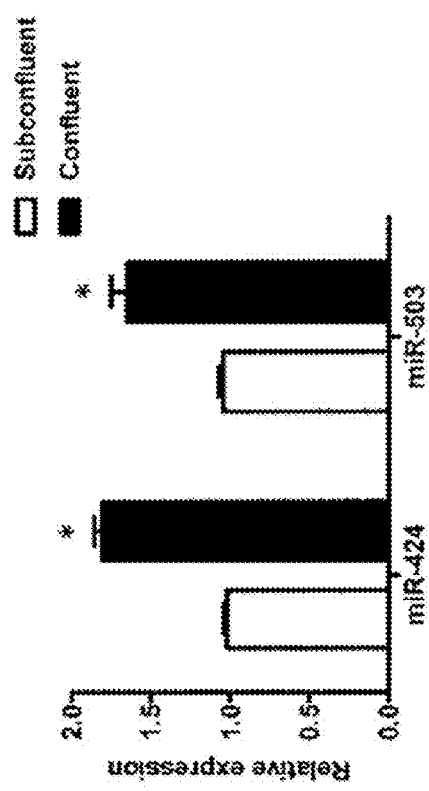
Figure 58B
Figure 58A

COMPOSITIONS AND METHODS OF USING MICRO RNAS

CROSS-REFERENCE TO RELATED APPLICATION

The present application is entitled to priority under 35 U.S.C. §119(e) to U.S. Provisional Patent Application No. 61/726,792, filed Nov. 15, 2012, which is hereby incorporated by reference in its entirety herein.

STATEMENT OF RIGHTS TO INVENTIONS MADE UNDER FEDERALLY SPONSORED RESEARCH

This invention was made with government support under HL095654 and HL101284 awarded by National Institute of Health. The government has certain rights in the invention.

BACKGROUND OF THE INVENTION

Pulmonary arterial hypertension (PAH) is a condition in which the pressure in the lung circulation increases, eventually causing heart failure and death. Although many causes and conditions are found to be associated with PAH, many of them share in common several fundamental pathophysiological features. One important feature among these processes is dysfunction of the endothelium, the internal cellular layer of all vessel walls, which is normally responsible for the production and metabolism of a large array of substances that regulate vessel tone and repair and inhibit clot formation. In the setting of PAH, vascular cell dysfunction can lead to excessive production of deleterious substances and impaired production of protective substances. Whether this is the primary event in the development of PAH or part of a downstream cascade remains unknown, but in either case it is an important factor in the progressive vasoconstriction and vascular proliferation that characterize the disease.

Apelin is highly expressed in the endothelial cells of both systemic and pulmonary vasculature. The apelin receptor (APLNR) is the only known receptor for apelin, and is also highly expressed in the lungs. Apelin knockout mice have been found to be more susceptible to hypoxia induced pulmonary hypertension, and administration of exogenous apelin has shown amelioration of experimental models of pulmonary hypertension. However, exogenous apelin is rapidly cleared from circulation with a plasma half-life of less than 8 mins.

Therefore, a need exists for restoring normal function within these cells to reduce or improve pulmonary arterial hypertension.

SUMMARY OF THE INVENTION

The present invention provides compositions and methods of using microRNAs.

Compositions and methods are disclosed that are useful for identifying a subject in need of therapeutic intervention to reduce or improve a symptom of pulmonary arterial hypertension, reducing proliferation of pulmonary vascular cells in a subject, or treating pulmonary arterial hypertension in a subject.

In one aspect, the compositions include an inhibitor of fibroblast growth factor 2 (FGF2) expression comprising at least one of: a mature sequence of miR-424 or miR-503; a pri-miRNA of miR-424 or miR-503; a pre-miRNA of miR-424 or miR-503; and the complement thereof. In one embodiment, the mature sequence includes a polynucleotide selected from the group consisting of: a nucleotide sequence as shown in SEQ ID NO: 9 or SEQ ID NO: 10; a nucleotide sequence consisting of 30 to 120 nucleotides which has an identity of at least 85% to the nucleotide sequence as shown in SEQ ID NO: 9 or SEQ ID NO: 10; or the complement thereof. In another embodiment, the inhibitor is expressed by a recombinant expression vector.

Pharmaceutical composition for reducing proliferation of pulmonary vascular cells in a subject in need thereof comprising the composition and a pharmaceutically acceptable carrier are also disclosed.

In another aspect, a method of identifying a subject in need of therapeutic intervention to reduce or improve a symptom of pulmonary arterial hypertension includes, detecting an alteration in the level of a biomarker selected from the group consisting of fibroblast growth factor 2 (FGF2), apelin (APLN), miR-424, and miR-503 in a sample from the subject relative to a reference, thereby identifying the subject as in need of therapeutic intervention to reduce or improve the symptom of pulmonary arterial hypertension. In some embodiments, the level of FGF2 is increased relative to the reference, and/or the level of APLN, miR-424, or miR-503 is decreased relative to the reference. In another embodiment, the biomarker further includes at least one of fibroblast growth factor receptor 1 (FGFR1), apelin receptor (APLNR), argonaute 2 (Ago2), miR-15a, miR-16, miR-195 and miR-497.

In yet another aspect, a method of reducing proliferation of pulmonary vascular cells in a subject in need thereof including administering to the pulmonary vascular cells of the subject a composition comprising an inhibitor of fibroblast growth factor 2 (FGF2) expression comprising at least one of: a mature sequence of miR-424 or miR-503; a pri-miRNA of miR-424 or miR-503; a pre-miRNA of miR-424 or miR-503; and the complement thereof, wherein the proliferation of pulmonary vascular cells is reduced in the subject following administration of the composition.

In still yet another aspect, a method of treating pulmonary arterial hypertension in a subject in need thereof including administering to the pulmonary vascular cells of the subject an inhibitor of fibroblast growth factor 2 (FGF2) expression comprising at least one of: a mature sequence of miR-424 or miR-503; a pri-miRNA of miR-424 or miR-503; a pre-miRNA of miR-424 or miR-503; and the complement thereof, and wherein the pulmonary arterial hypertension is reduced in the subject following administration of the inhibitor.

In one more aspect, a biomarker panel includes fibroblast growth factor 2 (FGF2), apelin (APLN), miR-424 and miR-503 or capture molecules that specifically bind the biomarkers. In a particular embodiment, the biomarker panel also includes fibroblast growth factor receptor 1 (FGFR1), apelin receptor (APLNR), argonaute 2 (Ago2), miR-15a, miR-16, miR-195 and miR-497 or capture molecules that specifically bind the biomarkers.

BRIEF DESCRIPTION OF THE DRAWINGS

FIG. 5 is a dot plot showing the correlation between APLN and FGF2 mRNA levels in PAECs from controls and subjects with PAH. The P value shown was calculated by unpaired two-tailed Student's t test;

FIG. 7A is a blot showing expression of FGF2 protein in total lung homogenates;

FIG. 7B is a blot showing expression of FGF2 protein in isolated LECs from wild-type (Apln+/+) and Apln-null (Apln-/-) mice (LECs were isolated from 5 to 6 mice per group).

FIG. 7C is a bar graph showing expression of FGF2 protein in isolated LECs from wild-type (Apln+/+) and Apln-null (Apln-/-) mice (LECs were isolated from 5 to 6 mice per group). *P<0.05 compared to wild type by unpaired two-tailed Student's t test. Error bars, s.e.m.;

Figure 23B:
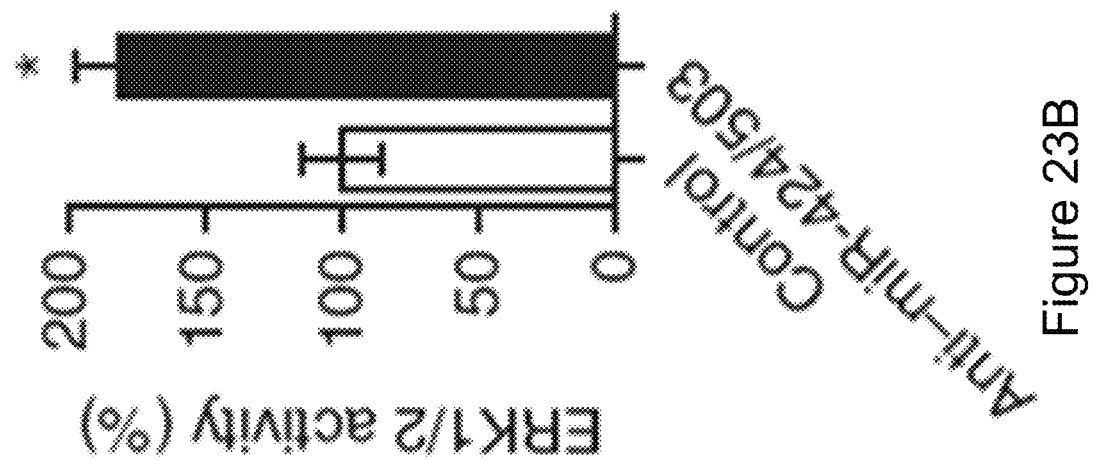
Figure 23A:
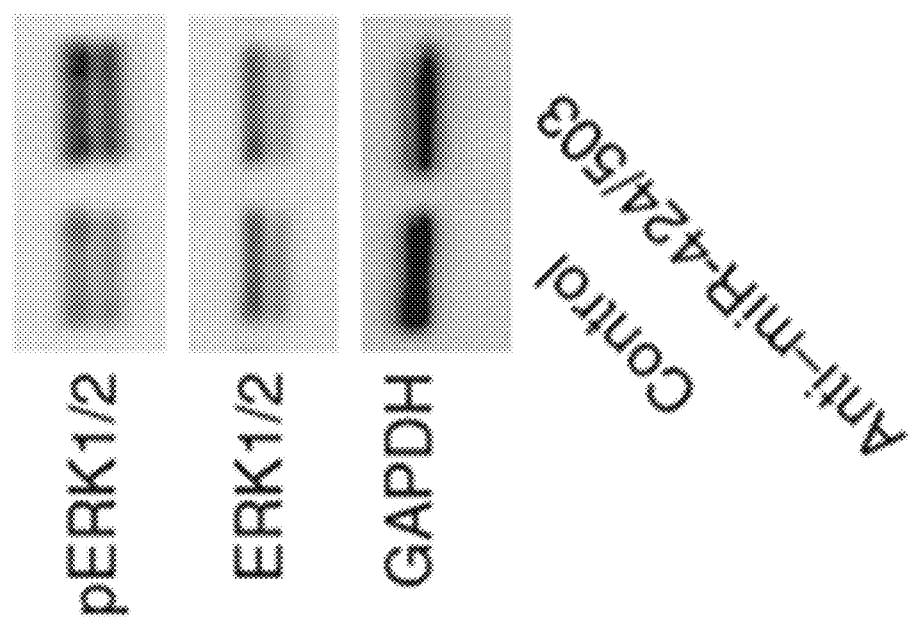
Figure 24:
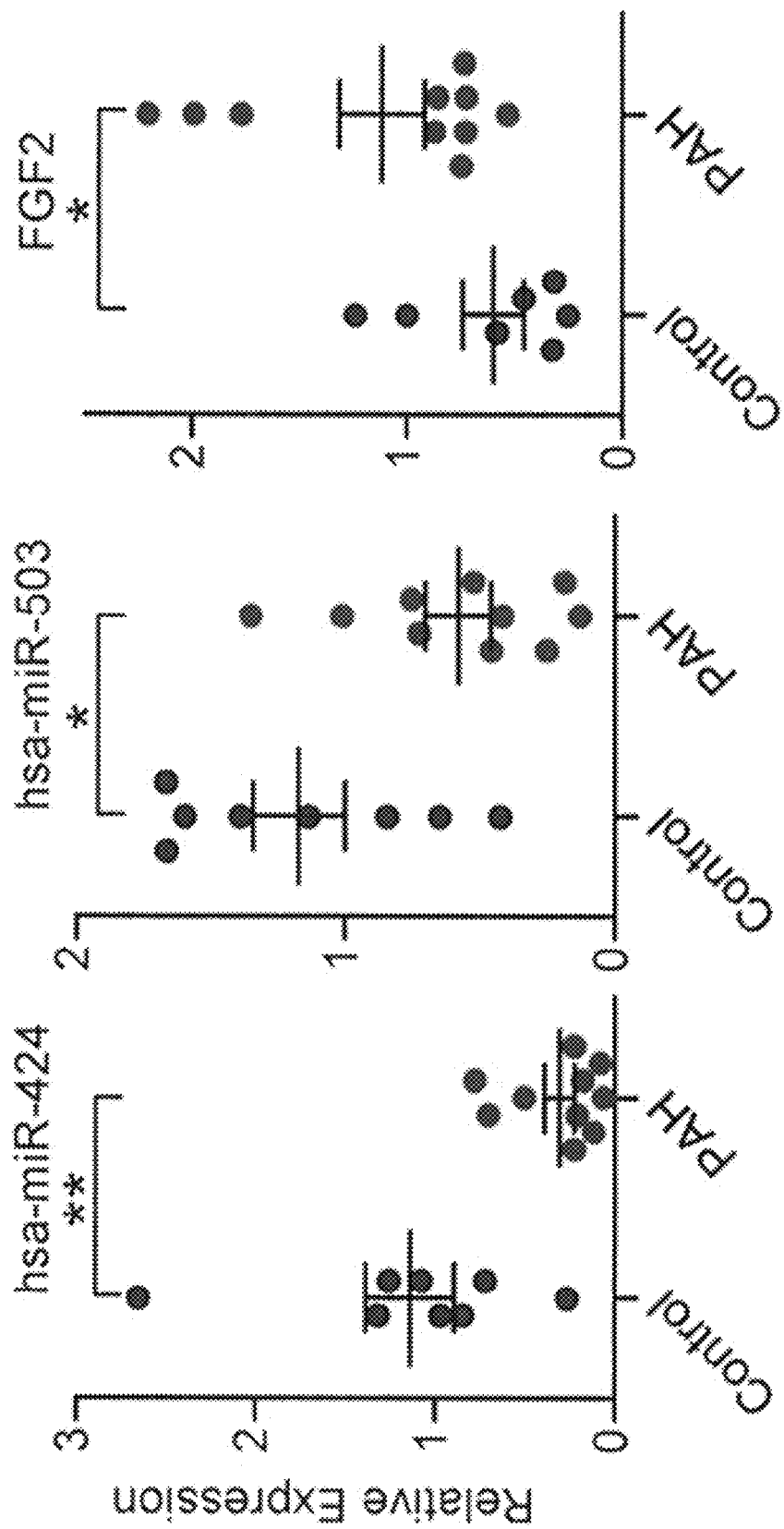
Figures 25A, 25B:
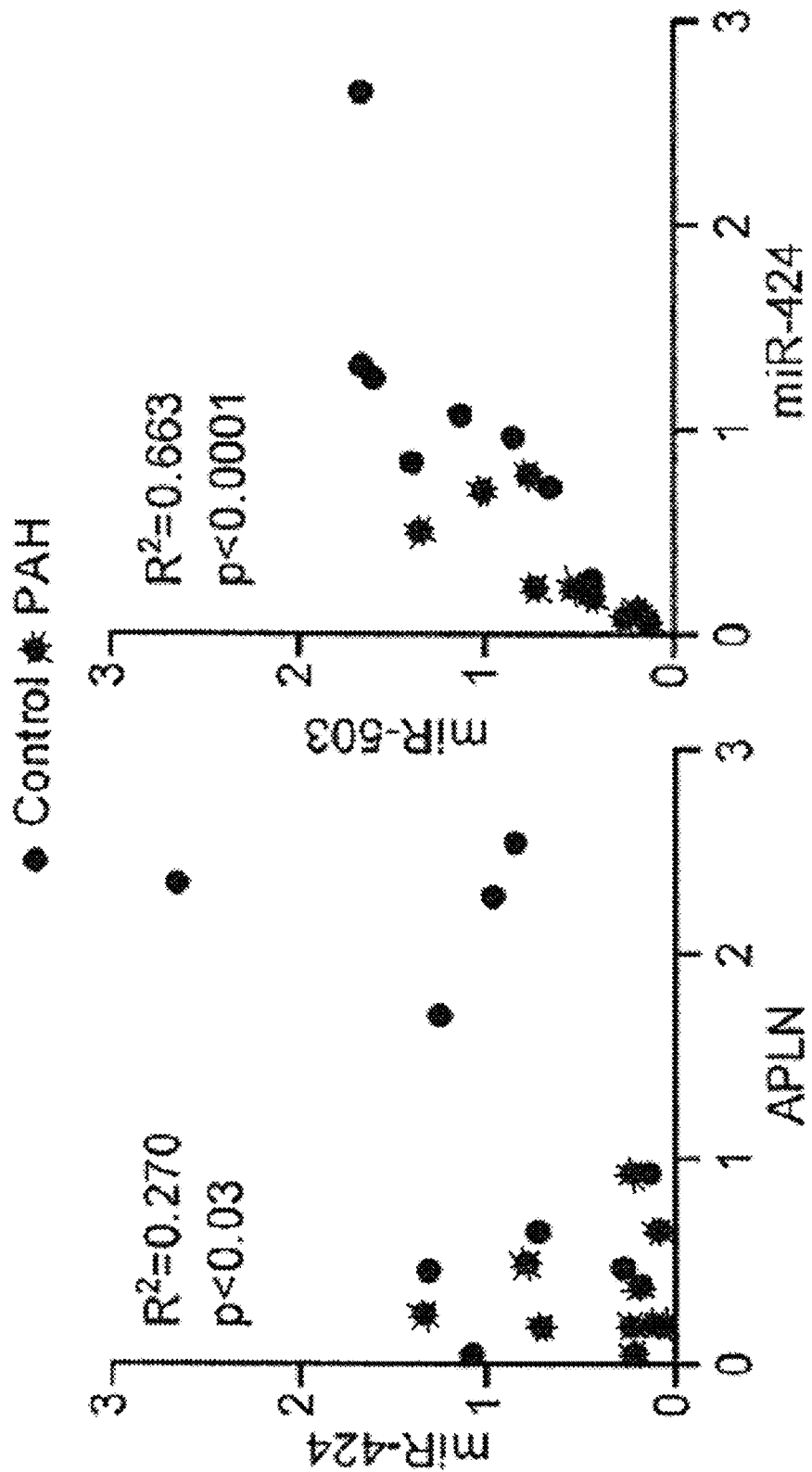
Figures 25C, 25D:
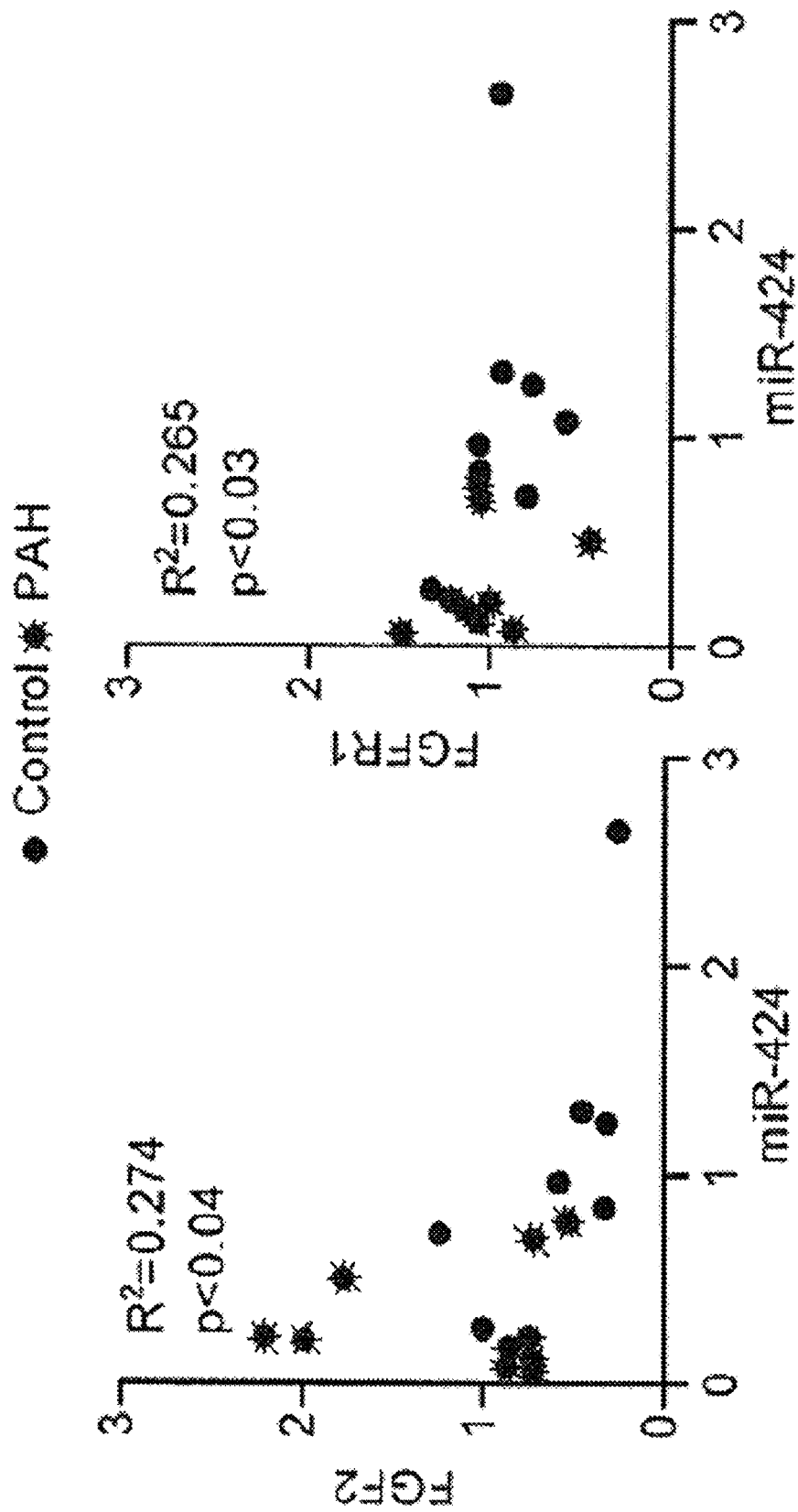
Figure 26:
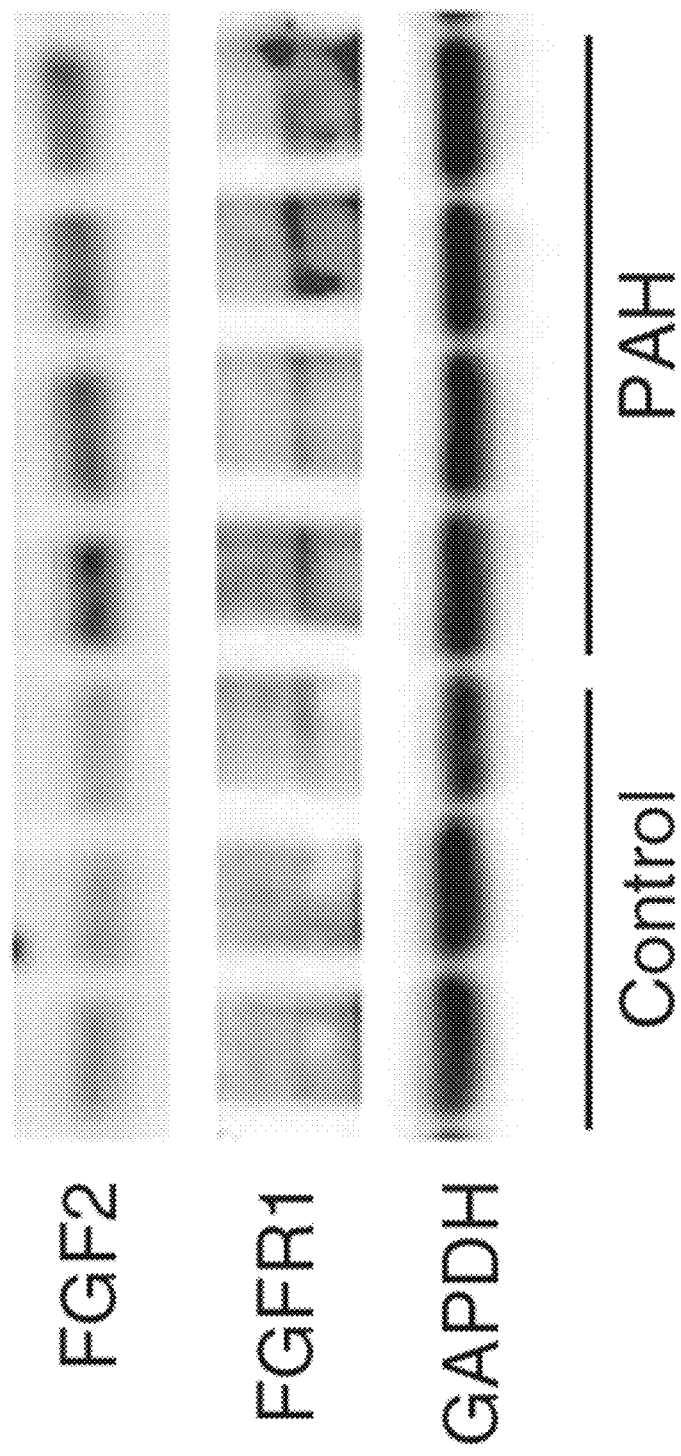
Figure 27:
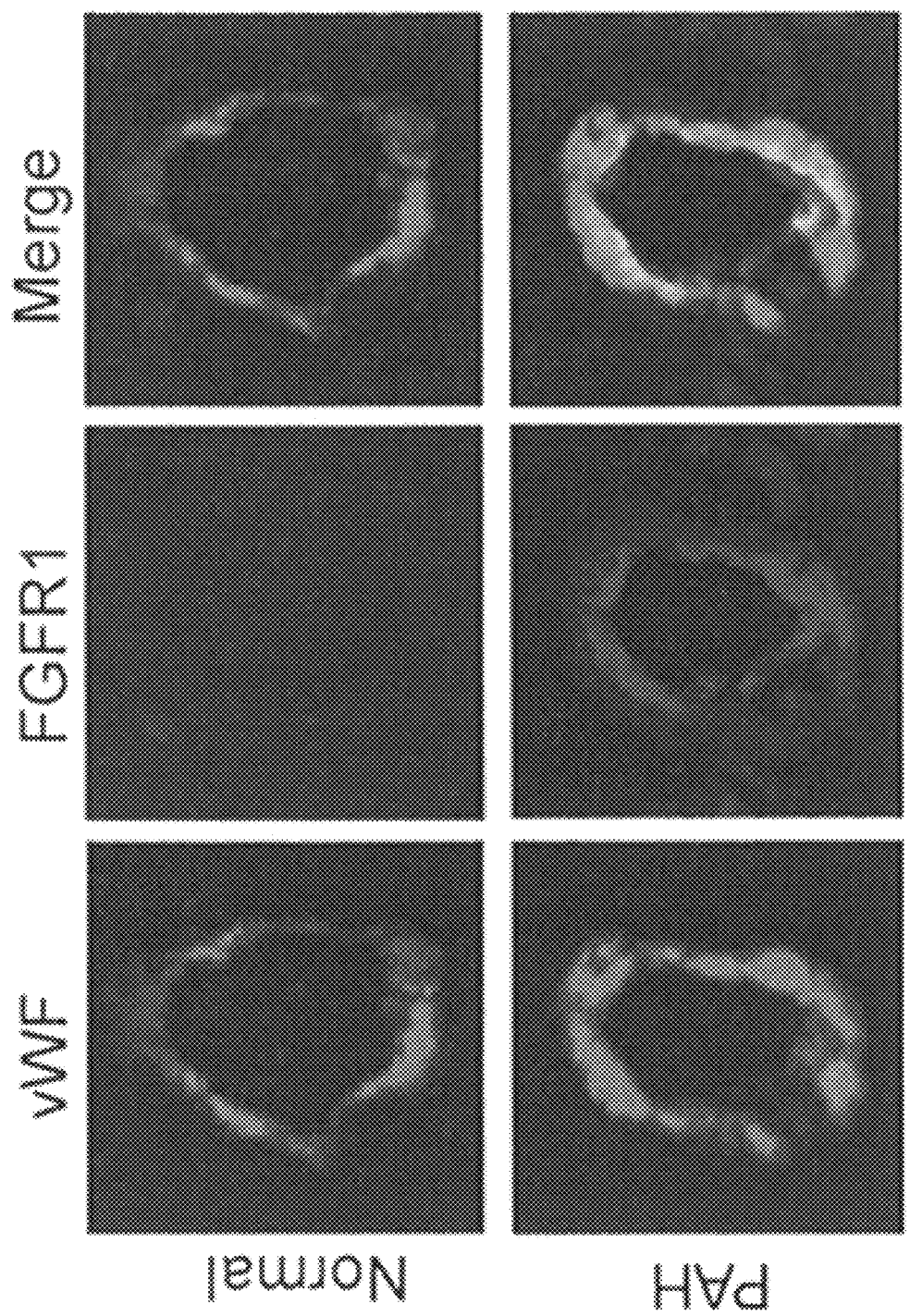
Figure 28A:
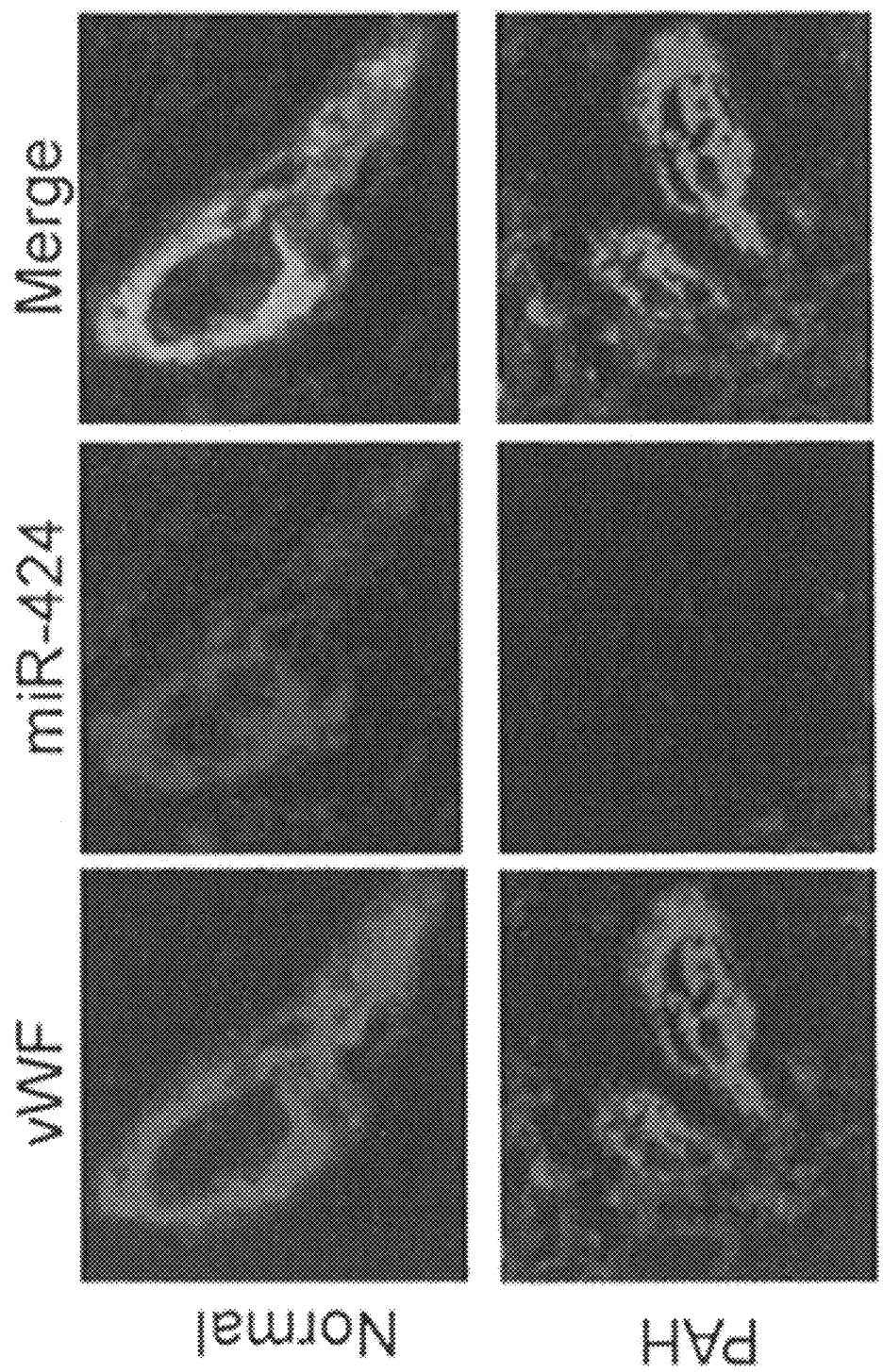
Figure 28B:
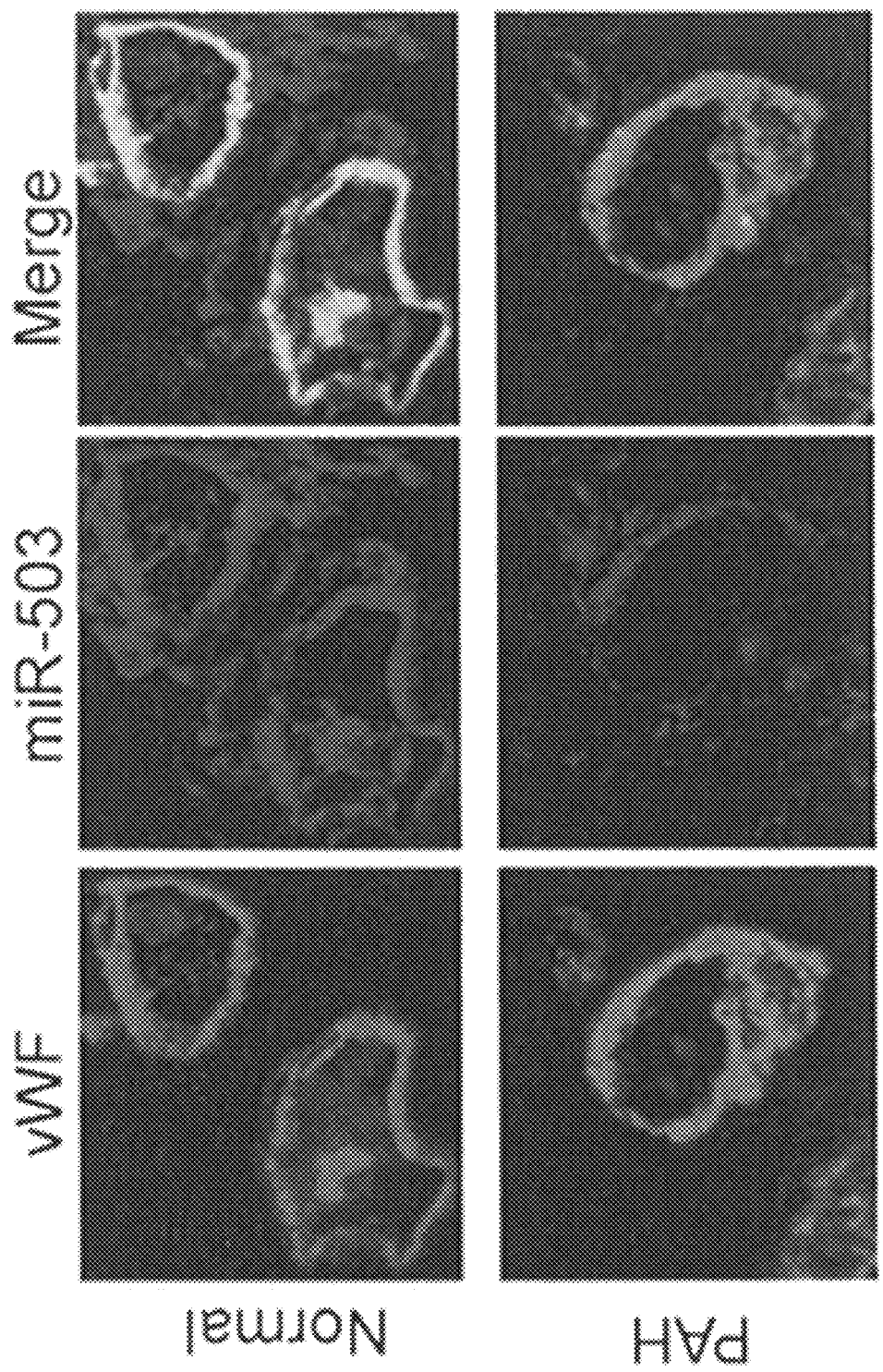
Figure 30:
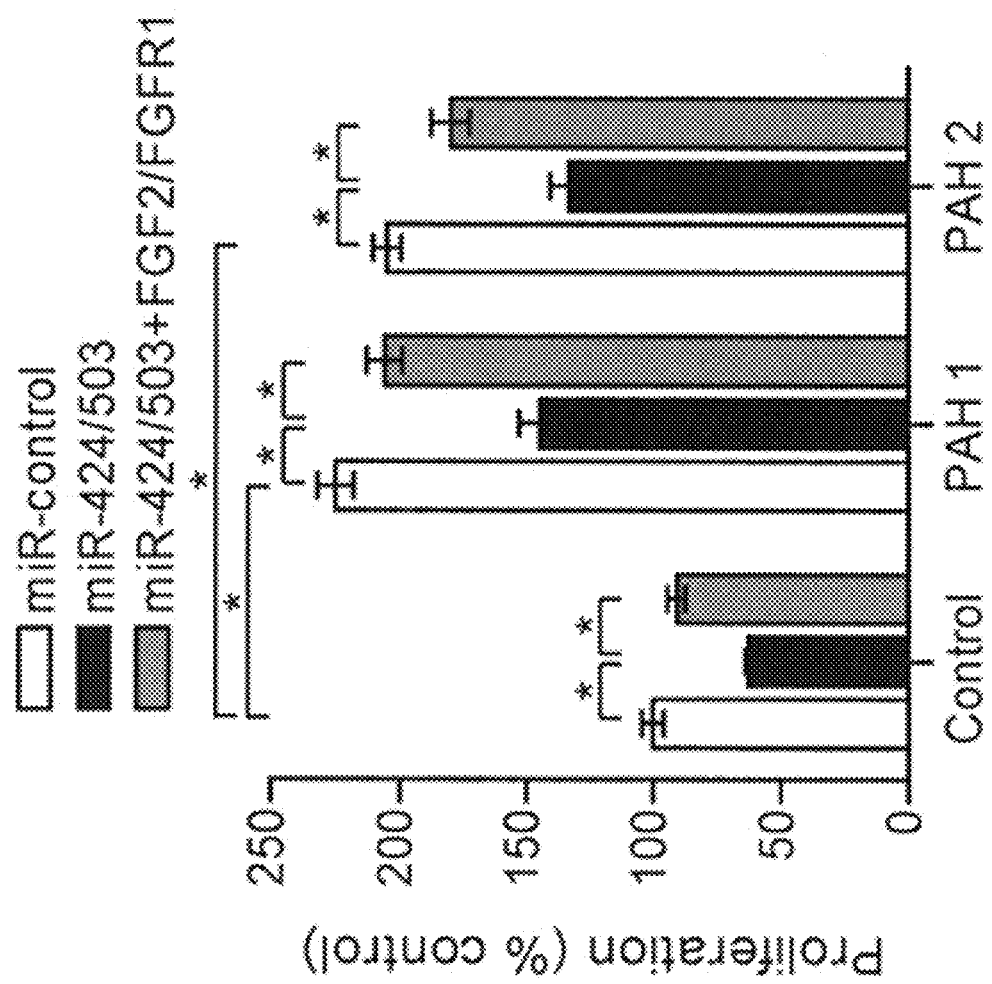
Figure 31:
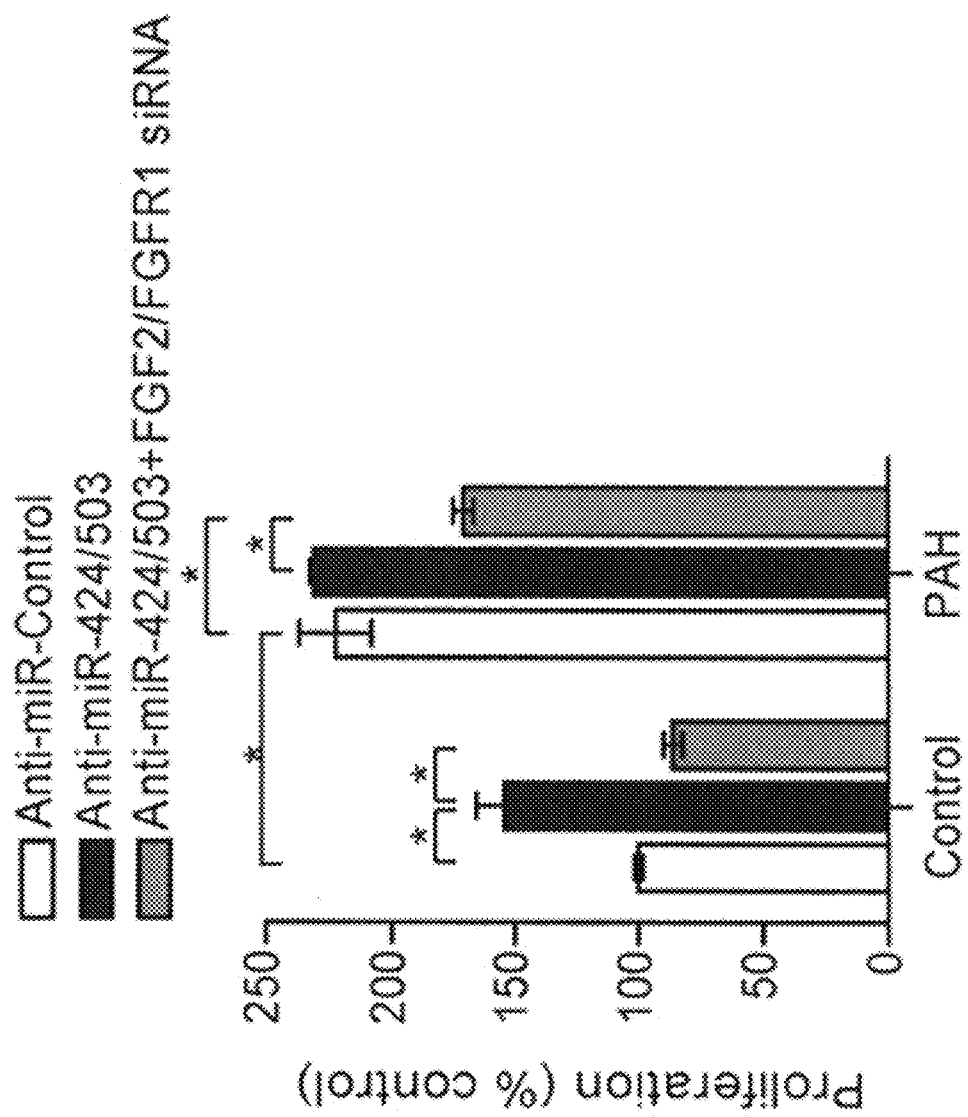
Figure 32A:
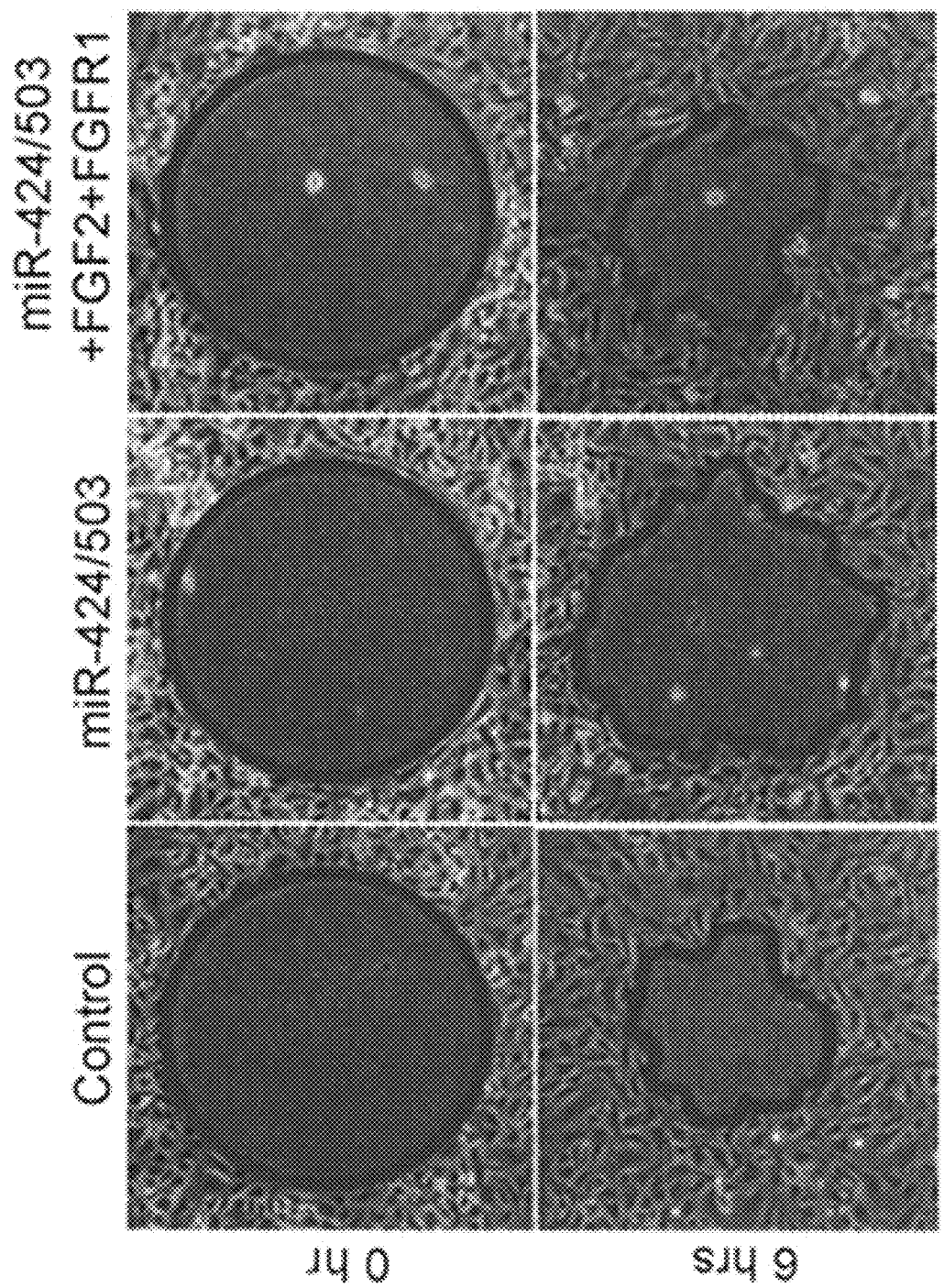
Figure 32B:
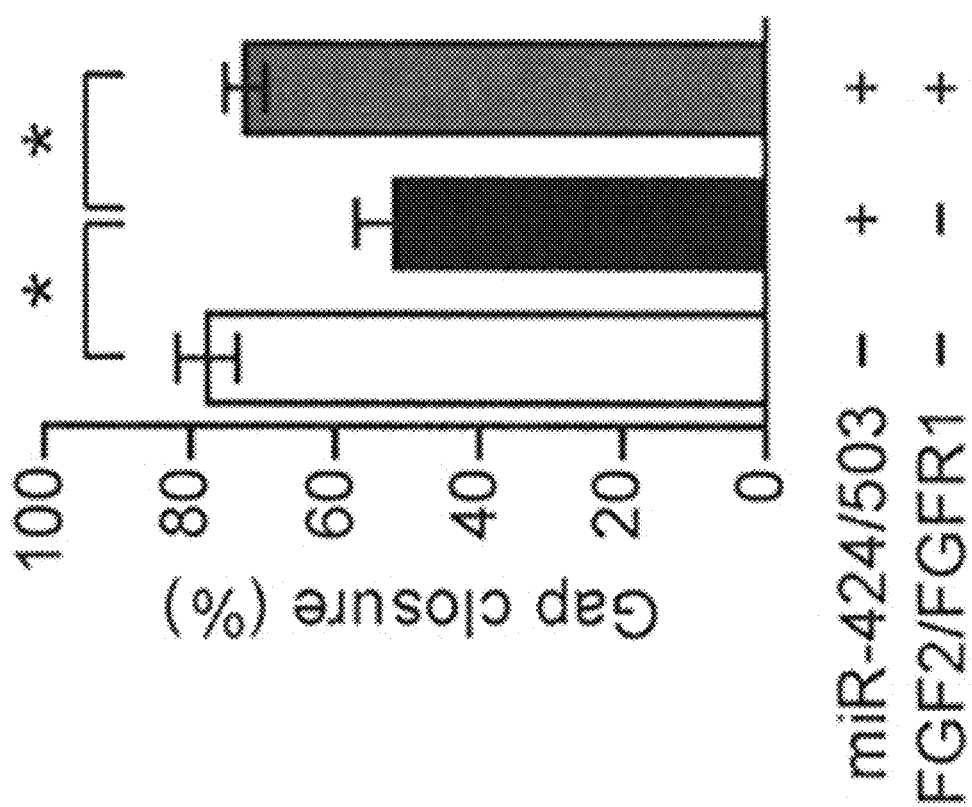
Figures 33A, 33B:
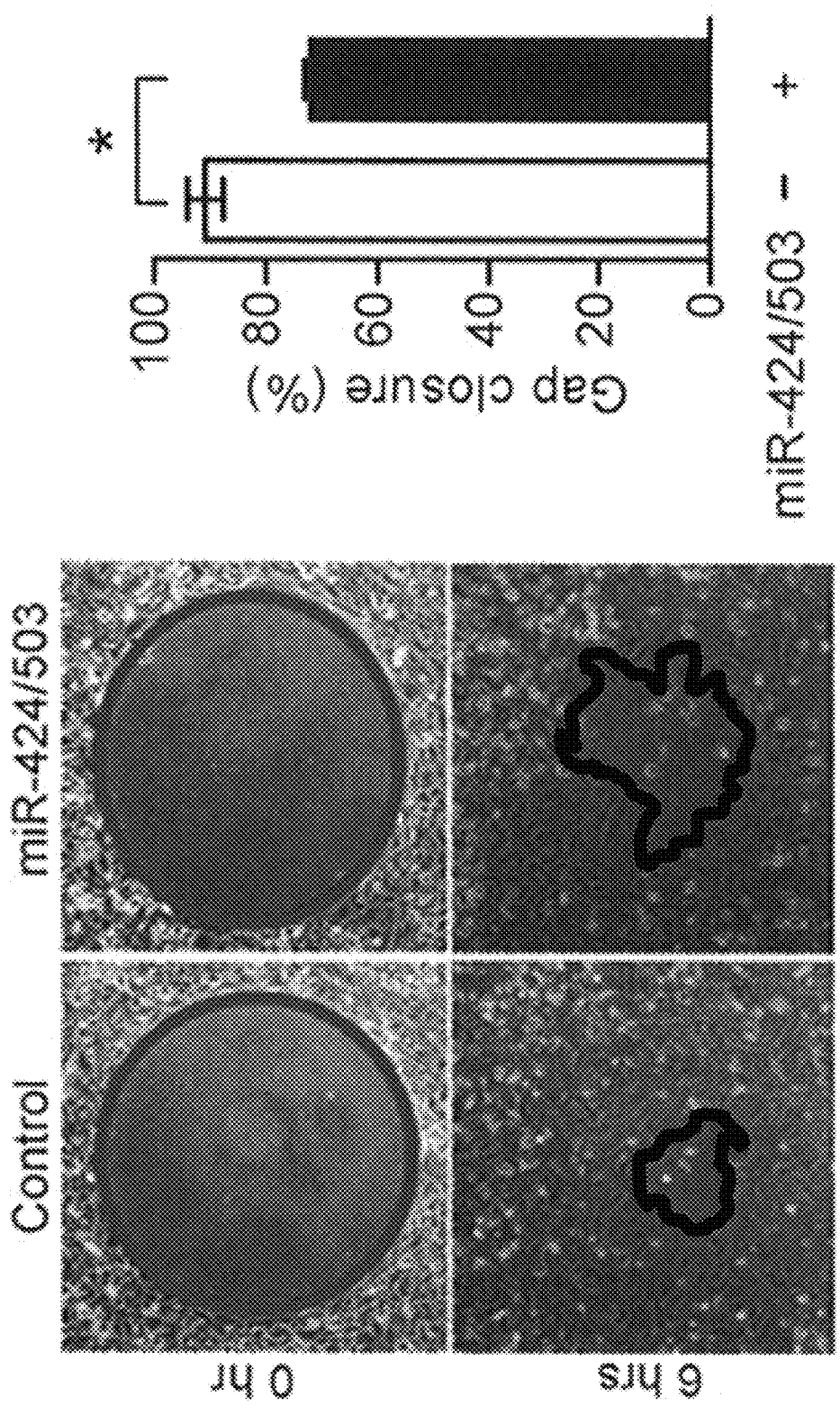
Figure 34:
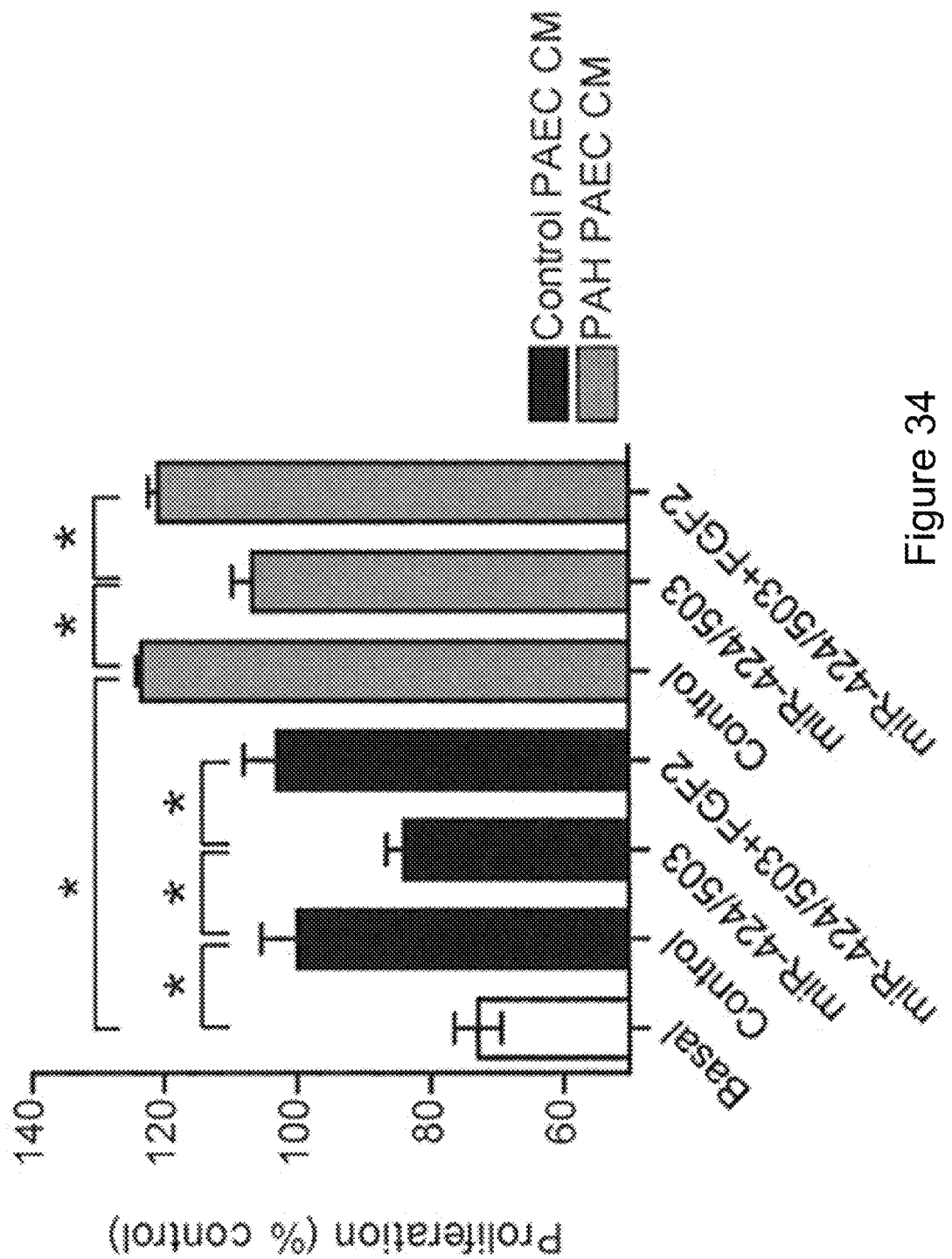
Figure 35:
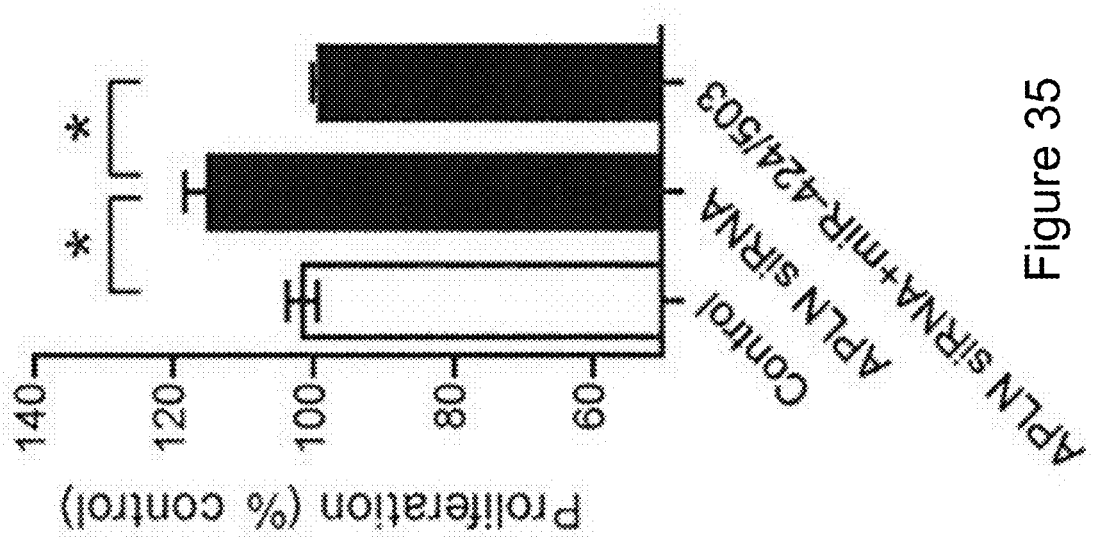
Figure 36:
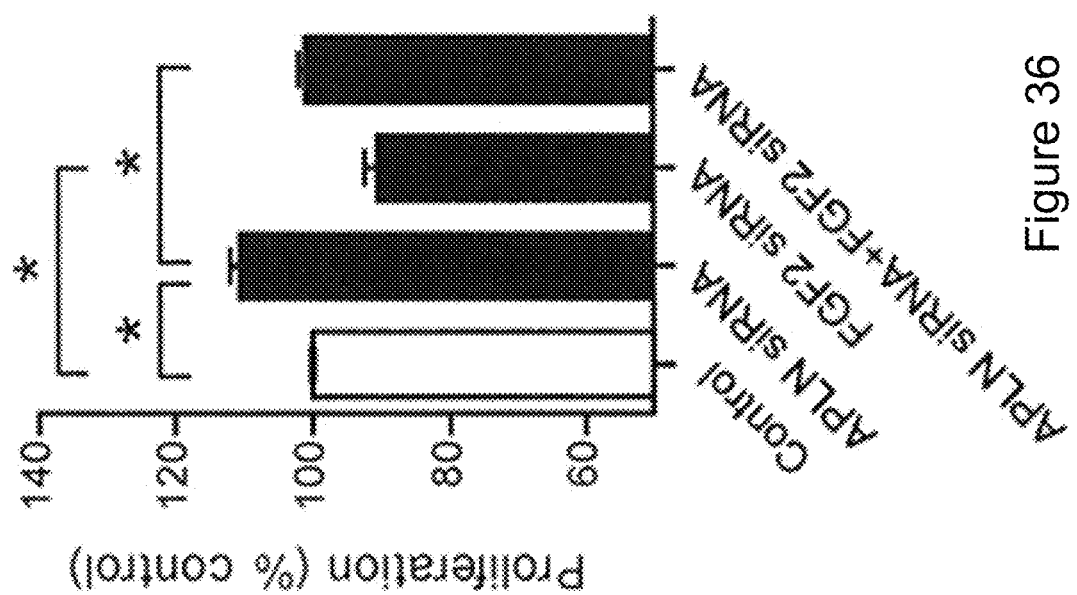
Figures 37A, 37B:
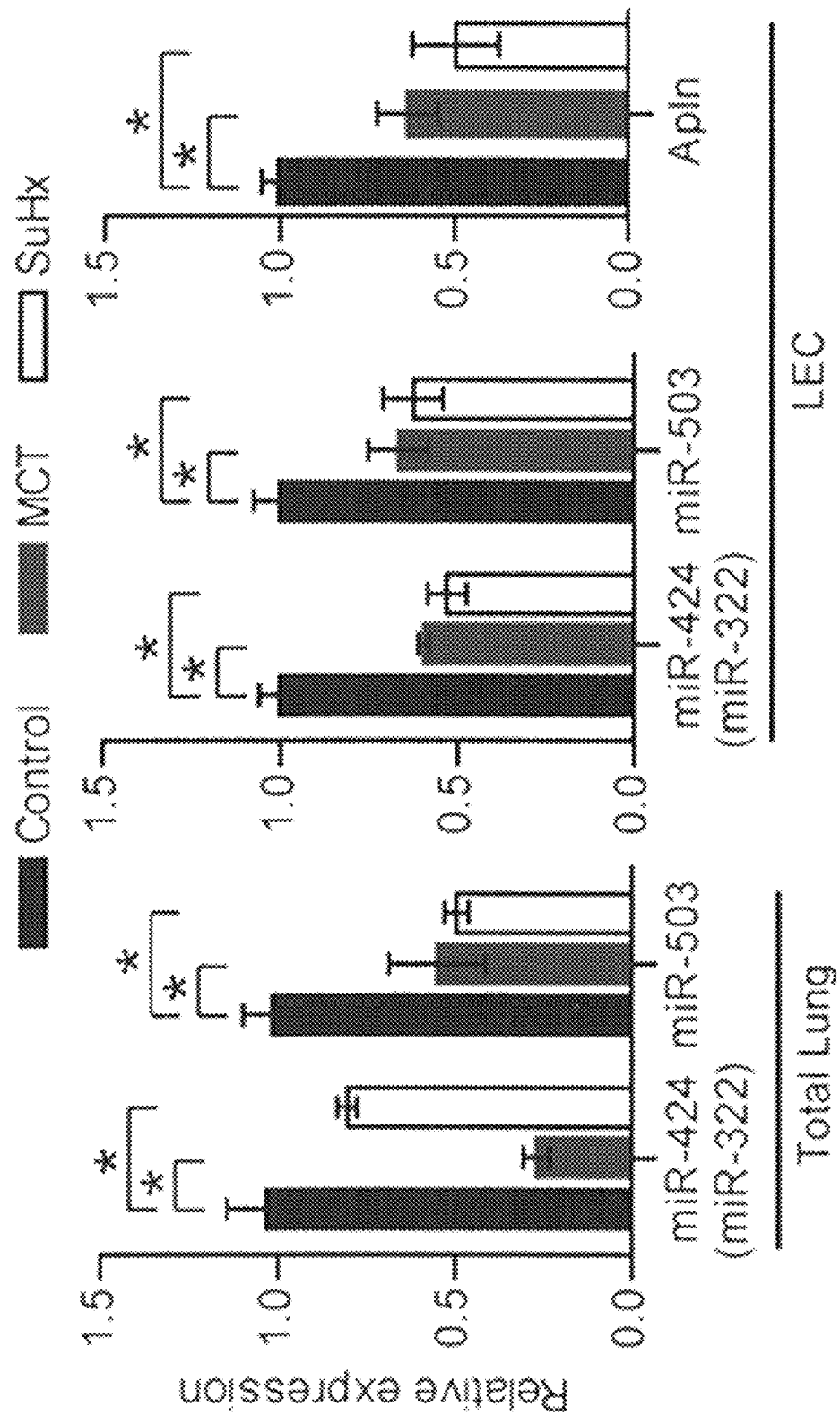
Figure 38:
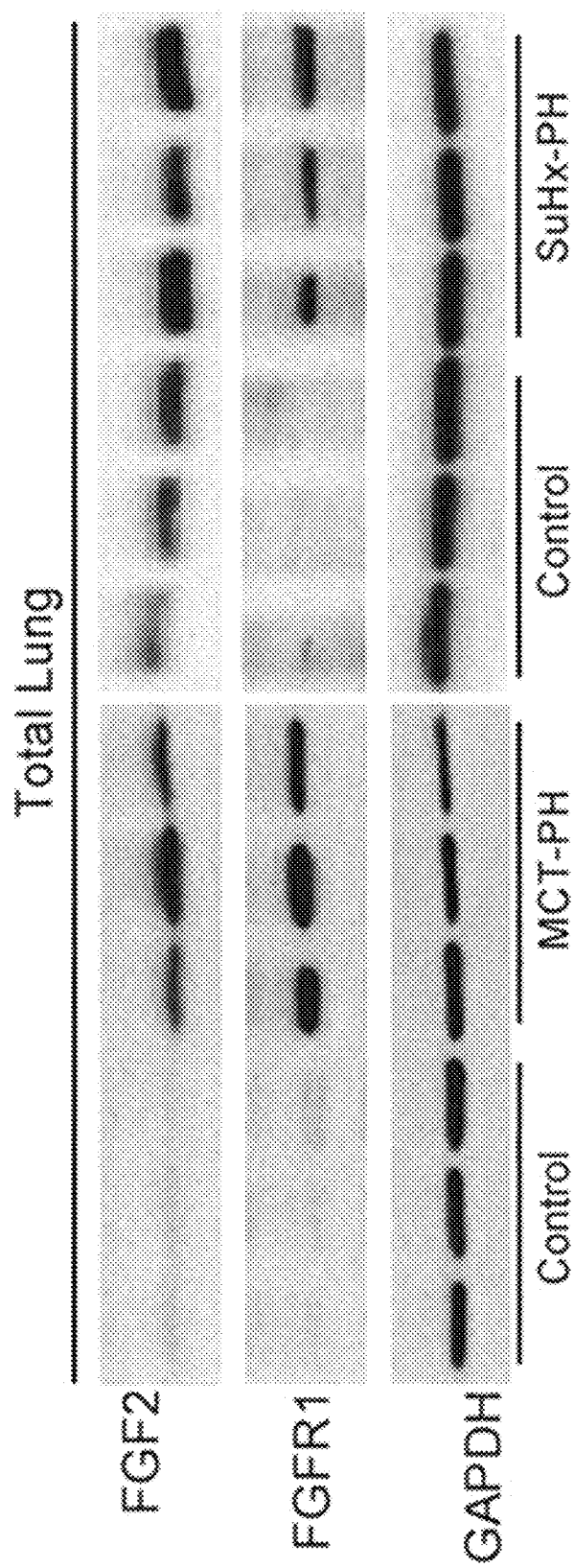
Figure 39:
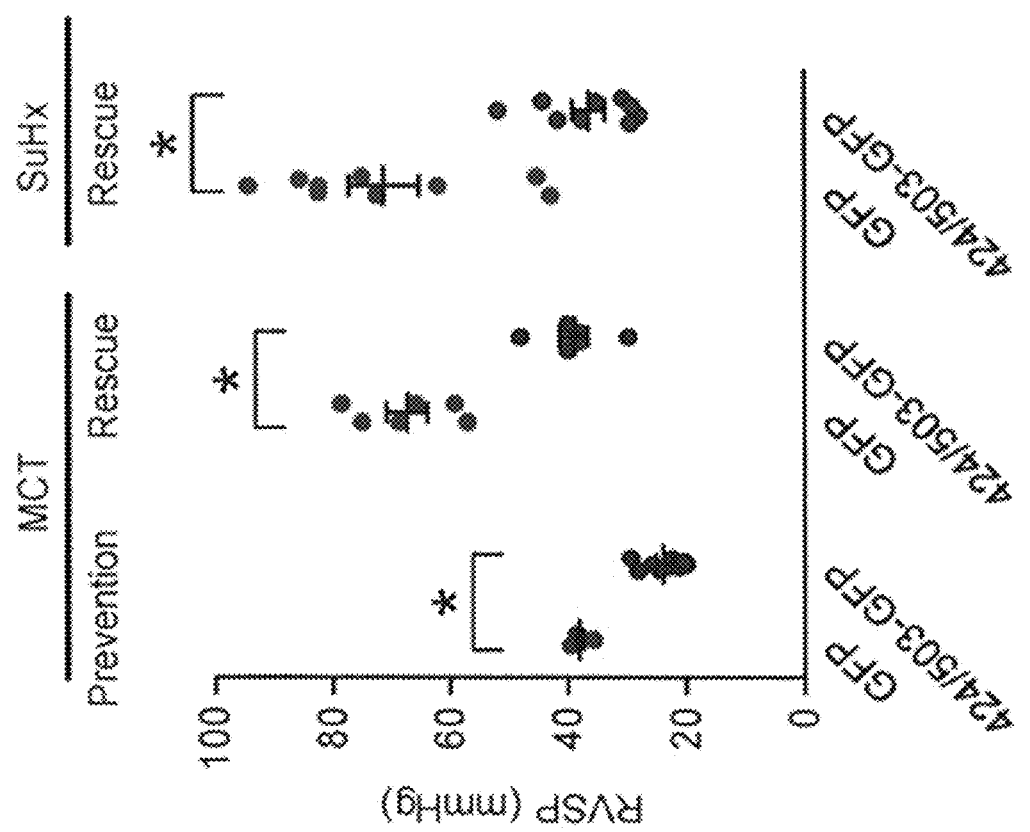
Figure 40A:
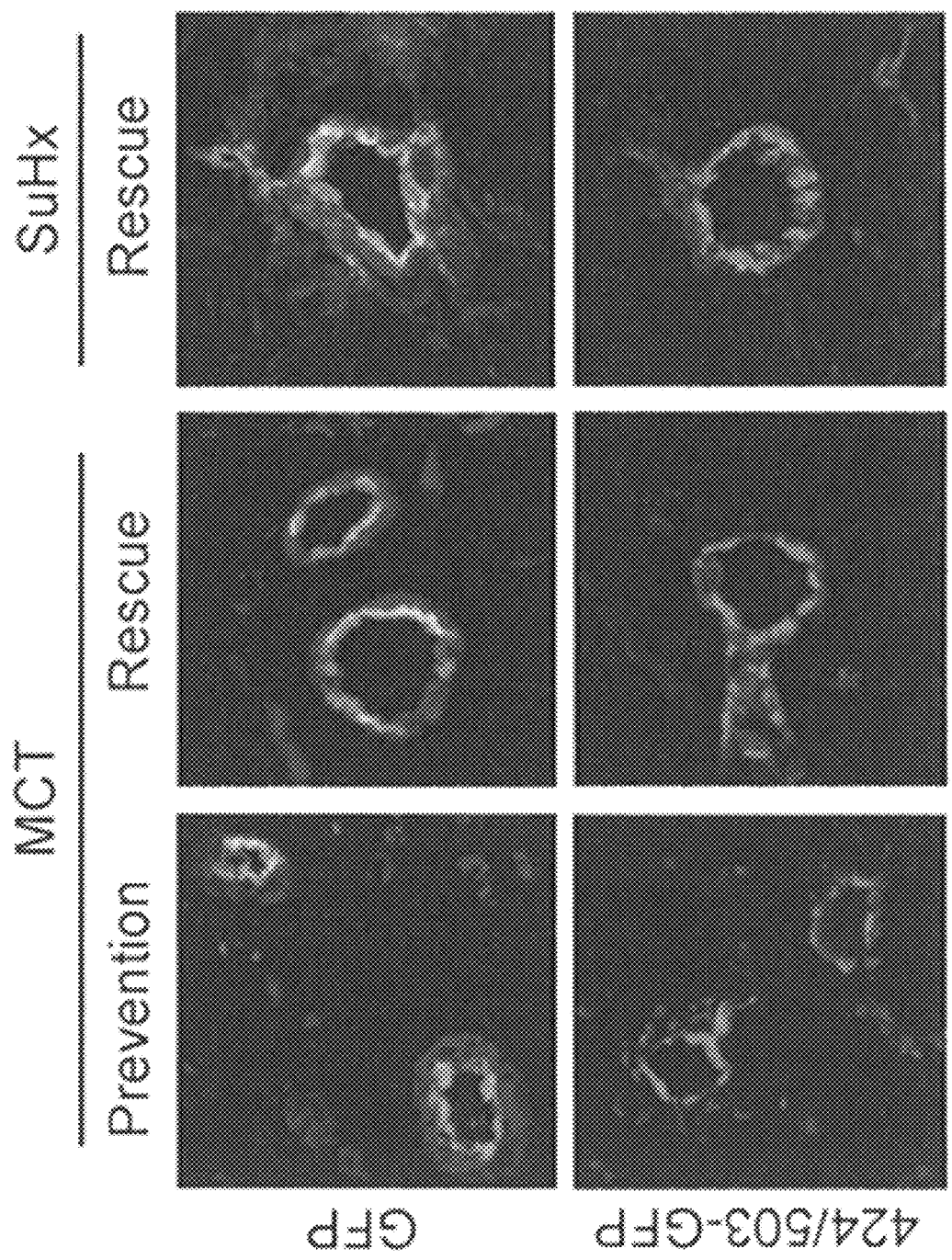
Figure 40B:
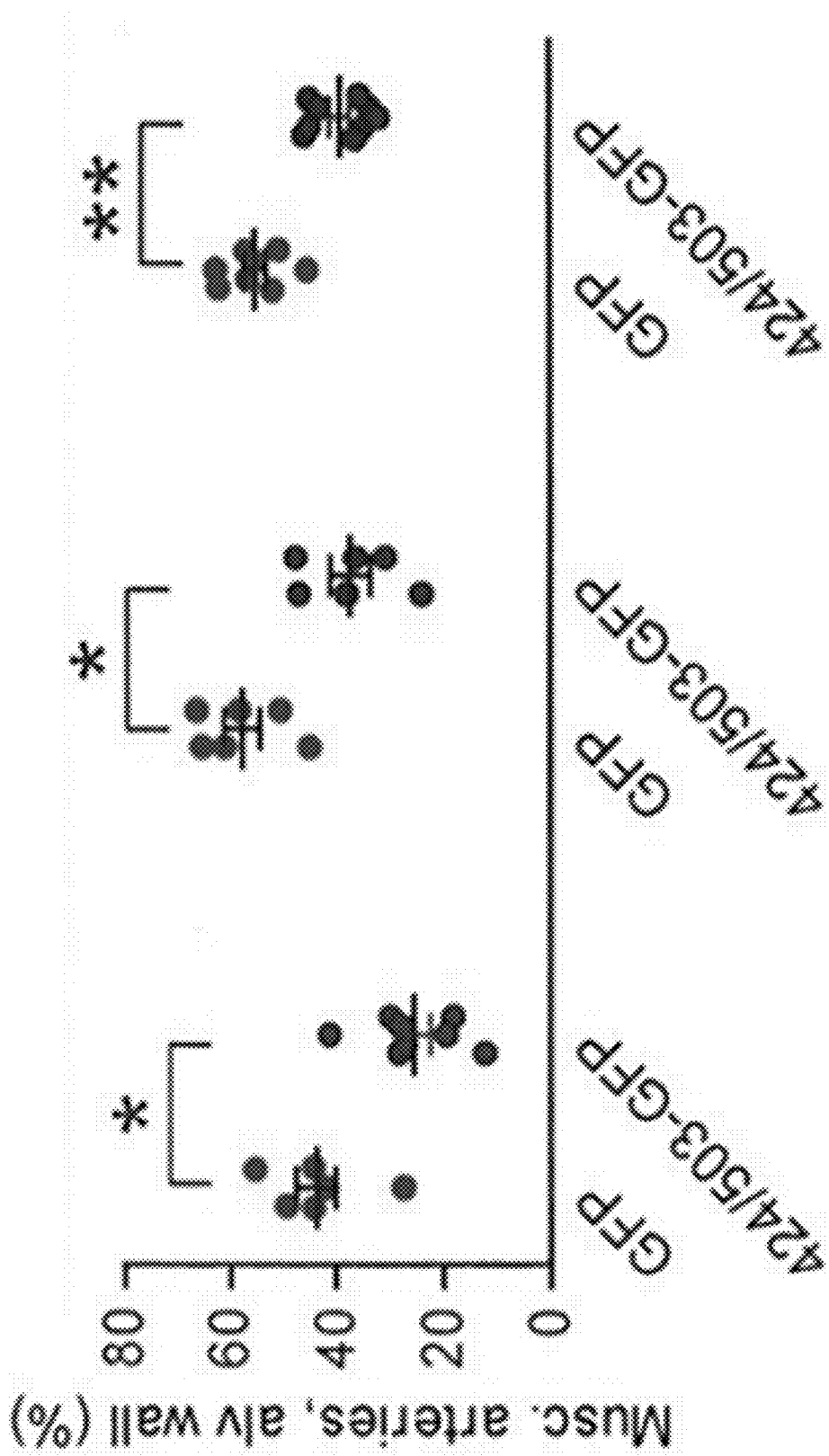
Figure 41A:
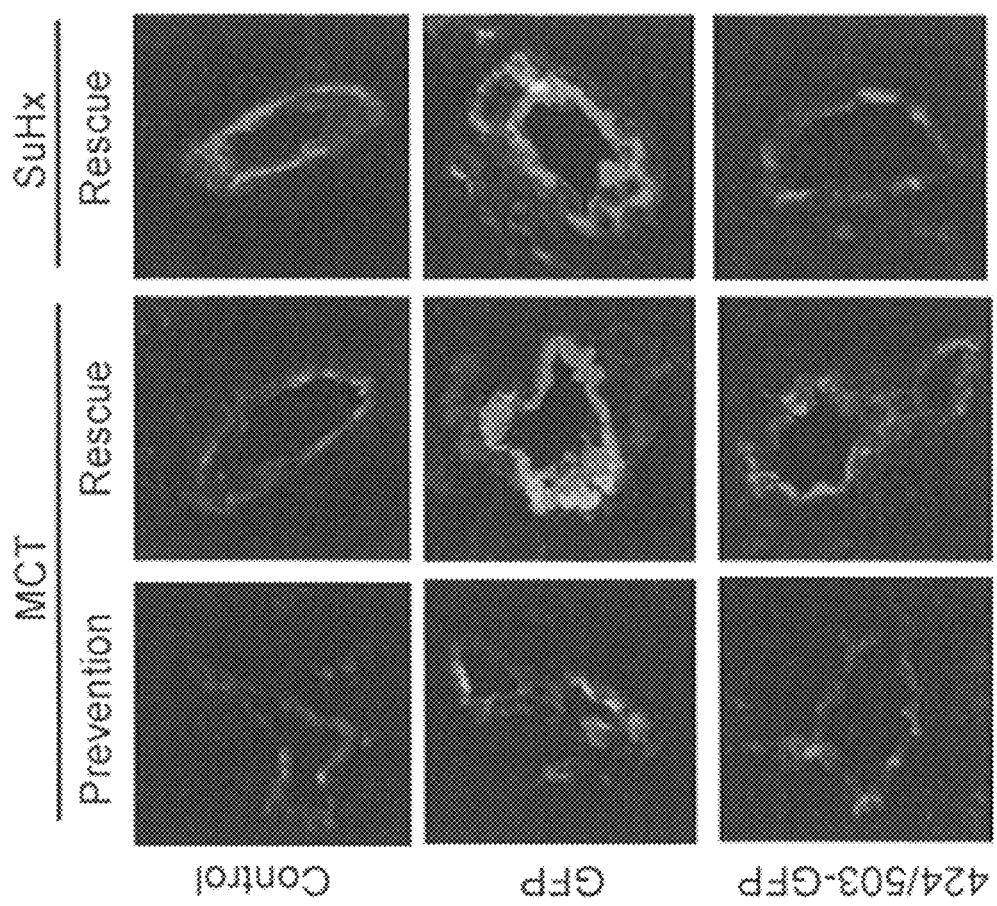

*P<0.05, †P<0.01 compared to control by unpaired two-tailed Student's t test. Error bars, s.e.m.;

FIG. 23A is a blot showing ERK1/2 phosphorylation in response to inhibition of miR-424 and miR-503 with anti-miRs (anti-miR-424/503) in PAECs. *P<0.01 compared to control by unpaired two-tailed Student's t test. Error bars, s.e.m.;

FIG. 23B is a bar graph showing ERK1/2 phosphorylation in response to inhibition of miR-424 and miR-503 with anti-miRs (anti-miR-424/503) in PAECs. *P<0.01 compared to control by unpaired two-tailed Student's t test. Error bars, s.e.m.;

FIG. 24 is a dot plot showing expression of miR-424, miR-503 and FGF2 mRNA in PAECs from controls and subjects with PAH. *P<0.01, **P<0.05 compared to controls by unpaired two-tailed Student's t test. Error bars, s.e.m.;

FIG. 25A is a correlation plot for the expression levels of APLN mRNA and miR-424 in PAECs from control and PAH subjects. The P values shown were calculated by unpaired two-tailed Student's t test;

FIG. 25B is a correlation plot for the expression levels of miR-424 and miR-503 in PAECs from control and PAH subjects. The P values shown were calculated by unpaired two-tailed Student's t test;

FIG. 25C is a correlation plot for the expression levels of FGF2 mRNA and miR-424 in PAECs from control and PAH subjects. The P values shown were calculated by unpaired two-tailed Student's t test;

FIG. 25D is a correlation plot for the expression levels of FGFR1 mRNA and miR-424 in PAECs from control and PAH subjects. The P values shown were calculated by unpaired two-tailed Student's t test;

FIG. 26 is a blot showing expression of FGF2 and FGFR1 proteins in PAECs from control and PAH subjects;

FIG. 27 shows vWF, FGFR1 and co-staining expression in normal and PAH lung microvascular endothelium. Scale bars, 50 μm;

FIG. 28A shows expression of vWF, either miR-424 or miR-503, and co-stained pulmonary endothelium by in situ hybridization n the microvasculature of normal and PAH lungs. Scale bars, 50 μm;

FIG. 28B shows expression of vWF, either miR-424 or miR-503, and co-stained pulmonary endothelium by in situ hybridization n the microvasculature of normal and PAH lungs. Scale bars, 50 μm;

FIG. 29A is a graph showing cell-cycle analysis of PAECs with control in normal PAECs;

FIG. 29B is a graph showing cell-cycle analysis of PAECs with miR-424/miR-503 overexpression in normal PAECs;

FIG. 29C is a graph showing cell-cycle analysis of PAECs with control in PAH PAECs;

FIG. 29D is a graph showing cell-cycle analysis of PAECs with miR-424/miR-503 overexpression in PAH PAECs;

FIG. 30 is a bar graph showing proliferation of control and PAH PAECs (derived from two subjects with PAH, PAH 1 and PAH 2) in response to overexpression of miR-424 and miR-503 with or without concurrent stimulation with exogenous FGF2 and transfection of an FGFR1 expression construct (FGF2/FGFR1). *P<0.01 for the indicated comparisons by unpaired two-tailed Student's t test. Error bars, s.e.m.;

FIG. 31 is a bar graph showing proliferation of control and PAH PAECs in response to inhibition of miR-424 and miR-503 by anti-miR (anti-miR-424/503) transfection with or without concurrent knockdown of FGF2 and FGFR1 (FGF2/FGFR1 siRNA). *P<0.01 for the indicated comparisons by unpaired two-tailed Student's t test. Error bars, s.e.m.;

FIG. 32A shows images of cell migration response to miR-424 and miR-503 overexpression with or without concurrent FGF2 stimulation and FGFR1 transfection (FGF2+FGFR1) in normal PAECs. Representative images of each condition are shown with the gap area demarcated by the dark outlines;

FIG. 32B is a bar graph showing cell migration response to miR-424 and miR-503 overexpression with or without concurrent FGF2 stimulation and FGFR1 transfection (FGF2+FGFR1) in normal PAECs. *P<0.05 for the indicated comparisons by unpaired two-tailed Student's t test. Scale bar, 500 Error bars, s.e.m.;

FIG. 33A shows images of cell migration response to overexpression of miR-424 and miR-503 in PAH PAECs;

FIG. 33B shows images of cell migration response to overexpression of miR-424 and miR-503 in PAH PAECs. *P<0.05 compared to control by unpaired two-tailed Student's t test. Scale bar, 500 Error bars, s.e.m.;

FIG. 34 is a bar graph showing PASMC proliferation in response to conditioned medium from PAECs of a normal donor (control PAEC CM) and a subject with PAH (PAH PAEC CM). Conditioned medium was used from untransfected cells (control on the x axis) or from cells transfected with miR-424 and miR-503 mimics (miR-424/503) with or without co-transfection with the FGF2 expression construct (FGF2). Basal indicates proliferation in the absence of conditioned medium. *P<0.01 for the indicated comparisons by unpaired two-tailed Student's t test. Error bars, s.e.m.;

FIG. 35 is a bar graph showing PASMC proliferation in response to conditioned medium from PAECs subjected to APLN knockdown alone or in conjunction with miR-424 and miR-503 overexpression. *P<0.05 for the indicated comparisons by unpaired two-tailed Student's t test. Error bars, s.e.m.;

FIG. 36 is a bar graph showing proliferation of PASMCs in response to conditioned medium from PAECs subjected to knockdown of APLN, FGF2 or both. *P<0.05 for the indicated comparisons by unpaired two-tailed Student's t test. Error bars, s.e.m.;

FIG. 37A is a bar graph showing expression levels of rno-miR-322 (the rat homolog of hsa-miR-424) and miR-503 in rat lungs 3 weeks after MCT injection and 4 weeks after SuHx. Also shown are expression levels of Apln mRNA in rat LECs (LECs were isolated from 4 rats per group). *P<0.01 for the indicated comparisons by unpaired two-tailed Student's t test. Error bars, s.e.m.;

FIG. 37B is a bar graph showing expression levels of rno-miR-322 (the rat homolog of hsa-miR-424) and miR-503 in isolated LECs 3 weeks after MCT injection and 4 weeks after SuHx. Also shown are expression levels of Apln mRNA in rat LECs (LECs were isolated from 4 rats per group). *P<0.01 for the indicated comparisons by unpaired two-tailed Student's t test. Error bars, s.e.m.;

FIG. 38 shows blots of expression of FGF2 and FGFR1 in rat lungs in the MCT- and SuHx models;

FIG. 39 is a dot plot showing RVSP measurements in rats receiving intranasal delivery of lentiviral miR-424 and miR-503 (424/503-GFP) compared to control lentivirus (GFP) in the MCT prevention and rescue models and the SuHx rescue model. *P<0.001 for the comparison to GFP in each model by unpaired two-tailed Student's t test. Error bars, s.e.m.;

FIG. 40A shows images of microvascular muscularization (Musc.) analysis of the alveolar (alv) wall of lungs from rats receiving either intranasal GFP or 424/503-GFP in the three models. Smooth-muscle actin and vWF co-staining;

FIG. 40B is a dot plot of the microvascular muscularization (Musc.) analysis of the alveolar (alv) wall of lungs from rats receiving either intranasal GFP or 424/503-GFP in the three models. *P<0.01, **P<0.001 compared to GFP by unpaired two-tailed Student's t test. Error bars, s.e.m.;

FIG. 41A shows images of PCNA expression in the lungs of the three models receiving either GFP or 424/503-GFP. PCNA and vWF co-staining.

Figure 41B:
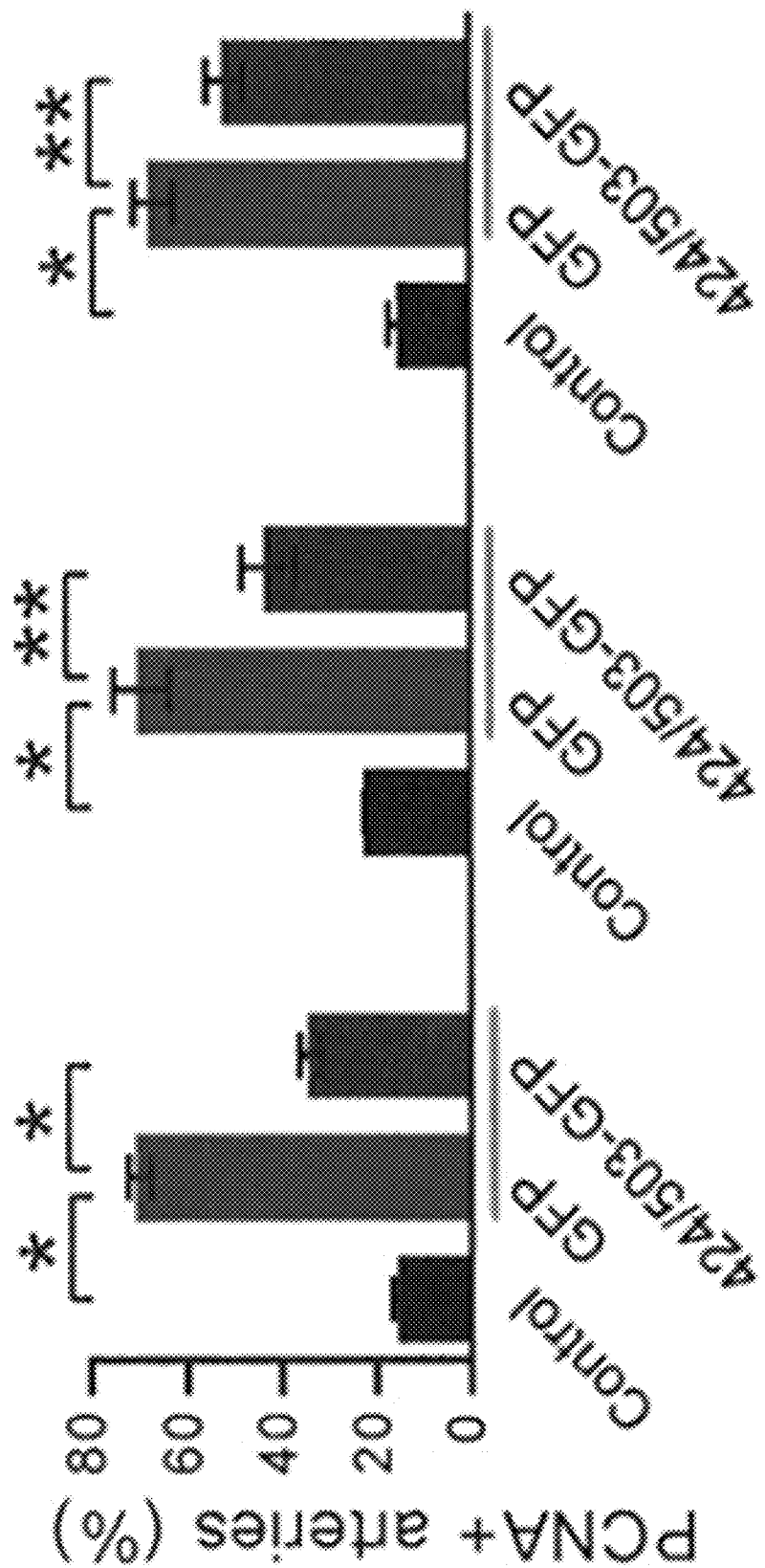
Figure 42B:
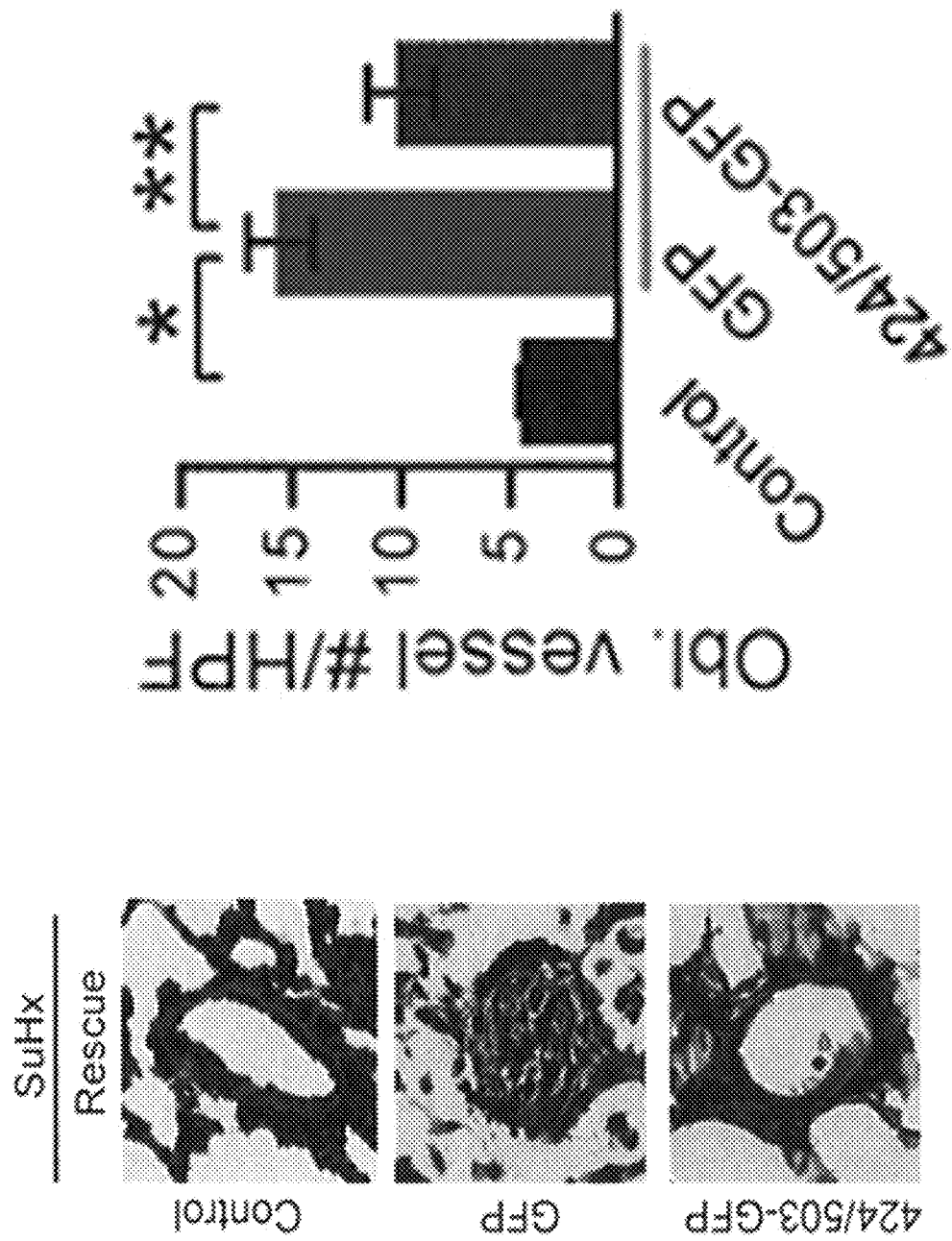
Figure 42A:
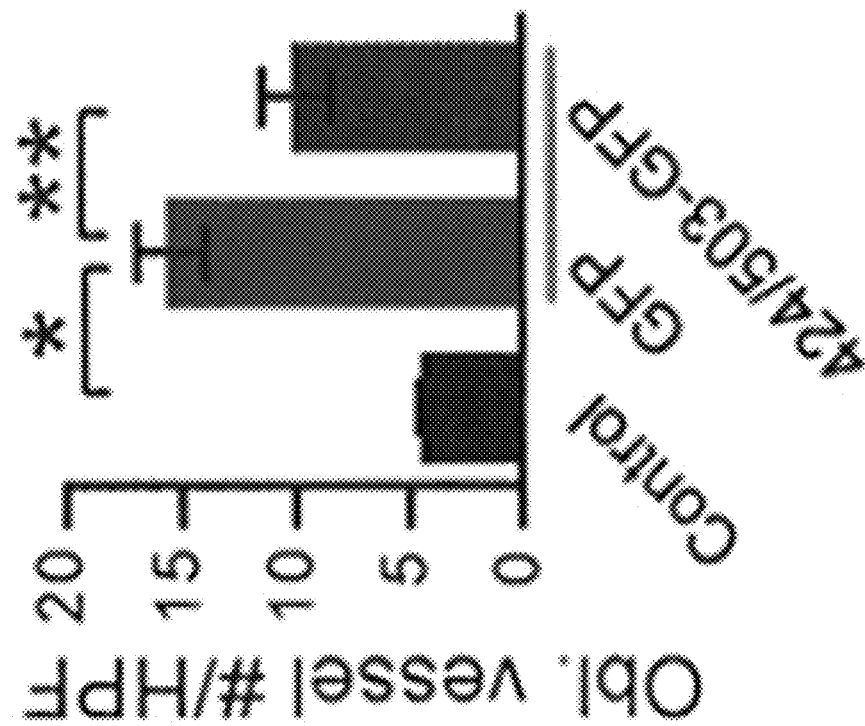
Figure 44:
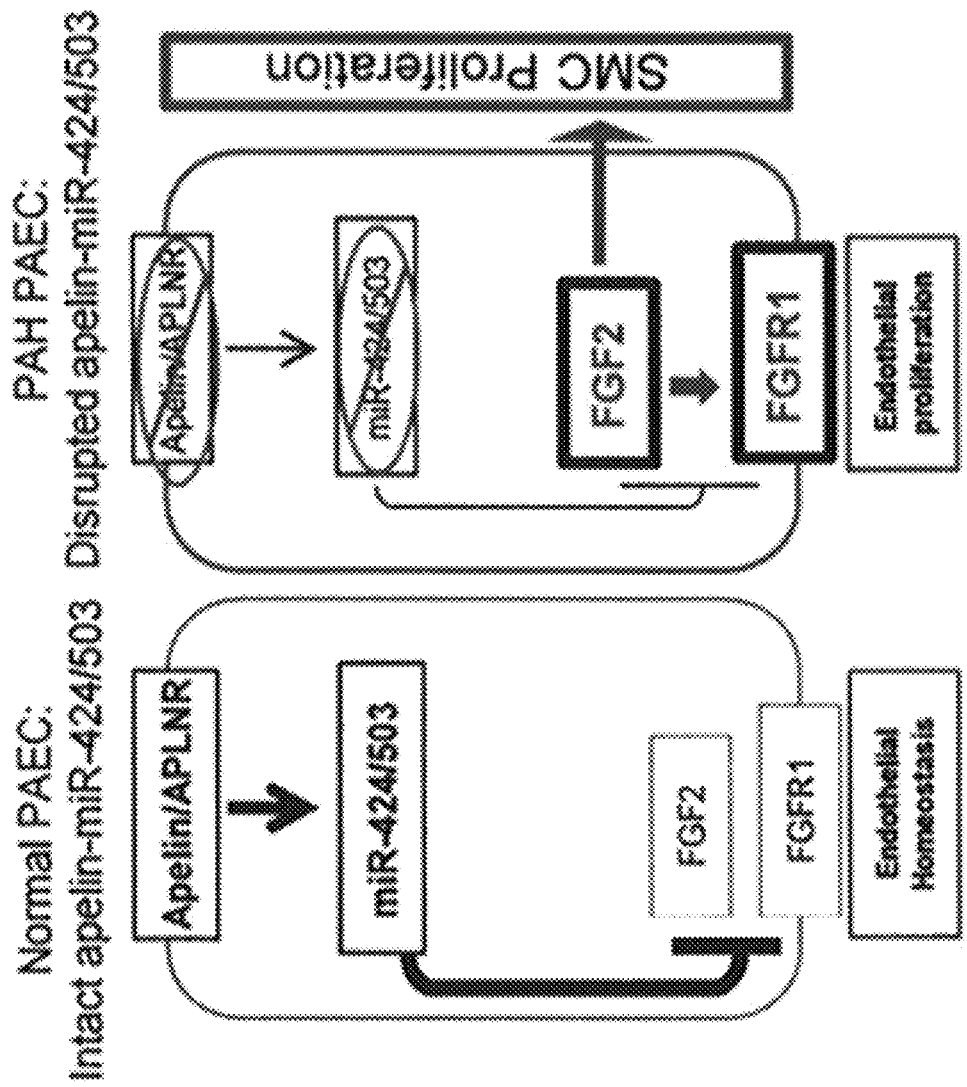
Figure 45B:
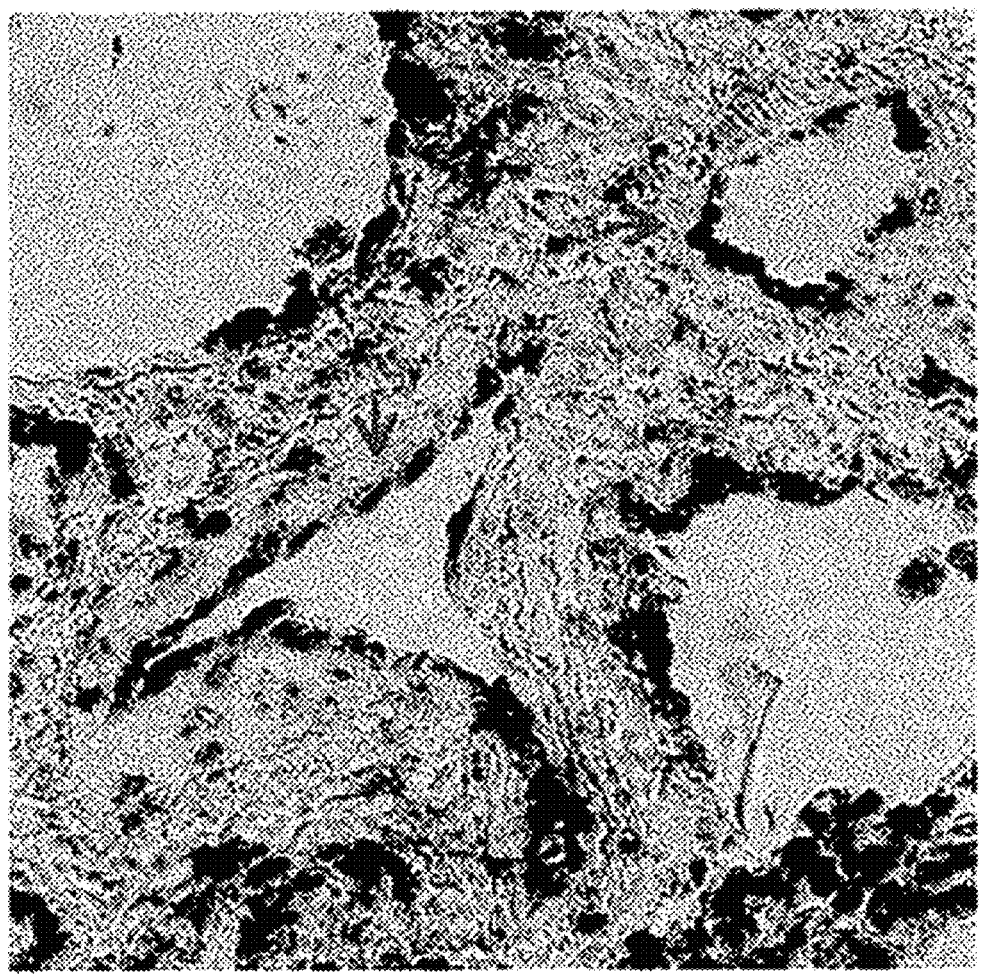
Figure 45A:
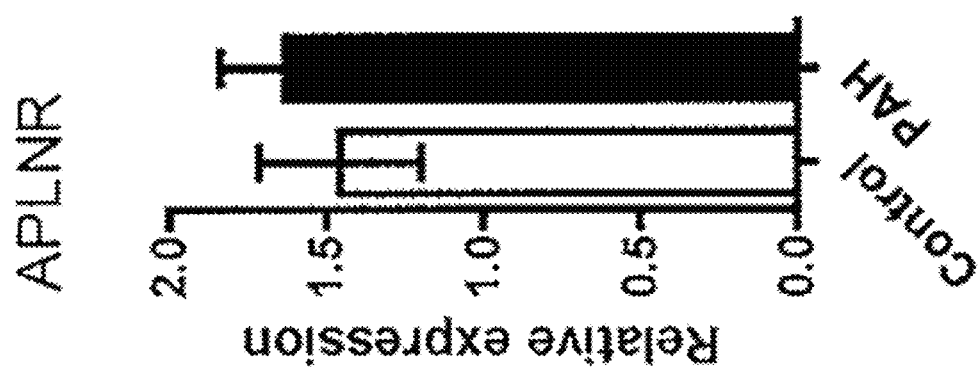
Figure 46:
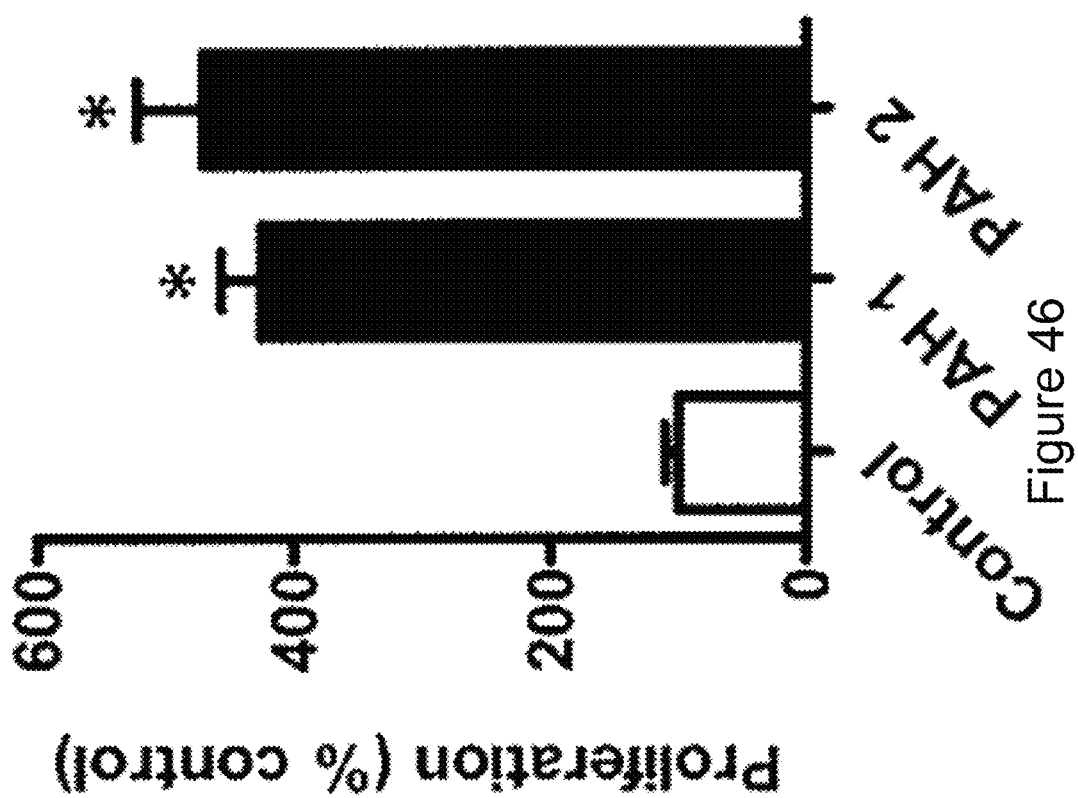

FIG. 41B is a bar graph of PCNA expression in the lungs of the three models receiving either GFP or 424/503-GFP, underlined bars denote the experimental pulmonary hypertension groups (n=7-9 rats per group). *P<0.001, **P<0.01 for the indicated comparisons by unpaired two-tailed Student's t test. Error bars, s.e.m.;

FIG. 42A shows H&E staining of the lungs from rats subjected to SuHx pulmonary hypertension induction receiving either GFP or 424/503-GFP;

FIG. 42B is a bar graph of the average number of obliterated vessels per microscopic field (Obl. vessels HPF-1), underlined bar denotes the experimental pulmonary hypertension groups (n=8-9 rats per group). *P<0.001, **P<0.02 for the indicated comparisons by unpaired two-tailed Student's t test. Error bars, s.e.m;

FIG. 43A shows FGF2 and FGFR1 protein expression in lung homogenates of rats in the three models with either GFP or 424/503-GFP treatment;

FIG. 43B shows FGF2 and FGFR1 expression in isolated LECs from the MCT and SuHx rescue models with GFP or 424/503-GFP treatment;

FIG. 43C is a bar graph showing FGF2 and FGFR1 expression in isolated LECs from the MCT and SuHx rescue models, underlined bars denote the experimental pulmonary hypertension groups (LECs were isolated from 4 rats per group). *P<0.05 for the indicated comparisons by unpaired two-tailed Student's t test. Error bars, s.e.m.;

FIG. 44 is a diagram of the proposed mechanism of endothelial signal linking APLN and its receptor (APLN/APLNR), miR-424 and miR-503 (miR-424/503), FGF2 and FGFR1 in normal and PAH PAECs;

FIG. 45A is a bar graph showing PAH PAEC APLNR expression is not significantly changed from control PAECS;

FIG. 45B is an image of in situ hybridization of control lungs that demonstrates high expression of APLNR in the luminal layer of pulmonary vessels;

FIG. 46 PAECs from PAH patients are hyperproliferative compared to control PAECS. *p<0.001.

Figure 48B:
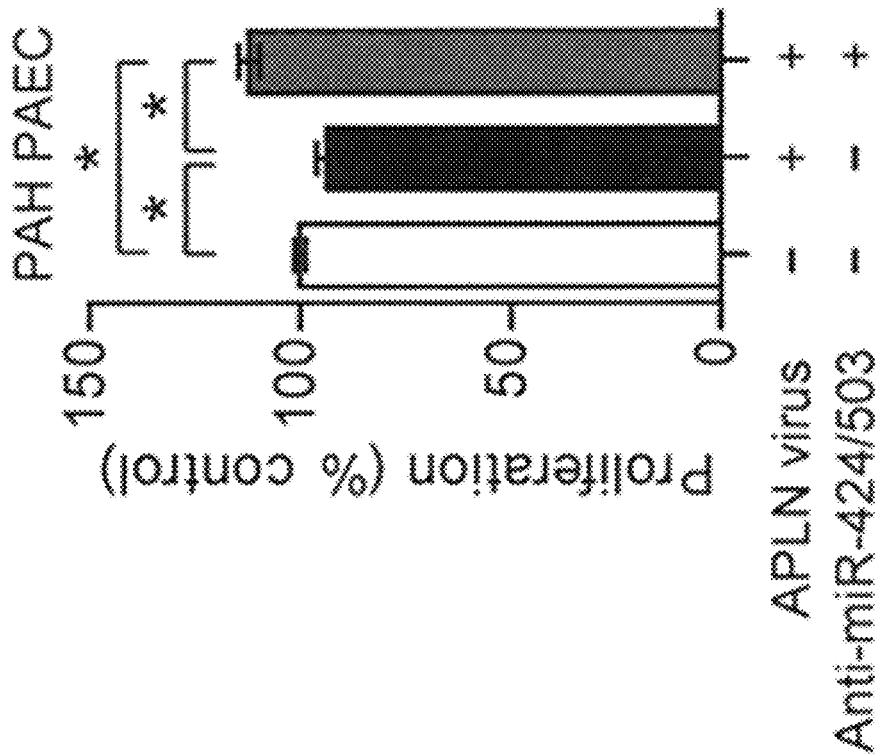
Figure 48A:
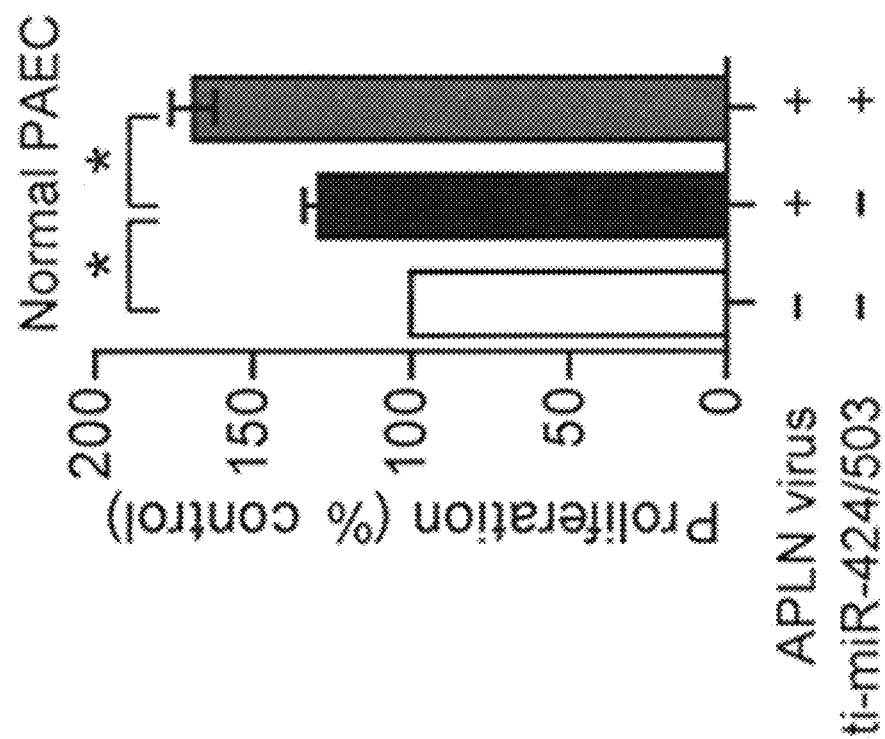
Figures 49A, 49B, 49C, 49D, 49E:
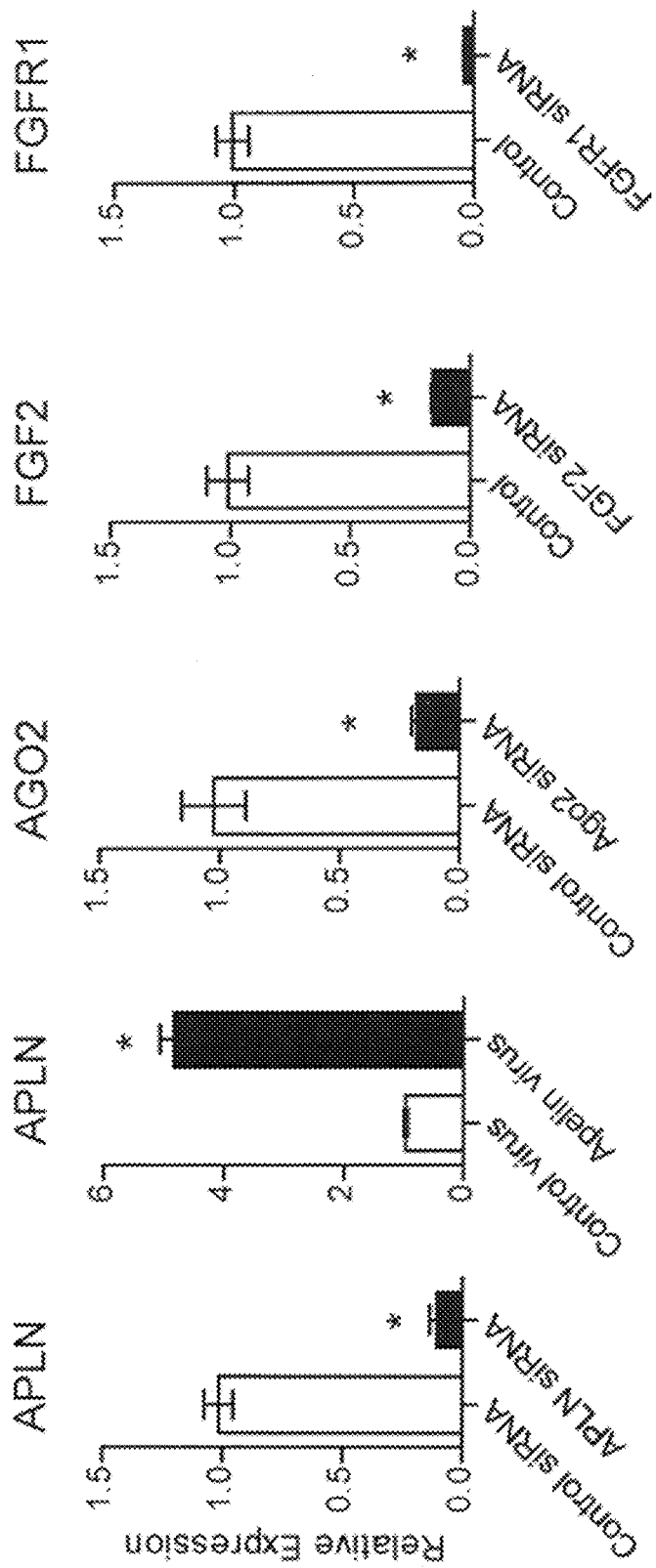
Figure 50A:
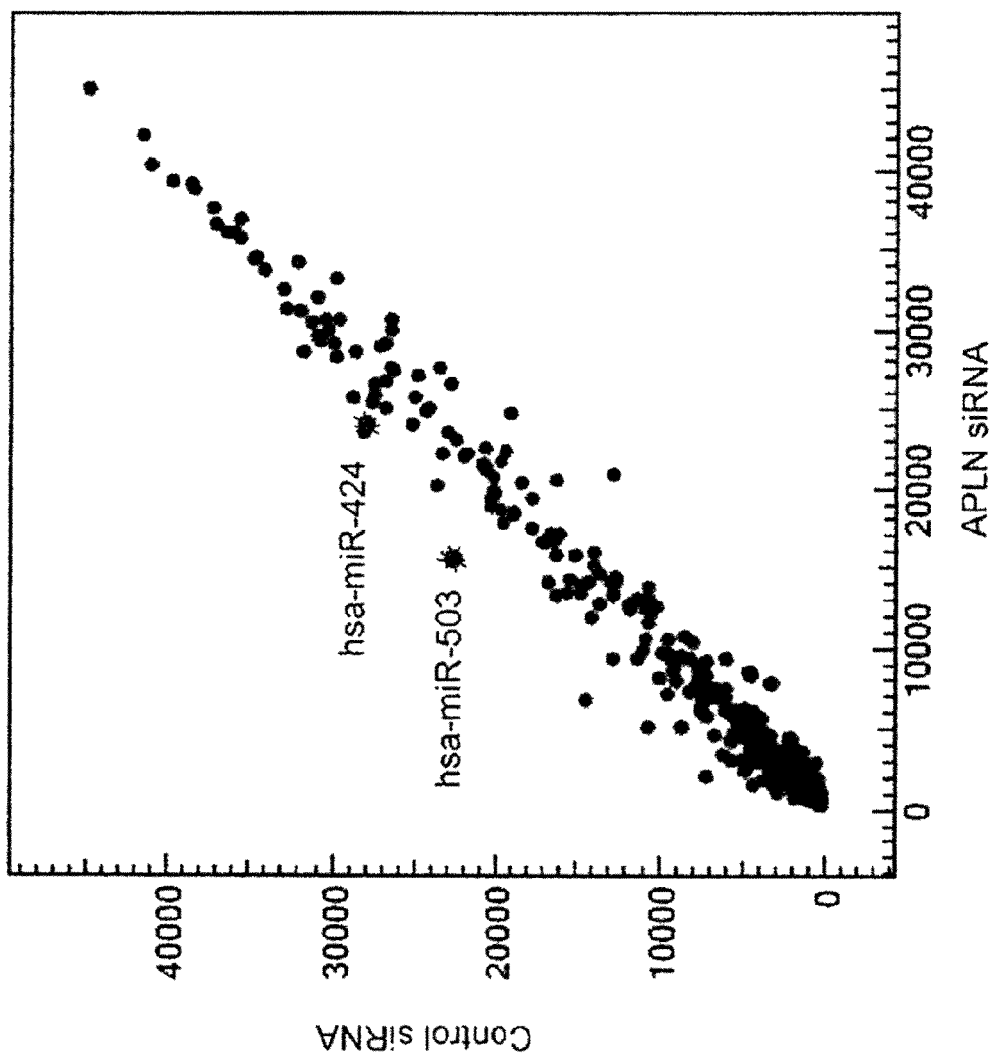
Figure 51C:
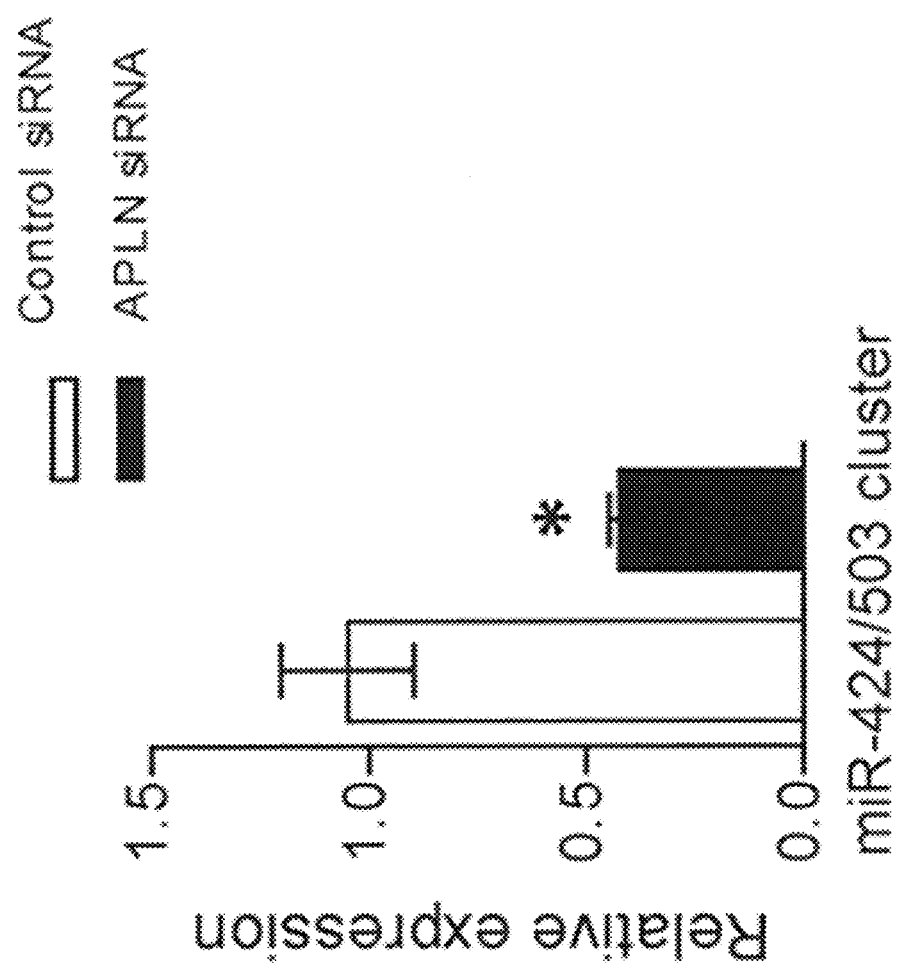
Figure 52:
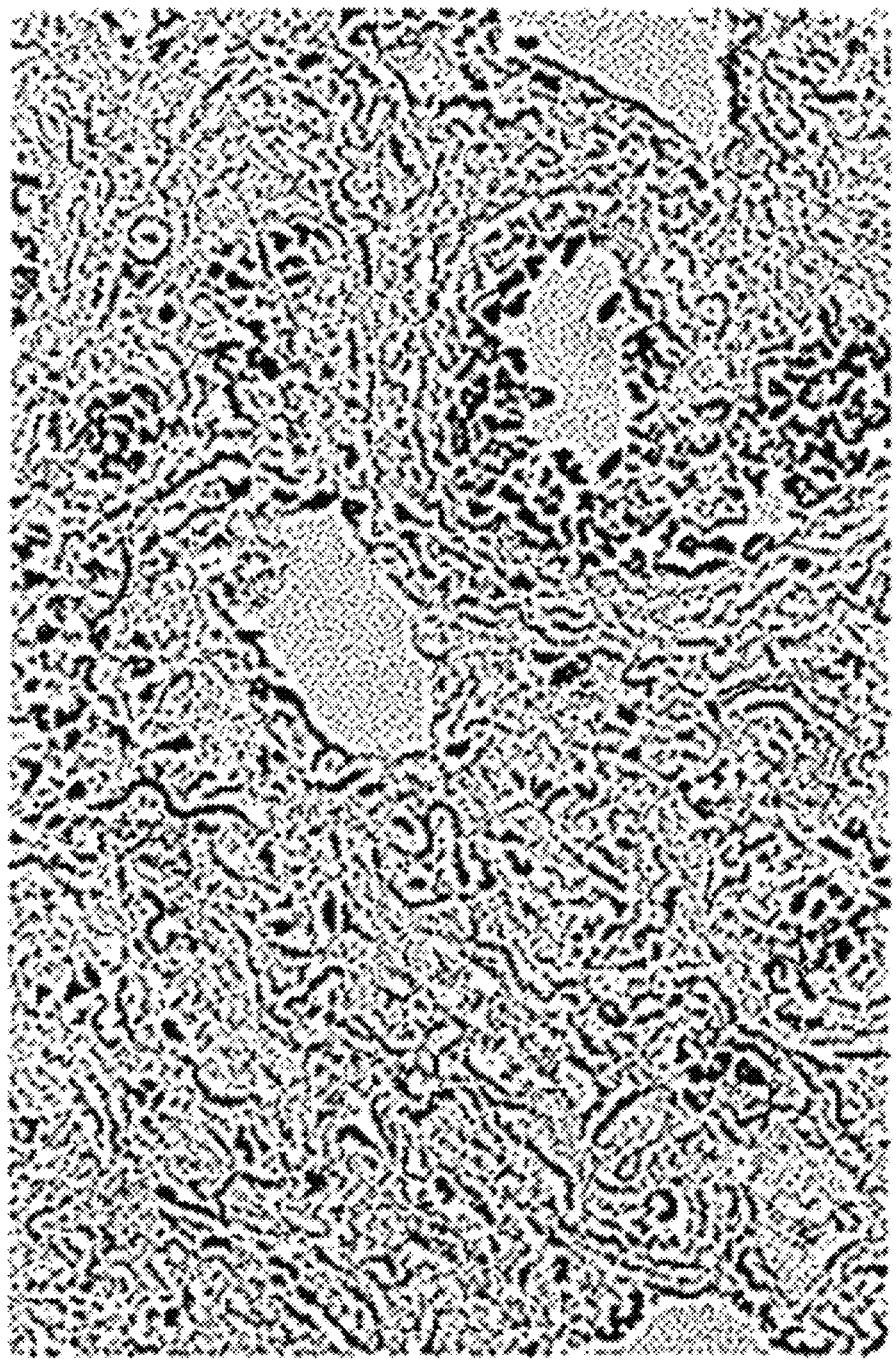
Figure 54A:
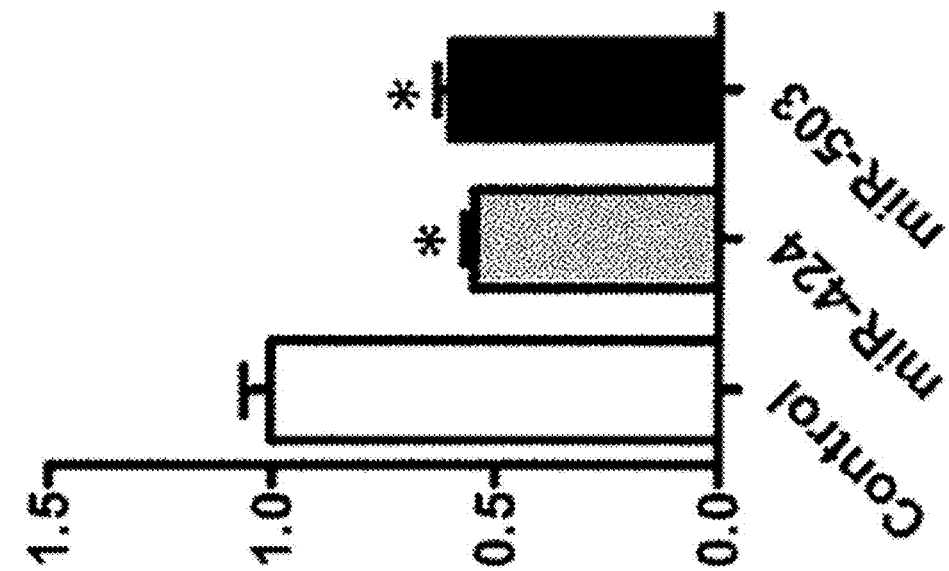
Figure 54B:
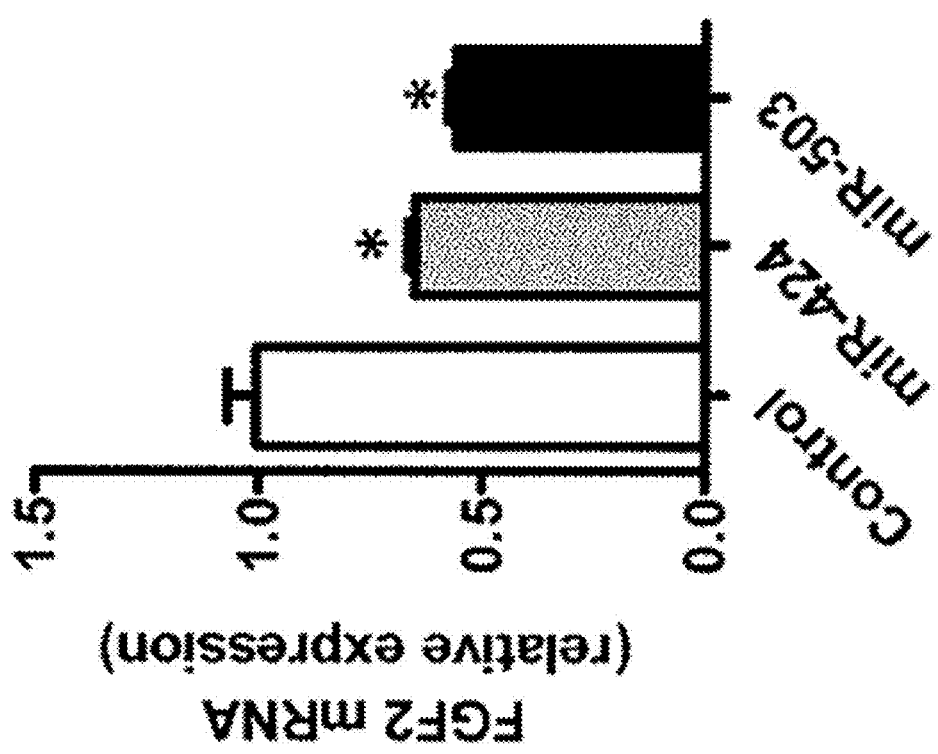
Figure 54C:
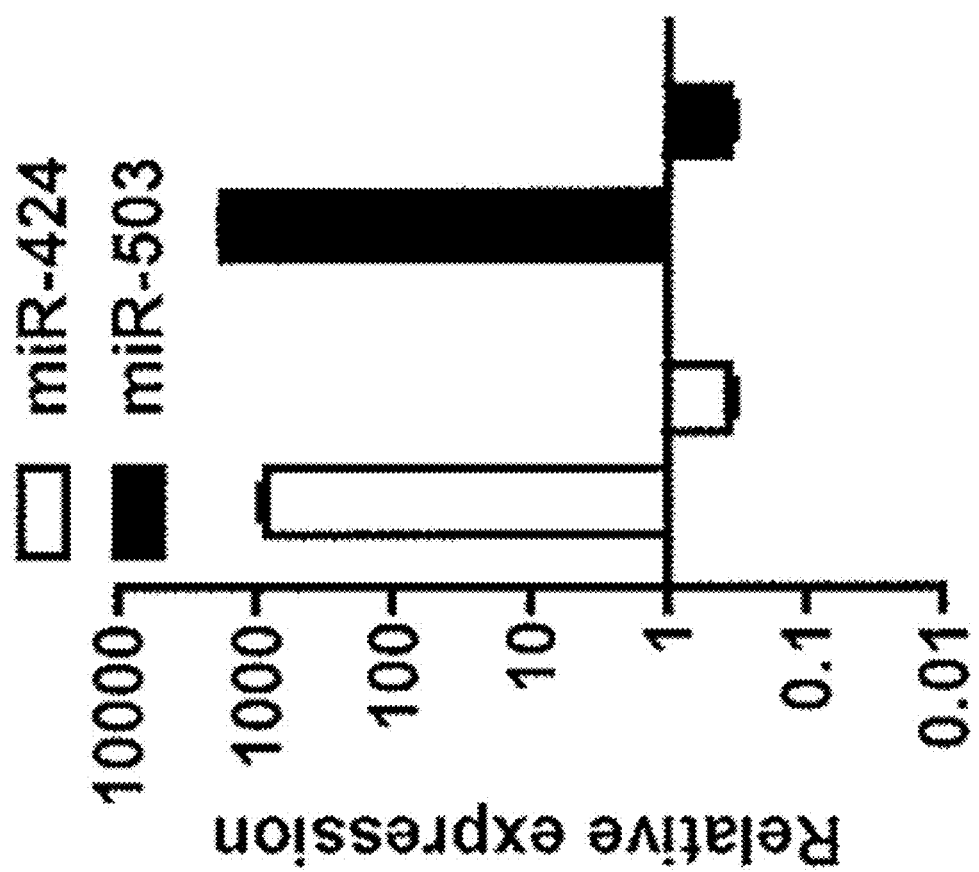
Figures 55A, 55B:
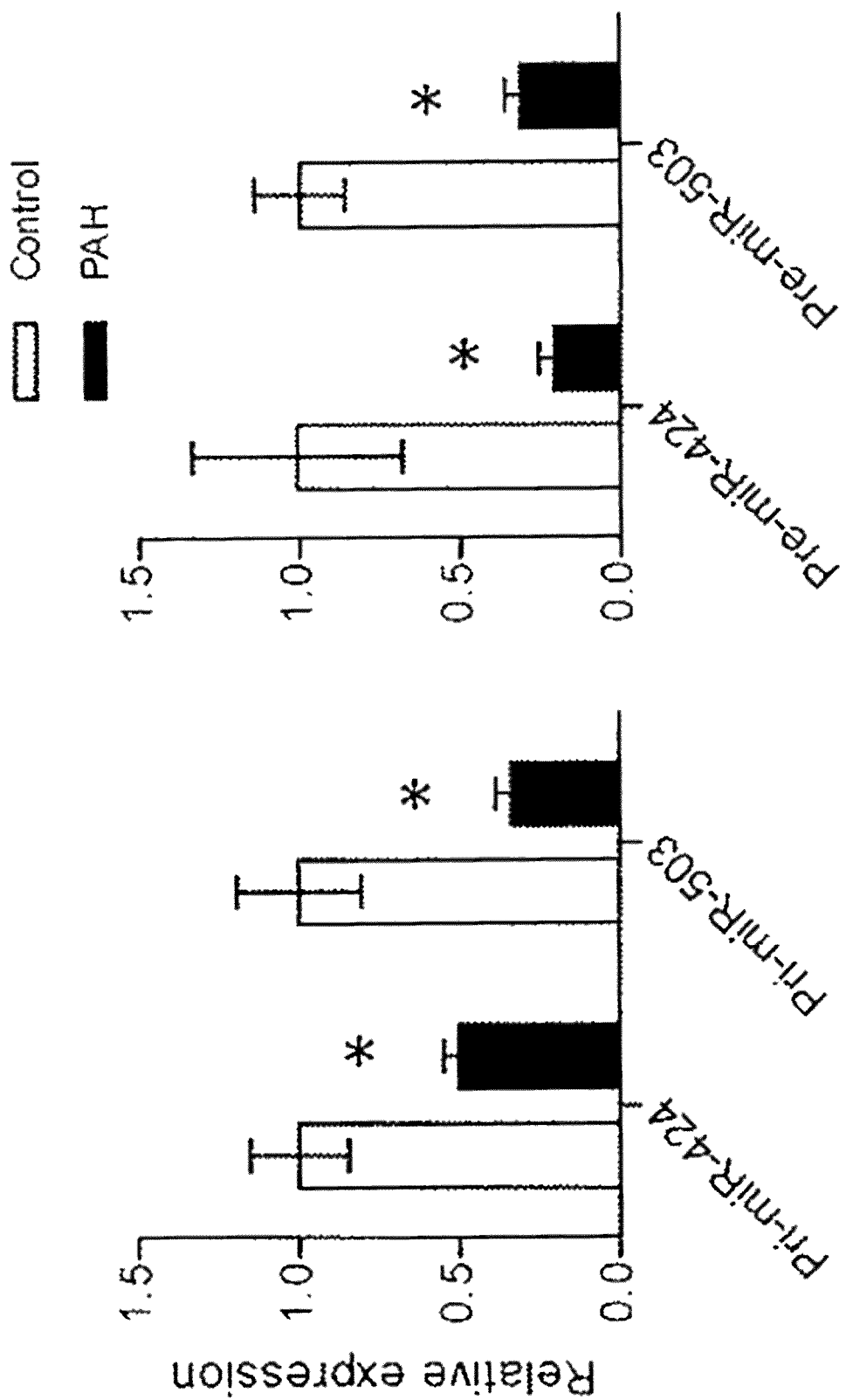
Figure 55C:
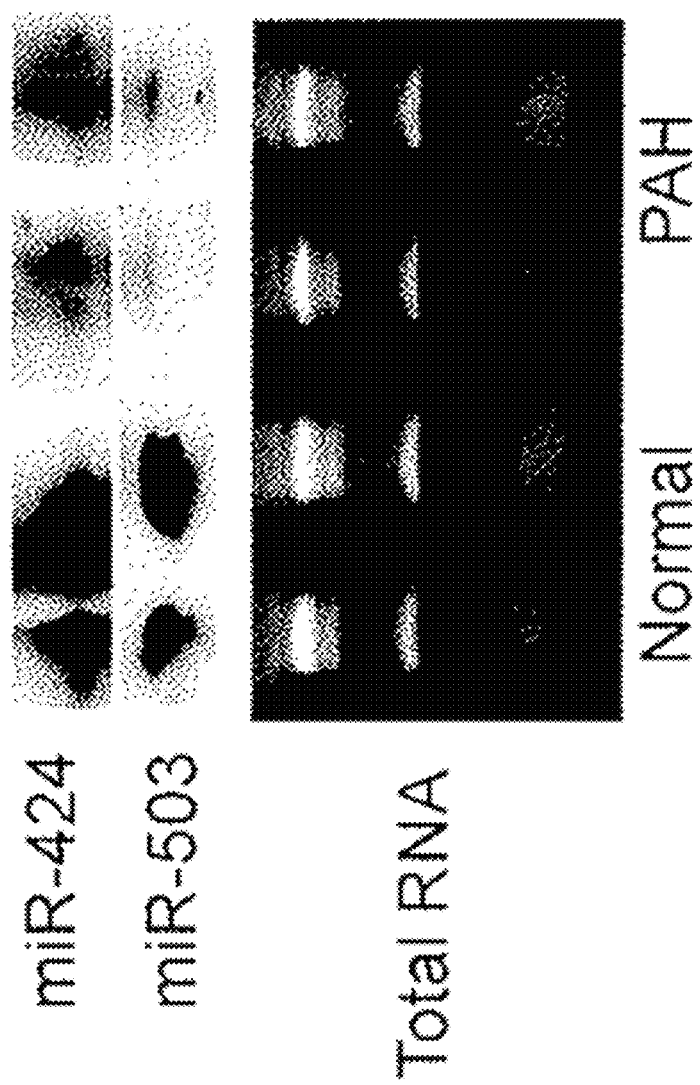
Figure 57:
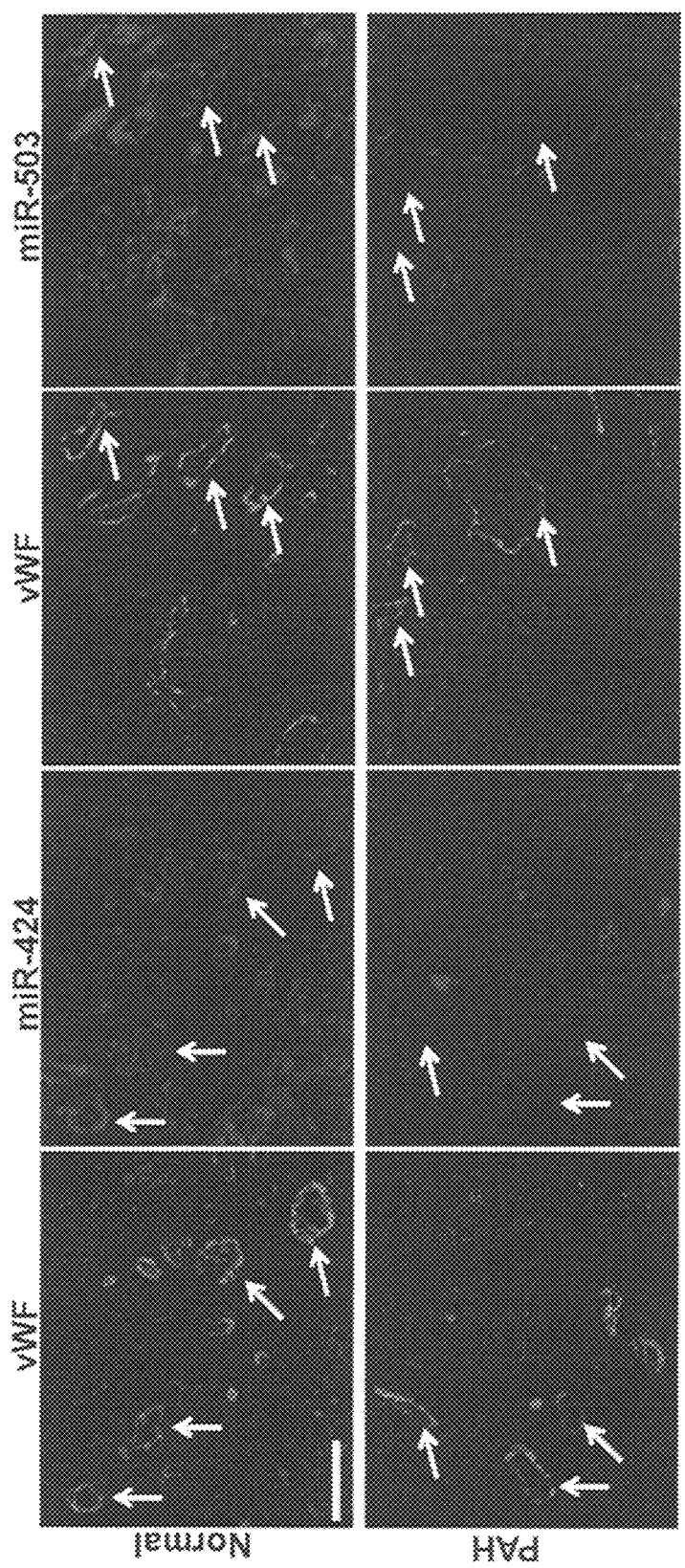
Figures 59A, 59B:
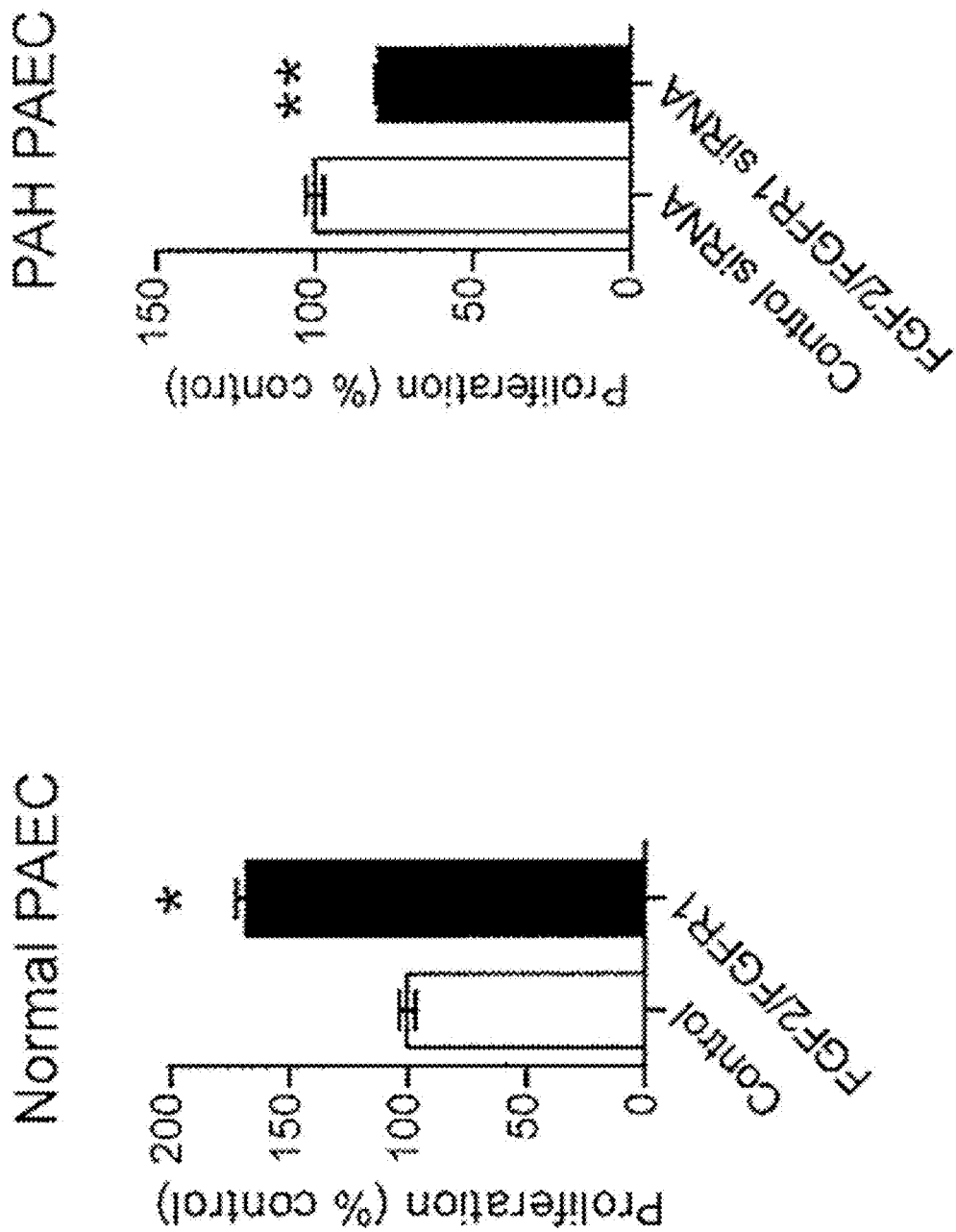
Figure 60:
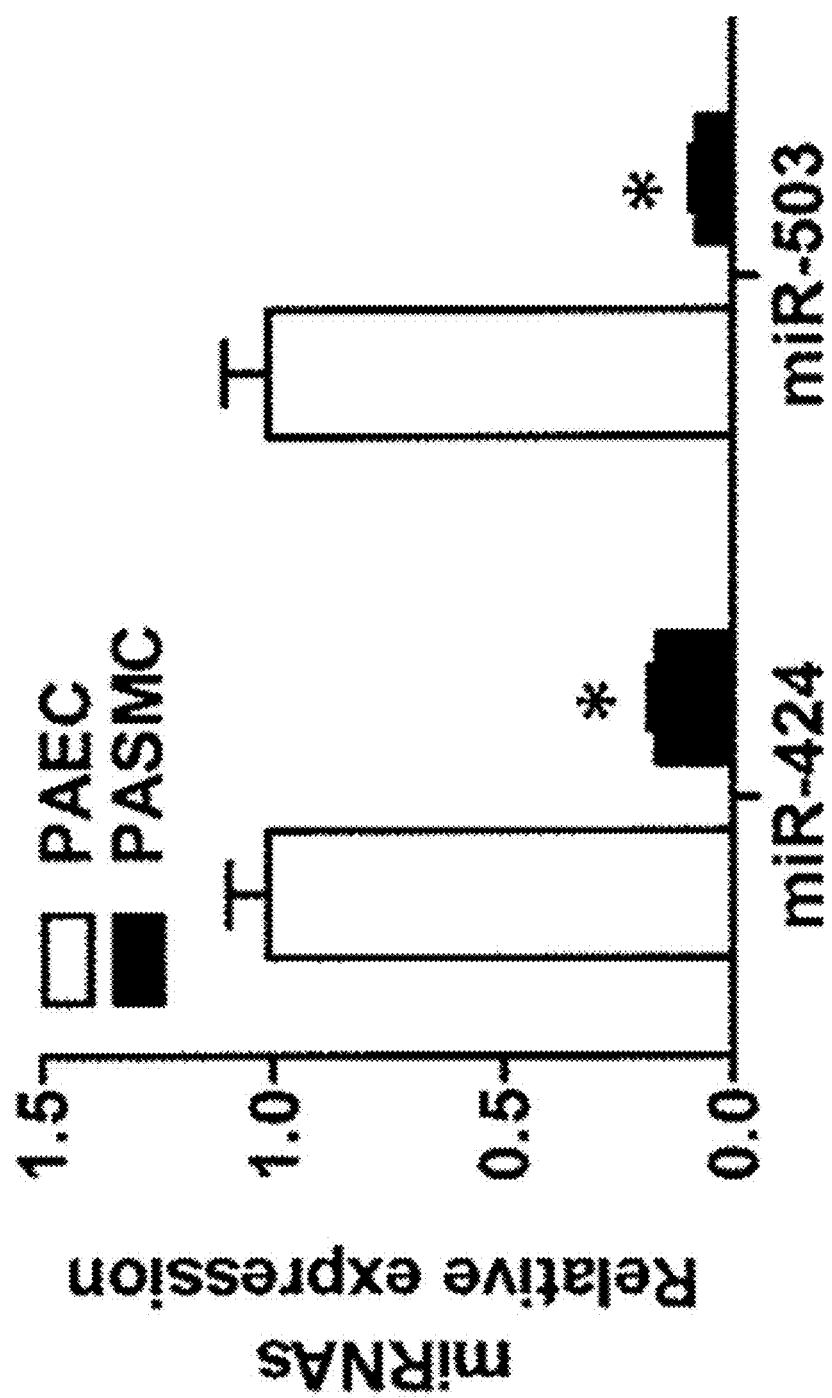
Figure 61:
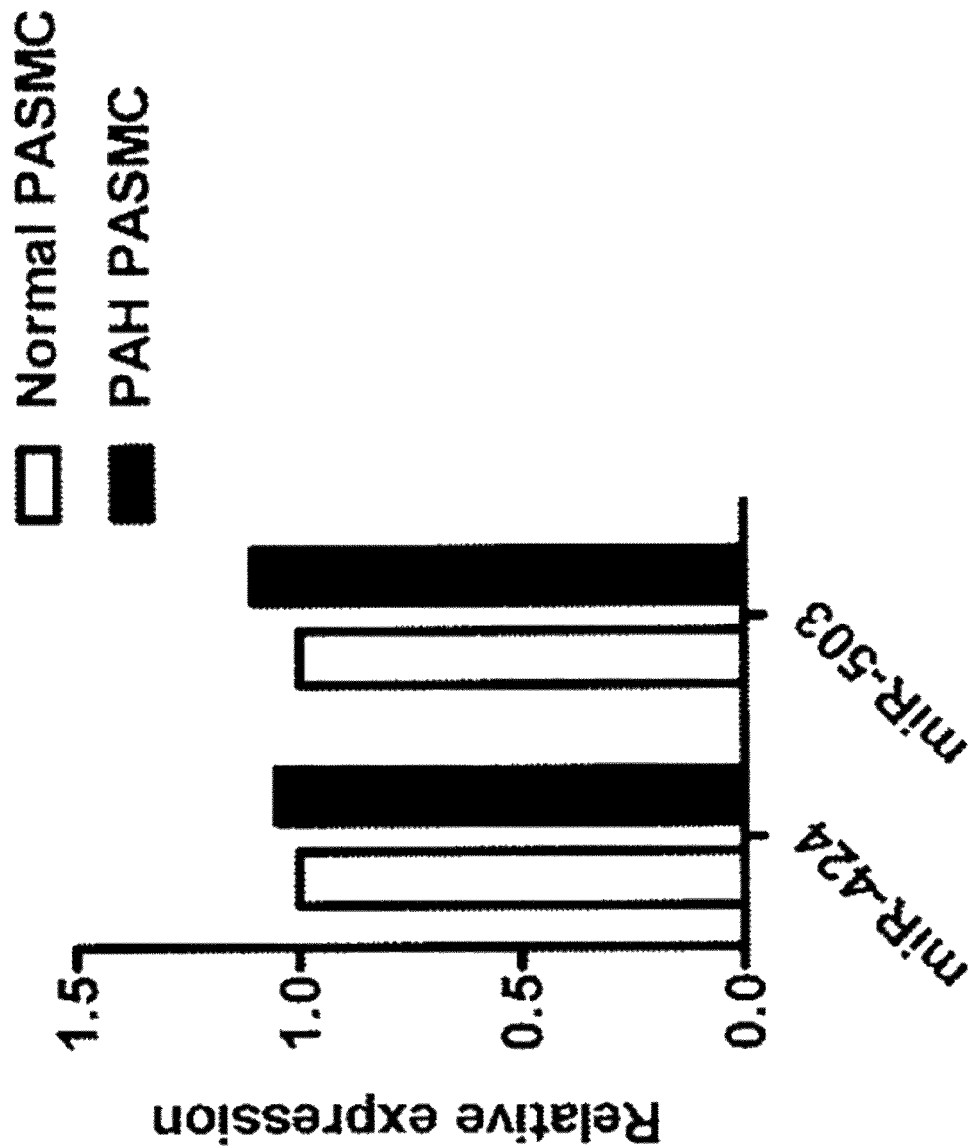
Figures 62A, 62B:
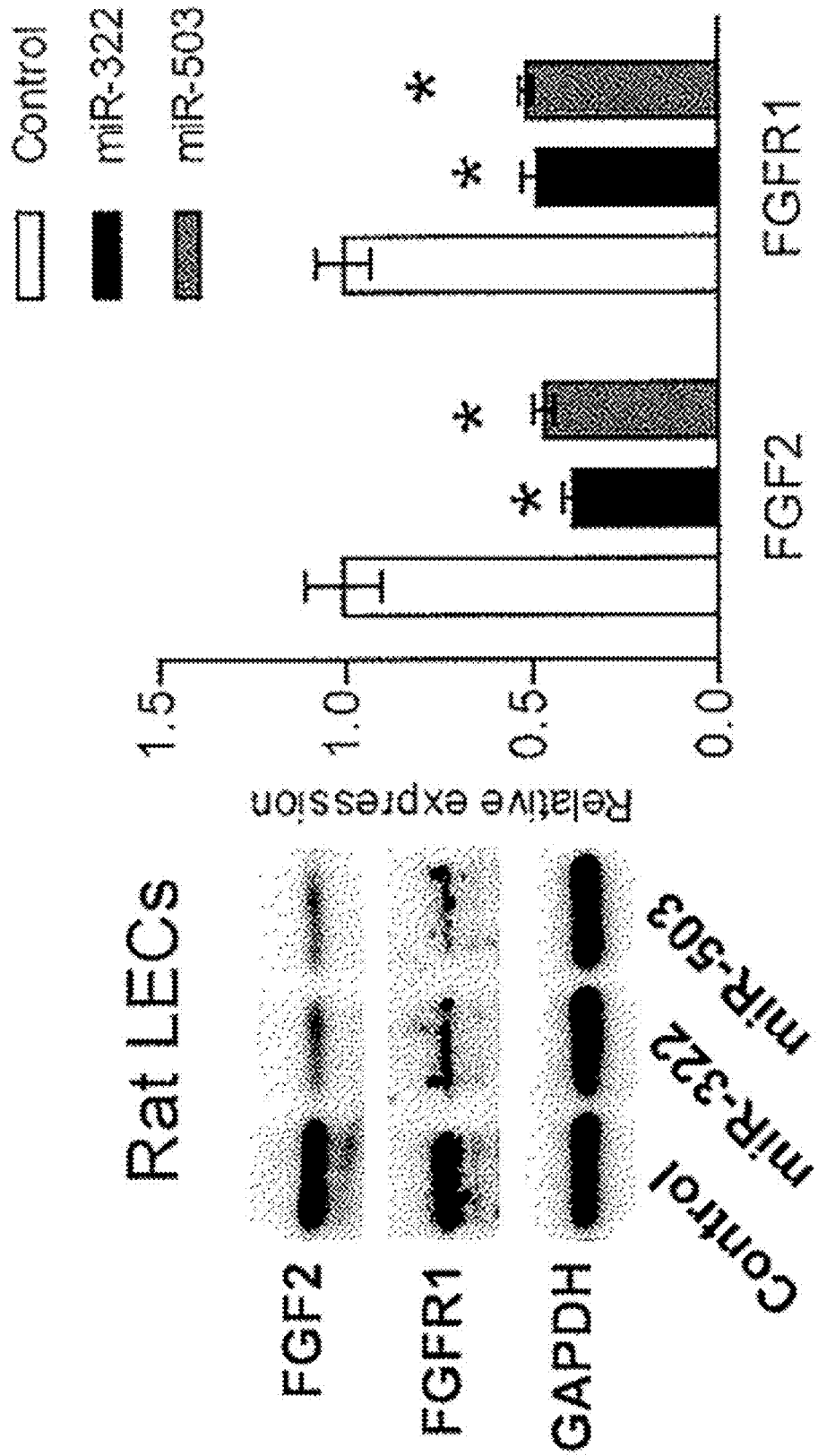
Figure 63:
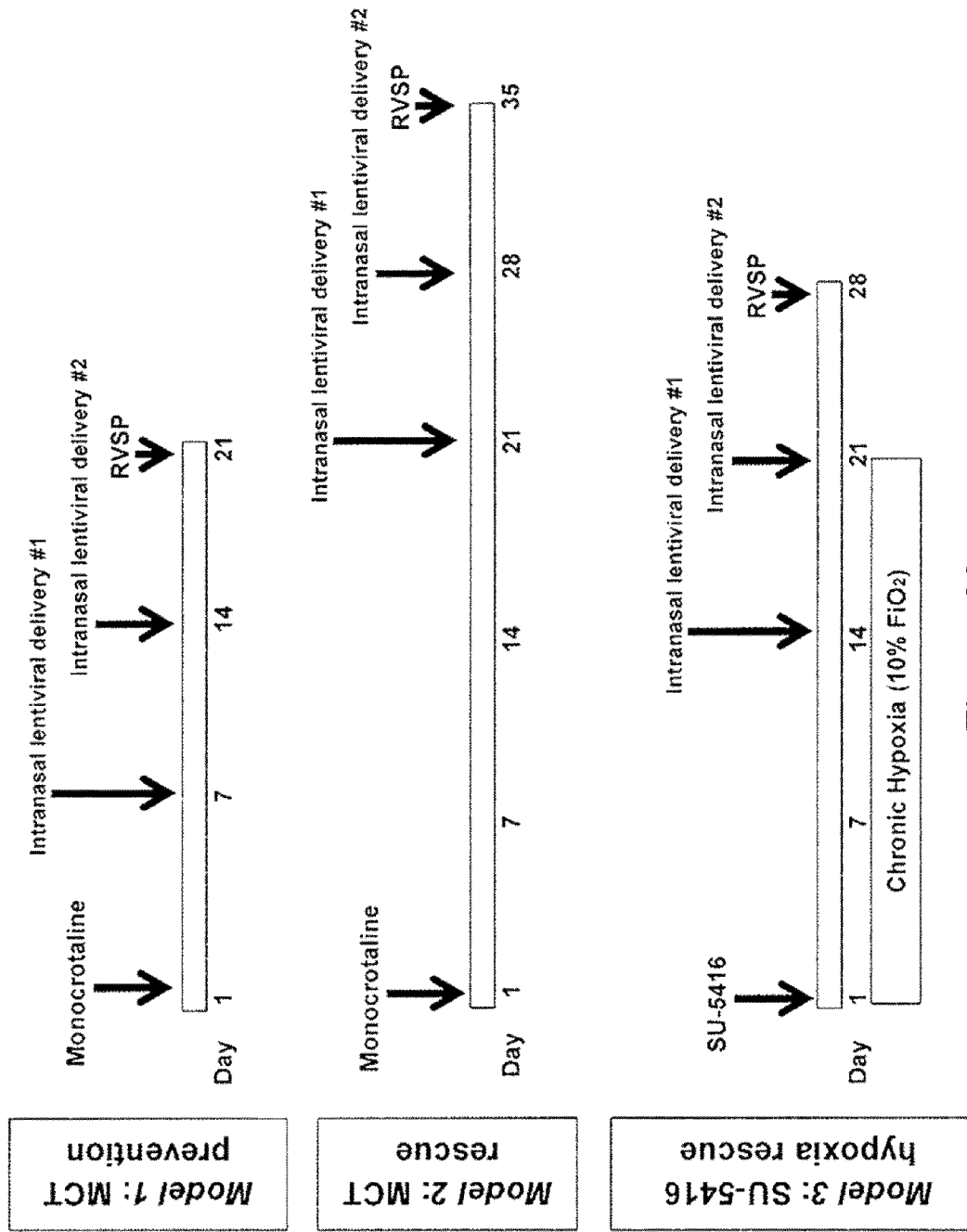
Figures 64A, 64B:
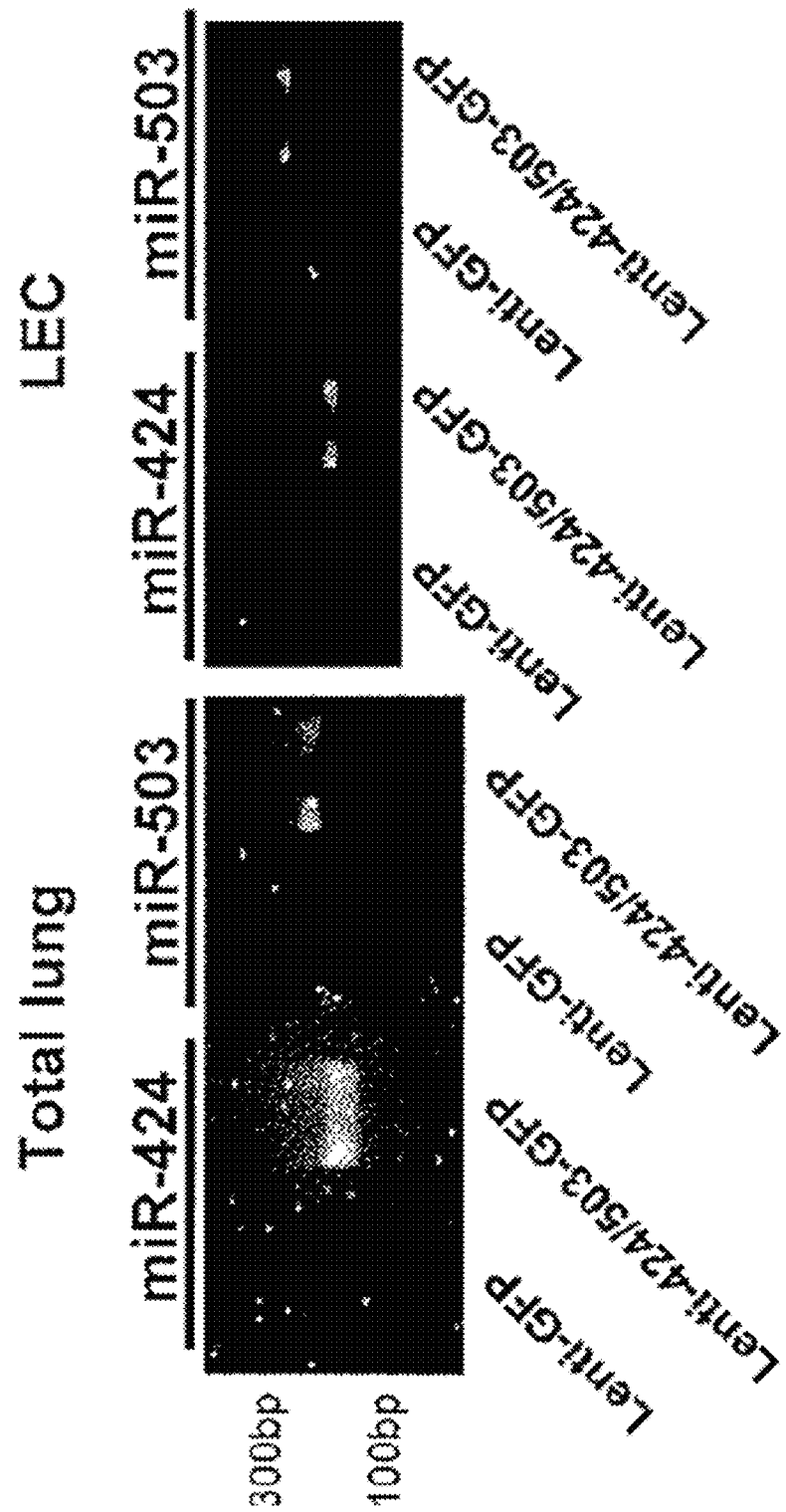
Figure 65:
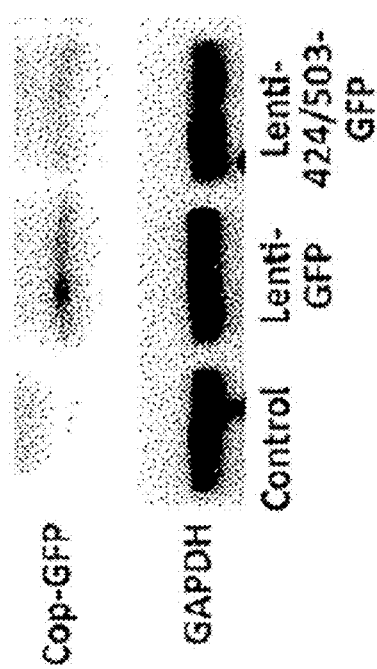
Figures 66A, 66B:
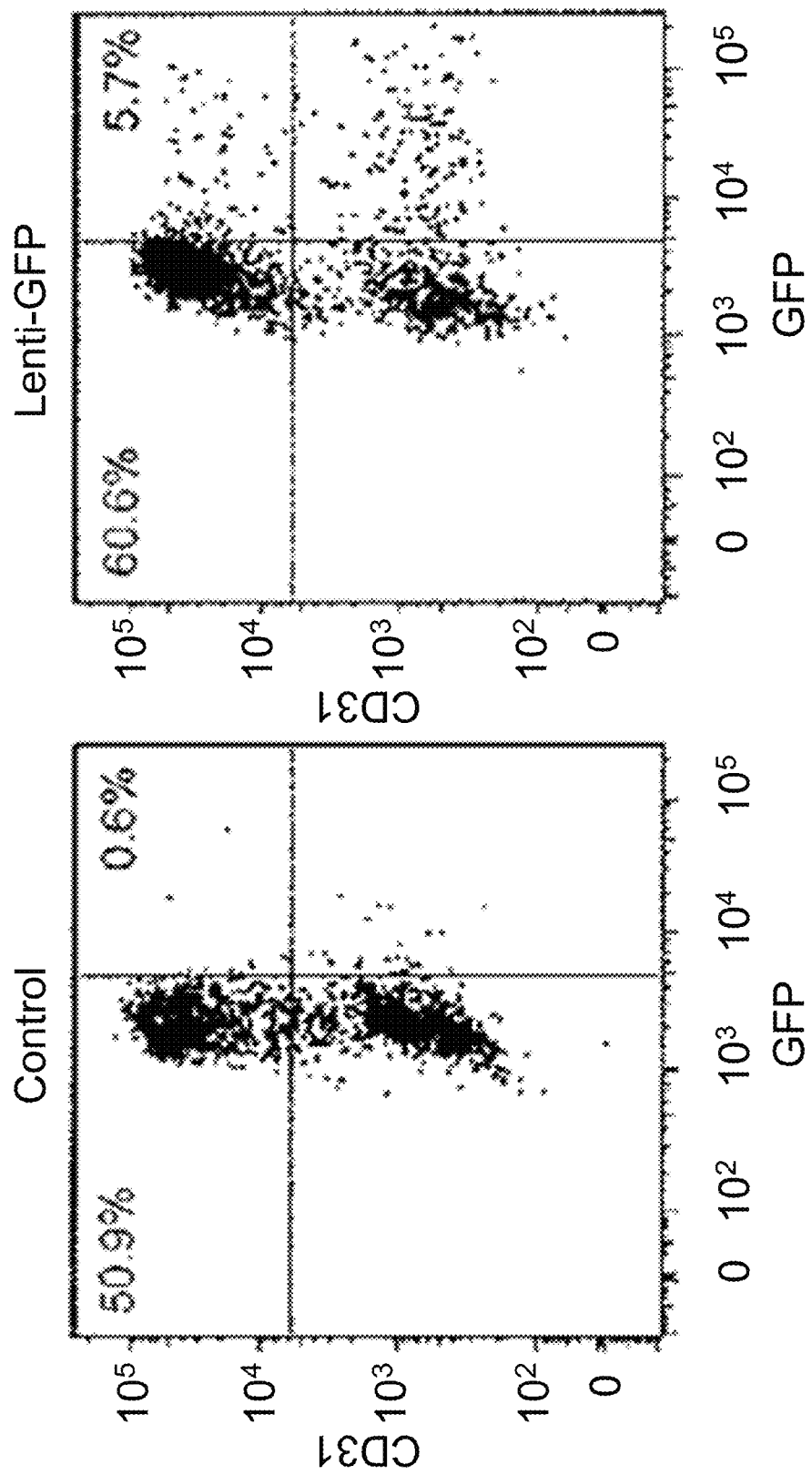
Figure 67:
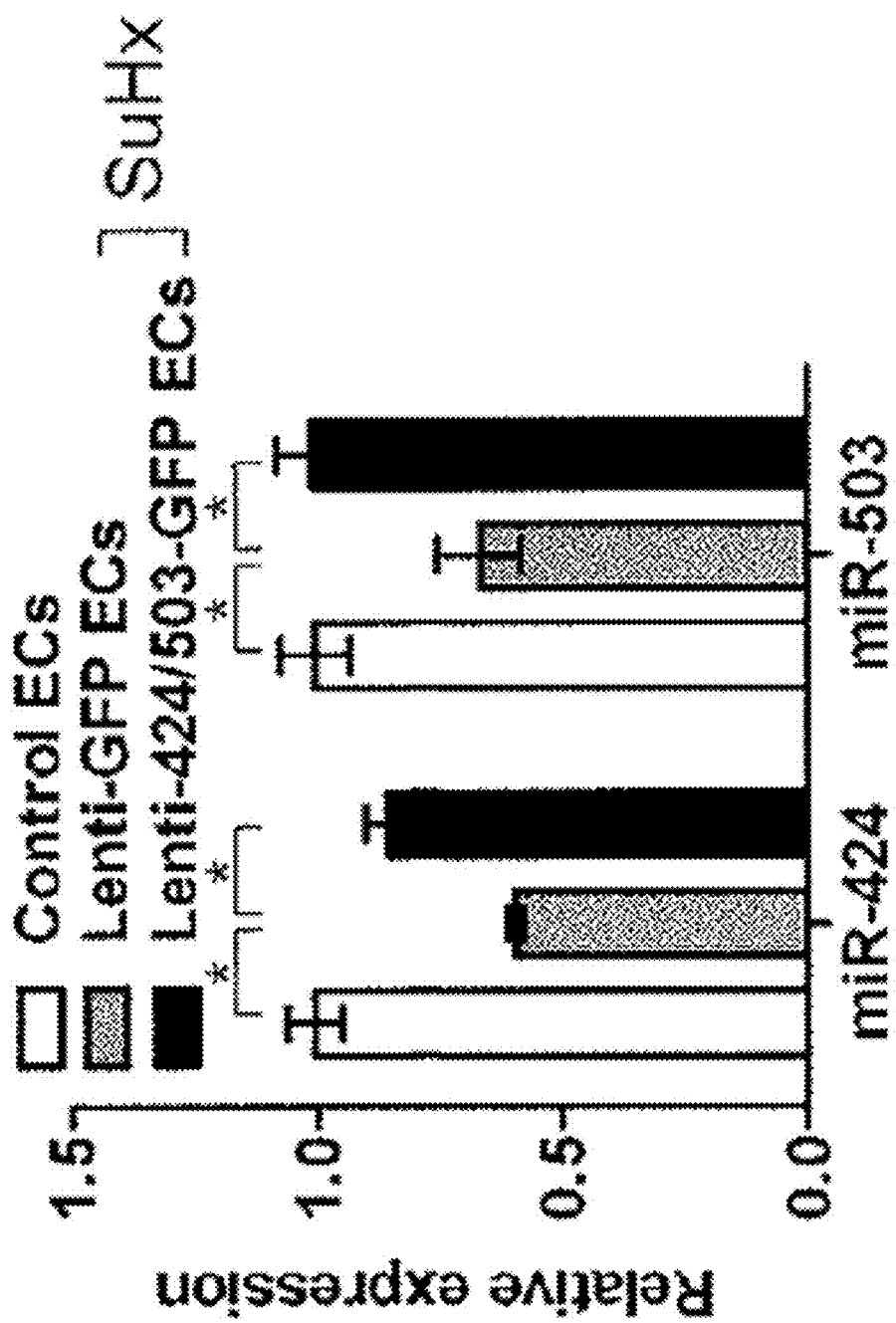
Figure 68:
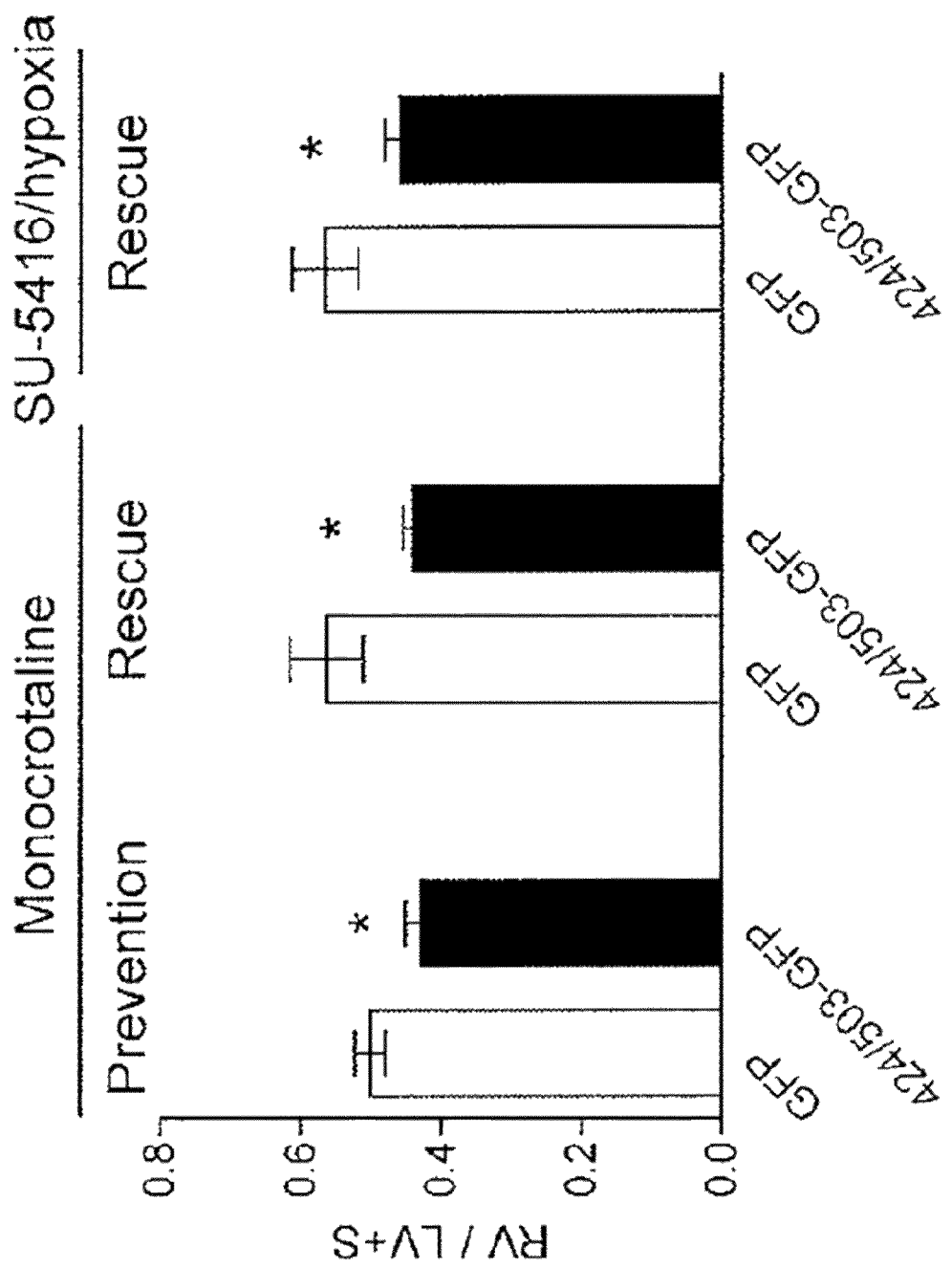

FIG. 47A is a graph showing APLN induced proliferation of normal PAECs. Control or PAH PAECs were stimulated with apelin-'13 peptide and proliferation response was assessed;

FIG. 47B is a graph showing decreased proliferation of PAH PAECs in response to APLN;

FIG. 47C is a graph showing decreased proliferation of PAH PAECs in response to APLN;

FIG. 48A is a bar graph showing increased proliferation of normal PAECs augmented by concurrent transfection of anti-miR-424/503. *p<0.05;

FIG. 48B is a bar graph showing that transfection of anti-miR-424/503 reverses the anti-proliferative effect of APLN on PAH PAECs. *p<0.05;

FIG. 49A is a bar graph showing knockdown of APLN in PAECs;

FIG. 49B is a bar graph showing overexpression of APLN in PAECs;

FIG. 49C is a bar graph showing knockdown of AGO2 in PAECs;

FIG. 49D is a bar graph showing knockdown of FGF2 in PAECs;

FIG. 49E is a bar graph showing knockdown of FGFR1 in PAECs *p<0.001;

FIG. 50A is a dot plot of MicroRNA microarray with APLN knockdown in PAECs leads to significantly decreased miR-424 and miR-503 expression;

FIG. 50B is a dot plot of MicroRNA microarray with APLNR knockdown in PAECs leads to significantly decreased miR-424 and miR-503 expression;

FIG. 51A is a diagram of MiR-424 and miR-503 transcribed as a single transcript. Lines indicate the location of two primers to determine whether a single transcript encompassing both miR-424 and miR-503;

FIG. 51B is a gel showing a single transcript encompasses both miR-424 and miR-503 in PAECs in RT-PCR analysis, control shows absence of the transcript;

FIG. 51C is a bar graph showing transcript level of miR-424/miR-503 is significantly decreased by APLN knockdown in PAECS. *p<0.001;

FIG. 52 is an image of negative control in situ hybridizations of human lung section;

FIG. 53A is a sequence alignment showing that FGF2 3' UTR has 3 unique target sequences shared by miR-424 and miR-503;

FIG. 53B is a sequence alignment showing that FGFRI 3' UTR has 2 unique target sequences shared by miR-424 and miR-503;

FIG. 54A is a bar graph showing FGF2 mRNA levels significantly reduced by miR-424 or miR-503 overexpression in normal PAECs. *p<0.01 vs. control;

FIG. 54B is a bar graph showing FGFRI mRNA levels significantly reduced by miR-424 or miR-503 overexpression in normal PAECs. *p<0.01 vs. control;

FIG. 54C is a bar graph showing levels of miR achieved with overexpression or knockdown in PAECs;

FIG. 55A is a bar graph showing pri-miR-424 and pri-miR-503 are significantly decreased in PAH PAECS;

FIG. 55B is a bar graph showing pre-miR-424 and pre-miR-503 are significantly decreased in PAH PAECS;

FIG. 55C is a Northern blot demonstrating decreased expression of miR-424 and miR-503 in PAH PAECs;

FIG. 56A is a dot plot showing expression of miR-503 in normal and PAH PAECs has a significant, inverse linear correlation with FGF2 mRNA levels;

FIG. 56B is a dot plot showing expression of miR-503 in normal and PAH PAECs has a significant, inverse linear correlation with FGFRI mRNA levels;

FIG. 57 shows images of microvascular endothelial expression of miR-424 and miR-503 significantly decreased in the lungs of PAH patient, as demonstrated by costaining with von Willebrand factor. Endothelial layer is designated by white arrows. Scale bar, 70 µm;

FIG. 58A is a bar graph showing expression levels of miR-424 and miR-503 as significantly increased with cell confluency in PAECS. *p<0.001;

FIG. 58B is a bar graph showing expression levels of miR-424 and miR-503 as significantly increased with serum starvation in PAECS. *p<0.001;

FIG. 59A is a bar graph showing augmentation of FGF signaling via FGF2 stimulation and FGFRI overexpression induces proliferation of normal PAECS, *p<0.001;

FIG. 59B is a bar graph showing knockdown of FGF2 and FGFRI in PAH PAECs inhibits proliferation, **p<0.05;

FIG. 60 is a bar graph showing PAECs express significantly higher levels of miR-424 and miR-503 compared to PASMCS. *p<0.001;

FIG. 61 is a bar graph showing levels of miR-424 and miR-503 are not significantly changed in PASMCS of PAH patients compared to control PASMCS;

FIG. 62A is a blot showing overexpression of rat miR-322 or miR-503 inhibits FGF2 and FGFR1 protein expression in isolated rat lung endothelial cells;

FIG. 62B is a bar graph showing overexpression of rat miR-322 or miR-503 inhibits FGF2 and FGFR1 mRNA expression in isolated rat lung endothelial cells. *p<0.01;

FIG. 63 is a schematic of experimental PH models used;

FIG. 64A is a gel showing detection of lentiviral miR-424 and miR-503 transcripts in the lungs of rats receiving Lenti-424/503-GFP but not Lenti-GFP;

FIG. 64B is a gel showing detection of lentiviral miR-424 and miR-503 transcripts in isolated LECs of rats receiving Lenti-424/503-GFP but not Lenti-GFP;

FIG. 65 is a blot showing expression of lentivirally expressed copGFP in lung homogenates of Lenti-GFP and Lenti-424/503-GFP groups;

FIG. 66A is a flow plot of CD31 and GFP of control cells;

FIG. 66B is a flow plot of CD31 and GFP of Lenti-GFP cells indicating ~8% of lung endothelial cells are GFP positive;

FIG. 67 is a bar graph showing Lenti-424/503-GFP delivered intranasally can restore miR-424 (hsa-miR-424+rno-miR-322) and miR-503 expression in LECs to basal levels in SU-5416/hypoxia (SuHx) induced PH. *p<0.05; and FIG. 68 is a bar graph showing the right ventricle to left ventricle+septum weight ratio is significantly decreased in rats receiving lenti-4241503-GFP compared to lenti-GFP in all three models. *p<0.05.

DETAILED DESCRIPTION OF THE INVENTION

Definitions

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or within 10%, 9%, 8%, 7%, 6%, 5%, 4%, 3%, 2%, 1%, 0.5%, 0.1%, 0.05%, or 0.01% of the specified value, as such variations are appropriate to perform the disclosed methods. Unless otherwise clear from context, all numerical values provided herein are modified by the term about.

By "apelin (APLN) polypeptide" is meant a protein substantially identical to the amino acid sequence of GenBank Accession No. NP_059109, or a fragment thereof, functions as the endogenous ligand for apelin receptor (APLNR). In one embodiment, an APLN polypeptide has at least about 85% amino acid sequence identity to the SEQ ID NO: 1 and the following amino acid sequence:

```
  1 mnlrlcvqal lllwlsltav cggslmplpd gngledgnvr hlvqprgsrn gpgpwqggrr
 61 kfrrqrprls hkgpmpf
```

By "APLN polynucleotide" is meant a nucleic acid molecule encoding an APLN polypeptide or fragment thereof. An exemplary APLN nucleic acid sequence (GenBank Accession No. NM_017413) is provided in SEQ ID NO.: 2 and below:

```
  1 gagcattctc tctggcagcc ggggtcacgg gcagttgcag ccgcggccga gcagccagcc
 61 gctaagaaag agctcgccgc tgccgctccc ggagccgccg aggccagctt cgcggcgctg
121 ccccgcggcg ggagaggagg ctgcagaaga gcggaggcgg ccagcgggag cggcggggct
181 cagcgcgcac actcagcggc cggggagcct cccgagctct gcgcccgcac gcgccagccg
241 cggctcgcgc ctttcttggc ctccgggcgc ccgacctctc ctccccgcg ccggctcgcc
301 ggggccgcgg cggcccaagg agcagcatga atctgcggct ctgcgtgcag gcgctcctgc
361 tgctctggct ctccttgacc gcggtgtgtg gagggtccct gatgccgctt cccgatggga
421 atgggctgga agacggcaat gtccgccacc tggtgcagcc cagagggtca aggaatgggc
481 cagggccctg gcagggaggt cggaggaaat tccgccgcca gcggccccgc ctctcccata
541 agggacccat gcctttctga agcaggactg aagggggccc caagtgccca ccccggcgg
601 ttatgtctcc tccatagatt ggtctgcttc tctggaggcc tcacgtccat tcagctctca
661 cctcgcacct gctgtagcca ccagtgggcc cagctcttct cacctgcctg cttccccag
721 tggcgtgctc ctggctgtag tttggatgat tcccgttctc tcacaagaat ccgtccagtc
781 catcttcctg gcccctccct ggactgactt tggagaccta gccccagaaa gcctcccttc
841 ttctccaggt ccctccgcc ctagtccctg cctgtctcat ctaacgcccc aaaccttcat
```

-continued

```
 901 ttgggccttc cttcctcatg tctgccctga gcgcggggtg gaagtgctcc cttctgtggg
 961 ctccagcaga tccttgttt tcctgtcagt tggacccctc acctggcctc cagggaagaa
1021 tgcagagaaa agcaaggaga gactctagtt aagaggtgct ggctgcgggg atccagacag
1081 ggcacattgg gggcatggaa gtgccagggt ggttttcagg agctctggtg aagtgggtgg
1141 agcatcagcg tttgctcagt taagggagag gtagagaggg gcccgtgaag tcctttgtca
1201 cttctcttgc cttagtgtgc ctcccaatac tcccttcttc ctgccccac accccatccc
1261 cagctagccc aagctccagg tcaggagggg agggtgctgg gcctgacatg gctatatacc
1321 ctcccaggag taaaagccaa gcaagaggtt gttttttgcca agaatcacag aatgttagag
1381 ctgacaggac ccttgaaggt cacttagcct tcttaggcaa acgcctgcaa aacagaagcc
1441 tggagagggg agtgacctgc tcagagtcat tgcagagccg ggatggggac caggtctccc
1501 atctcctact ttatgacgcc ctcttccctc ttgatgatgt cttttcaaag caaatgaagt
1561 gccttttccc gaggctgggg ctgggggtgg ctgggagggg aagggaaggg agaggcaagc
1621 tggctgtgaa ctgtcctgtt gtggggctgg agctgctccc acctccctga cctacccctg
1681 ctgcaccatt cccccagctg ggctggaagg ttccataact ggccagctgc ccccataact
1741 ggcagcattc ccagacccag ggtactctaa taggggcggc tcaggcactg agactaccgc
1801 tcaaccccag ggtggttttc aggagtccga ggtagccttc aatcactgga ctccatggcc
1861 ttcccttcgt gttgaccgga ccttccttcc agggcttttc ctttggggga ggcggagagg
1921 ggagaagaag gaagggaagg gcagaaggaa ggagggaaga aaagaaagca aaggaacaga
1981 aggaaggaaa gaaagatggg aggaagtgca gcaggaatag caccctctcc ccgggaggcc
2041 ctagcttccg tgaggggcca tcaccagcca ttccttggag ggggctttct cccttttgc
2101 ttgagcaggg ttcccaggag ggagaaagag aagacaagag cctgatgccc aactttgtgt
2161 gtgtggggac gggggagtca gggcccccca agtcccacaa tagccccaat gtttgcctat
2221 ccacctcccc caagcccctt tacctatgct gctgctaacg ctgctgctgc tgctgctgct
2281 gcttaaaggc tcatgcttgg agtggggact ggtcggtgcc cagaaagtct cttctgccac
2341 tgacgccccc atcagggatt gggccttctt tccccttcc tttctgtgtc tcctgcctca
2401 tcggcctgcc atgacctgca gccaagccca gccccgtggg gaaggggaga aagtggggga
2461 tggctaagaa agctgggaga tagggaacag aagagggtag tgggtgggct aggggggctg
2521 ccttatttaa agtggttgtt tatgattctt atactaattt atacaaagat attaaggccc
2581 tgttcattaa gaaattgttc ccttcccctg tgttcaatgt ttgtaaagat tgttctgtgt
2641 aaatatgtct ttataataaa cagttaaaag ctgacagttc gcccttactc ttggaggtca
2701 tgttcaggag gggcattcct ttcccctggg ggtcatgggt gtccccatgc ccacatattg
2761 cacgtgcagg gaggtaagtg cctgcatccc aaatcggttc taggtcaact ggcctcaaac
2821 tgatttgcca tgagctcaca aaatgaatcc ctatgcttaa tgaccaggtc acataaaatc
2881 cagcccactt acaggttttc tggcatctgt ttgggtgtcc taatttttt ggcagtgtca
2941 tttgaagaat ttttttaaag cagtttattt aagaacatac tgattaaatg caggatcgct
3001 actaaaaatt gttttgtatc cttggtgggt gtcttctgct attttatcta cttttgaaca
3061 cttcaggac ttttagcca gtttgccttt cttgaaaat gttatgtttt cagcaataaa
3121 tacatttgat aatgactttg tttgtatcat tttatgtttc acaaagtaga gttgcttgat
3181 gaatgagata gcctgaaaaa taaaatgcaa agagttcaat ataaaaaaaa aaaaaaa
```

By "apelin receptor (APLNR or APJ) polypeptide" is meant a protein substantially identical to the amino acid sequence of GenBank Accession No. NP_005152, or a fragment thereof, functions as the endogenous ligand for apelin receptor (APLNR or APJ). In one embodiment, an APLNR or APJ polypeptide has at least about 85% amino acid sequence identity to SEQ ID NO: 3 and the following amino acid sequence:

```
  1 meeggdfdny ygadnqsece ytdwkssgal ipaiymlvfl lgttgnglvl wtvfrssrek 61 rrsadifias lavadltfvv tlplwatyty rdydwpfgtf fcklssylif vnmyasvfcl 121 tglsfdryla ivrpvanarl rlrvsgavat avlwvlaall ampvmvlrtt gdlenttkvq 181 cymdysmvat vssewawevg lgvssttvgf vvpftimltc yffiaqtiag hfrkeriegl 241 rkrrrllsii vvlvvtfalc wmpyhlvktl ymlgsllhwp cdfdlflmni fpyctcisyv 301 nsclnpflya ffdprfrqac tsmlccgqsr cagtshsssg eksasyssgh sqgpgpnmgk 361 ggeqmheksi pysqetivvd
```

By "APLNR or APJ polynucleotide" is meant a nucleic acid molecule encoding an APLNR or APJ polypeptide or fragment thereof. An exemplary APLNR or APJ nucleic acid sequence (GenBank Accession No. NM_017413) is in SEQ ID NO: 4 and provided below:

```
   1 ggaaagccga cttgcaaaac cacagataat gttcagccca gcacagtagg ggtcaatttg 61 gtccacttgc tcagtgacaa aaagaaaaaa aaagtgggct gtcactaaag attttgactc 121 acaagagagg ggctggtctg gaggtgggag gagggagtga cgagtcaagg aggagacagg 181 gacgcaggag ggtgcaagga agtgtcttaa ctgagacggg ggtaaggcaa gagagggtgg 241 aggaaattct gcaggagaca ggcttcctcc agggtctgga gaacccagag gcagctcctc 301 ctgagtgctg ggaaggactc tgggcatctt cagcccttct tactctctga ggctcaagcc 361 agaaattcag gctgcttgca gagtgggtga cagagccacg gagctggtgt ccctgggacc 421 ctctgcccgt cttctctcca ctccccagca tggaggaagg tggtgatttt gacaactact 481 atggggcaga caaccagtct gagtgtgagt acacagactg gaaatcctcg ggggccctca 541 tccctgccat ctacatgttg gtcttcctcc tgggcaccac gggcaacggt ctggtgctct 601 ggaccgtgtt tcggagcagc cgggagaaga ggcgctcagc tgatatcttc attgctagcc 661 tggcggtggc tgacctgacc ttcgtggtga cgctgcccct gtgggctacc tacacgtacc 721 gggactatga ctggcccttt gggaccttct tctgcaagct cagcagctac ctcatcttcg 781 tcaacatgta cgccagcgtc ttctgcctca ccggcctcag cttcgaccgc tacctggcca 841 tcgtgaggcc agtggccaat gctcggctga ggctgcgggt cagcggggcc gtggccacgg 901 cagttctttg ggtgctggcc gccctcctgg ccatgcctgt catggtgtta cgcaccaccg 961 gggacttgga gaacaccact aaggtgcagt gctacatgga ctactccatg gtggccactg 1021 tgagctcaga gtgggcctgg gaggtgggcc ttggggtctc gtccaccacc gtgggctttg 1081 tggtgccctt caccatcatg ctgacctgtt acttcttcat cgcccaaacc atcgctggcc 1141 acttccgcaa ggaacgcatc gagggcctgc ggaagcggcg ccggctgctc agcatcatcg 1201 tggtgctggt ggtgaccttt gccctgtgct ggatgcccta ccacctggtg aagacgctgt 1261 acatgctggg cagcctgctg cactggccct gtgactttga cctcttcctc atgaacatct 1321 tcccctactg cacctgcatc agctacgtca acagctgcct caaccccttc ctctatgcct 1381 ttttcgaccc ccgcttccgc caggcctgca cctccatgct ctgctgtggc cagagcaggt 1441 gcgcaggcac ctcccacagc agcagtgggg agaagtcagc cagctactct tcggggcaca 1501 gccaggggcc cggcccaaac atgggcaagg gtggagaaca gatgcacgag aaatccatcc
```

-continued

```
1561 cctacagcca ggagacccct gtggttgact agggctggga gcagagagaa gcctggcgcc 1621 ctcggccctc cccggccttt gcccttgctt tctgaaaatc aggtagtgtg gctactcctt 1681 gtcctatgca catcctttaa ctgtccctg attctgcccc gccctgtcct cctctactgc 1741 tttattcttt ctcagaggtt tgtggtttag gggaaagaga ctgggctcta cagacctgac 1801 cctgcacaag ccatttaatc tcactcagcc tcagtttctc cattggtatg aaatgggga 1861 aagtcatatt gatcctaaaa tgttgaagcc tgagtctgga cgcagtaaaa gcttgtttcc 1921 ctctgctgct ttcttagatc tgcaatcgtc tttcctccct tctttccttg tagttttcc 1981 cccaccactc tctgcagctg ccgctcctta tccctgcctt ctggcaccaa tcccctccta 2041 cagctcgtcc ccctccctcc atccatcctt ctccctgtc tactttcttg ttctgaaggg 2101 ctactaaggg ttaaggatcc caaagcttgc agagactgac cctgtttaag ctttctatcc 2161 tgttttctga gtgtgaggca gggaatgggc tgggccggg ggtgggctgt gtgtcagcag 2221 ataattagtg ctccagccct tagatctggg agctccagag cttgccctaa aattggatca 2281 cttccctgtc attttgggca ttggggctag tgtgattcct gcagttcccc catggcacca 2341 tgacactgac tagatatgct ttctccaaat tgtccgcaga cccttcatc cttcctctat 2401 tttctatgag aattggaagg cagcagggct gatgaatgga tgtactcctt ggtttcatta 2461 tgtgagtggg gagttgggaa gggcaactag agagagagga tggaggggtg tctgcattta 2521 gtccagacac tgcttggctc gctccccgag tcctcctgtt tctgacttcc tgcataactg 2581 tgagctgaag ggtttcctca tctccccatc ttaccccatc atactgattt ctttcttggg 2641 cactggtgct acttggtgcc aagaatcatg ttgtttggga tggagatgcc tgcctcttgt 2701 ctgtgtgtgt tgtacttata tgtctatatg gatgagcctg gcatgaacag cagtgtgcct 2761 gggtcatttg gacaaatctc ctcccacccc ccaatccact gcaactctgc tgttcacaca 2821 ttacccttgg caggggtgg tgggggcag ggacacactg aggcaatgaa aaatgtagaa 2881 taaaaatgag tccacccct actgggattg ggggctccaa cggctggtcc gtgctttagg 2941 agcgaagtta atgtttgcac caggcttcct gtagggagat ccctcccaa agcagctggc 3001 gccaaggctt gggggcgtcc tactgagctg ggttcctgct ccttcttggg ctccatgaag 3061 gaagtaagag gctagttgag agcctccctt ggccccttc cggtgcctcc ccgcctggct 3121 tcaaatttat gagcattgcc ctcatcgtcc tttcttgttc cagggtcagt ggccctcttc 3181 ctaaggaggc ctcctgcttg ccatgggcca aaaggcacgg ggtgggtttt ttctctccct 3241 acccctcagga ttggacctct tggcttctgc tggattgggg atctgggaat agggactgga 3301 gcaagtgtgc agatagcatg atgtctacac tgccagagag accgtgagga tgaaattaat 3361 agtggggcct ttgtgagcta gaggctggga gtgtctattc cgggttttgt tcttggagga 3421 ctatgaaagt gaaggacaag acatgagcga tggagataag aaaagcccag cttgatgtga 3481 atggacatct tgaccctccc tggaatgacg ccagctctgg gggcagaggg aggaggagag 3541 gggaaggggc tcctcacagc ctagtctccc catcttaaga tagcatcttt cacagagtca 3601 cctcctctgc ccagagctgt cctcaaagca tccagtgaac actggaagag gcttctagaa 3661 gggaagaaat tgtccctctg aggccgccgt gggtgacctg cagagacttc ctgcctggaa 3721 ctcatctgtg aactgggaca gaagcagagg aggctgcctg ctgtgatacc cccttacctc 3781 ccccagtgcc ttcttcagaa tatctgcact gtcttctgat cctgttagtc actgtggttc 3841 atcaaataaa actgtttgtg caactgttgt gtccaaaaaa aaaaaaaaa aaaaaaaaa 3901 aaaaa
```

By "fibroblast growth factor receptor 1 (FGFR1) polypeptide" is meant a protein substantially identical to the amino acid sequence of GenBank Accession No. NP_001167534, or a fragment thereof, is the receptor for fibroblast growth factors, setting in motion a cascade of downstream signals, ultimately influencing mitogenesis and differentiation. In one embodiment, a FGFR1 polypeptide has at least about 85% amino acid sequence identity to SEQ ID NO: 5 and the following amino acid sequence:

```
  1 mwswkcllfw avlvtatlct arpsptlpeq aqpwgapvev esflvhpgdl lqlrcrlrdd
 61 vqsinwlrdg vqlaesnrtr itgeevevqd svpadsglya cvtsspsgsd ttyfsvnvsd
121 alpssedddd dddssseeke tdntkpnrmp vapywtspek mekklhavpa aktvkfkcps
181 sgtpnptlrw lkngkefkpd hriggykvry atwsiimdsv vpsdkgnytc iveneygsin
241 htyqldvver sphrpilqag lpanktvalg snvefmckvy sdpqphiqwl khievngski
301 gpdnlpyvqi lktagvnttd kemevlhlrn vsfedageyt clagnsigls hhsawltvle
361 aleerpavmt splyleiiiy ctgafliscm vgsvivykmk sgtkksdfhs qmavhklaks
421 iplrrqvsad ssasmnsgvl lvrpsrlsss gtpmlagvse yelpedprwe lprdrlvlgk
481 plgegcfgqv vlaeaigldk dkpnrvtkva vkmlksdate kdlsdlisem emmkmigkhk
541 niinllgact qdgplyvive yaskgnlrey lqarrppgle ycynpshnpe eqlsskdlvs
601 cayqvargme ylaskkcihr dlaarnvlvt ednvmkiadf glardihhid yykkttngrl
661 pvkwmapeal fdriythqsd vwsfgvllwe iftlggspyp gvpveelfkl lkeghrmdkp
721 snctnelymm mrdcwhavps qrptfkqlve dldrivalts nqeyldlsmp ldqyspsfpd
781 trsstcssge dsvfsheplp eepclprhpa glangglkrr
```

By "FGFR1 polynucleotide" is meant a nucleic acid molecule encoding a FGFR1 polypeptide or fragment thereof. An exemplary FGFR1 nucleic acid sequence (GenBank Accession No. NM_001174063) is in SEQ ID NO: 6 and provided below:

```
  1 agatgcaggg gcgcaaacgc caaaggagac caggctgtag gaagagaagg gcagagcgcc
 61 ggacagctcg gcccgctccc cgtcctttgg ggccgcggct ggggaactac aaggcccagc
121 aggcagctgc aggggcgga ggcggaggag ggaccagcgc gggtgggagt gagagagcga
181 gccctcgcgc cccgccggcg catagcgctc ggagcgctct tgcggccaca ggcgcggcgt
241 cctcggcggc gggcggcagc tagcggagc cgggacgccg gtgcagccgc agcgcgcgga
301 ggaacccggg tgtgccggga gctgggcggc cacgtccgga cgggaccgag acccctcgta
361 gcgcattgcg gcgacctcgc cttccccggc cgcgagcgcg ccgctgcttg aaaagccgcg
421 gaacccaagg acttttctcc ggtccgagct cggggcgccc cgcagggcgc acggtacccg
481 tgctgcagtc gggcacgccg cggcgccggg gcctccgcag ggcgatggag cccggtctgc
541 aaggaaagtg aggcgccgcc gctgcgttct ggaggagggg ggcacaaggt ctgagaccc
601 cgggtggcgg acgggagccc tccccccgcc ccgcctccgg ggcaccagct ccggctccat
```

-continued

```
 661 tgttcccgcc cgggctggag gcgccgag-
ca ccgagcgccg ccgggagtcg agcgccggcc 721 gcggagctct tgcgacccccg ccaggac-
ccg aacagagccc gggggcggcg ggccggagcc 781 ggggacgcgg gcacacgccc gctcgca-
caa gccacggcgg actctcccga ggcggaacct 841 ccacgccgag cgagggt-
cag tttgaaaagg aggatcgagc tcactgtgga gtatccatgg 901 agatgtggag ccttgtcacc aac-
ctctaac tgcagaactg ggatgtggag ctggaagtgc 961 ctcctcttct gggctgtgct ggtca-
cagcc acactctgca ccgctaggcc gtccccgacc 1021 ttgcctgaac aagcccagcc ctggg-
gagcc cctgtggaag tggagtcctt cctggtccac 1081 cccggtgacc tgctgcagct tcgct-
gtcgg ctgcgggacg atgtgcagag catcaactgg 1141 ctgcgggacg gggtgcagct ggcg-
gaaagc aaccgcaccc gcatcacagg ggaggaggtg 1201 gaggtgcagg actccgtgcc cgca-
gactcc ggcctctatg cttgcgtaac cagcagcccc 1261 tcgggcagtg acaccaccta cttctc-
cgtc aatgtttcag atgctctccc ctcctcggag 1321 gatgatgatg atgatgatga ctcctct-
tca gaggagaaag aaacagataa caccaaacca 1381 aaccgtatgc ccgtagctcc atattgga-
ca tccccagaaa agatggaaaa gaaattgcat 1441 gcagtgccgg ctgccaagac agtgaagt-
tc aaatgcccctt ccagtgggac cccaaacccc 1501 acactgcgct ggttgaaaaa tggcaaa-
gaa ttcaaacctg accacagaat tggaggctac 1561 aaggtccgtt atgccacctg gagcat-
cata atggactctg tggtgccctc tgacaagggc 1621 aactacacct gcattgtgga gaatgag-
tac ggcagcatca accacacata ccagctggat 1681 gtcgtggagc ggtcccctca ccggc-
ccatc ctgcaagcag ggttgcccgc caacaaaaca 1741 gtggccctgg gtagcaacgt ggagt-
tcatg tgtaaggtgt acagtgaccc gcagccgcac 1801 atccagtggc taaagcacat cgaggt-
gaat gggagcaaga ttgcccccaga caacctgcct 1861 tatgtccaga tcttgaagac tgctg-
gagtt aataccaccg acaaagagat ggaggtgctt 1921 cacttaagaa atgtctcctt tgaggacg-
ca ggggagtata cgtgcttggc gggtaactct 1981 atcggactct cccatcactc tgcatggt-
tg accgttctgg aagccctgga agagaggccg 2041 gcagtgatga cctcgcccct gtacctg-
gag atcatcatct attgcacagg ggccttcctc 2101 atctcctgca tggtggggtc ggt-
catcgtc tacaagatga agagtggtac caagaagagt 2161 gacttccaca gccagatggc tgtgca-
caag ctggccaaga gcatccctct gcgcagacag 2221 gtgtctgctg actccagtgc atccat-
gaac tctggggttc ttctggttcg gccatcacgg 2281 ctctcctcca gtgggactcc catgctag-
ca ggggtctctg agtatgagct tcccgaagac
```

-continued

```
2341 cctcgctggg agctgcctcg ggaca-
gactg gtcttaggca aaccctggg agagggctgc 2401 tttgggcagg tggtgttggc agaggc-
tatc gggctggaca aggacaaacc caaccgtgtg 2461 accaaagtgg ctgtgaagat gt-
tgaagtcg dacgcaacag agaaagactt gtcagacctg 2521 atctcagaaa tggagatgat gaagat-
gatc gggaagcata agaatatcat caacctgctg 2581 ggggcctgca cgcaggatgg tcccttg-
tat gtcatcgtgg agtatgcctc caagggcaac 2641 ctgcgggagt acctgcaggc ccggaggc-
cc ccagggctgg aatactgcta caacccagc 2701 cacaacccag aggagcagct ctcctc-
caag gacctggtgt cctgcgccta ccaggtggcc 2761 cgaggcatgg agtatctggc ctccaa-
gaag tgcatacacc gagacctggc agccaggaat 2821 gtcctggtga cagaggacaa tgtgat-
gaag atagcagact ttggcctcgc acgggacatt 2881 caccacatcg actactataa aaaga-
caacc aacggccgac tgcctgtgaa gtggatggca 2941 cccgaggcat tatttgaccg gatcta-
cacc caccagagtg atgtgtggtc tttcggggtg 3001 ctcctgtggg agatcttcac tctgggcg-
gc tccccatacc ccggtgtgcc tgtggaggaa 3061 cttttcaagc tgctgaagga gggtcac-
cgc atggacaagc ccagtaactg caccaacgag 3121 ctgtacatga tgatgcggga ctgctg-
gcat gcagtgccct cacagagacc caccttcaag 3181 cagctggtgg aagacctgga ccg-
catcgtg gccttgacct ccaaccagga gtacctggac 3241 ctgtccatgc ccctggacca gtactc-
cccc agctttcccg acacccggag ctctacgtgc 3301 tcctcagggg aggattccgt cttctct-
cat gagccgctgc ccgaggagcc ctgcctgccc 3361 cgacacccag cccagcttgc caatggcg-
ga ctcaaacgcc gctgactgcc acccacacgc 3421 cctccccaga ctccaccgtc agctg-
taacc ctcacccaca gccctgctg ggcccaccac 3481 ctgtccgtcc ctgtcccctt cctgctg-
gc aggagccggc tgcctaccag gggcttcct 3541 gtgtggcctg ccttcacccc actcagct-
ca cctctccctc cacctcctct ccacctgctg 3601 gtgagaggtg caaagaggca-
gatctttgct gccagccact tcatcccctc ccagatgttg 3661 gaccaacacc cctccctgcc accag-
gcact gcctggaggg cagggagtgg gagccaatga 3721 acaggcatgc aagtgagagc ttcct-
gagct ttctcctgtc ggtttggtct gttttgcctt 3781 cacccataag cccctcgcac tctggtg-
gca ggtgccttct cctcagggct acagcagtag 3841 ggaggtcagt gcttcgtgcc tcgat-
tgaag gtgacctctg ccccagatag gtggtgccag 3901 tggcttatta attccgatac-
tagtttgctt tgctgaccaa atgcctggta ccagaggatg 3961 gtgaggcgaa ggccaggttg ggggcagt-
gt tgtggccctg ggcccagcc ccaaactggg
```

-continued

```
4021 ggctctgtat atagctatga agaaaaca-
ca aagtgtataa atctgagtat atatttacat 4081 gtctttttaa aagggtcgtt acca-
gagatt tacccatcgg gtaagatgct cctggtggct 4141 gggaggcatc agttgctata tat-
taaaaac aaaaagaaa aaaaaggaaa atgttttaa 4201 aaaggtcata tattttttgc-
tacttttgct gttttatttt tttaaattat gttctaaacc 4261 tattttcagt ttaggtccct-
caataaaaat tgctgctgct tcatttatct atgggctgta 4321 tgaaagggt gggaatgtcc actggaaa-
ga agggacaccc acgggccctg gggctaggtc 4381 tgtcccgagg gcaccgcatg ctcccg-
gcgc aggttccttg taacctcttc ttcctaggtc 4441 ctgcacccag acctcacgac gcacctc-
ctg cctctccgct gcttttggaa agtcagaaaa 4501 agaagatgtc tgcttcgagg gcaggaac-
cc catccatgca gtagaggcgc tgggcagaga 4561 gtcaaggccc agcagccatc gaccatg-
gat ggtttcctcc aaggaaaccg gtggggttgg 4621 gctggggagg gggcacctac ctaggaat-
ag ccacggggta gagctacagt gattaagagg 4681 aaagcaaggg cgcggttgct cacgcctg-
ta atcccagcac tttgggacac cgaggtgggc 4741 agatcacttc aggtcaggag tttgagac-
ca gcctggccaa cttagtgaaa ccccatctct 4801 actaaaaatg caaaaattat ccag-
gcatgg tggcacacgc ctgtaatccc agctccacag 4861 gaggctgagg cagaatccct-
tgaagctggg aggcggaggt tgcagtgagc cgagattgcg 4921 ccattgcact ccagcctggg caaca-
gagaa aacaaaaagg aaaacaaatg atgaaggtct 4981 gcagaaactg aaacccagac atgtgtct-
gc cccctctatg tgggcatggt tttgccagtg 5041 cttctaagtg caggagaaca tgtcacct-
ga ggctagtttt gcattcaggt ccctggcttc 5101 gtttcttgtt ggtatgcctc ccca-
gatcgt ccttcctgta tccatgtgac cagactgtat 5161 ttgttgggac tgtcgcagat cttggct-
tct tacagttctt cctgtccaaa ctccatcctg 5221 tccctcagga acgggggaa aattctc-
cga atgttttgg ttttttggct gcttggaatt 5281 tacttctgcc acctgctggt catcact-
gtc ctcactaagt ggattctggc tcccccgtac 5341 ctcatggctc aaactaccac tcct-
cagtcg ctatattaaa gcttatattt tgctggatta 5401 ctgctaaata caaaagaaag ttcaatat-
gt tttcatttct gtaggaaaaa tgggattgct 5461 gctttaaatt tctgagctag g-
gatttttg gcagctgcag tgttggcgac tattgtaaaa 5521 ttctctttgt ttctctctgt aaatag-
cacc tgctaacatt acaatttgta tttatgttta 5581 aagaaggcat catttggtga acagaac-
tag gaaatgaatt tttagctctt aaaagcattt 5641 gctttgagac cgcacaggag tgtctttc-
ct tgtaaaacag tgatgataat ttctgccttg
```

```
5701  gccctacctt gaagcaatgt tgtgt-
gaagg gatgaagaat ctaaaagtct tcataagtcc 5761  ttgggagagg tgctagaaaa atataag-
gca ctatcataat tacagtgatg tccttgctgt 5821  tactactcaa atcacccaca aatttc-
ccca aagactgcgc tagctgtcaa ataaaagaca 5881  gtgaaattga cctga
```

By "fibroblast growth factor 2 (FGF2) polypeptide" is meant a protein substantially identical to the amino acid sequence of GenBank Accession No. NP_001997, or a fragment thereof, functions in basement membranes and in the subendothelial extracellular matrix of blood vessels. In one embodiment, a FGF2 polypeptide has at least about 85% amino acid sequence identity to SEQ ID NO: 7 and the following amino acid sequence:

```
  1  mvgvgggdve dvtprpggcq isgrgargcn gipgaaawea alprrrprrh psvnprsraa
 61  gsprtrgrrt eerpsgsrlg drgrgralpg grlggrgrgr apervggrgr grgtaapraa
121  paargsrpgp agtmaagsit tlpalpedgg sgafppghfk dpkrlyckng gfflrihpdg
181  rvdgvreksd phiklqlqae ergvvsikgv canrylamke dgrllaskcv tdecffferl
241  esnnyntyrs rkytswyval krtgqyklgs ktgpgqkail flpmsaks
```

By "FGF2 polynucleotide" is meant a nucleic acid molecule encoding a FGF2 polypeptide or fragment thereof. An exemplary FGF2 nucleic acid sequence (GenBank Accession No. NM_002006) is SEQ ID NO: 8 and provided below:

```
   1  cggccccaga aacccgagc gagtaggggg cggcgcgcag gagggaggag aactgggggc
  61  gcgggaggct ggtgggtgtg gggggtggag atgtagaaga tgtgacgccg cggcccggcg
 121  ggtgccagat tagcggacgc ggtgcccgcg gttgcaacgg gatcccgggc gctgcagctt
 181  gggaggcggc tctccccagg cggcgtccgc ggagacaccc atccgtgaac cccaggtccc
 241  gggccgccgg ctcgccgcgc accaggggcc ggcggacaga agagcggccg agcggctcga
 301  ggctggggga ccgcgggcgc ggccgcgcgc tgccgggcgg gaggctgggg ggccggggcc
 361  ggggccgtgc cccggagcgg gtcggaggcc ggggccgggg ccggggacg gcggctcccc
 421  gcgcggctcc agcggctcgg ggatcccggc cgggccccgc agggaccatg gcagccggga
 481  gcatcaccac gctgcccgcc ttgcccgagg atggcggcag cggcgccttc ccgcccggcc
 541  acttcaagga cccaagcgg ctgtactgca aaaacggggg cttcttcctg cgcatccacc
 601  ccgacggccg agttgacggg gtccgggaga agagcgaccc tcacatcaag ctacaacttc
 661  aagcagaaga gagaggagtt gtgtctatca aggagtgtg tgctaaccgt tacctggcta
 721  tgaaggaaga tggaagatta ctggcttcta aatgtgttac ggatgagtgt ttcttttttg
 781  aacgattgga atctaataac tacaatactt accggtcaag gaaatacacc agttggtatg
 841  tggcactgaa acgaactggg cagtataaac ttggatccaa acaggacct gggcagaaag
 901  ctatactttt tcttccaatg tctgctaaga gctgatttta atggccacat ctaatctcat
 961  ttcacatgaa agaagaagta tattttagaa atttgttaat gagagtaaaa gaaataaat
1021  gtgtatagct cagtttggat aattggtcaa acaattttt atccagtagt aaaatatgta
1081  accattgtcc cagtaaagaa aaataacaaa agttgtaaaa tgtatattct ccctttata
1141  ttgcatctgc tgttacccag tgaagcttac ctagagcaat gatcttttc acgcatttgc
```

-continued

```
1201 tttattcgaa agaggctttt taaaatgtgc atgtttagaa acaaaatttc ttcatggaaa
1261 tcatatacat tagaaaatca cagtcagatg tttaatcaat ccaaaatgtc cactatttct
1321 tatgtcattc gttagtctac atgtttctaa acatataaat gtgaatttaa tcaattcctt
1381 tcatagttttt ataattctct ggcagttcct tatgatagag tttataaaac agtcctgtgt
1441 aaactgctgg aagttcttcc acagtcaggt caattttgtc aaacccttct ctgtacccat
1501 acagcagcag cctagcaact ctgctggtga tgggagttgt attttcagtc ttcgccaggt
1561 cattgagatc catccactca catcttaagc attcttcctg gcaaaatttt atggtgaatg
1621 aatatggctt taggcggcag atgatataca tatctgactt cccaaaagct ccaggatttg
1681 tgtgctgttg ccgaatactc aggacggacc tgaattctga ttttatacca gtctcttcaa
1741 aaacttctcg aaccgctgtg tctcctacgt aaaaaaagag atgtacaaat caataataat
1801 tacactttta gaaactgtat catcaaagat tttcagttaa agtagcatta tgtaaaggct
1861 caaaacatta ccctaacaaa gtaaagtttt caatacaaat tctttgcctt gtggatatca
1921 agaaatccca aaatattttc ttaccactgt aaattcaaga agcttttgaa atgctgaata
1981 tttctttggc tgctacttgg aggcttatct acctgtacat ttttggggtc agctcttttt
2041 aacttcttgc tgctcttttt cccaaaaggt aaaaatatag attgaaaagt taaaacattt
2101 tgcatggctg cagttccttt gtttcttgag ataagattcc aaagaactta gattcatttc
2161 ttcaacaccg aaatgctgga ggtgtttgat cagtttcaa gaaacttgga atataaataa
2221 ttttataatt caacaaaggt tttcacattt tataaggttg atttttcaat taaatgcaaa
2281 tttgtgtggc aggattttta ttgccattaa catattttg tggctgcttt ttctacacat
2341 ccagatggtc cctctaactg ggctttctct aattttgtga tgttctgtca ttgtctccca
2401 aagtatttag gagaagccct ttaaaaagct gccttcctct accactttgc tggaaagctt
2461 cacaattgtc acagacaaag attttttgttc caatactcgt tttgcctcta tttttcttgt
2521 ttgtcaaata gtaaatgata tttgcccttg cagtaattct actggtgaaa acatgcaaa
2581 gaagaggaag tcacagaaac atgtctcaat tcccatgtgc tgtgactgta gactgtctta
2641 ccatagactc tcttacccat cccctggata tgctcttgtt ttttccctct aatagctatg
2701 gaaagatgca tagaaagagt ataatgtttt aaaacataag gcattcgtct gccattttc
2761 aattacatgc tgacttccct tacaattgag atttgcccat aggttaaaca tggttagaaa
2821 caactgaaag cataaaagaa aaatctaggc cgggtgcagt ggctcatgcc tatattccct
2881 gcactttggg aggccaaagc aggaggatcg cttgagccca ggagttcaag accaacctgg
2941 tgaaaccccg tctctacaaa aaaacacaaa aaatagccag gcatggtggc gtgtacatgt
3001 ggtctcagat acttgggagg ctgaggtggg agggttgatc acttgaggct gagaggtcaa
3061 ggttgcagtg agccataatc gtgccactgc agtccagcct aggcaacaga gtgagacttt
3121 gtctcaaaaa aagagaaatt ttccttaata agaaaagtaa ttttactct gatgtgcaat
3181 acatttgtta ttaaatttat tatttaagat ggtagcacta gtcttaaatt gtataaaata
3241 tcccctaaca tgtttaaatg tccatttttta ttcattatgc tttgaaaaat aattatgggg
3301 aaatacatgt ttgttattaa atttattatt aaagatagta gcactagtct taaatttgat
3361 ataacatctc ctaacttgtt taaatgtcca ttttttattct ttatgtttga aaataaatta
3421 tgggatcct atttagctct tagtaccact aatcaaaagt tcggcatgta gctcatgatc
3481 tatgctgttt ctatgtcgtg gaagcaccgg atggggtag tgagcaaatc tgccctgctc
3541 agcagtcacc atagcagctg actgaaaatc agcactgcct gagtagtttt gatcagttta
3601 acttgaatca ctaactgact gaaaattgaa tgggcaaata agtgcttttg tctccagagt
```

-continued

```
3661 atgcgggaga cccttccacc tcaagatgga tatttcttcc ccaaggattt caagatgaat 3721 tgaaattttt aatcaagata gtgtgcttta ttctgttgta ttttttatta ttttaatata 3781 ctgtaagcca aactgaaata acatttgctg ttttataggt ttgaagaaca taggaaaaac 3841 taagaggttt tgttttatt tttgctgatg aagagatatg tttaaatatg ttgtattgtt 3901 ttgtttagtt acaggacaat aatgaaatgg agtttatatt tgttatttct attttgttat 3961 atttaataat agaattagat tgaaataaaa tataatggga aataatctgc agaatgtggg 4021 ttttcctggt gtttccctct gactctagtg cactgatgat ctctgataag gctcagctgc 4081 tttatagttc tctggctaat gcagcagata ctcttcctgc cagtggtaat acgattttt 4141 aagaaggcag tttgtcaatt ttaatcttgt ggatacctt atactcttag ggtattattt 4201 tatacaaaag ccttgaggat tgcattctat tttctatatg accctcttga tatttaaaaa 4261 acactatgga taacaattct tcatttacct agtattatga agaatgaag gagttcaaac 4321 aaatgtgttt cccagttaac tagggtttac tgtttgagcc aatataaatg tttaactgtt 4381 tgtgatggca gtattcctaa agtacattgc atgttttcct aaatacagag tttaaataat 4441 ttcagtaatt cttagatgat tcagcttcat cattaagaat atcttttgtt ttatgttgag 4501 ttagaaatgc cttcatatag acatagtctt tcagacctct actgtcagtt ttcatttcta 4561 gctgctttca gggttttatg aattttcagg caaagcttta atttatacta agcttaggaa 4621 gtatggctaa tgccaacggc agttttttc ttcttaattc cacatgactg aggcatatat 4681 gatctctggg taggtgagtt gttgtgacaa ccacaagcac ttttttttt tttaaagaaa 4741 aaaaggtagt gaattttaa tcatctggac tttaagaagg attctggagt atacttaggc 4801 ctgaaattat atatatttgg cttggaaatg tgttttcctt caattacatc tacaagtaag 4861 tacagctgaa attcagagga cccataagag ttcacatgaa aaaatcaat ttatttgaaa 4921 aggcaagatg caggagagag gaagccttgc aaacctgcag actgctttt gcccaatata 4981 gattgggtaa ggctgcaaaa cataagctta attagctcac atgctctgct ctcacgtggc 5041 accagtggat agtgtgagag aattaggctg tagaacaaat ggccttctct ttcagcattc 5101 acaccactac aaaatcatct tttatatcaa cagaagaata agcataaact aagcaaaagg 5161 tcaataagta cctgaaacca agattggcta gagatatatc ttaatgcaat ccatttctg 5221 atggattgtt acgagttggc tatataatgt atgtatggta ttttgatttg tgtaaaagtt 5281 ttaaaaatca agctttaagt acatggacat ttttaaataa aatatttaaa gacaatttag 5341 aaaattgcct taatatcatt gttggctaaa tagaataggg gacatgcata ttaaggaaaa 5401 ggtcatggag aaataatatt ggtatcaaac aaatacattg atttgtcatg atacacattg 5461 aatttgatcc aatagtttaa ggaataggta ggaaaatttg gtttctattt ttcgatttcc 5521 tgtaaatcag tgacataaat aattcttagc ttatttata tttccttgtc ttaaatactg 5581 agctcagtaa gttgtgttag gggattattt ctcagttgag actttcttat atgacattt 5641 actatgtttt gacttcctga ctattaaaaa taaatagtag atacaatttt cataaagtga 5701 agaattatat aatcactgct ttataactga ctttattata tttatttcaa agttcattta 5761 aaggctacta ttcatcctct gtgatggaat ggtcaggaat ttgttttctc atagtttaat 5821 tccaacaaca atattagtcg tatccaaaat aaccttaat gctaaacttt actgatgtat 5881 atccaaagct tctcattttc agacagatta atccagaagc agtcataaac agaagaatag 5941 gtggtatgtt cctaatgata ttatttctac taatggaata aactgtaata ttagaaatta 6001 tgctgctaat tatatcagct ctgaggtaat ttctgaaatg ttcagactca gtcggaacaa
```

```
-continued
6061 attggaaaat ttaaattttt attcttagct ataaagcaag aaagtaaaca cattaatttc 6121 ctcaacattt ttaagccaat taaaaatata aaagatacac accaatatct tcttcaggct 6181 ctgacaggcc tcctggaaac ttccacatat ttttcaactg cagtataaag tcagaaaata 6241 aagttaacat aactttcact aacacacaca tatgtagatt tcacaaaatc cacctataat 6301 tggtcaaagt ggttgagaat atattttta gtaattgcat gcaaaatttt tctagcttcc 6361 atcctttctc cctcgtttct tcttttttg ggggagctgg taactgatga aatcttttcc 6421 caccttttct cttcaggaaa tataagtggt tttgtttggt taacgtgata cattctgtat 6481 gaatgaaac attggaggga aacatctact gaatttctgt aatttaaaat attttgctgct 6541 agttaacta tgaacagata gaagaatctt acagatgctg ctataaataa gtagaaaatat 6601 aaatttcat cactaaaata tgctatttta aaatctattt cctatattgt atttctaatca 6661 gatgtatta ctcttattat ttctattgta tgtgttaatg attttatgta aaaatgtaatt 6721 gcttttcat gagtagtatg aataaaattg attagtttgt gttttcttgt ctccc
```

By "microRNA" or "miRNA" or "miR" is meant a small non-coding RNA, which functions in transcriptional and/or post-transcriptional regulation of gene expression.

"Pre-miRNA" or "pre-miR" means a non-coding RNA having a hairpin structure, which is the product of cleavage of a pri-miR by double-stranded RNA-specific ribonuclease.

"Pri-miRNA" or "pri-miR" means a non-coding RNA having a hairpin structure that is a substrate for double-stranded RNA-specific ribonuclease.

By the phrase "miRNA precursor" means a transcript that originates from a genomic DNA and that comprises a non-coding, structured RNA comprising one or more miRNA sequences. For example, in certain embodiments, a miRNA precursor is a pre-miRNA. In certain embodiments, a miRNA precursor is a pri-miRNA.

By "miR-424" is meant human miR-424, and is substantially identical to the nucleic acid sequence of GenBank Accession No. NR_029946, or a fragment thereof. In one embodiment, an miR-424 has at least about 85% nucleic acid sequence identity to SEQ ID NO: 9 and the sequence provided below:

```
 1 cgaggggata cagcagcaat tcatgttttg aagtgttcta aatggttcaa aacgtgaggc 61 gctgctatac cccctcgtgg ggaaggtaga aggtgggg
```

By "miR-503" is meant human miR-503, and is substantially identical to the nucleic acid sequence of GenBank Accession No. NR_030228, or a fragment thereof. In one embodiment, an miR 503 has at least about 85% nucleic acid sequence identity to SEQ ID NO: 10 and the sequence provided below:

```
 1 tgccctagca gcgggaacag ttctgcagtg agcgatcggt gctctggggt attgtttccg 61 ctgccagggt a
```

By "pulmonary arterial hypertension" or "pulmonary hypertension" is meant a condition, disorder or disease characterized by abnormally high blood pressure in the arteries of the lungs with a markedly decreased exercise tolerance and increased risk of heart failure. A pressure of greater than 25 mm Hg at rest is abnormally high and is classified as pulmonary hypertension. By "disease" is meant any condition or disorder that damages or interferes with the normal function of a cell, tissue, or organ. Examples of diseases include pulmonary arterial hypertension.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "biomarker" or "marker" is meant any protein or polynucleotide having an alteration in expression level or activity that is associated with a disease or disorder.

By "complementary sequence" or "complement" is meant a nucleic acid base sequence that can form a double-stranded structure by matching base pairs to another polynucleotide sequence. Base pairing occurs through the formation of hydrogen bonds, which may be Watson-Crick, Hoogsteen or reversed Hoogsteen hydrogen bonding, between complementary nucleobases. For example, adenine and thymine are complementary nucleobases that pair through the formation of hydrogen bonds.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the biomarker to be detected.

The phrase "differentially present" refers to differences in the quantity and/or the frequency of a biomarker present in a sample taken from subjects having a disease as compared to a control subject. A biomarker can be differentially present in terms of quantity, frequency or both. A polypeptide or polynucleotide is differentially present between two samples if the amount of the polypeptide or polynucleotide in one sample is statistically significantly different from the amount of the polypeptide or polynucleotide in the other sample, such as a reference. Alternatively or additionally, a polypeptide or polynucleotide is differentially present between two sets of samples if the frequency of detecting the polypeptide or polynucleotide in diseased subjects' samples is statistically significantly higher or lower than in the control samples. A biomarker that is present in one sample, but undetectable in another sample is differentially present.

By "effective amount" is meant the amount required to reduce or improve at least one symptom of a disease relative to an untreated patient. The effective amount of active compound(s) used to practice the present invention for therapeutic treatment of a disease varies depending upon the manner of administration, the age, body weight, and general health of the subject.

The term "expression" as used herein is defined as the transcription and/or translation of a particular nucleotide sequence driven by its promoter.

By "fragment" is meant a portion of a polynucleotide or nucleic acid molecule. This portion contains, preferably, at least 10%, 20%, 30%, 40%, 50%, 60%, 70%, 80%, or 90% of the entire length of the reference nucleic acids. A fragment may contain 10, 20, 30, 40, 50, 60, 70, 80, 90, or 100, 200, 300, 400, 500, 600, 700, 800, 900, 1000, 1500, 2000 or 2500 (and any integer value in between) nucleotides. The fragment, as applied to a nucleic acid molecule, refers to a subsequence of a larger nucleic acid. A "fragment" of a nucleic acid molecule may be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

As used herein, the term "inhibit" is meant to refer to a decrease in biological state. For example, the term "inhibit" may be construed to refer to the ability to negatively regulate the expression, stability or activity of a protein, including but not limited to transcription of a protein mRNA, stability of a protein mRNA, translation of a protein mRNA, stability of a protein polypeptide, a protein post-translational modifications, a protein activity, a protein signaling pathway or any combination thereof.

Further, the term "inhibit" may be construed to refer to the ability to negatively regulate the expression, stability or activity of a miRNA, wherein such inhibition of the miRNA may affect modulation of a gene, protein mRNA, stability of a protein mRNA, translation of a protein mRNA, stability of a protein, a protein post-translational modifications, and/or a protein activity.

"Instructional material," as that term is used herein, includes a publication, a recording, a diagram, or any other medium of expression that may be used to communicate the usefulness of the compounds of the invention. In some instances, the instructional material may be part of a kit useful for effecting alleviating or treating the various diseases or disorders recited herein. Optionally, or alternately, the instructional material may describe one or more methods of alleviating the diseases or disorders in a cell or a tissue of a mammal. The instructional material of the kit may, for example, be affixed to a container that contains the compounds of the invention or be shipped together with a container that contains the compounds. Alternatively, the instructional material may be shipped separately from the container with the intention that the recipient uses the instructional material and the compound cooperatively. For example, the instructional material is for use of a kit; instructions for use of the compound; or instructions for use of a formulation of the compound.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which may be hydrolyzed into the monomeric "nucleotides." The monomeric nucleotides may be hydrolyzed into nucleosides. As used herein polynucleotides include, but are not limited to, all nucleic acid sequences that are obtained by any means available in the art, including, without limitation, recombinant means, i.e., the cloning of nucleic acid sequences from a recombinant library or a cell genome, using ordinary cloning technology and PCR™, and the like, and by synthetic means. The following abbreviations for the commonly occurring nucleic acid bases are used. "A" refers to adenosine, "C" refers to cytosine, "G" refers to guanosine, "T" refers to thymidine, and "U" refers to uridine. The term "RNA" as used herein is defined as ribonucleic acid. The term "recombinant DNA" as used herein is defined as DNA produced by joining pieces of DNA from different sources.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

As used herein, the terms "prevent," "preventing," "prevention," and the like refer to reducing the probability of developing a disorder or condition in a subject, who does not have, but is at risk of or susceptible to developing a disorder or condition.

By "reduces" or "decreases" is meant a negative alteration of at least 10%, 25%, 50%, 75%, or 100%.

By "reference" is meant a standard or control. A "reference" is also a defined standard or control used as a basis for comparison.

As used herein, "sample" or "biological sample" refers to anything, which may contain the biomarker (e.g., polypeptide, polynucleotide, or fragment thereof) for which a biomarker assay is desired. The sample may be a biological sample, such as a biological fluid or a biological tissue. In one embodiment, a biological sample is a tissue sample including pulmonary vascular cells. Such a sample may include diverse cells, proteins, and genetic material. Examples of biological tissues also include organs, tumors, lymph nodes, arteries and individual cell(s). Examples of biological fluids include urine, blood, plasma, serum, saliva, semen, stool, sputum, cerebral spinal fluid, tears, mucus, amniotic fluid or the like.

As used herein, the term "sensitivity" is the percentage of biomarker-detected subjects with a particular disease.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

A "subject" or "patient," as used therein, may be a human or non-human mammal. Non-human mammals include, for example, livestock and pets, such as ovine, bovine, porcine, canine, feline and murine mammals. Preferably, the subject is human.

As used herein, the terms "treat," treating," "treatment," and the like refer to reducing or improving a disorder and/or symptom associated therewith. It will be appreciated that, although not precluded, treating a disorder or condition does not require that the disorder, condition or symptoms associated therewith be completely ameliorated or eliminated.

A "vector" is a composition of matter that comprises an isolated nucleic acid and that may be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression may be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

MicroRNAs in PAH

Pulmonary arterial hypertension (PAH) is a vascular disease of the pulmonary vasculature that primarily targets the small pulmonary arteries. The hallmark of terminal PAH is aberrant proliferation of both the pulmonary artery endothelial cells and pulmonary artery smooth muscle cells (PAECs and PASMCs), pulmonary vascular cells, ultimately culminating in the formation of lumen obliterating plexiform lesions. Research into the molecular events originating in pulmonary endothelial cells that contribute to the PAH have found that levels of apelin and fibroblast growth factor 2 (FGF2) are increased in PAH pulmonary endothelial cells.

MicroRNAs (miRNAs), small non-coding RNAs that downregulate target gene expression by inhibiting target messenger RNA stability and translatability, target cognitive sites in the 3'-untranslated regions (3'UTRs). As described herein, the discovery that miR-424 and miR-503 target the FGF2 3' UTR and are significantly downregulated in apelin-apelin receptor knockdown models provides an important advance in the treatment of PAH. By targeting fibroblast growth factor 2 to inhibit its expression, miR-424 and miR-503 play a role in FGF2 regulation.

Compositions

The present invention provides compositions of microRNAs. The present invention further provides compositions that are useful for treating pulmonary arterial hypertension or symptoms thereof by reducing proliferation of pulmonary vascular cells. Thus, one embodiment is a composition that includes an inhibitor of fibroblast growth factor 2 (FGF2) expression including at least one of: a mature sequence of miR-424 or miR-503; a pri-miRNA of miR-424 or miR-503; a pre-miRNA of miR-424 or miR-503; and the complement thereof.

As used herein, treatment with miRNAs refers to administration or in situ generation of oligonucleotide molecules or their derivatives which specifically hybridize (e.g., bind) under cellular conditions with the cellular mRNA and/or genomic DNA, thereby inhibiting transcription and/or translation of that gene. The binding may be by conventional base pair complementarity, or, for example, in the case of binding to DNA duplexes, through specific interactions in the major groove of the double helix. In general, treatment with miRNAs refers to the range of techniques generally employed in the art, and includes any therapy which relies on specific binding to oligonucleotide sequences.

In particular embodiments, a composition is disclosed that includes an inhibitor of fibroblast growth factor 2 (FGF2) expression, where the inhibitor is at least one of: a mature sequence of miR-424 or miR-503; a pri-miRNA of miR-424 or miR-503; a pre-miRNA of miR-424 or miR-503; and the complement thereof. In a more particular embodiment, the mature sequence includes a polynucleotide selected from the group consisting of: a nucleotide sequence as shown in SEQ ID NO: 9 or SEQ ID NO: 10; a nucleotide sequence consisting of 30 to 120 nucleotides which has an identity of at least 85% to the nucleotide sequence as shown in SEQ ID NO: 9 or SEQ ID NO: 10; or the complement thereof.

In some embodiments, it is desirable to use one or more miRNA, the complement of the primary miRNA (pri-miRNA) transcript, or the complement of the mature miRNA to inhibit fibroblast growth factor 2 (FGF2) expression. In similar embodiments, the complement of the pri-miRNA may be used. For example, in an exemplary embodiment, a composition includes an inhibitor of fibroblast growth factor 2 (FGF2) expression and the inhibitor is a mature sequence of miR-424 or miR-503; a pri-miRNA of miR-424 or miR-503; a pre-miRNA of miR-424 or miR-503; and the complement thereof. One of skill in the art will appreciate that a complementary sequence need not be an exact complement, and that it is within the scope of the present invention to employ miRNA fragments, fragments of complement sequences, or sequences which are similar to the miRNA or its complement. As one example, a composition includes an inhibitor of fibroblast growth factor 2 (FGF2) expression and the inhibitor is miR-424 or miR-503 complement, a fragment of the -424 or miR-503 complement, or, e.g., a sequence which is 80%, 85%, 90%, 95%, or 99% identical to the complement of miR-424 or miR-503.

The miRNAs may be provided in expression vectors as compositions of the invention. The expression vectors express the miRNA under the control of highly cell-type specific promoters and amplification promoter elements, can be administered to any mammal, including a human. Many such vectors are commercially available, and other suitable vectors can be readily prepared and obvious to the skilled artisan. The exact design of the vector depends on such factors as the choice of the host cell to be transformed and/or the type of protein desired to be expressed. Suitable vectors can be produced by ligating the desired construct into a plasmid or viral vector suitable for expression in eukaryotic cells (see, for example, Broach, et al., Experimental Manipulation of Gene Expression, ed. M. Inouye (Academic Press, 1983) p. 83; Molecular Cloning: A Laboratory Manual, 4th Ed., ed. Sambrook, et al. (Cold Spring Harbor Laboratory Press, 2012) Chapters 14 through 19, the entireties of which are incorporated by reference herein).

Transducing viral (e.g., retroviral, adenoviral, lentiviral and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding an inhibitory nucleic acid molecule can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77 S-83S, 1995). Examples of vectors that can be used include, but are not limited to, plasmids such as pBR322, pUC, or ColE1; adenovirus; Sindbis virus; simian virus 40; cytomegalovirus; and retroviral vectors such as murine sarcoma virus, mouse mammary tumor virus, Moloney murine leukemia virus, and Rous sarcoma virus. Bacterial vectors can be used, such as *Salmonella* ssp., *Yersinia enterocolitica*, *Shigella* spp., *Vibrio cholerae*, *Mycobacterium* strain BCG, and *Listeria monocytogenes*. Minichromosomes such as MC and MCI, bacteriophages, cosmids (plasmids into which phage lambda cos sites have been inserted) and replicons (genetic elements that are capable of independent extrachromosomal replication).

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Additionally, the non-viral based delivery can be nano-based or aerosolized.

Biomarkers

Analysis of apelin downregulation in pulmonary endothelial cells lead to the discovery of multiple biomarkers alternatively expressed in pulmonary arterial hypertension (PAH). Biomarkers present in a sample can be used for identifying a subject in need of therapeutic intervention to reduce or improve a symptom of pulmonary arterial hypertension, reducing proliferation of pulmonary vascular cells, and/or treating pulmonary arterial hypertension in a subject in need thereof. In particular, biomarkers, such as fibroblast growth factor 2 (FGF2), apelin (APLN), miR-424, and miR-503 polynucleotides, are particularly relevant. A second major class of biomarkers are fibroblast growth factor receptor 1 (FGFR1), apelin receptor (APLNR), argonaute 2 (Ago2), miR-15a, miR-16, miR-195 and miR-497 polynucleotides.

Fibroblast growth factor 2 (FGF2) is a member of the fibroblast growth factor (FGF) family. FGF family members bind heparin and possess broad mitogenic and angiogenic activities. FGF2 has been implicated in diverse biological processes, such as limb and nervous system development, wound healing, and tumor growth. FGF2 has also been shown to be markedly overproduced by pulmonary endothelial cells in PAH and contributes significantly to smooth muscle hyperplasia and disease progression. Excessive FGF2 expression in malignancy exerts pathologic effects on tumor cells by paracrine and autocrine mechanisms. Thus, FGF2 expression levels in pulmonary vascular cells are important due to the association with diseased states.

Fibroblast growth factor receptor 1 (FGFR1) is the receptor for FGF2 and consists of an extracellular region, composed of three immunoglobulin-like domains, a single hydrophobic membrane-spanning segment and a cytoplasmic tyrosine kinase domain. The extracellular portion of the protein interacts with fibroblast growth factors, setting in motion a cascade of downstream signals, ultimately influencing mitogenesis and differentiation. FGFR1 have been associated with Pfeiffer syndrome, Jackson-Weiss syndrome, Antley-Bixler syndrome, osteoglophonic dysplasia, and autosomal dominant Kallmann syndrome 2 and chromosomal aberrations involving FGFR1 are associated with stem cell myeloproliferative disorder and stem cell leukemia lymphoma syndrome. FGFR1 is included as a biomarker for PAH because of its role in inducing mitogenesis and its associated with proliferative disorders.

Apelin (APLN) and its G-protein coupled apelin receptor (APLNR) are expressed in several tissues. Apelin is localized in vascular endothelial cells while the APLNR is localized in both endothelial and smooth muscle cells in vessels and in the heart. Apelin is regulated by hypoxia inducible factor-1α and bone morphogenetic protein receptor-2. Patients with PAH have lower levels of plasma-apelin, and decreased apelin expression in pulmonary endothelial cells. Apelin also plays a role in angiogenesis and regulates endothelial and smooth muscle cell apoptosis and proliferation. Thus, APLN and APLNR are also biomarkers for PAH.

As disclosed herein, the discovery of microRNAs role in PAH also provides a multiplex method of identification and treatment. This is an important advance given that there are no cures for PAH despite pharmacological therapy. In one embodiment, a biomarker panel includes but is not limited to any one or more of fibroblast growth factor 2 (FGF2), apelin (APLN), miR-424, and miR-503, fibroblast growth factor receptor 1 (FGFR1), apelin receptor (APLNR), argonaute 2 (Ago2), miR-15a, miR-16, miR-195 and miR-497 polynucleotides. In another embodiment, a biomarker panel includes but is not limited to any one or more of FGF2, APLN, FGFR1, APLNR, and Ago2 polypeptides.

To test whether levels of one or more of these biomarkers are indicative of pulmonary arterial hypertension, the levels of multiple biomarkers in cells of the lungs of PAH patients and control pulmonary vascular cells from unused donor lungs were measured, a correlation with multiple biomarkers (e.g. FGF2, APLN, miR-424, and miR-503 polynucleotides and/or FGF2, APLN, FGFR1, APLNR, and Ago2 polypeptides) was observed as disclosed elsewhere herein. Thus, in some embodiments, a biomarker panel includes, but is not limited to, fibroblast growth factor 2 (FGF2), apelin (APLN), miR-424, and miR-503 polynucleotides and/or FGF2, APLN, FGFR1, APLNR, and Ago2 polypeptides that specifically bind the biomarkers. These polynucleotide biomarkers can be used alone, or in combination with any one or all of the other polynucleotide biomarkers delineated herein (e.g., FGFR1, APLNR, Ago2, miR-15a, miR-16, miR-195 and miR-497 polynucleotides) in tests to determine expression levels.

Also provided is a biomarker panel to detect or identify the presence of biomarkers in a sample. The panel includes such biomarkers as fibroblast growth factor 2 (FGF2), apelin (APLN), miR-424 and miR-503, fibroblast growth factor receptor 1 (FGFR1), apelin receptor (APLNR), argonaute 2 (Ago2), miR-15a, miR-16, miR-195 and miR-497 polynucleotides and/or FGF2, APLN, FGFR1, APLNR, and Ago2 polypeptides that specifically bind the biomarkers.

Clinical Indicators

The present invention provides biomarkers whose expression level is altered in a biological sample derived from a subject with pulmonary arterial hypertension (PAH). Such biomarkers, which include inhibitors of FGF2, may be used individually or in combination with clinical indicators or measurements or symptoms, such as blood pressure, stress testing for chest pain, fatigue or lethargy, heart rate and swelling and/or edema of the extremities, to provide a method of diagnosing and/or monitoring PAH or a propensity to develop PAH. In some embodiments, the clinical measurements of the subject are compared to the measurements present in a reference (e.g., a healthy control subject). In particular embodiments, the subject's clinical measurements, such as blood pressure, stress test, and heart rate, are increased relative to measurements obtained from a reference. The subject's clinical status can also include increased elevation of blood pressure and exercise heart rate relative to the reference (e.g., relative to exercise heart rate in a healthy control subject without PAH).

Diagnostics

Samples from subjects suffering from PAH have altered levels of particular biomarkers. In particular, subjects are identified as having PAH, or a propensity to develop such a condition by detecting an alteration in the levels of one or more of FGF2, APLN, miR-424, and miR-503 polynucleotides and/or FGF2, APLN, FGFR1, APLNR, and Ago2 polypeptides in a sample obtained from the subject relative the level of such biomarkers in a reference. Alterations in the levels of such biomarkers (or any other marker delineated herein) are detected using standard methods. In another approach, diagnostic methods are used to assess the level of FGF2, APLN, miR-424, and miR-503 polynucleotides and/or FGF2, APLN, FGFR1, APLNR, and Ago2 polypeptides in a biological sample relative to a reference (e.g., the level of such polynucleotides or polypeptides present in a corresponding control sample). In one embodiment, the levels of FGF2, APLN, miR-424, and miR-503 polynucleotides and/or FGF2, APLN, FGFR1, APLNR, and Ago2 polypeptides are detected using a probe that specifically binds the biomarker of interest.

In general, the measurement of the level of a biomarker in a subject sample is compared with a reference. A difference between the level of a biomarker and the reference distinguishes between PAH or a propensity to develop PAH and the absence of such a condition. The skilled artisan will appreciate that the particular amount used can be adjusted to increase sensitivity or specificity of the assay. In general, any significant increase (e.g., at least about 10%, 15%, 30%, 50%, 60%, 75%, 80%, or 90%) in the level of a polynucleotide or polypeptide biomarker in the subject sample relative to a reference may be used to diagnose PAH or a propensity to develop such a condition. In one embodiment, the reference is the level of the polynucleotide or polypeptide biomarker present in a control sample obtained from a patient that does not have PAH or a propensity to develop such a condition. In another embodiment, the reference is a baseline level of a polynucleotide or polypeptide biomarker present in a biologic sample derived from a patient prior to, during, or after treatment for PAH. In yet another embodiment, the reference is a standardized curve.

In another approach, the diagnostic methods of the invention are used to assess the levels of FGF2, APLN, miR-424, and miR-503 polynucleotides and/or FGF2, APLN, FGFR1, APLNR, and Ago2 polypeptides in a biological sample relative to a reference (e.g., the expression level of such biomarkers present in a corresponding control sample). In one embodiment, the levels of FGF2, APLN, miR-424, and miR-503 polynucleotides and/or FGF2, APLN, FGFR1, APLNR, and Ago2 polypeptides are detected using a probe that specifically binds the biomarker. Exemplary probes that specifically bind such biomarkers are described herein. Methods for measuring or detecting a probe-biomarker complex include any suitable method and are readily known in the art. Practice of the invention can be achieved with one or a combination of methods that can detect and, preferably, quantify the markers. These methods include, without limitation, hybridization-based methods, including those employed in biochip arrays, mass spectrometry (e.g., laser desorption/ionization mass spectrometry), fluorescence (e.g. sandwich immunoassay), surface plasmon resonance, ellipsometry and atomic force microscopy. Levels of biomarkers (e.g., FGF2, APLN, miR-424, and miR-503 polynucleotides and/or FGF2, APLN, FGFR1, APLNR, and Ago2 polypeptides) are compared using procedures well known in the art, such as RT-PCR, Northern blotting, Western blotting, flow cytometry, immunocytochemistry, binding to magnetic and/or antibody-coated beads, in situ hybridization, fluorescence in situ hybridization (FISH), flow chamber adhesion assay, ELISA, microarray analysis, or colorimetric assays. Methods may further include, one or more of electrospray ionization mass spectrometry (ESI-MS), ESI-MS/MS, ESI-MS/(MS)$^n$, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS)$_n$, quadrupole mass spectrometry, fourier transform mass spectrometry (FTMS), and ion trap mass spectrometry, where n is an integer greater than zero.

Accordingly, a biomarker profile may be obtained from a subject sample and compared to a reference biomarker profile obtained from a reference population, so that it is possible to classify the subject as belonging to or not belonging to the reference population. The correlation may take into account the presence or absence of the biomarkers in a test sample and the frequency of detection of the same biomarkers in a control. The correlation may take into account both of such factors to facilitate a diagnosis of PAH.

Any marker, individually, is useful in aiding in the diagnosis of PAH status. First, the selected biomarker is detected in a subject sample using the methods described herein (e.g. RT-PCR). Then, the result is compared with a control that distinguishes PAH status from non-PAH status. As is well understood in the art, the techniques can be adjusted to increase sensitivity or specificity of the diagnostic assay depending on the preference of the diagnostician.

While individual biomarkers are useful diagnostic biomarkers, in some instances, a combination of biomarkers provides greater predictive value than single biomarkers alone. The detection of a plurality of biomarkers (or absence thereof, as the case may be) in a sample can increase the percentage of true positive and true negative diagnoses and decrease the percentage of false positive or false negative diagnoses. Thus, one method provides for the measurement of more than one marker.

Microarrays

The methods of the invention may also be used in the context of microarray-based assays that provide for the high-throughput analysis of biomarkers, such as FGF2, APLN, miR-424, miR-503, FGFR1, APLNR, Ago2, miR-15a, miR-16, miR-195 and miR-497. The biomarkers are useful as hybridizable array elements in such a microarray. The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference.

Biomarker levels present in a biological sample taken from a patient, such as a tissue (e.g., a tissue including pulmonary vascular cells) may be measured using a probe or other molecule derived from a nucleic acid, or chemical library. Hybridization conditions (e.g., temperature, pH, protein concentration, and ionic strength) are optimized to promote specific interactions. Such conditions are known to the skilled artisan and are described, for example, in Harlow, E. and Lane, D., Using Antibodies: A Laboratory Manual. 1998, New York: Cold Spring Harbor Laboratories. After removal of non-specific probes, specifically bound probes are detected, for example, by fluorescence, enzyme activity (e.g., an enzyme-linked calorimetric assay), direct immunoassay, radiometric assay, or any other suitable detectable method known to the skilled artisan.

Monitoring

Methods of monitoring subjects receiving therapeutic intervention to reduce or improve a symptom of pulmonary arterial hypertension are also useful in managing treatment. Provided are methods where the biomarkers (or specific combinations of biomarkers) are measured. In some cases, the biomarkers are measured before and again after subject management or treatment. In these cases, the methods are used to monitor the status of pulmonary arterial hypertension, or a propensity to develop such conditions, e.g., proliferation of pulmonary artery vascular cells.

For example, biomarkers (e.g., FGF2, APLN, miR-424, and miR-503) can be used to monitor a subject's response to certain treatments of PAH. The level of a marker delineated herein may be measured before treatment, during treatment, or following the conclusion of a treatment regimen. In some embodiments, multiple measurements (e.g., 2, 3, 4, 5) are made at one or more of those times. Measurements are made, for example, using a fluorescent, enzyme activity (e.g., an enzyme-linked calorimetric assay), direct immunoassay, radiometric assay, or other standard method to determine the expression profile of one or more biomarkers. If desired, levels of the biomarkers are compared to reference levels of the biomarkers to determine if alterations in the biomarkers are present. Such monitoring may be useful, for example, in assessing the efficacy of a particular treatment in a patient. Therapeutics that normalize the expression of any of FGF2, APLN, miR-424, and miR-503 biomarkers are taken as particularly useful.

Kits

In one aspect, kits for diagnosing, detecting and/or monitoring PAH, wherein the kits can be used to detect the biomarkers described herein. For example, the kits can be used to detect any one or more of the biomarkers potentially differentially present in samples of test subjects vs. normal subjects (e.g., FGF2, APLN, miR-424, and miR-503 polynucleotides and/or FGF2, APLN, FGFR1, APLNR, and Ago2 polypeptides) or control proteins. If desired a kit includes any one or more of the following: capture molecules that bind FGF2, APLN, miR-424, and miR-503 polynucleotides and/or FGF2, APLN, FGFR1, APLNR, and Ago2 polypeptides and other biomarkers. The kits have many used in the context of the present invention. For example, the kits can be used to differentiate if a subject has PAH, or has a propensity to develop PAH, thus aiding PAH diagnosis. The kits can also be used to identify agents that modulate expression of one or more of the herein-described biomarkers in in vitro or in vivo animal models for PAH.

Methods of Use

The methods herein include a method of identifying a subject in need of therapeutic intervention to reduce or improve a symptom of pulmonary arterial hypertension, a method of reducing proliferation of pulmonary vascular cells in a subject in need thereof, and a method of treating pulmonary arterial hypertension in a subject in need thereof. Identifying a subject in need of such treatment can be in the judgment of a subject or a health care professional and can be subjective (e.g. opinion) or objective (e.g. measurable by a test or diagnostic method). Identification of those subjects "at risk" can be made by any objective or subjective determination by a diagnostic test or opinion of a subject or health care provider (e.g., genetic test, enzyme or protein marker, Marker (as defined herein), family history, and the like). In particular, detecting an alteration in the level of a identifying the subject as in need of therapeutic intervention to prevent or treat pulmonary arterial hypertension.

The therapeutic methods (which include prophylactic treatment) to reduce proliferation of pulmonary vascular cells or to treat pulmonary arterial hypertension in a subject include administration of a therapeutically effective amount of an inhibitor of fibroblast growth factor 2 (FGF2) expression including at least one of: a mature sequence of miR-424 or miR-503; a pri-miRNA of miR-424 or miR-503; a pre-miRNA of miR-424 or miR-503; and the complement thereof, to a subject (e.g., animal, human) in need thereof, including a mammal, particularly a human. Such treatment will be suitably administered to subjects, particularly humans, suffering from, having, susceptible to, or at risk for pulmonary arterial hypertension or a symptom thereof.

Pharmaceutical Compositions and Formulations

The invention also encompasses the use of a pharmaceutical composition of the invention to practice the methods of the invention. Such a pharmaceutical composition may be provided in a form suitable for administration to a subject, and may be comprise one or more pharmaceutically acceptable carriers, one or more additional ingredients, or some combination of these. The at least one composition of the invention may comprise a physiologically acceptable salt, such as a compound contemplated within the invention in combination with a physiologically acceptable cation or anion, as is well known in the art.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment, the compositions of the invention are formulated using one or more pharmaceutically acceptable excipients or carriers. In one embodiment, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

Administration/Dosing

In the clinical settings, delivery systems for the therapeutic composition can be introduced into a patient by any of a number of methods, each of which is familiar in the art. For instance, a pharmaceutical composition can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen, et al. PNAS 91: 3054-3057 (1994)).

In one exemplary implementation, the pharmaceutical composition is directly injected into pulmonary arterial tissue. U.S. Ser. No. 10/914,829 describes a protocol for direct injection. Direct injection or application of a viral vector into pulmonary arterial tissue can restrict expression of the miRNAs to pulmonary arterial tissue (Gutzman et al, Circ. Res. (1993); French et al., Circulation. (1994)). The preparation may also be provided to cells ex vivo. Cells containing the miRNAs (e.g., miR-424 and/or miR-503) are then administered to the patient.

The regimen of administration may affect what constitutes an effective amount. The therapeutic formulations may be administered to the patient either prior to or after the manifestation of symptoms associated with the disease or condition. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or condition in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

Routes of Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Results of the experiments disclosed herein are now described.

Impaired APLN Signaling Leads to Increased FGF2 Expression.

Figure 1:
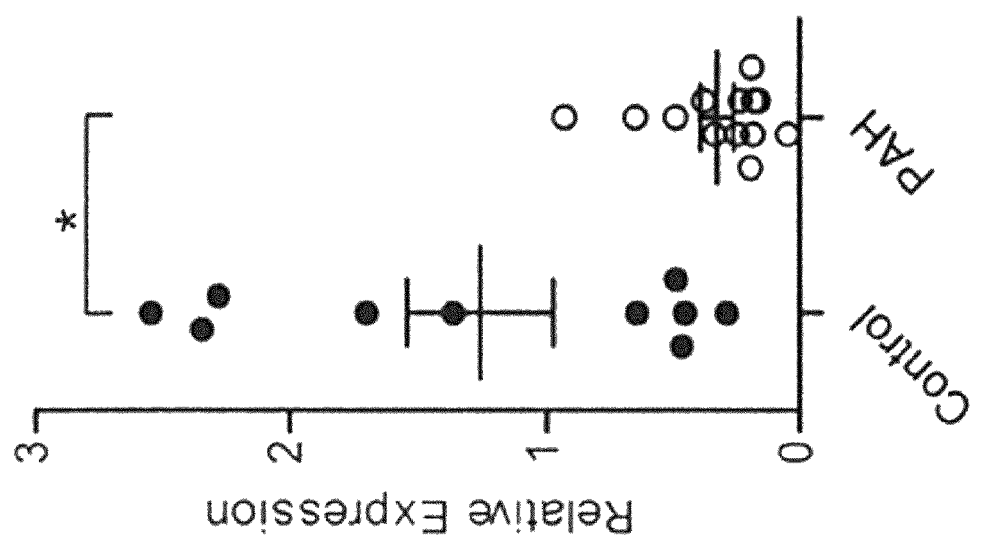
FIG. 1 is a dot plot showing APLN mRNA expression in PAECs of controls and subjects with PAH. *$P<0.005$ compared to controls by unpaired two-tailed Student's t test. Error bars, s.e.m.
Figure 2:
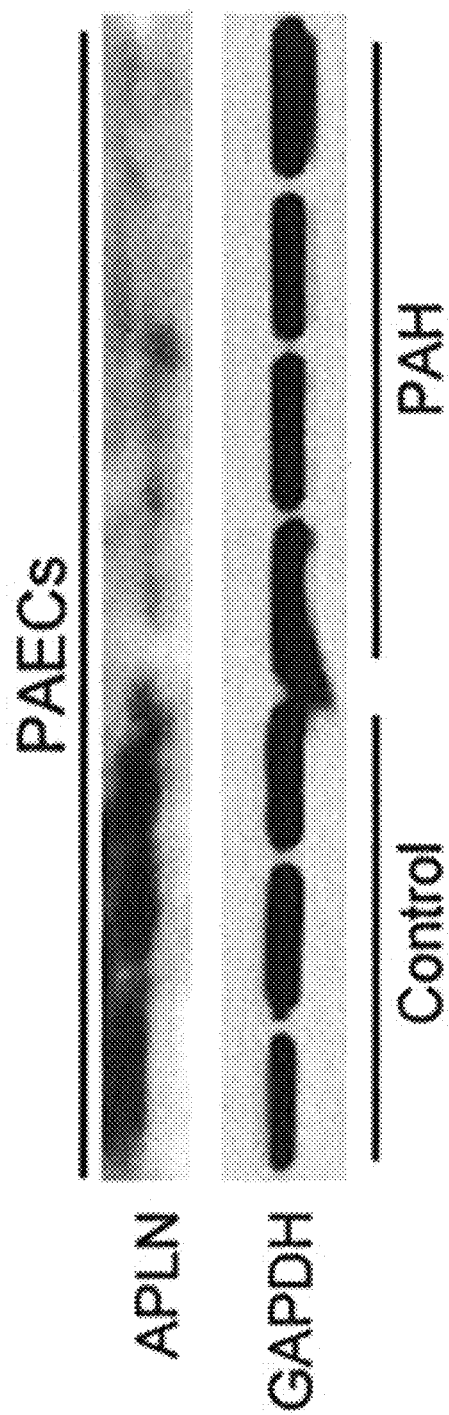
FIG. 2 is a blot showing APLN protein expression in PAECs of controls and subjects with PAH. GAPDH, glyceraldehyde-3-phosphate dehydrogenase.
Figure 3:
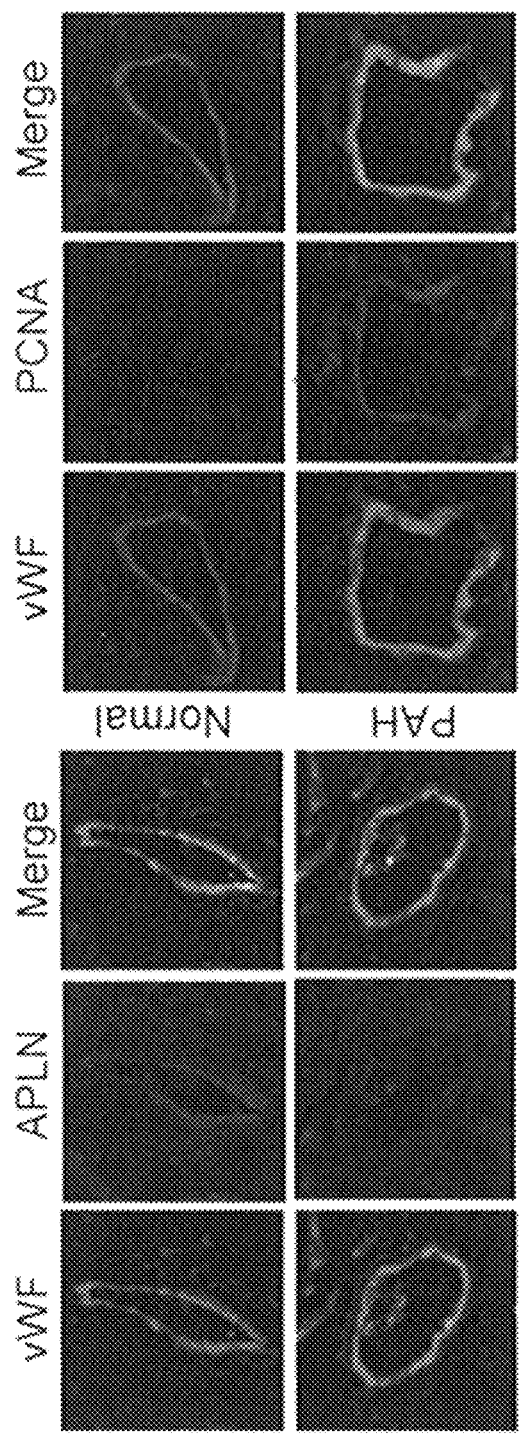
FIG. 3 shows immunofluorescence staining showing APLN expression and PCNA staining in the lung endothelium of a control subject and a subject with PAH. vWF and APLN and PCNA staining are shown. Scale bars, 50 µm.

Previous studies have demonstrated that APLN expression is significantly reduced in the serum and pulmonary microvascular endothelium of subjects with PAH, as well as in the lungs of rats with monocrotaline (MCT)-induced pulmonary hypertension. In line with these data, APLN expression was significantly decreased in multiple PAEC lines derived from the lungs of subjects with idiopathic or familial PAH (IPAH or FPAH, respectively, referred to generally as PAH herein) compared to control PAECs from unused, explanted normal donor lungs (FIGS. 1-3). No significant difference in the mRNA levels of APLNR was found, which was predominantly expressed by the microvascular endothelial layers of the pulmonary vessels, between the two groups (FIGS. 45A-B). Increased proliferating cellular nuclear antigen (PCNA) staining in the endothelium of PAH microvasculature was found, as well as increased proliferative responses of PAH PAECs (FIGS. 3 and 46). Whereas augmentation of APLN signaling in normal PAECs led to an increase in PAEC proliferation as previously described, augmentation of APLN signaling in PAH PAECs had the reverse effect and inhibited proliferation (FIGS. 47A-C and FIGS. 48A-B).

Figure 4:
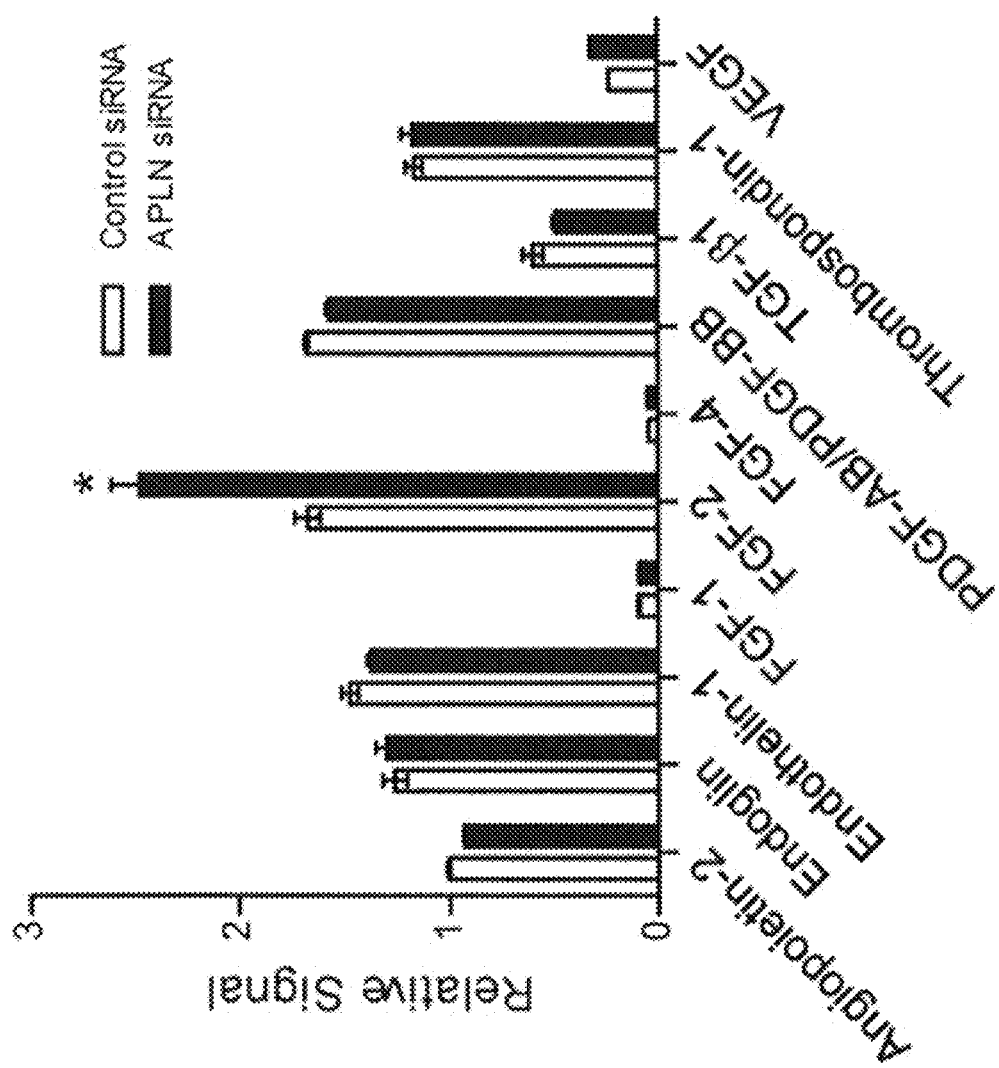
FIG. 4 is a bar graph showing cytokine array data and relative changes in cytokine expression in response to APLN knockdown by siRNA in PAECs. *P<0.01 compared to control siRNA by unpaired two-tailed Student's t test. Error bars, s.e.m.
Figure 6B:
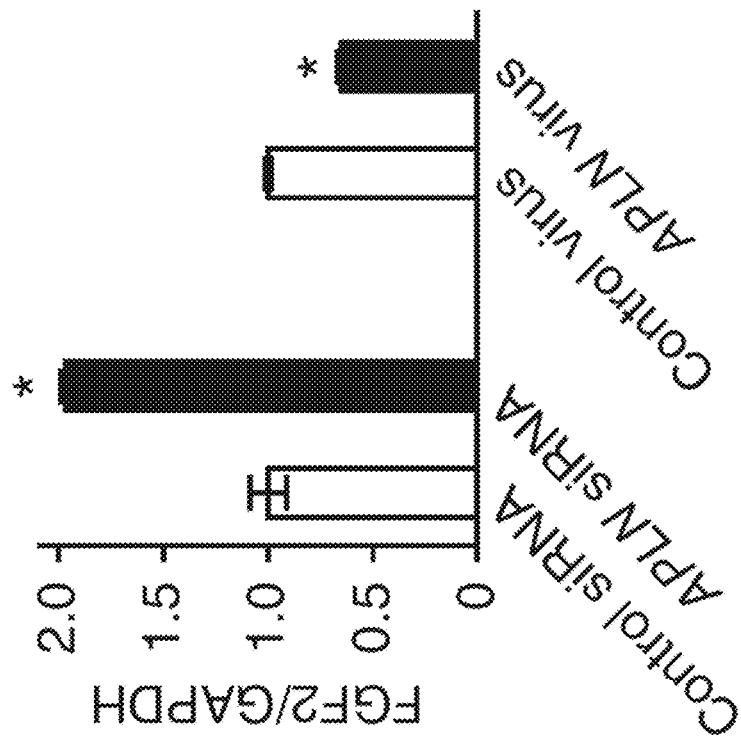
FIG. 6B is a bar graph showing expression of FGF2 protein in response to either APLN knockdown by siRNA or lentiviral APLN overexpression in PAECs. *P<0.01 compared to control siRNA or control lentivirus by unpaired two-tailed Student's t test. Error bars, s.e.m.
Figure 6A:
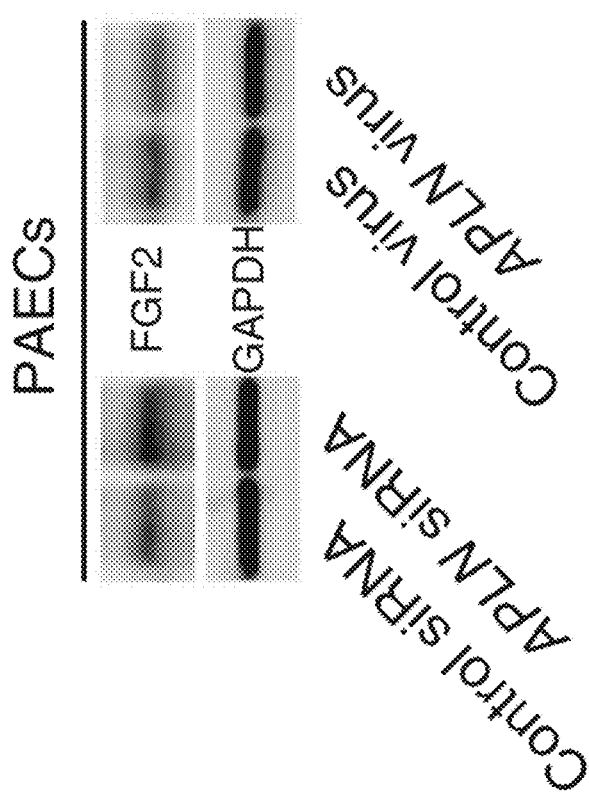
FIG. 6A is a blot and a bar graph showing expression of FGF2 protein in response to either APLN knockdown by siRNA or lentiviral APLN overexpression in PAECs. *P<0.01 compared to control siRNA or control lentivirus by unpaired two-tailed Student's t test. Error bars, s.e.m.

Given these findings, downregulation of APLN in PAH PAECs might contribute to the aberrant activation of a secondary signaling cascade, leading to increased proliferation of PAECs. The expression of an array of angiogenic growth factors was evaluated in normal PAECs subjected to APLN knockdown (FIGS. 49A-E) and found that FGF2 expression was significantly increased (FIG. 4). An inverse correlation between APLN and FGF2 mRNA levels was found in PAECs from controls and subjects with PAH (FIG. 5). This relationship was confirmed by showing a robust increase in FGF2 expression with APLN knockdown and reciprocally decreased FGF2 expression with APLN overexpression (FIGS. 6A-B). Moreover, significantly increased FGF2 expression was found in both total lung homogenates and isolated mouse lung endothelial cells (LECs) of Apln-null mice 18 compared to wild-type mice (FIGS. 7A-C).

FGF2 is Regulated by miRNAs Downstream of APLN Signaling.

Figure 8B:
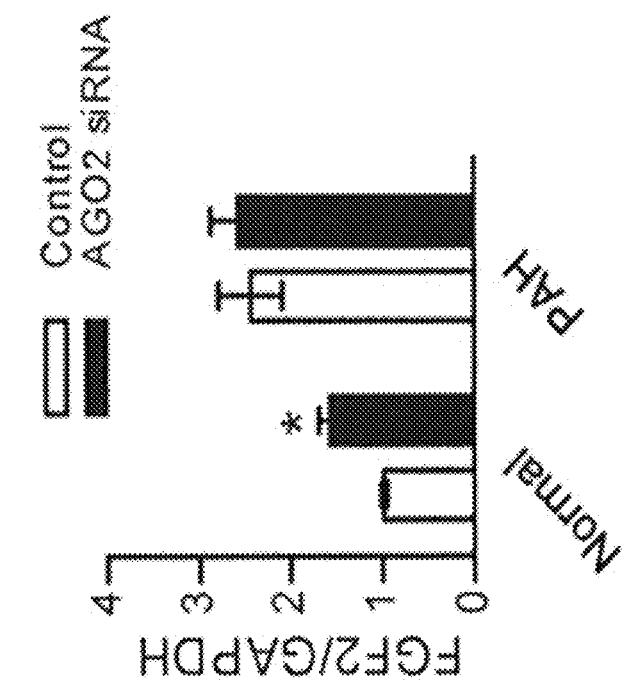
FIG. 8B is a bar graph showing FGF2 expression in response to knockdown of AGO2 by siRNA in normal and PAH PAECs. *P<0.01 compared to control siRNA by unpaired two-tailed Student's t test. Error bars, s.e.m.
Figure 8A:
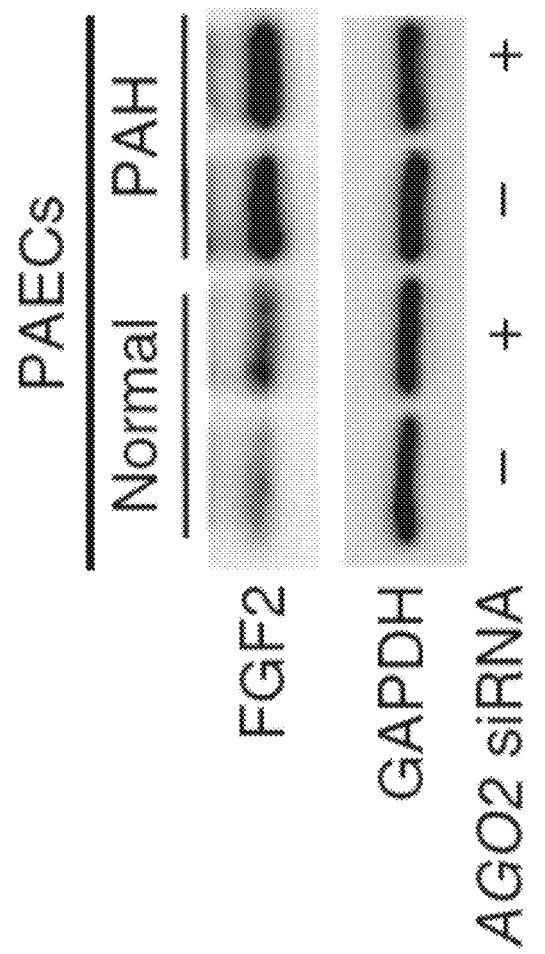
FIG. 8A is a blot showing FGF2 expression in response to knockdown of AGO2 by siRNA in normal and PAH PAECs. *P<0.01 compared to control siRNA by unpaired two-tailed Student's t test. Error bars, s.e.m.
Figure 9B:
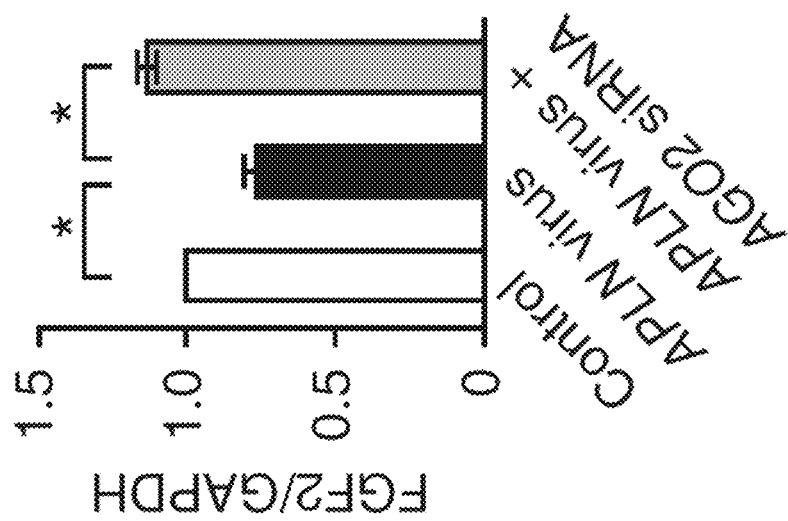
FIG. 9B is a bar graph showing FGF2 expression in PAECs in response to lentiviral APLN overexpression and AGO2 knockdown by siRNA. *P<0.01 for the comparisons indicated by unpaired two-tailed Student's t test. Error bars, s.e.m.
Figure 9A:
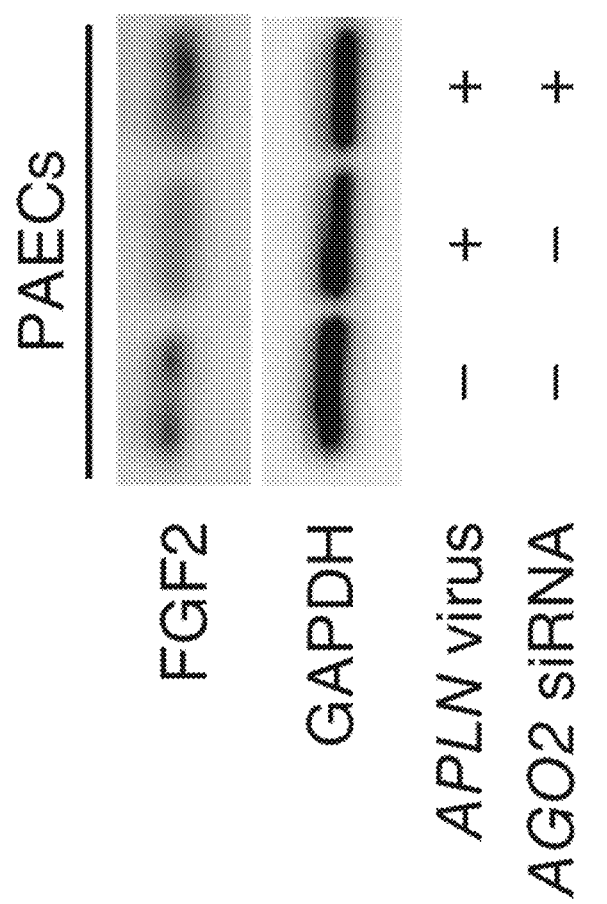
FIG. 9A is a blot showing FGF2 expression in PAECs in response to lentiviral APLN overexpression and AGO2 knockdown by siRNA. *P<0.01 for the comparisons indicated by unpaired two-tailed Student's t test. Error bars, s.e.m.

The regulation of FGF2 by APLN might be mediated by miRNAs that affect the stability of FGF2 mRNA. To test this hypothesis, it was determined whether knockdown of AGO2 (encoding argonaute 2), a key catalytic core component of the RNA-induced silencing complex, affected FGF2 expression in PAECs. AGO2 knockdown (FIGS. 49A-E) led to a robust increase in FGF2 protein expression in normal PAECs, suggesting the presence of basal miRNA-directed regulation of FGF2 in PAECs (FIGS. 8A-B). AGO2 knockdown did not further increase FGF2 expression in PAH PAECs, suggesting that miRNA-mediated control of FGF2 expression may be compromised in these PAECs (FIGS. 8A-B). In addition, the reduced FGF2 expression seen with APLN overexpression was abrogated by concurrent AGO2 knockdown (FIGS. 9A-B).

Figure 10:
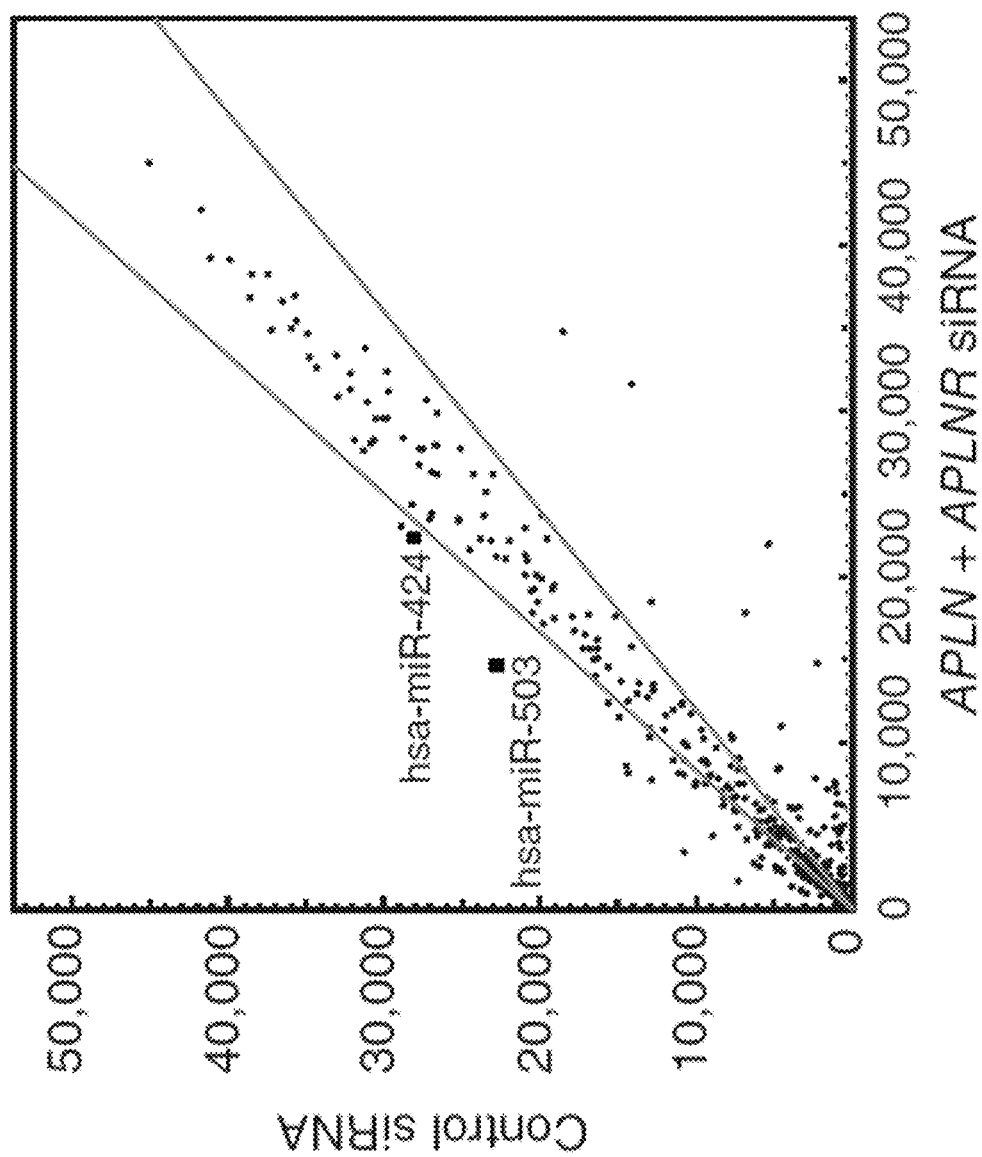
FIG. 10 is a dot plot showing miRNA microarray analysis of PAECs subjected to combined APLN and APLNR knockdown with siRNA. miR-424 and miR-503 are shown. Lines demarcate a 1.2-fold change from baseline expression.
Figure 11:
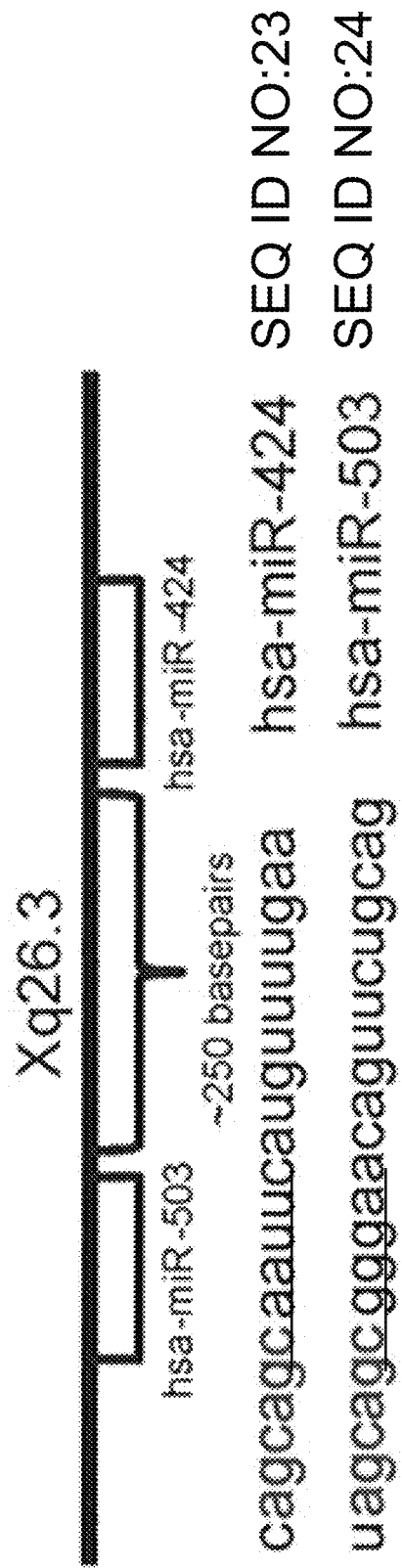
FIG. 11 depicts the chromosomal location of miR-424 and miR-503 and the sequences of the mature miRNAs. The homology in the seed sequences is shown.
Figure 12:
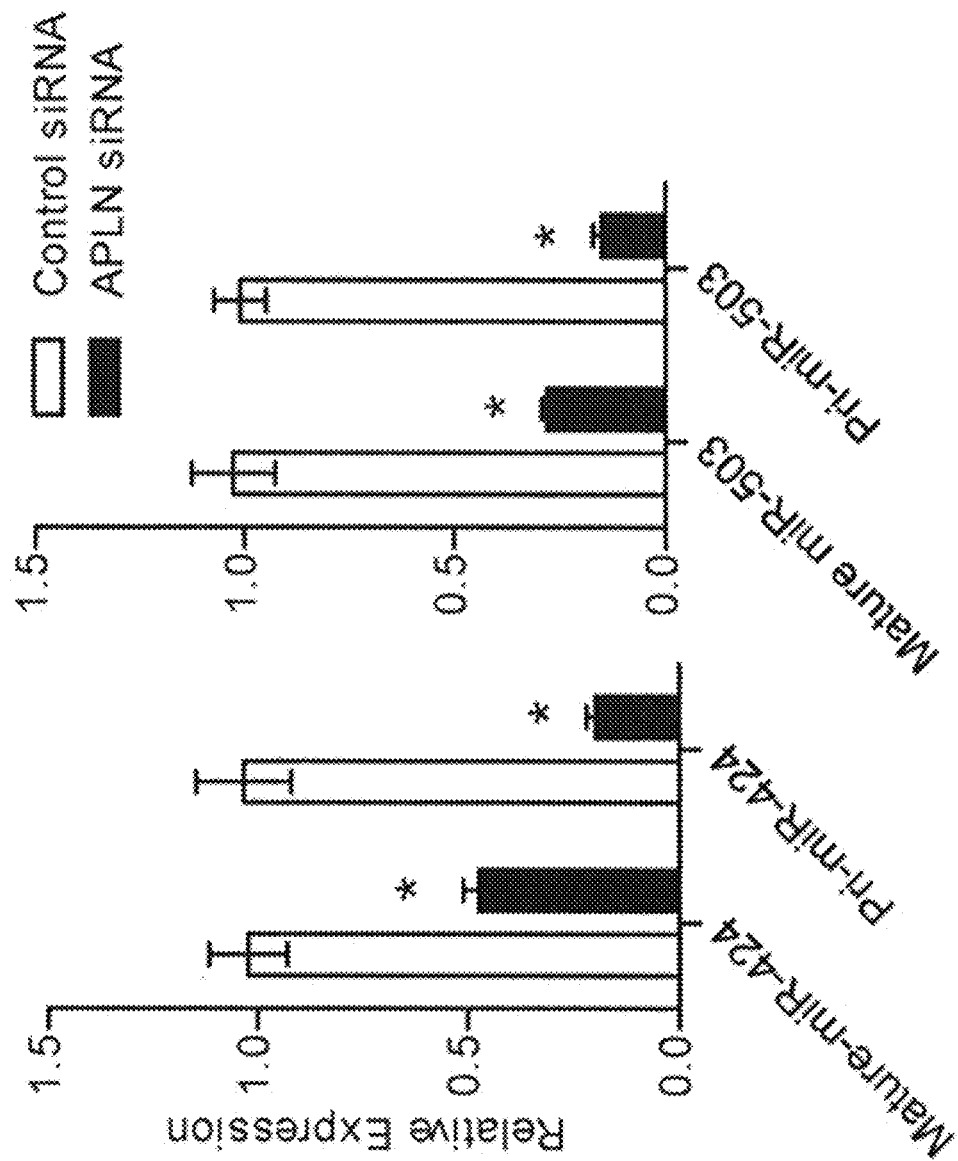
FIG. 12 is a bar graph showing quantitative PCR expression of the mature and pri forms of miR-424 and miR-503 in response to APLN knockdown by siRNA in PAECs. *P<0.01 compared to control siRNA by unpaired two-tailed Student's t test. Error bars, s.e.m.
Figure 13:
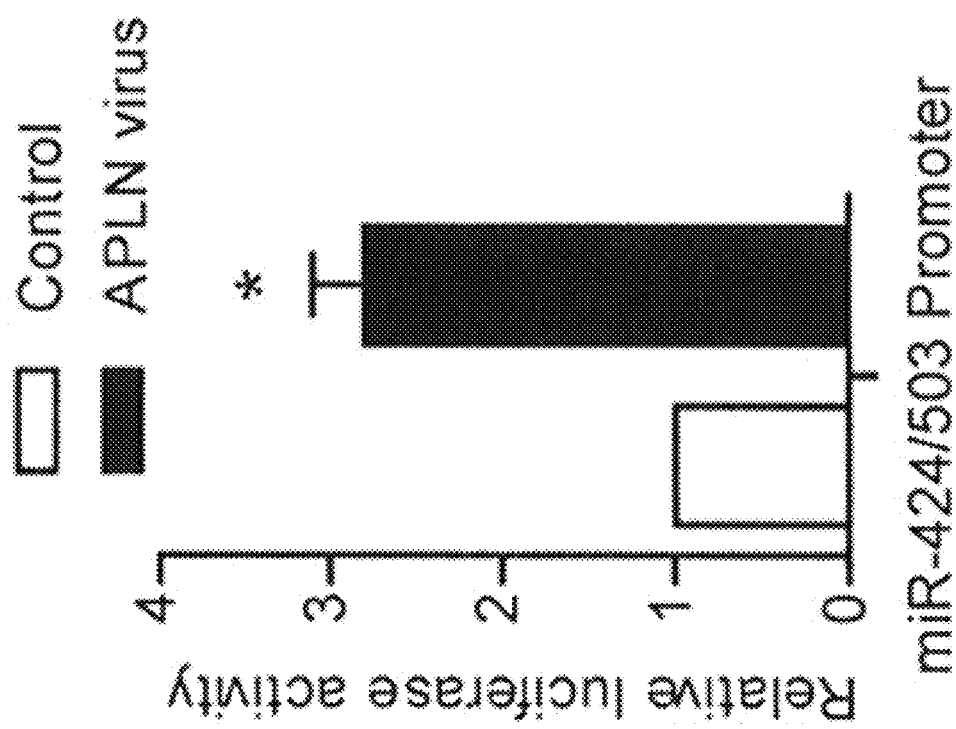
FIG. 13 is a bar graph of the relative luciferase activity of PAECs transfected with the miR-424 and miR-503 promoter luciferase reporter construct in response to lentiviral APLN overexpression. *P<0.001 compared to control lentivirus by unpaired two-tailed Student's t test. Error bars, s.e.m.
Figure 14:
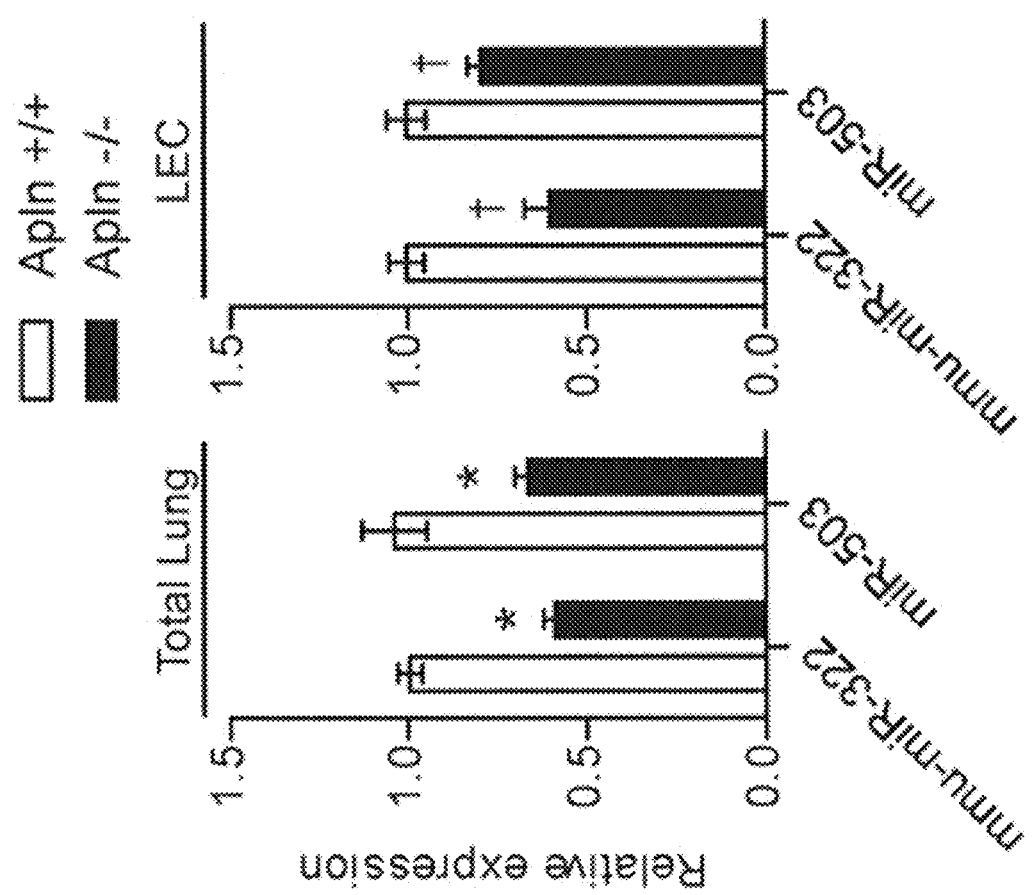
FIG. 14 is a bar graph showing expression of mmu-miR-322 (the mouse homolog of hsa-miR-424) and mmu-miR-503 in total lung homogenates and LECs of Apln-deficient (Apln-/-) mice (LECs were isolated from 5 to 6 mice per group). *P<0.001, †P<0.01 compared to wild type by unpaired two-tailed Student's t test. Error bars, s.e.m.
Figure 15:
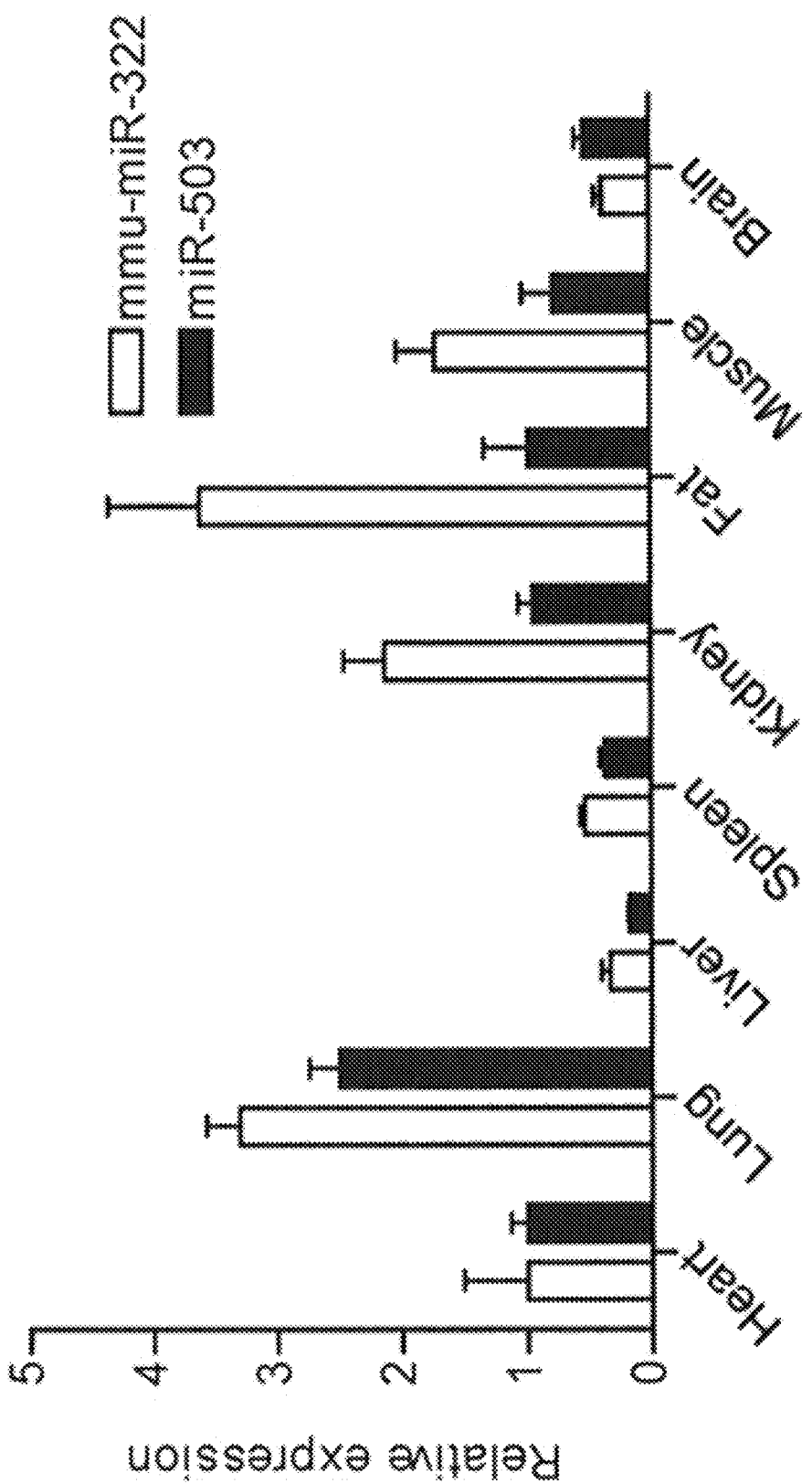
FIG. 15 is a bar graph showing quantitative PCR of mmu-miR-322 and mmu-miR-503 in mouse tissues (n=3). Error bars, s.e.m.
Figure 16A:
FIG. 16A shows in situ hybridization of human lungs for miR-424 and miR-503. Arrows indicate positively staining cells. Scale bar, 100 µm.
Figure 16B:
FIG. 16B shows in situ hybridization of human lungs for miR-424 and miR-503. Arrows indicate positively staining cells. Scale bar, 100 µm.
Figure 17B:
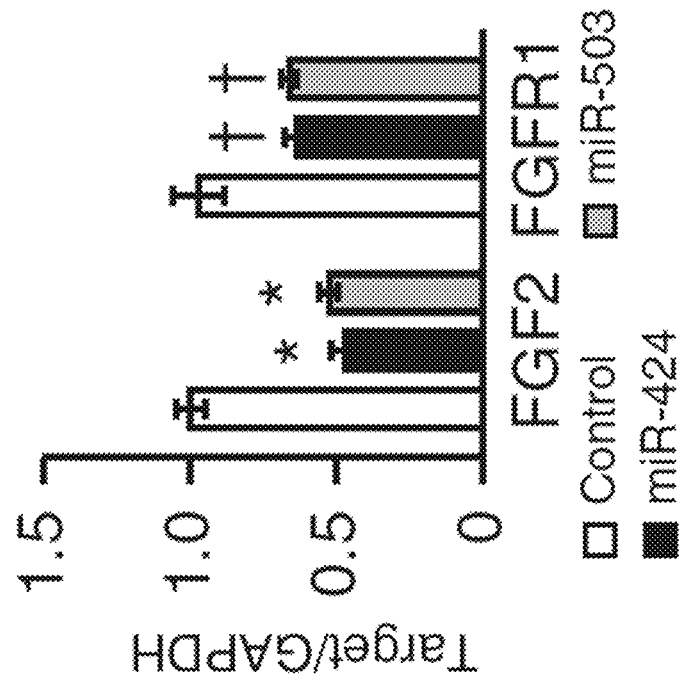
FIG. 17B is a bar graph showing FGF2 and FGFR1 protein expression in response to overexpression of miR-424, miR-503 or both (miR-424/503) in normal PAECs. *P<0.01, †P<0.05 compared to control by unpaired two-tailed Student's t test. Error bars, s.e.m.
Figure 17A:
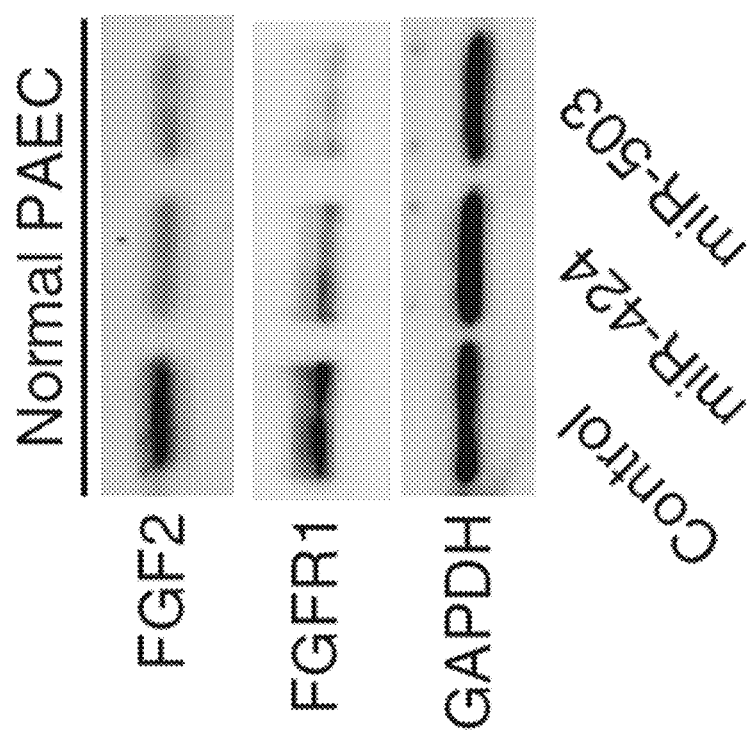
FIG. 17A is a blot showing FGF2 and FGFR1 protein expression in response to overexpression of miR-424, miR-503 or both (miR-424/503) in normal PAECs.
Figure 18B:
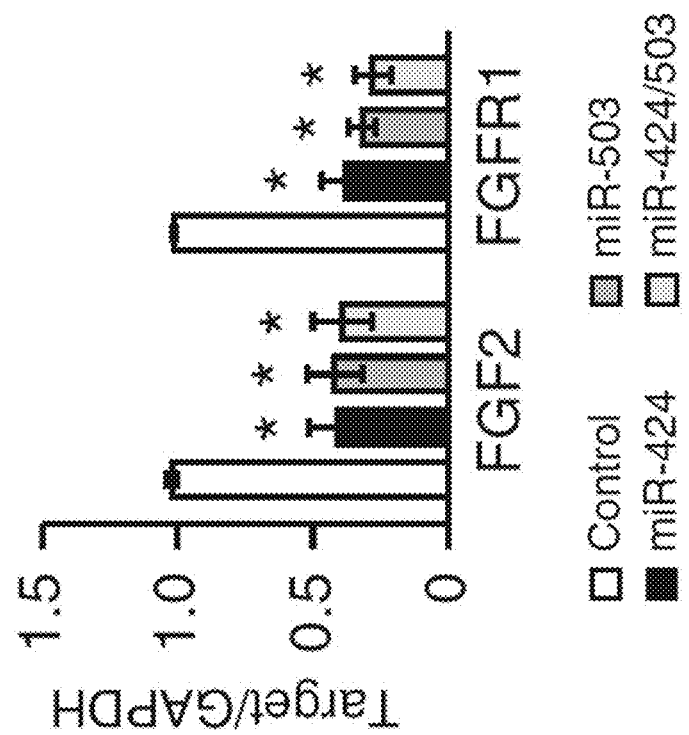
FIG. 18B is a bar graph showing FGF2 and FGFR1 protein expression in response to overexpression of miR-424, miR-503 or both (miR-424/503) in PAH PAECs. *P<0.01, †P<0.05 compared to control by unpaired two-tailed Student's t test. Error bars, s.e.m.
Figure 18A:
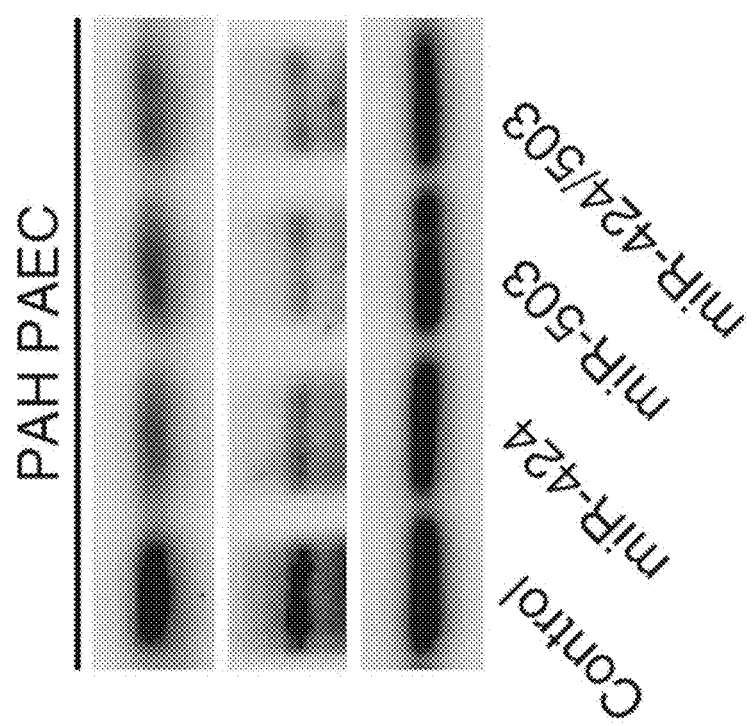
FIG. 18A is a blot showing FGF2 and FGFR1 protein expression in response to overexpression of miR-424, miR-503 or both (miR-424/503) in PAH PAECs.
Figure 19B:
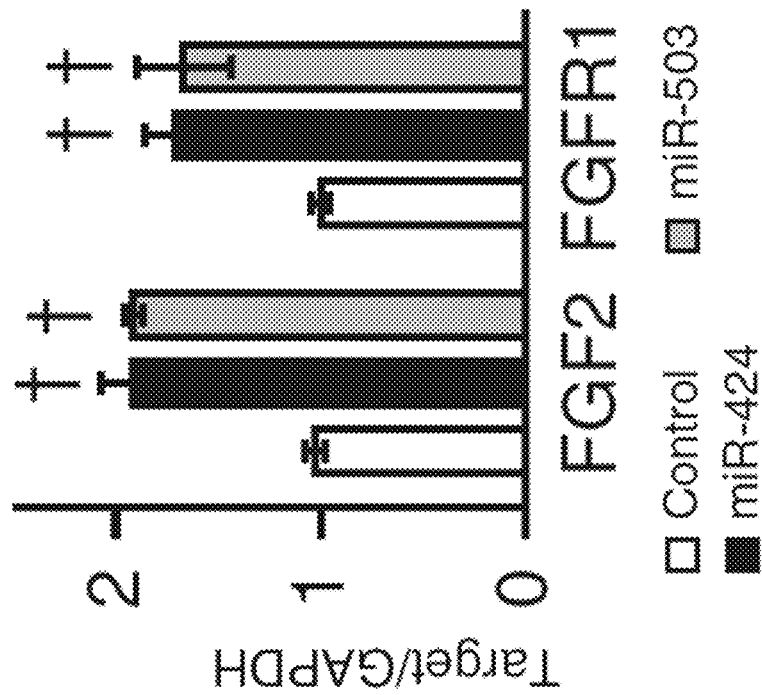
FIG. 19B a bar graph showing FGF2 and FGFR1 protein expression in response to inhibition of miR-424 or miR-503 with anti-miRs in normal PAECs. *P<0.01, †P<0.05 compared to control by unpaired two-tailed Student's t test. Error bars, s.e.m.
Figure 19A:
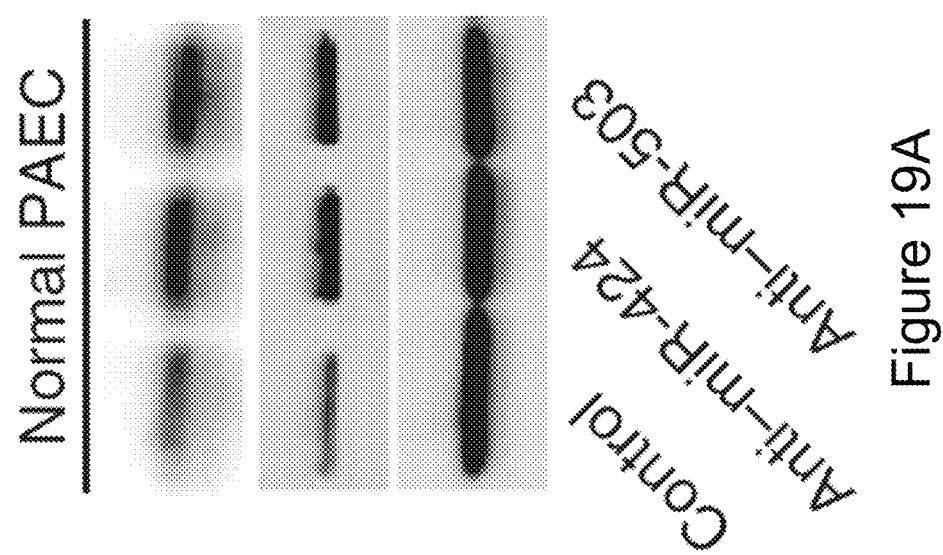
FIG. 19A is a blot showing FGF2 and FGFR1 protein expression in response to inhibition of miR-424 or miR-503 with anti-miRs in normal PAECs.

On the basis of these findings, experiments were performed to identify miRNAs regulated by APLN that might be involved in FGF2 regulation. miRNA microarray analyses were conducted using normal PAECs subjected to knockdown of APLN, APLNR or both (FIGS. 10 and 50A-B). From a total of 14 miRNAs that were significantly downregulated in each of the three conditions (Table 1), in silico analysis identified two that were predicted to target the FGF2 3' untranslated region (UTR): miR-424 and miR-503. These two miRNAs are separated by 250 by on the X chromosome and share substantial sequence identity in their seed sequences (FIG. 11). Other miRNAs predicted to target FGF2 in the in silico analysis, including miR-15a, miR-16, miR-195 and miR-497, were not significantly downregulated in these microarray experiments (data not shown). Using real-time quantitative PCR, confirmation of both the pri and mature forms of miR-424 and miR-503 were significantly downregulated by APLN knockdown (FIG. 12), suggesting that the transcription of these miRNAs, rather than their post-transcriptional maturation, is regulated by APLN signaling. It was also found that these two miRNAs are transcribed as a single transcript, which was also downregulated by APLN knockdown (FIGS. 51A-B). The putative promoter of reporter construct was used. The activity of this reporter was robustly induced by APLN overexpression in PAECs (FIG. 13). Moreover, decreased levels of mmu-miR-322 (the mouse homolog of hsa-miR-424) and miR-503 were found in both total lung homogenates and LECs from Apln-null mice (FIG. 14). Expression profiling of various organ tissues from control mice showed high expression of miR-424 and miR-503 in the lungs, where the highest expression of APLN and APLNR had been previously reported (FIG. 15). In situ hybridization of normal human lungs demonstrated robust expression of miR-424 and miR-503 in the luminal layer of the pulmonary microvasculature (FIGS. 16A-B and 52).

TABLE 1

List of microRNAs significantly upregulated or downregulated in all three conditions.

| Upregulated | Downregulated |
| --- | --- |
| hsa-miR-27a* | hsa-miR-23a |
| | hsa-miR-95 |
| | hsa-miR-139-5p |
| | hsa-miR-149 |
| | hsa-miR-200a |
| | hsa-miR-210 |
| | hsa-miR-328 |
| | hsa-miR-424 |
| | hsa-miR-424. |
| | hsa-miR450a |
| | hsa-miR-450b-5p |
| | hsa-miR-503 |
| | hsa-miR-542-5p |
| | hsa-miR-551a |

Figures 20A, 20B:
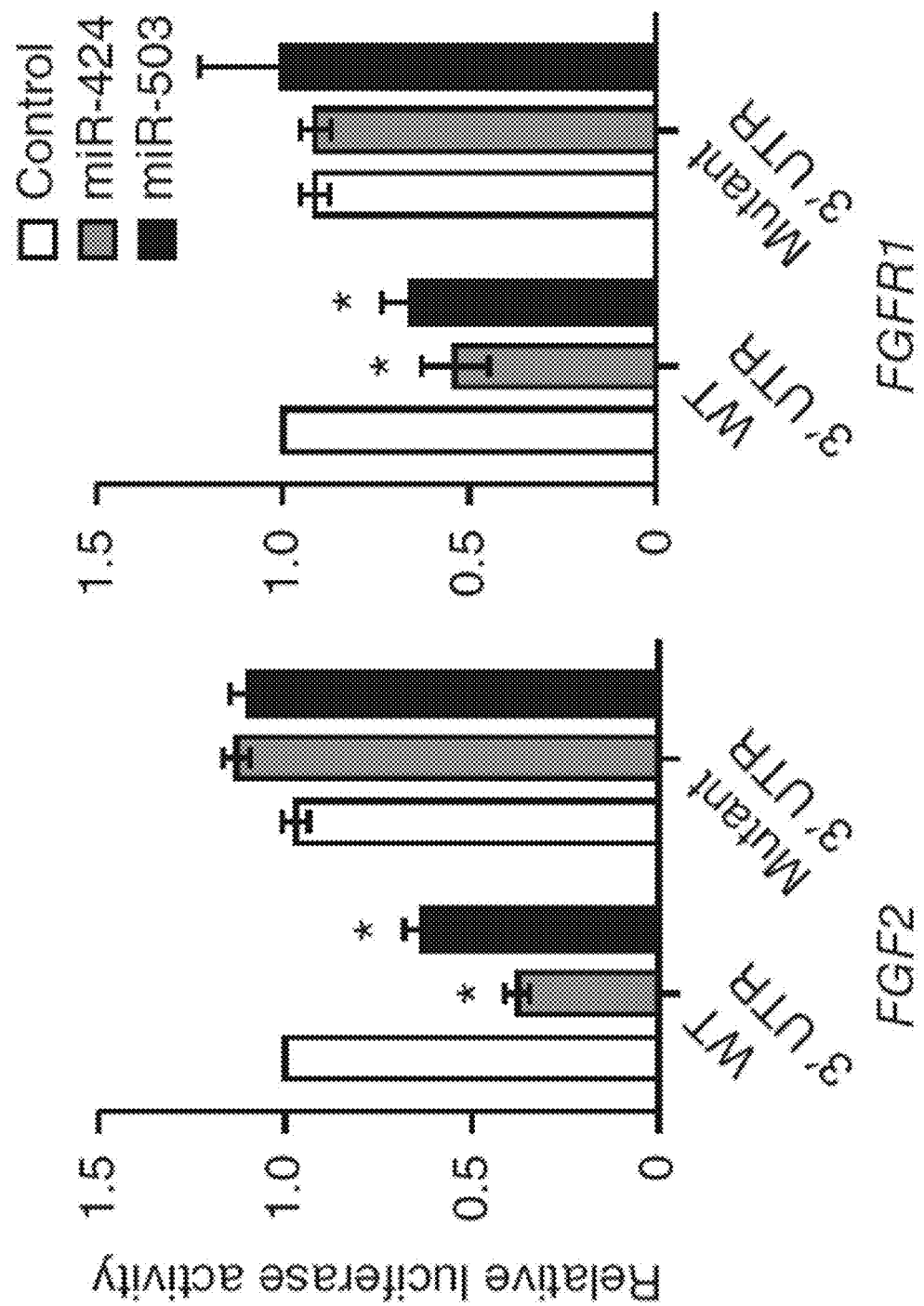
FIG. 20A is a bar graph showing luciferase activity for constructs targeting wildtype and mutant FGF2 3' UTRs by overexpression of miR-424 or miR-503 in HeLa cells. *P<0.01 compared to control by unpaired two-tailed Student's t test. Error bars, s.e.m.
FIG. 20B is a bar graph showing luciferase activity for constructs targeting wildtype and mutant FGFR1 3' UTRs by overexpression of miR-424 or miR-503 in HeLa cells. *P<0.01 compared to control by unpaired two-tailed Student's t test. Error bars, s.e.m.

To validate the predicted targeting of FGF2 by miR-424 and miR-503, the effects of miR-424 and miR-503 overexpression or knockdown on FGF2 expression in PAECs were assessed. miR-424 and miR-503 were predicted to target the FGF2 3' UTR at three separate sites (FIGS. 53A-B). miR-424 or miR-503 overexpression in normal or PAH PAECs led to significantly decreased FGF2 expression, whereas inhibition of endogenous miR-424 or miR-503 by transfection of anti-miRs in normal PAECs led to increased FGF2 expression (FIGS. 17A-B, 18A-B, 19A-B and 54A-C). Furthermore, luciferase constructs with the 3' UTR sequence of FGF2 were generated and it was discovered that miR-424 and miR-503 overexpression led to a robust decrease of luciferase activity (FIGS. 20A-B). This response was abrogated by mutation of the miR-424- and miR-503-targeted seed sequences (FIG. 20A).

miR-424 and miR-503 Target FGFR1 and Inhibit FGF Signaling.

Figures 21A, 21B:
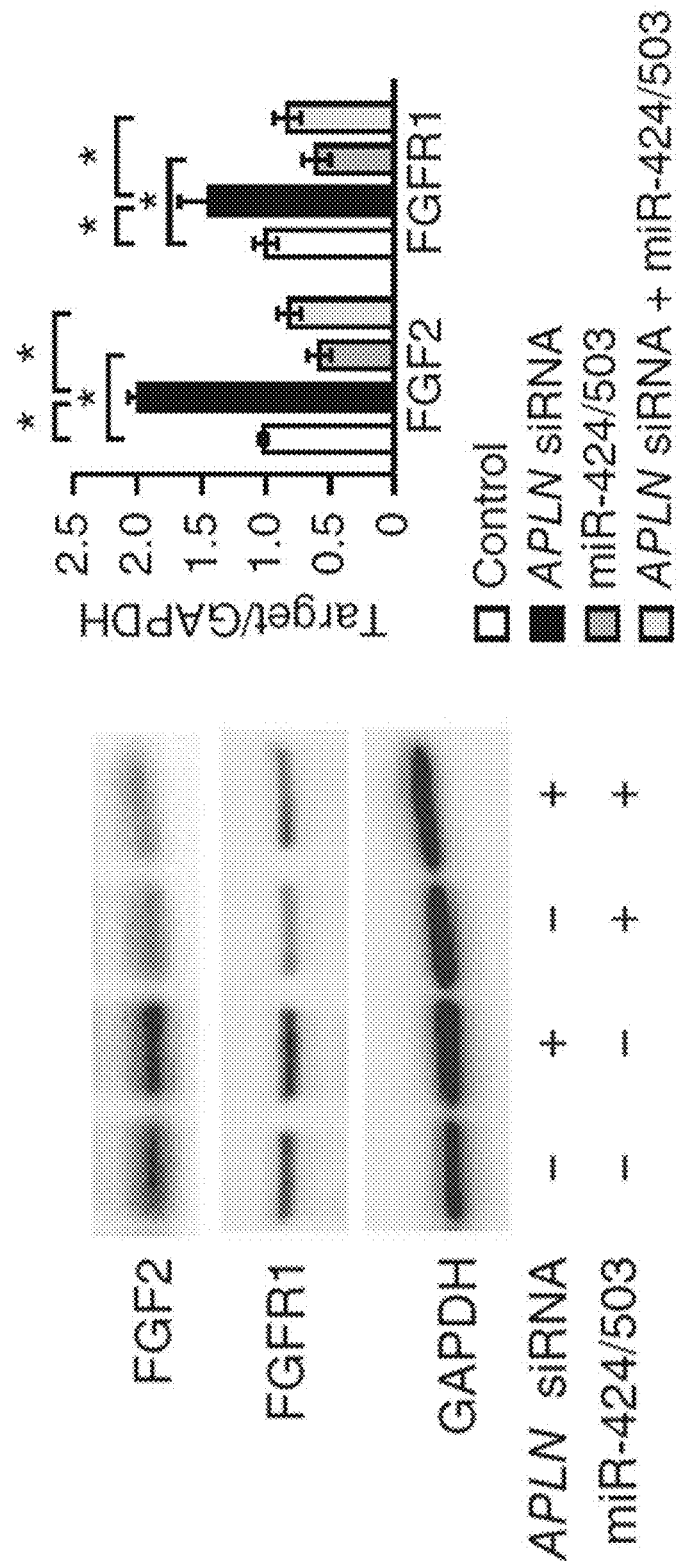
FIG. 21A is a western blot showing FGF2 and FGFR1 expression in response to knockdown of APLN by siRNA in PAECs with concurrent overexpression of miR-424 and miR-503.
FIG. 21B is a bar graph showing FGF2 and FGFR1 expression in response to knockdown of APLN by siRNA in PAECs with concurrent overexpression of miR-424 and miR-503. *P<0.01 for the comparisons indicated by unpaired two-tailed Student's t test. Error bars, s.e.m.

The in silico data were analyzed to identify additional potential targets of miR-424 and miR-503 that might have a role in FGF signaling. FGFR1, encoding FGF receptor 1, was predicted to be targeted by miR-424 and by miR-503, as it has two distinct miR-424- and miR-503-binding sites in its 3' UTR (FIGS. 53A-B). Overexpression and knockdown of miR-424 and miR-503 in normal and PAH PAECs had effects on FGFR1 that were similar to those on FGF2 expression (FIGS. 17A-B, 18A-B, 19A-B and 54A-C). A luciferase reporter bearing the 3' UTR of FGFR1 was also similarly affected by miR-424 and miR-503 overexpression (FIG. 20A). Mutation of the miR-424- and miR-503-targeted seed sequences in the FGFR1 3' UTR led to complete abrogation of miR-424- and miR-503-mediated inhibition of luciferase reporter activity (FIG. 20A). Moreover, APLN knockdown resulted in robust increases of FGF2 and FGFR1 expression that were abrogated with concurrent overexpression of miR-424 and miR-503 (FIGS. 21A-B).

Figure 22B:
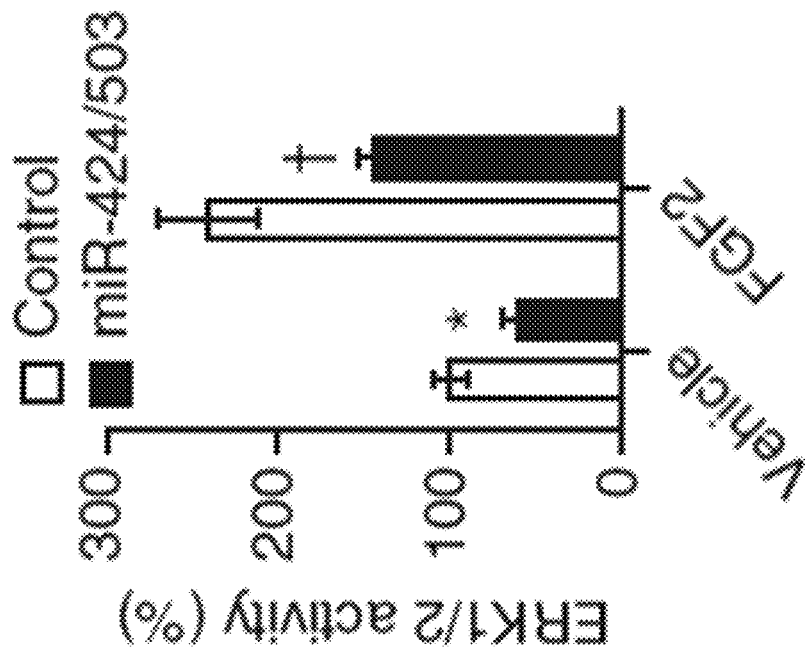
FIG. 22B is a bar graph showing ERK1/2 phosphorylation (pERK1/2) in response to overexpression of miR-424 and miR-503 in PAECs at baseline and with FGF2 stimulation.
Figure 22A:
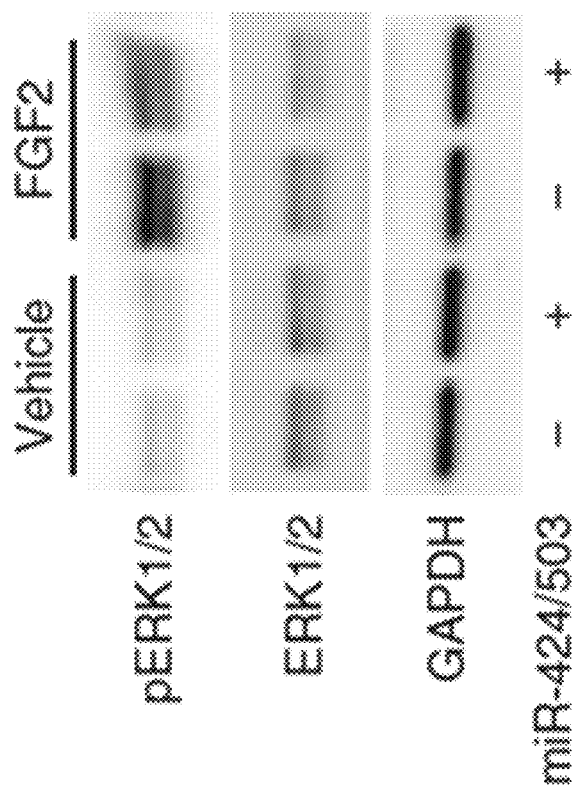
FIG. 22A is a blot showing ERK1/2 phosphorylation (pERK1/2) in response to overexpression of miR-424 and miR-503 in PAECs at baseline and with FGF2 stimulation.

It was next determined whether perturbation of miR-424 and miR-503 expression affected the phosphorylation of ERK1 and ERK2 (ERK1/2), key downstream targets of FGF2-FGFR1 signaling in endothelial cells. ERK1/2 phosphorylation was decreased by miR-424 and miR-503 overexpression both in the basal state and with exogenous FGF2 stimulation (FIGS. 22A-B); this effect may be secondary to a reduction of FGFR1 expression. In addition, transfection of anti-miRs targeting miR-424 and miR-503 led to a significant increase in ERK1/2 phosphorylation (FIGS. 23A-B).

Altered miRNA-FGF Axis in PAH PAECs.

The finding that APLN expression is decreased in PAH PAECs prompted analysis as to whether miR-424 and miR-503 expression would also be reduced in these cells. Indeed, significantly decreased expression of the mature, pri and pre forms of miR-424 and miR-503 was found in PAECs derived from subjects with PAH as compared to PAECs from control subjects (FIGS. 24 and 55A-C). Moreover, FGF2 mRNA levels were also increased in PAH PAECs (FIG. 24).

There was a significant linear correlation between the mRNA levels of APLN and miR-424 as well as between expression of miR-424 and miR-503 (FIGS. 25A-D). A significant inverse correlation was found between the levels of miR-424 and those of FGF2 and FGFR1, and between the levels of miR-503 and those of FGF2 and FGFR1 (FIGS. 25A-D and 56A-B). As assessed by western blotting, FGF2 and FGFR1 protein expression were markedly higher in PAH PAECs (FIG. 26). In addition, immunohistochemistry in lung samples of unused explanted normal donors and subjects with PAH showed substantially higher expression of FGFR1 in the endothelial layer of the PAH lung, as demonstrated by colocalization with von Willebrand factor (vWF) (FIG. 27). In situ hybridization of lungs from subjects with PAH showed markedly lower levels of miR-424 and miR-503 in the microvasculature compared to control donor lungs (FIGS. 28A-B and 57).

miR-424 and miR-503 Promote PAEC Quiescence.

Human PAECs were studied in cell culture to further evaluate the functional roles of miR-424 and miR-503. The endogenous expression levels of miR-424 and miR-503 were increased as the PAECs reached a confluent state or in serum-starvation conditions (FIGS. 58A-B). Cell-cycle analysis showed that miR-424 and miR-503 overexpression using miRNA mimics induced cell-cycle arrest at the G0/G1 stage in both normal and PAH PAECs (FIGS. 29A-D). Overexpression of miR-424 and miR-503 also led to significantly decreased proliferation of both normal and PAH PAECs, whereas FGFR1 transfection (lacking its 3' UTR) in conjunction with FGF2 stimulation reversed the inhibition of proliferation resulting from miR-424 and miR-503 overexpression in both normal and PAH PAECs (FIGS. 30 and 59A-B). Moreover, the increased proliferation of normal PAECs in response to APLN overexpression was further augmented with concurrent inhibition of miR-424 and miR-503, and inhibition of miR-424 and miR-503 reversed the antiproliferative effect of APLN overexpression in PAH PAECs (FIGS. 47B-C).

Transfection of siRNAs targeting FGF2 and FGFR1 (FIGS. 49A-E) led to significantly (P<0.05) reduced proliferation of PAH PAECs (FIGS. 59A-B). Inhibition of miR-424 and miR-503 led to significantly increased proliferation of normal PAECs but had minimal effect on PAH PAECs (FIG. 31). In addition, concurrent knockdown of FGF2 and FGFR1 completely antagonized the proliferative effects of miR-424 and miR-503 inhibition in control PAECs and inhibited proliferation of PAH PAECs, which were unaffected by miR-424 and miR-503 inhibition (FIG. 31). Overexpression of miR-424 and miR-503 in control and PAH PAECs also reduced cell migration (FIGS. 32A-B and 33A-B); this effect in control PAECs was reversed by restoration of FGF2 and FGFR1 expression (FIGS. 32A-B).

Endothelial miR-424 and miR-503 inhibit PASMC proliferation. PAH is a vascular disease that is characterized by hyperproliferation of both PAECs and PASMCs. miR-424 and miR-503 expression in control and PAH PASMCs was therefore assessed. PASMCs had significantly (P<0.001) lower transcript levels of miR-424 and miR-503 than PAECs (FIG. 60). Moreover, miR-424 or miR-503 expression in PAH PASMCs was not significantly different as compared to control PASMCs (FIG. 61).

Next, it was evaluated whether overexpression of miR-424 and miR-503 in PAECs affected the proliferation of PASMCs in a paracrine manner. Incubation of normal PASMCs with conditioned medium from normal PAECs resulted in a significant increase in PASMC proliferation, and this effect was even greater using conditioned medium from PAH PAECs (FIG. 34). Conditioned medium from either normal or PAH PAECs transfected with miR-424 and miR-503 had a significantly (P<0.01) reduced effect on PASMC proliferation as compared to conditioned medium from control normal or PAH PAECs, respectively. Moreover, this effect of miR-424 and miR-503 transfection was abrogated by concurrent transfection with an FGF2 overexpression construct, demonstrating the ability of FGF2 to reverse the paracrine effects of miR-424 and miR-503 (FIG. 34). Further, conditioned medium from normal PAECs subjected to APLN knockdown induced a significantly higher level of PASMC proliferation as compared to conditioned medium from control cells; this effect of APLN knockdown was abrogated by concurrent overexpression of miR-424 and miR-503 (FIG. 35). Conditioned medium from normal PAECs subjected to FGF2 knockdown medium from control cells, and concurrent knockdown of FGF2 abrogated the effect of APLN knockdown in this assay (FIG. 36).

miR-424 and miR-503 Ameliorate Pulmonary Hypertension.

The expression levels of rno-miR-322 (the rat homolog of hsa-miR-424), miR-503, FGF2 and FGFR1 were evaluated in two experimental rat models of pulmonary hypertension: the MCT model and the SU-5416/hypoxia (SuHx) model. Compared to control rats, rats subjected to MCT or SuHx had significantly decreased expression of miR-322 and miR-503 in their lungs and in isolated LECs and decreased Apln expression in LECs, as well as robust increases in FGF2 and FGFR1 expression in the lungs (FIGS. 37A-B and 38). The signaling axis comprising miR-322 (miR-424), miR-503, FGF2 and FGFR1 was validated in rats by demonstrating that expression of FGF2 and FGFR1 in isolated rat LECs were significantly ($P<0.01$) downregulated by overexpression of rno-miR-322 or rno-miR-503 mimics (FIGS. 60 and 61) or human miR-424 or miR-503 (data not shown). The efficacy of miR-424 and miR-503 restoration was evaluated in ameliorating the severity of pulmonary hypertension in three experimental models: (i) the MCT prevention model, (ii) the MCT rescue model and (iii) the SuHx rescue model (FIG. 63). Intranasal delivery was used of either GFP-expressing control lentivirus (GFP) or lentivirus expressing miR-424, miR-503 and GFP (424/503-GFP, $2\times10^{10}$ PFU per intranasal delivery) to induce expression of these miRNAs in the lungs (n=6-9 mice in each group). Expression of the lentiviral-encoded miRNAs was confirmed by detection of lentiviral-specific miR-424 and miR-503 transcripts in lung homogenates and isolated LECs of 424/503-GFP-treated rats, which were absent in the GFP treatment group (FIGS. 64A-B). The efficacy of our delivery method was confirmed by detection of lentivirally expressed GFP in lungs from both 424/503-GFP-treated and GFP-treated rats but not in lungs from control rats not subjected to intranasal lentivirus delivery (FIG. 65). Endothelial infection was confirmed by flow cytometry that identified a CD31+GFP+ cell population (~8% of total CD31+ cells) in the lentiviral groups (FIGS. 66A-B). In addition, 424/503-GFP treatment in the SuHx model restored miR-424 (rno-miR-322 and lentivirally expressed hsa-miR-424) and miR-503 levels in isolated LECs to levels comparable to those in the nondiseased control state (FIG. 67).

In all three models, right ventricular systolic pressure (RVSP) was significantly increased (FIG. 39). RVSP was markedly reduced in rats that received intranasal 424/503-GFP compared to those that received GFP in all three models (FIG. 39). A significant reduction ($P<0.05$) was found in the right ventricle to the left ventricle plus septum weight ratio in the 424/503-GFP treatment groups in the three models (FIG. 68). The number of muscularized microvessels was also significantly lower in the 424/503-GFP treatment groups in each of the three models (FIG. 40A-B). To evaluate vascular cell proliferation, PCNA staining was performed in conjunction with vWF staining. The number of PCNA-positive microvessels was increased in pulmonary hypertension rats in the GFP treatment groups as compared to nondiseased controls, whereas the 424/503-GFP treatment groups had significantly fewer PCNA-positive microvessels compared to the GFP treatment groups (FIGS. 41A-B). Similarly, the number of obliterated vessels was increased in the GFP treatment group in the SuHx model as compared to nondiseased controls, an effect that was ameliorated by 424/503-GFP treatment (FIGS. 42A-B). The expression of FGF2 and FGFR1 was significantly decreased in total lung homogenates of the 424/503-GFP treatment groups compared to the respective GFP treatment groups (FIGS. 43A-C). Moreover, isolated LECs in the GFP treatment groups of the MCT and SuHx models also had significantly elevated FGF2 and FGFR1 expression, which was significantly reduced in the respective 424/503-GFP treatment groups (FIGS. 43A-C), further validating the miR-424, miR-503, FGF2 and FGFR1 signaling axis.

Recent studies have associated decreased APLN expression with clinical PAH. In addition, abnormally elevated FGF2 expression has also been linked with PAH. Described herein is miRNA-driven regulation of FGF signaling by APLN, integrating these isolated clinical observations into a cohesive mechanism.

The importance of APLN signaling in pulmonary vascular homeostasis has been demonstrated by studies showing exacerbation of hypoxia-induced pulmonary hypertension in Apln-null mice and the reversal of disease by exogenous APLN peptide administration in both the MCT model and endothelial-specific peroxisome proliferator activated receptor γ (PPAR-γ) knockout mice. These findings provide four major possibilities: (i) disruption of APLN signaling in PAECs results in increased expression of FGF2 and FGFR1; (ii) APLN regulates miR-424 and miR-503 expression, which in turn target two key components of endothelial FGF signaling, FGF2 and FGFR1; (iii) downregulation of APLN, miR-424 and miR-503 in PAH PAECs is associated with increased FGF2 and FGFR1 expression and hyperproliferation of PAECs and PASMCs, and (iv) restoration of miR-424 and miR-503 in the lungs inhibits FGF2 and FGFR1 expression and ameliorates pathology in experimental models of pulmonary hypertension.

The downstream targets of APLN in the context of the pulmonary vasculature remain to be fully elucidated. These current findings demonstrate that APLN signaling, in a miR-424- and miR-503-dependent manner, has a crucial role in regulating the magnitude of FGF signaling in the pulmonary vasculature (FIG. 44). Although basal FGF signaling activity has been found to be essential for endothelial homeostasis, pathological augmentation of FGF signaling is associated with the cellular hyperproliferation and vascular remodeling found in PAH. These findings indicate that the maintenance of delicately balanced FGF signaling is essential for the preservation of pulmonary vascular homeostasis.

Previous studies have suggested proliferative effects of APLN on endothelial cells. However, these effects have been modest at best, and another study was unable to confirm such findings, suggesting strong context dependence for the effects of APLN on the endothelium. APLN seems to have the greatest proliferative and migratory effects in the developing vasculature, but these findings have not been convincingly extended to the mature endothelium. Rather, emerging evidence suggests that the role of APLN signaling in mature vessels is to preserve a differentiated and quiescent endothelial layer. This role is mediated at least in part by induction of KLF2 expression and nitric oxide synthase 3 (NOS3 or eNOS) expression and activity. APLN also enhances endothelial layer integrity by maintenance of membranous CDH5 (VE-cadherin) expression. These current data point to a third role in which APLN induces miR-424 and miR-503 expression to repress aberrant, pathologic cellular growth and proliferation. It is worth noting that in addition to the cellular growth-inhibitory effects described here of the APLN, miR-424 and miR-503 axis, APLN signaling can also promote cellular growth through other signaling targets, as has been previously described. Nevertheless, this demonstration of a marked reduction in APLN, miR-424 and miR-503 expression and the consequent signaling perturbations in PAH PAECs demonstrates the importance of this signaling axis in the pulmonary vasculature.

Prior work demonstrated that increased production of FGF2 from the PAECs may have an important role in the pathogenesis of PAH. However, the mechanism of this dysregulation has remained undefined. This study identifies a cell-intrinsic, miRNA-mediated regulation of FGF signaling that is disrupted in the pulmonary endothelium of subjects with PAH. These data also provide a mechanism by which restoration of miR-424 and miR-503 expression in PAECs can regulate PASMC growth in a paracrine manner. These findings lend further support to the emerging role of PAEC-PASMC crosstalk that likely has an important role in the pathogenesis of PAH.

Although no prior studies have demonstrated a role for miR-424 or miR-503 in PAH, miR-322 (miR-424) was found to be significantly downregulated in array analyses evaluating the MCT model of pulmonary hypertension in rats. Studies have also implicated miR-424 and miR-503 in promoting the differentiation of monocytes, macrophages and skeletal muscle. A recent study demonstrated targeting of vascular endothelial growth factor (VEGF), VEGFR2 and FGFR1 by miR-424 in human umbilical vein endothelial cells, but a separate study indicated that miR-424 may have a proangiogenic function in hypoxic endothelial cells, suggesting a context-dependent role for miR-424.

Although other validated targets of miR-424 and miR-503, such as cyclin E1 (CCNE1), cdc25A, mitogen-activated protein kinase 1 (MEK1), VEGF and VEGFR2 may also contribute to the PAEC phenotype of subjects with PAH, no significant changes in their expression levels in PAH PAECs. Furthermore, the restoration or abrogation of FGF signaling was found to be sufficient to fully counter the effects of either overexpression or knockdown of miR-424 and miR-503 in PAECs, respectively. It is possible that additional predicted but not yet validated targets of miR-424 and miR-503 may also contribute to the cellular and in vivo consequences of modulating these miRNAs. The current study focused on the regulatory mechanism that links APLN signaling to the FGF2 signaling cascade in the pulmonary vasculature, future studies will be needed to evaluate the role of targets of miR-424 and miR-503 in the context of PAH.

These findings delineate a relationship between the APLN and FGF signaling pathways in the pulmonary vasculature that is mediated by two APLN-responsive miRNAs: miR-424 and miR-503. Downregulation of these miRNAs is associated with both human PAH and established experimental rodent models. These findings support development of new therapeutic strategies designed to augment APLN, miR-424 and miR-503 signaling, as well as to inhibit FGF signaling.

The Materials and Methods used in the performance of the experiments disclosed herein are now described.

Oligonucleotide Primers.

All primers were obtained from the Keck Oligonucleotide Synthesis Resource at Yale University.

TABLE 2

Primer sequences and SEQ ID NOs.

| | 5' Primer | SEQ ID NO. | 3' Primer | SEQ ID NO. |
|---|---|---|---|---|
| FGF2-3' UTR | TAGGCGATCGCTCGAGCAGACAGATTAATCCAGAAGC | 11 | TTGCGGCCAGCGGCCGCGGGAGACAAGAAAACACAAA | 12 |
| FGFR1-3' UTR | TAGGCGATCGCTCGAGATTGAAGGTGACCTCTGCC | 13 | TTGCGGCCAGCGGCCGCCTCTCCCAAGGACTTATGAA | 14 |
| Human miR-424 transcript | GGCTTCCTTCAGTCATCCAGT | 15 | ACCTTCTACCTTCCCCACGA | 16 |
| Human miR-503 transcript | GGAAGGTAGAAGGTGGGGTC | 17 | GGAAACAATACCCCAGAGCA | 18 |
| Human miR-424/503 combined transcript | GGCTTCCTTCAGTCATCCAGT | 19 | GCGGAAACAATACCCCAGAG | 20 |
| Human miR-424/503 promoter | TTTCTCTATCGATAGGTACCCCATTTTCGAGTGGAGCC | 21 | CCGGAATGCCAAGCTTGAGTCAATGAAGGGGATC | 22 |

MicroRNA Array.

The Illumina microRNA expression profiling panel (based on miRbase release 9.0) was used for miRNA analysis according to the manufacturer's recommendation (Illumina, inc., San Diego, Calif.). Human PAECs (Lonza) subjected to 1) control, 2) APLN, 3) APLNR, or 4) APLN+APLNR siRNA transfection. Each experimental condition was performed in triplicate. RNA samples (200 ng) from each condition were first labeled and then hybridized to each array using standard Illumina protocols. Sample array matrices were scanned on an Illumina BeadArray reader. Data were imported into GenomeStudio (Illumina), quantile normalized and log 2-transformed in R.

Isolation of Mouse and Rat Lung Endothelial Cells.

Mouse and rat lung endothelial cells (LECs) were isolated by digesting whole lung tissue with collagenase (2mglml) with gentle agitation for 45 minutes at 37° C. Using a 30 cc syringe attached firmly to a cannula, suspension was triturated 12 times, the cell suspension was filtered through 70 pm cell strainers, and centrifuged at 4009 for five minutes at 4° C. Cells were resuspended in 2 mL of cold PBS+0.1% BSA and the cell suspension was incubation with sheep anti-mouse lgG Dynabeads (lnvitrogen) coated with purified anti-CD31 antibodies (BD Pharmingen). Second sorting was performed to ensure the purity of the LECs.

Vectors and Plasmids/Luciferase Assays.

Human FGF2 3'-UTR (874 bp) and FGFRI 3'-UTR (1906 bp) that included the predictedmiR-4241503 seed sequences were amplified using from a human genomic DNA by PCR and confirmed by sequencing. The FGF2 3'-UTR and FGFR1 3'-UTR were cloned into the Xhol and Notl sites of psiCHECK-2 (Promega). CTGCT in the three predicted seed sequences of FGF2 and two predicted seed sequences of FGFR1 (FIGS. 47A-C and 48A-B) were mutated to TAATA. HeLa cells were transfected with the luciferase reporter constructs containing the 3' UTR variants and with 30 nM of either miR-4241503 mimics or negative control miRNA using Lipofectamine 2000 (Invitrogen). The cells were lysed and luciferase activity was measured 24 hours post-transfection by Dual Luciferase Assay System (Promega). The FGFR1 and FGF2 expression constructs lacking the 3' UTR were used (Addgene and Origene). Putative human miR-4241503 promoter sequence was amplified using primers from human genomic DNA by PCR and confirmed by sequencing. The PCR product was cloned into the Kpnl and Hindlll sites of PGL3 vector (Promega) using In-Fusion@ PCR Cloning System (Clontech). PAECs were transfected with miR-4241503 promoter-luciferase, renilla-luciferase, and APLN constructs (Origene). At 24 h post-transfection, luciferase activity was quantified using the Dual-Luciferase Reporter Assay kit (Promega).

Protein Methods.

Western blotting was performed. Each western blot was a representative of three independent experiments done in triplicates. For generation of cell lysates, RIPA lysis buffer (Thermo Scientific) containing Halt Protease and Phosphatase Inhibitor cocktail (Thermo Scientific) was used. Protein contents were measured using a Bio-Rad DC assay kit.

RNA Extraction, Reverse Transcription PGR and miRNA Profiling.

RNA was extracted with the miRNeasy RNA isolation kit (Qiagen). Purified RNA was reverse transcribed with iScriptrMoDNA Synthesis Kit (Bio-Rad). RT-PCR was performed with TaqMan probes for both genes and miRNAs (Applied Biosystems). RT-PCR for miR-424 detected both the human (hsa-miR-424) and rodent (rno-miR-322 and mmu-miR-322) variants. All miRNA data were normalized to the internal control small RNAs RNU19 and HY3 for human samples and U87 for rat samples. For the mRNA samples, ribosomal 18S was used as an internal control. Individual RT-PCRs were performed on a CFX96 (Bio-Rad) according to the manufacturers' instructions. RT-PCR analyses from cell cultures were performed in triplicate as three independent experiments.

Northern Blots for microRNAs.

For northern blot analysis, total RNA (10 Ug) was resolved on a 15o/o denaturing polyacrylamide gel and transferred to Hybond N+ nylon membrane (Amersham). The membranes were crosslinked using stratagene UV crosslinker and prehybridization were performed at 58° C. in DIG Easy Hyb (Roche). Probes for miR-424 and miR-503 (DlG labeled LNA probes, Exiqon) were mixed with DIG Easy Hyb and incubated overnight at 58'C and were washed with 2×SSC, 0.1% SDS for 15 min at 50° C. and then with 0.5×SSC, 0.1% SDS for an additional 15 min at 50° C. The blot was blocked with 5% milk powder in PBST for 30 min at RT and incubated with anti-DlG-AP (Roche) in blocking buffer for 1 hour at room temperature. After washing, detection was performed with CDP-star chemiluminescent substrate (Roche).

Lentivirus Production.

Lenti-miR microRNA precursors for hsa-miR-424 and hsa-miR-503 were used (System Biosciences). For APLN overexpression in PAECs, full length human APLN cDNA (Origene) was cloned into CD511B-1 lentiviral vector (System Biosciences). The Lenti-X HTX Packaging System (Clontech) with Lenti-X Concentrator was used to generate the lentivirus particles for intranasal delivery and in vitro cellular transduction.

Animal Studies.

Animal experiments performed in this study were approved by the Institutional Animal Care and Use Committee of Yale University. Apln knockout mice have been described previously (Chandra et al., *Arterioscler. Thromb. Vasc. Biol.* 31, 814-820 (2011)).

Monocrotaline and SU-541G/Hypoxia Induction of Pulmonary Hypertension and Intranasal Administration of Lentivirus.

Sprague Dawley rats (200-250 grams) were subcutaneously injected with monocrotaline (60 mg/kg) (Sigma). For the SU-5416/hypoxia model, SU-5416 (20 mg/kg) (Sigma) was resuspended in DMSO and injected subcutaneously. Rats were subsequently exposed to hypoxia (10% $FlO_2$) for three weeks. Intranasal administration of either the lenti-GFP or lenti-424/503-GFP ($2 \times 10^{10}$ pfu/intranasal delivery/rat) was performed at the designated times (FIG. 63)). Rats were first anesthetized with inhaled isoflurane and subsequently lentiviral droplets (~250 µL) was placed over their nares for inhalation.

Immunohistochemistry of Lung Sections.

Small pieces of fixed human and rat lung tissue were rehydrated through an ethanol series to 1×PBS and cryo-protected in 30% sucrose/1×PBS at 4° C. overnight. Tissue was then embedded in OCT (Sakura Tissue-Tek), frozen solid in cryomolds, sectioned on a Leica CM1950 at 10 µm and stored at −20° C. Cryosections were then air-dried for 10 minutes at room temperature, and rehydrated in 1×PBS for 15 minutes at room temperature. Sections were treated with 5% $H_2O_2$/1× PBS for 30 min at room temperature to reduce auto fluorescence from elastic lamina and red blood cells. Sections were washed in 1×PBS, blocked in 5% heat-inactivated goat serum in 1×PBS for 1 h at room temperature, and then probed with primary antibody overnight at 4° C. After incubation, slides were washed with 1×PBS, blocked for 1 hour at room temperature, and probed with Alexa 488 goat a rabbit and DAPI at 10 µg/ml overnight at 4° C. After washing, slides were mounted in mounting media (DAKO) and sealed with nail polish. Hematoxylin and eosin staining was performed using standard methods.

Proliferation Assays.

PAECs ($5 \times 10^3$ cells/well) were plated to a 96-well plate and transfected with miRNA or anti-miRNAs with Lipofectamine RNAiMax (Invitrogen). PAEC proliferation was assessed under basal condition (2% FCS). For the MTT assay, cell proliferation was measured by the CellTiter 96® AQueous One Solution Cell Proliferation Assay kit (Promega). To assess PASMC proliferation, PASMCs were seeded at $2 \times 10^4$ cells per well in a 24-well plate. The cells were allowed to adhere for 24 h then washed three times and starved in serum free media for 48 h. These quiescent cells were then stimulated with conditioned media and proliferation measured using the MTT assay. To assess dynamic cell proliferation, the xCELLigence system (Roche) was used, which monitors cell growth in response to APLN treatment in real-time in PAH ECs. PAH ECs were seeded at 2,000 cells per well in 96 well E-Plates. The cells were monitored every 30 minutes for the indicated period.

Cell Cycle Analysis/Flow Cytometry.

PAECs transfected with miRNA mimics or antago-miRs were fixed in ethanol, treated with RNase A and subsequently stained with propidium iodide (PI). DNA content was analyzed by flow cytometry (BD FACScan). Data quantification was performed using FlowJo 7.6. Flow cytometry for CD31/GFP was performed using BD FACScan and data analyzed using FlowJo 7.6.

Cell Migration Assay.

PAEC migration was analyzed using a 24-well cell-migration assay (Radius Assay, Cell Biolabs, Inc.) per manufacturer's protocol. Migration images were captured with microscope and migration closure was measured using image J software.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. A composition comprising an effective amount of an inhibitor of fibroblast growth factor 2 (FGF2) expression comprising at least one of: a mature sequence of miR-424 and miR-503; a pri-miRNA of miR-424 and miR-503; a pre-miRNA of miR-424 and miR-503; and the complement thereof, wherein the composition is formulated for delivery to a pulmonary endothelial cell and wherein the composition reduces proliferation of the pulmonary endothelial cell.

2. The composition of claim 1, wherein the mature sequence comprises a polynucleotide selected from the group consisting of: a nucleotide sequence as shown in SEQ ID NO: 9 or SEQ ID NO: 10; a nucleotide sequence consisting of 30 to 120 nucleotides which has an identity of at least 85% to the nucleotide sequence as shown in SEQ ID NO: 9 or SEQ ID NO: 10; or the complement thereof.

3. The composition of claim 1, wherein the inhibitor is expressed by a recombinant expression vector.

4. A pharmaceutical composition for reducing proliferation of pulmonary vascular cells in a subject in need thereof comprising the composition of claim 1 and a pharmaceutically acceptable carrier.

5. A method of reducing proliferation of pulmonary vascular cells in a subject in need thereof comprising administering to the pulmonary vascular cells of the subject the composition of claim 1, wherein the proliferation of pulmonary vascular cells is reduced in the subject following administration of the composition.

6. The method of claim 5, wherein the mature sequence comprises a polynucleotide selected from the group consisting of: a nucleotide sequence as shown in SEQ ID NO: 9 or SEQ ID NO: 10; a nucleotide sequence consisting of 30 to 120 nucleotides which has an identity of at least 85% to the nucleotide sequence as shown in SEQ ID NO: 9 or SEQ ID NO: 10; or the complement thereof, wherein the pulmonary arterial hypertension is reduced in the subject following administration of the composition.

7. A method of treating pulmonary arterial hypertension in a subject in need thereof comprising administering to the pulmonary vascular cells of the subject the composition of claim 1, wherein the pulmonary arterial hypertension is reduced in the subject following administration of the inhibitor.

8. The method of claim 7, wherein the mature sequence comprises a polynucleotide selected from the group consisting of: a nucleotide sequence as shown in SEQ ID NO: 9 or SEQ ID NO: 10; a nucleotide sequence consisting of 30 to 120 nucleotides which has an identity of at least 85% to the nucleotide sequence as shown in SEQ ID NO: 9 or SEQ ID NO: 10; or the complement thereof.

9. The method of claim 7, wherein the step of administering the inhibitor further comprises administering a recombinant expression vector comprising the inhibitor.

\* \* \* \* \*

SEQUENCE LISTING

```
<160> NUMBER OF SEQ ID NOS: 29

<210> SEQ ID NO 1
<211> LENGTH: 77
<212> TYPE: PRT
<213> ORGANISM: Homo sapiens

<400> SEQUENCE: 1

Met Asn Leu Arg Leu Cys Val Gln Ala Leu Leu Leu Trp Leu Ser
1               5                   10                  15

Leu Thr Ala Val Cys Gly Gly Ser Leu Met Pro Leu Pro Asp Gly Asn
                20                  25                  30

Gly Leu Glu Asp Gly Asn Val Arg His Leu Val Gln Pro Arg Gly Ser
            35                  40                  45

Arg Asn Gly Pro Gly Pro Trp Gln Gly Gly Arg Arg Lys Phe Arg Arg
        50                  55                  60

Gln Arg Pro Arg Leu Ser His Lys Gly Pro Met Pro Phe
65                  70                  75

<210> SEQ ID NO 2
<211> LENGTH: 3238
<212> TYPE: DNA
<213> ORGANISM: Homo sapiens

<400> SEQUENCE: 2
gagcattctc tctggcagcc ggggtcacgg gcagttgcag ccgcggccga gcagccagcc        60
gctaagaaag agctcgccgc tgccgctccc ggagccgccg aggccagctt cgcggcgctg       120
ccccgcggcg ggagaggagg ctgcagaaga gcggaggcgg ccagcgggag cggcggggct       180
cagcgcgcac actcagcggc cggggagcct cccgagctct gcgcccgcac gcgccagccg       240
cggctcgcgc ctttcttggc ctccgggcgc ccgacctctc ctccccgcg ccggctcgcc        300 ggggccgcgg cggcccaagg agcagcatga atctgcggct ctgcgtgcag gcgctcctgc      360
tgctctggct ctccttgacc gcggtgtgtg gagggtccct gatgccgctt cccgatggga      420
atgggctgga agacggcaat gtccgccacc tggtgcagcc cagagggtca aggaatgggc      480
cagggccctg gcagggaggt cggaggaaat tccgccgcca gcggccccgc ctctcccata       540
agggacccat gcctttctga agcaggactg aagggccccc caagtgccca ccccggcgg       600 ttatgtctcc tccatagatt ggtctgcttc tctggaggcc tcacgtccat tcagctctca      660
cctcgcacct gctgtagcca ccagtgggcc cagctcttct cacctgcctg cttcccccag      720
tggcgtgctc ctggctgtag tttggatgat tcccgttctc tcacaagaat ccgtccagtc      780
catcttcctg gcccctccct ggactgactt tggagaccta gccccagaaa gcctcccttc      840
ttctccaggt cccctccgcc ctagtccctg cctgtctcat ctaacgcccc aaaccttcat      900
ttgggccttc cttcctcatg tctgccctga gcgcggggtg gaagtgctcc cttctgtggg      960
```

```
ctccagcaga tcccttgttt tcctgtcagt tggacccctc acctggcctc cagggaagaa    1020
tgcagagaaa agcaaggaga gactctagtt aagaggtgct ggctgcgggg atccagacag    1080
ggcacattgg gggcatggaa gtgccagggt ggttttcagg agctctggtg aagtgggtgg    1140
agcatcagcg tttgctcagt taagggagag gtagagaggg gcccgtgaag tcctttgtca    1200
cttctcttgc cttagtgtgc ctcccaatac tcccttcttc ctgcccccac accccatccc    1260
cagctagccc aagctccagg tcaggagggg agggtgctgg gcctgacatg gctatatacc    1320
ctcccaggag taaaagccaa gcaagaggtt gttttttgcca agaatcacag aatgttagag    1380
ctgacaggac ccttgaaggt cacttagcct tcttaggcaa acgcctgcaa aacagaagcc    1440
tggagagggg agtgacctgc tcagagtcat tgcagagccg ggatggggac caggtctccc    1500
atctcctact ttatgacgcc ctcttccctc ttgatgatgt cttttcaaag caaatgaagt    1560
gccttttccc gaggctgggg ctggggggtgg ctgggagggg aagggaaggg agaggcaagc    1620
tggctgtgaa ctgtcctgtt gtggggctgg agctgctccc acctccctga cctacccctg    1680
ctgcaccatt cccccagctg ggctggaagg ttccataact ggccagctgc ccccataact    1740
ggcagcattc ccagacccag ggtactctaa taggggcggc tcaggcactg agactaccgc    1800
tcaaccccag ggtggttttc aggagtccga ggtagccttc aatcactgga ctccatggcc    1860
ttcccttcgt gttgaccgga ccttccttcc agggcttttc ctttggggga ggcggagagg    1920
ggagaagaag gaagggaagg gcagaaggaa ggagggaaga aaagaaagca aaggaacaga    1980
aggaaggaaa gaaagatggg aggaagtgca gcaggaatag caccctctcc ccgggaggcc    2040
ctagcttccg tgaggggcca tcaccagcca ttccttggag ggggctttct cccctttgc     2100
ttgagcaggg ttcccaggag ggagaaagag aagacaagag cctgatgccc aactttgtgt    2160
gtgtggggac gggggagtca gggccccca agtcccacaa tagccccaat gtttgcctat    2220
ccacctcccc caagccccctt tacctatgct gctgctaacg ctgctgctgc tgctgctgct    2280
gcttaaaggc tcatgcttgg agtggggact ggtcggtgcc cagaaagtct cttctgccac    2340
tgacgccccc atcagggatt gggccttctt tccccttcc tttctgtgtc tcctgcctca    2400
tcggcctgcc atgacctgca gccaagccca gccccgtggg gaaggggaga agtgggggga    2460
tggctaagaa agctgggaga tagggaacag aagagggtag tgggtgggct agggggctg    2520
ccttatttaa agtggttgtt tatgattctt atactaattt atacaaagat attaaggccc    2580
tgttcattaa gaaattgttc ccttcccctg tgttcaatgt ttgtaaagat tgttctgtgt    2640
aaatatgtct ttataataaa cagttaaaag ctgacagttc gcccttactc ttggaggtca    2700
tgttcaggag gggcattcct ttcccctggg ggtcatgggt gtcccatgc ccacatattg     2760
cacgtgcagg gaggtaagtg cctgcatccc aaatcggttc taggtcaact ggcctcaaac    2820
tgatttgcca tgagctcaca aaatgaatcc ctatgcttaa tgaccaggtc acataaaatc    2880
cagcccactt acaggttttc tggcatctgt ttgggtgtcc taattttttt ggcagtgtca    2940
tttgaagaat ttttttaaag cagtttattt aagaacatac tgattaaatg caggatcgct    3000
actaaaaatt gttttgtatc cttggtgggt gtcttctgct attttatcta cttttgaaca    3060
ctttcaggac ttttttagcca gtttgccttt cttgaaaaat gttatgtttt cagcaataaa    3120
tacatttgat aatgactttg tttgtatcat tttatgtttc acaaagtaga gttgcttgat    3180
gaatgagata gcctgaaaaa taaaatgcaa agagttcaat ataaaaaaaa aaaaaaaa     3238

<210> SEQ ID NO 3
<211> LENGTH: 380
```

```
<212> TYPE: PRT
<213> ORGANISM: Homo sapiens

<400> SEQUENCE: 3

Met Glu Glu Gly Gly Asp Phe Asp Asn Tyr Tyr Gly Ala Asp Asn Gln
1               5                   10                  15

Ser Glu Cys Glu Tyr Thr Asp Trp Lys Ser Ser Gly Ala Leu Ile Pro
            20                  25                  30

Ala Ile Tyr Met Leu Val Phe Leu Leu Gly Thr Thr Gly Asn Gly Leu
        35                  40                  45

Val Leu Trp Thr Val Phe Arg Ser Arg Glu Lys Arg Arg Ser Ala
    50                  55                  60

Asp Ile Phe Ile Ala Ser Leu Ala Val Ala Asp Leu Thr Phe Val Val
65                  70                  75                  80

Thr Leu Pro Leu Trp Ala Thr Tyr Thr Tyr Arg Asp Tyr Asp Trp Pro
                85                  90                  95

Phe Gly Thr Phe Phe Cys Lys Leu Ser Ser Tyr Leu Ile Phe Val Asn
            100                 105                 110

Met Tyr Ala Ser Val Phe Cys Leu Thr Gly Leu Ser Phe Asp Arg Tyr
        115                 120                 125

Leu Ala Ile Val Arg Pro Val Ala Asn Ala Arg Leu Arg Leu Arg Val
    130                 135                 140

Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

Thr Lys Val Gln Cys Tyr Met Asp Tyr Ser Met Val Ala Thr Val Ser
            180                 185                 190

Ser Glu Trp Ala Trp Glu Val Gly Leu Gly Val Ser Ser Thr Thr Val
        195                 200                 205

Gly Phe Val Val Pro Phe Thr Ile Met Leu Thr Cys Tyr Phe Phe Ile
    210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Val Leu Val Val Thr
                245                 250                 255

Phe Ala Leu Cys Trp Met Pro Tyr His Leu Val Lys Thr Leu Tyr Met
            260                 265                 270

Leu Gly Ser Leu Leu His Trp Pro Cys Asp Phe Asp Leu Phe Leu Met
        275                 280                 285

Asn Ile Phe Pro Tyr Cys Thr Cys Ile Ser Tyr Val Asn Ser Cys Leu
    290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335

Ser Ser Ser Gly Glu Lys Ser Ala Ser Tyr Ser Ser Gly His Ser Gln
            340                 345                 350

Gly Pro Gly Pro Asn Met Gly Lys Gly Gly Glu Gln Met His Glu Lys
        355                 360                 365

Ser Ile Pro Tyr Ser Gln Glu Thr Leu Val Val Asp
    370                 375                 380

<210> SEQ ID NO 4
```

<211> LENGTH: 3905
<212> TYPE: DNA
<213> ORGANISM: Homo sapiens

<400> SEQUENCE: 4

| | | | | | |
|---|---|---|---|---|---|
| ggaaagccga | cttgcaaaac | cacagataat | gttcagccca | gcacagtagg | ggtcaatttg | 60 |
| gtccacttgc | tcagtgacaa | aagaaaaaa | aagtgggct | gtcactaaag | attttgactc | 120 |
| acaagagagg | ggctggtctg | gaggtgggag | gagggagtga | cgagtcaagg | aggagacagg | 180 |
| gacgcaggag | ggtgcaagga | agtgtcttaa | ctgagacggg | ggtaaggcaa | gagagggtgg | 240 |
| aggaaattct | gcaggagaca | ggcttcctcc | agggtctgga | gaacccagag | gcagctcctc | 300 |
| ctgagtgctg | ggaaggactc | tgggcatctt | cagcccttct | tactctctga | ggctcaagcc | 360 |
| agaaattcag | gctgcttgca | gagtgggtga | cagagccacg | gagctggtgt | ccctgggacc | 420 |
| ctctgcccgt | cttctctcca | ctccccagca | tggaggaagg | tggtgatttt | gacaactact | 480 |
| atggggcaga | caaccagtct | gagtgtgagt | acacagactg | gaaatcctcg | ggggccctca | 540 |
| tccctgccat | ctacatgttg | gtcttcctcc | tgggcaccac | gggcaacggt | ctggtgctct | 600 |
| ggaccgtgtt | tcggagcagc | cgggagaaga | ggcgctcagc | tgatatcttc | attgctagcc | 660 |
| tggcggtggc | tgacctgacc | ttcgtggtga | cgctgccccct | gtgggctacc | tacacgtacc | 720 |
| gggactatga | ctggcccttt | gggaccttct | tctgcaagct | cagcagctac | ctcatcttcg | 780 |
| tcaacatgta | cgccagcgtc | ttctgcctca | ccggcctcag | cttcgaccgc | tacctggcca | 840 |
| tcgtgaggcc | agtggccaat | gctcggctga | ggctgcgggt | cagcggggcc | gtggccacgg | 900 |
| cagttctttg | ggtgctggcc | gccctcctgg | ccatgcctgt | catggtgtta | cgcaccaccg | 960 |
| gggacttgga | gaacaccact | aaggtgcagt | gctacatgga | ctactccatg | gtggccactg | 1020 |
| tgagctcaga | gtgggcctgg | gaggtgggcc | ttggggtctc | gtccaccacc | gtgggctttg | 1080 |
| tggtgccctt | caccatcatg | ctgacctgtt | acttcttcat | cgcccaaacc | atcgctggcc | 1140 |
| acttccgcaa | ggaacgcatc | gagggcctgc | ggaagcggcg | ccggctgctc | agcatcatcg | 1200 |
| tggtgctggt | ggtgaccttt | gccctgtgct | ggatgcccta | ccacctggtg | aagacgctgt | 1260 |
| acatgctggg | cagcctgctg | cactggccct | gtgactttga | cctcttcctc | atgaacatct | 1320 |
| tcccctactg | cacctgcatc | agctacgtca | acagctgcct | caacccctte | ctctatgcct | 1380 |
| ttttcgaccc | ccgcttccgc | caggcctgca | cctccatgct | ctgctgtggc | cagagcaggt | 1440 |
| gcgcaggcac | ctcccacagc | agcagtgggg | agaagtcagc | cagctactct | cgggggcaca | 1500 |
| gccaggggcc | cggccccaac | atgggcaagg | gtggagaaca | gatgcacgag | aaatccatcc | 1560 |
| cctacagcca | ggagacccct | gtggttgact | agggctggga | gcagagagaa | gcctggcgcc | 1620 |
| ctcggccctc | cccggccttt | gcccttgctt | tctgaaaatc | aggtagtgtg | gctactcctt | 1680 |
| gtcctatgca | catcctttaa | ctgtcccctg | attctgcccc | gccctgtcct | cctctactgc | 1740 |
| tttattcttt | ctcagaggtt | tgtggtttag | gggaaagaga | ctgggctcta | cagacctgac | 1800 |
| cctgcacaag | ccatttaatc | tcactcagcc | tcagtttctc | cattggtatg | aaatggggga | 1860 |
| aagtcatatt | gatcctaaaa | tgttgaagcc | tgagtctgga | cgcagtaaaa | gcttgtttcc | 1920 |
| ctctgctgct | tcttagatc | tgcaatcgtc | tttcctccct | tctttccttg | tagtttttcc | 1980 |
| cccaccactc | tctgcagctg | ccgctcctta | tccctgcctt | ctggcaccaa | tcccctccta | 2040 |
| cagctcgtcc | ccctccctcc | atccatcctt | ctccctgtc | tactttcttg | ttctgaaggg | 2100 |
| ctactaaggg | ttaaggatcc | caagcttgc | agagactgac | cctgtttaag | cttttctatcc | 2160 |
| tgttttctga | gtgtgaggca | gggaatgggc | tggggccggg | ggtgggctgt | gtgtcagcag | 2220 |

-continued

```
ataattagtg ctccagccct tagatctggg agctccagag cttgccctaa aattggatca    2280
cttccctgtc attttgggca ttggggctag tgtgattcct gcagttcccc catggcacca    2340
tgacactgac tagatatgct ttctccaaat tgtccgcaga ccctttcatc cttcctctat    2400
tttctatgag aattggaagg cagcagggct gatgaatgga tgtactcctt ggtttcatta    2460
tgtgagtggg gagttgggaa gggcaactag agagagagga tggaggggtg tctgcattta    2520
gtccagacac tgcttggctc gctccccgag tcctcctgtt tctgacttcc tgcataactg    2580
tgagctgaag ggtttcctca tctccccatc ttaccccatc atactgattt ctttcttggg    2640
cactggtgct acttggtgcc aagaatcatg ttgtttggga tggagatgcc tgcctcttgt    2700
ctgtgtgtgt tgtacttata tgtctatatg gatgagcctg gcatgaacag cagtgtgcct    2760
gggtcatttg gacaaatctc ctcccacccc ccaatccact gcaactctgc tgttcacaca    2820
ttacccttgg caggggtgg tggggggcag ggacacactg aggcaatgaa aaatgtagaa    2880
taaaaatgag tccaccccct actggatttg ggggctccaa cggctggtcc gtgctttagg    2940
agcgaagtta atgtttgcac caggcttcct gtagggagat ccctccccaa agcagctggc    3000
gccaaggctt gggggcgtcc tactgagctg ggttcctgct ccttcttggg ctccatgaag    3060
gaagtaagag gctagttgag agcctccctt ggccccttc cggtgcctcc ccgcctggct    3120
tcaaatttat gagcattgcc ctcatcgtcc tttcttgttc cagggtcagt ggccctcttc    3180
ctaaggaggc ctcctgcttg ccatgggcca aaggcacgg ggtgggtttt ttctctccct    3240
accctcagga ttggacctct tggcttctgc tggattgggg atctgggaat agggactgga    3300
gcaagtgtgc agatagcatg atgtctacac tgccagagag accgtgagga tgaaattaat    3360
agtggggcct ttgtgagcta gaggctggga gtgtctattc cgggttttgt tcttggagga    3420
ctatgaaagt gaaggacaag acatgagcga tggagataag aaaagcccag cttgatgtga    3480
atggacatct tgaccctccc tggaatgacg ccagctctgg gggcagaggg aggaggagag    3540
gggaaggggc tcctcacagc ctagtctccc catcttaaga tagcatcttt cacagagtca    3600
cctcctctgc ccagagctgt cctcaaagca tccagtgaac actggaagag gcttctagaa    3660
gggaagaaat tgtccctctg aggccgccgt gggtgacctg cagagacttc ctgcctggaa    3720
ctcatctgtg aactgggaca gaagcagagg aggctgcctg ctgtgatacc cccttacctc    3780
ccccagtgcc ttcttcagaa tatctgcact gtcttctgat cctgttagtc actgtggttc    3840
atcaaataaa actgtttgtg caactgttgt gtccaaaaaa aaaaaaaaa aaaaaaaaa    3900
aaaaa                                                                 3905
```

<210> SEQ ID NO 5
<211> LENGTH: 820
<212> TYPE: PRT
<213> ORGANISM: Homo sapiens

<400> SEQUENCE: 5

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60
```

```
Asn Trp Leu Arg Asp Gly Val Gln Leu Ala Glu Ser Asn Arg Thr Arg
 65                  70                  75                  80

Ile Thr Gly Glu Glu Val Glu Val Gln Asp Ser Val Pro Ala Asp Ser
                 85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Ser Ser Glu Glu Lys Glu Thr Asp Asn Thr
130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365

Met Thr Ser Pro Leu Tyr Leu Glu Ile Ile Ile Tyr Cys Thr Gly Ala
370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Ser Ala Asp Ser Ser
            420                 425                 430

Ala Ser Met Asn Ser Gly Val Leu Leu Val Arg Pro Ser Arg Leu Ser
        435                 440                 445

Ser Ser Gly Thr Pro Met Leu Ala Gly Val Ser Glu Tyr Glu Leu Pro
450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
```

```
                    485                 490                 495
Gly Leu Asp Lys Asp Lys Pro Asn Arg Val Thr Lys Val Ala Val Lys
                500                 505                 510
Met Leu Lys Ser Asp Ala Thr Glu Lys Asp Leu Ser Asp Leu Ile Ser
            515                 520                 525
Glu Met Glu Met Met Lys Met Ile Gly Lys His Lys Asn Ile Ile Asn
        530                 535                 540
Leu Leu Gly Ala Cys Thr Gln Asp Gly Pro Leu Tyr Val Ile Val Glu
545                 550                 555                 560
Tyr Ala Ser Lys Gly Asn Leu Arg Glu Tyr Leu Gln Ala Arg Arg Pro
                565                 570                 575
Pro Gly Leu Glu Tyr Cys Tyr Asn Pro Ser His Asn Pro Glu Glu Gln
                580                 585                 590
Leu Ser Ser Lys Asp Leu Val Ser Cys Ala Tyr Gln Val Ala Arg Gly
            595                 600                 605
Met Glu Tyr Leu Ala Ser Lys Lys Cys Ile His Arg Asp Leu Ala Ala
        610                 615                 620
Arg Asn Val Leu Val Thr Glu Asp Asn Val Met Lys Ile Ala Asp Phe
625                 630                 635                 640
Gly Leu Ala Arg Asp Ile His His Ile Asp Tyr Tyr Lys Lys Thr Thr
                645                 650                 655
Asn Gly Arg Leu Pro Val Lys Trp Met Ala Pro Glu Ala Leu Phe Asp
                660                 665                 670
Arg Ile Tyr Thr His Gln Ser Asp Val Trp Ser Phe Gly Val Leu Leu
            675                 680                 685
Trp Glu Ile Phe Thr Leu Gly Gly Ser Pro Tyr Pro Gly Val Pro Val
        690                 695                 700
Glu Glu Leu Phe Lys Leu Leu Lys Glu Gly His Arg Met Asp Lys Pro
705                 710                 715                 720
Ser Asn Cys Thr Asn Glu Leu Tyr Met Met Met Arg Asp Cys Trp His
                725                 730                 735
Ala Val Pro Ser Gln Arg Pro Thr Phe Lys Gln Leu Val Glu Asp Leu
                740                 745                 750
Asp Arg Ile Val Ala Leu Thr Ser Asn Gln Glu Tyr Leu Asp Leu Ser
            755                 760                 765
Met Pro Leu Asp Gln Tyr Ser Pro Ser Phe Pro Asp Thr Arg Ser Ser
        770                 775                 780
Thr Cys Ser Ser Gly Glu Asp Ser Val Phe Ser His Glu Pro Leu Pro
785                 790                 795                 800
Glu Glu Pro Cys Leu Pro Arg His Pro Ala Gln Leu Ala Asn Gly Gly
                805                 810                 815
Leu Lys Arg Arg
            820

<210> SEQ ID NO 6
<211> LENGTH: 5895
<212> TYPE: DNA
<213> ORGANISM: Homo sapiens

<400> SEQUENCE: 6
agatgcaggg gcgcaaacgc caaaggagac caggctgtag gaagagaagg gcagagcgcc      60
ggacagctcg gcccgctccc cgtcctttgg ggccgcggct ggggaactac aaggcccagc     120
aggcagctgc agggggcgga ggcggaggag ggaccagcgc gggtgggagt gagagagcga     180
```

-continued

```
gccctcgcgc cccgccggcg catagcgctc ggagcgctct tgcggccaca ggcgcggcgt    240
cctcggcggg gggcggcagc tagcgggagc cgggacgccg gtgcagccgc agcgcgcgga    300
ggaacccggg tgtgccggga gctgggcggc cacgtccgga cgggaccgag acccctcgta    360
gcgcattgcg gcgacctcgc cttccccggc cgcgagcgcg ccgctgcttg aaaagccgcg    420
gaacccaagg acttttctcc ggtccgagct cggggcgccc cgcagggcgc acggtacccg    480
tgctgcagtc gggcacgccg cggcgccggg gcctccgcag ggcgatggag cccggtctgc    540
aaggaaagtg aggcgccgcc gctgcgttct ggaggagggg ggcacaaggt ctggagaccc    600
cgggtggcgg acgggagccc tcccccgcc ccgcctccgg ggcaccagct ccggctccat    660
tgttcccgcc cgggctggag gcgccgagca ccgagcgccg ccgggagtcg agcgccggcc    720
gcggagctct tgcgacccg ccaggaccg aacagagccc gggcggcg ggccggagcc    780 ggggacgcgg gcacacgccc gctcgcacaa gccacggcgg actctcccga ggcggaacct    840
ccacgccgag cgagggtcag tttgaaaagg aggatcgagc tcactgtgga gtatccatgg    900
agatgtggag ccttgtcacc aacctctaac tgcagaactg ggatgtggag ctggaagtgc    960
ctcctcttct gggctgtgct ggtcacagcc acactctgca ccgctaggcc gtccccgacc   1020
ttgcctgaac aagcccagcc ctggggagcc cctgtggaag tggagtcctt cctggtccac   1080
cccggtgacc tgctgcagct tcgctgtcgg ctgcgggacg atgtgcagag catcaactgg   1140
ctgcgggacg gggtgcagct ggcggaaagc aaccgcaccc gcatcacagg ggaggaggtg   1200
gaggtgcagg actccgtgcc cgcagactcc ggcctctatg cttgcgtaac cagcagcccc   1260
tcgggcagtg acaccaccta cttctccgtc aatgtttcag atgctctccc ctcctcggag   1320
gatgatgatg atgatgatga ctcctcttca gaggagaaag aaacagataa caccaaacca   1380
aaccgtatgc ccgtagctcc atattggaca tccccagaaa agatggaaaa gaaattgcat   1440
gcagtgccgg ctgccaagac agtgaagttc aaatgcccctt ccagtgggac cccaaacccc   1500
acactgcgct ggttgaaaaa tggcaaagaa ttcaaacctg accacagaat ggaggctac   1560 aaggtccgtt atgccaccctg agcatcata atggactctg tggtgccctc tgacaagggc   1620
aactacacct gcattgtgga gaatgagtac ggcagcatca ccacacata ccagctggat   1680 gtcgtggagc ggtcccctca ccggcccatc ctgcaagcag ggttgcccgc caacaaaaca   1740
gtggccctgg gtagcaacgt ggagttcatg tgtaaggtgt acagtgaccc gcagccgcac   1800
atccagtggc taaagcacat cgaggtgaat gggagcaaga ttggcccaga caacctgcct   1860
tatgtccaga tcttgaagac tgctggagtt aataccaccg acaaagagat ggaggtgctt   1920
cacttaagaa atgtctcctt tgaggacgca ggggagtata cgtgcttggc gggtaactct   1980
atcggactct cccatcactc tgcatggttg accgttctgg aagccctgga agagaggccg   2040
gcagtgatga cctcgcccct gtacctggag atcatcatct attgcacagg ggccttcctc   2100
atctcctgca tggtggggtc ggtcatcgtc tacaagatga agagtggtac caagaagagt   2160
gacttccaca gccagatggc tgtgcacaag ctggccaaga gcatccctct cgcagacag   2220 gtgtctgctg actccagtgc atccatgaac tctgggttc ttctggttcg gccatcacgg   2280
ctctcctcca gtgggactcc catgctagca ggggtctctg agtatgagct tcccgaagac   2340
cctcgctggg agctgcctcg ggacagactg gtcttaggca aacccctggg agagggctgc   2400
tttgggcagg tggtgttggc agaggctatc gggctggaca aggacaaacc caaccgtgtg   2460
accaaagtgg ctgtgaagat gttgaagtcg acgcaacag agaaagactt gtcagacctg   2520
atctcagaaa tggagatgat gaagatgatc gggaagcata agaatatcat caacctgctg   2580
```

```
ggggcctgca cgcaggatgg tcccttgtat gtcatcgtgg agtatgcctc caagggcaac      2640
ctgcgggagt acctgcaggc ccggaggccc cagggctgg aatactgcta caaccccagc       2700
cacaacccag aggagcagct ctcctccaag acctggtgt cctgcgccta ccaggtggcc       2760
cgaggcatgg agtatctggc ctccaagaag tgcatacacc gagacctggc agccaggaat     2820
gtcctggtga cagaggacaa tgtgatgaag atagcagact ttggcctcgc acgggacatt      2880
caccacatcg actactataa aaagacaacc aacggccgac tgcctgtgaa gtggatggca     2940
cccgaggcat tatttgaccg gatctacacc caccagagtg atgtgtggtc tttcggggtg      3000
ctcctgtggg agatcttcac tctgggcggc tccccatacc ccgtgtgcc tgtggaggaa      3060 cttttcaagc tgctgaagga gggtcaccgc atggacaagc ccagtaactg caccaacgag     3120
ctgtacatga tgatgcggga ctgctggcat gcagtgccct cacagagacc caccttcaag     3180
cagctggtgg aagacctgga ccgcatcgtg gccttgacct ccaaccagga gtacctggac    3240
ctgtccatgc ccctggacca gtactccccc agctttcccg acacccggag ctctacgtgc     3300
tcctcagggg aggattccgt cttctctcat gagccgctgc ccgaggagcc ctgcctgccc     3360
cgacacccag cccagcttgc caatggcgga ctcaaacgcc gctgactgcc acccacacgc    3420
cctccccaga ctccaccgtc agctgtaacc ctcacccaca gccctgctg gcccaccac      3480 ctgtccgtcc ctgtcccctt tcctgctggc aggagccggc tgcctaccag ggccttcct    3540 gtgtggcctg ccttcacccc actcagctca cctctccctc cacctcctct ccacctgctg    3600
gtgagaggtg caaagaggca gatctttgct gccagccact tcatcccctc ccagatgttg    3660
gaccaacacc cctccctgcc accaggcact gcctggaggg cagggagtgg gagccaatga   3720
acaggcatgc aagtgagagc ttcctgagct ttctcctgtc ggtttggtct gttttgcctt      3780
cacccataag cccctcgcac tctggtggca ggtgccttgt cctcagggct acagcagtag    3840
ggaggtcagt gcttcgtgcc tcgattgaag gtgacctctg ccccagatag gtggtgccag    3900
tggcttatta attccgatac tagtttgctt tgctgaccaa atgcctggta ccagaggatg    3960
gtgaggcgaa ggccaggttg ggggcagtgt tgtggccctg gggcccagcc ccaaactggg    4020
ggctctgtat atagctatga agaaaacaca aagtgtataa atctgagtat atatttacat     4080 gtcttttaa aagggtcgtt accagagatt tacccatcgg gtaagatgct cctggtggct    4140
gggaggcatc agttgctata tattaaaaac aaaaagaaa aaaaggaaa atgtttttaa      4200 aaaggtcata tattttttgc tactttgct gttttatttt tttaaattat gttctaaacc      4260 tatttcagt ttaggtccct caataaaat tgctgctgct tcatttatct atgggctgta      4320 tgaaagggt gggaatgtcc actggaaaga agggacaccc acgggccctg ggctaggtc      4380 tgtcccgagg gcaccgcatg ctcccggcgc aggttccttg taacctcttc ttcctaggtc    4440
ctgcacccag acctcacgac gcacctcctg cctctccgct gcttttggaa agtcagaaaa    4500
agaagatgtc tgcttcgagg gcaggaaccc catccatgca gtagaggcgc tgggcagaga    4560
gtcaaggccc agcagccatc gaccatggat ggtttcctcc aaggaaaccg gtgggggttgg    4620 gctggggagg gggcacctac ctaggaatag ccacggggta gagctacagt gattaagagg    4680
aaagcaaggg cgcggttgct cacgcctgta atcccagcac tttgggacac cgaggtgggc    4740
agatcacttc aggtcaggag tttgagacca gcctggccaa cttagtgaaa ccccatctct    4800
actaaaaatg caaaaattat ccaggcatgg tggcacacgc ctgtaatccc agctccacag    4860
gaggctgagg cagaatccct tgaagctggg aggcggaggt tgcagtgagc cgagattgcg    4920
```

| | | | | |
|---|---|---|---|---|
| ccattgcact | ccagcctggg | caacagagaa | acaaaaagg | aaaacaaatg | atgaaggtct | 4980 |
| gcagaaactg | aaacccagac | atgtgtctgc | cccctctatg | tgggcatggt | tttgccagtg | 5040 |
| cttctaagtg | caggagaaca | tgtcacctga | ggctagtttt | gcattcaggt | ccctggcttc | 5100 |
| gtttcttgtt | ggtatgcctc | cccagatcgt | ccttcctgta | tccatgtgac | cagactgtat | 5160 |
| ttgttgggac | tgtcgcagat | cttggcttct | tacagttctt | cctgtccaaa | ctccatcctg | 5220 |
| tccctcagga | acgggggaa | aattctccga | atgttttgg | ttttttggct | gcttggaatt | 5280 |
| tacttctgcc | acctgctggt | catcactgtc | ctcactaagt | ggattctggc | tcccccgtac | 5340 |
| ctcatggctc | aaactaccac | tcctcagtcg | ctatattaaa | gcttatattt | tgctggatta | 5400 |
| ctgctaaata | caaaagaaag | ttcaatatgt | tttcatttct | gtagggaaaa | tgggattgct | 5460 |
| gctttaaatt | tctgagctag | ggattttttg | gcagctgcag | tgttggcgac | tattgtaaaa | 5520 |
| ttctctttgt | ttctctctgt | aaatagcacc | tgctaacatt | acaatttgta | tttatgttta | 5580 |
| aagaaggcat | catttggtga | acagaactag | gaaatgaatt | tttagctctt | aaaagcattt | 5640 |
| gctttgagac | cgcacaggag | tgtctttcct | tgtaaaacag | tgatgataat | ttctgccttg | 5700 |
| gccctacctt | gaagcaatgt | tgtgtgaagg | gatgaagaat | ctaaaagtct | tcataagtcc | 5760 |
| ttgggagagg | tgctagaaaa | atataaggca | ctatcataat | tacagtgatg | tccttgctgt | 5820 |
| tactactcaa | atcacccaca | aatttcccca | aagactgcgc | tagctgtcaa | ataaaagaca | 5880 |
| gtgaaattga | cctga | | | | | 5895 |

<210> SEQ ID NO 7
<211> LENGTH: 288
<212> TYPE: PRT
<213> ORGANISM: Homo sapiens

<400> SEQUENCE: 7

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Arg
                85                  90                  95

Gly Arg Gly Arg Ala Pro Glu Arg Val Gly Gly Arg Gly Arg Gly Arg
            100                 105                 110

Gly Thr Ala Ala Pro Arg Ala Ala Pro Ala Ala Arg Gly Ser Arg Pro
        115                 120                 125

Gly Pro Ala Gly Thr Met Ala Ala Gly Ser Ile Thr Thr Leu Pro Ala
    130                 135                 140

Leu Pro Glu Asp Gly Gly Ser Gly Ala Phe Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys

```
                195                 200                 205
Gly Val Cys Ala Asn Arg Tyr Leu Ala Met Lys Glu Asp Gly Arg Leu
    210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285

<210> SEQ ID NO 8
<211> LENGTH: 6774
<212> TYPE: DNA
<213> ORGANISM: Homo sapiens

<400> SEQUENCE: 8
```

| | | | | | |
|---|---|---|---|---|---|
| cggccccaga | aacccgagc | gagtagggg | cggcgcgcag | gagggaggag | aactgggggc | 60 |
| gcgggaggct | ggtgggtgtg | gggggtggag | atgtagaaga | tgtgacgccg | cggcccggcg | 120 |
| ggtgccagat | tagcggacgc | ggtgcccgcg | gttgcaacgg | gatcccgggc | gctgcagctt | 180 |
| gggaggcggc | tctccccagg | cggcgtccgc | ggagacaccc | atccgtgaac | cccaggtccc | 240 |
| gggccgccgg | ctcgccgcgc | accaggggcc | ggcggacaga | agagcggccg | agcggctcga | 300 |
| ggctggggga | ccgcgggcgc | ggccgcgcgc | tgccggggcgg | gaggctgggg | ggccggggcc | 360 |
| ggggccgtgc | cccggagcgg | gtcggaggcc | ggggccgggg | ccggggacg | gcggctcccc | 420 |
| gcgcggctcc | agcggctcgg | ggatcccggc | cgggccccgc | agggaccatg | gcagccggga | 480 |
| gcatcaccac | gctgcccgcc | ttgcccgagg | atggcggcag | cggcgccttc | ccgcccggcc | 540 |
| acttcaagga | ccccaagcgg | ctgtactgca | aaaacgggggg | cttcttcctg | cgcatccacc | 600 |
| ccgacggccg | agttgacggg | gtccgggaga | gagcgaccc | tcacatcaag | ctacaacttc | 660 |
| aagcagaaga | gagaggagtt | gtgtctatca | aaggagtgtg | tgctaaccgt | tacctggcta | 720 |
| tgaaggaaga | tggaagatta | ctggcttcta | aatgtgttac | ggatgagtgt | ttcttttttg | 780 |
| aacgattgga | atctaataac | tacaatactt | accggtcaag | gaaatacacc | agttggtatg | 840 |
| tggcactgaa | acgaactggg | cagtataaac | ttggatccaa | aacaggacct | gggcagaaag | 900 |
| ctatactttt | tcttccaatg | tctgctaaga | gctgatttta | atggccacat | ctaatctcat | 960 |
| ttcacatgaa | agaagaagta | tattttagaa | atttgttaat | gagagtaaaa | gaaaataaat | 1020 |
| gtgtatagct | cagtttggat | aattggtcaa | acaattttt | atccagtagt | aaaatatgta | 1080 |
| accattgtcc | cagtaaagaa | aaataacaaa | agttgtaaaa | tgtatattct | ccctttata | 1140 |
| ttgcatctgc | tgttacccag | tgaagcttac | ctagagcaat | gatcttttc | acgcatttgc | 1200 |
| tttattcgaa | aagaggcttt | taaaatgtgc | atgtttagaa | acaaaatttc | ttcatggaaa | 1260 |
| tcatatacat | tagaaaatca | cagtcagatg | tttaatcaat | ccaaaatgtc | cactatttct | 1320 |
| tatgtcattc | gttagtctac | atgttttctaa | acatataaat | gtgaatttaa | tcaattcctt | 1380 |
| tcatagtttt | ataattctct | ggcagttcct | tatgatagag | tttataaaac | agtcctgtgt | 1440 |
| aaactgctgg | aagttcttcc | acagtcaggt | caatttgtc | aaaccttct | ctgtacccat | 1500 |
| acagcagcag | cctagcaact | ctgctggtga | tgggagttgt | atttcagtc | ttcgccaggt | 1560 |
| cattgagatc | catccactca | catcttaagc | attcttcctg | gcaaaaattt | atggtgaatg | 1620 |

```
aatatggctt taggcggcag atgatataca tatctgactt cccaaaagct ccaggatttg   1680
tgtgctgttg ccgaatactc aggacggacc tgaattctga ttttataccg gtctcttcaa   1740
aaacttctcg aaccgctgtg tctcctacgt aaaaaagag atgtacaaat caataataat    1800
tacactttta gaaactgtat catcaaagat tttcagttaa agtagcatta tgtaaaggct   1860
caaaacatta ccctaacaaa gtaaagtttt caatacaaat tctttgcctt gtggatatca   1920
agaaatccca aaatattttc ttaccactgt aaattcaaga agcttttgaa atgctgaata   1980
tttcttttgc tgctacttgg aggcttatct acctgtacat ttttggggtc agctcttttt   2040
aacttcttgc tgctctttt cccaaaaggt aaaaatatag attgaaaagt taaaacattt    2100
tgcatggctg cagttccttt gtttcttgag ataagattcc aaagaactta gattcatttc   2160
ttcaacaccg aaatgctgga ggtgtttgat cagttttcaa gaaacttgga atataaataa   2220
ttttataatt caacaaaggt tttcacattt tataaggttg attttcaat taaatgcaaa    2280 tttgtgtggc aggatttta ttgccattaa catattttg tggctgcttt ttctacacat     2340
ccagatggtc cctctaactg gctttctct aattttgtga tgttctgtca ttgtctccca    2400
aagtatttag gagaagccct ttaaaaagct gccttcctct accactttgc tggaaagctt   2460
cacaattgtc acagacaaag atttttgttc caatactcgt tttgcctcta tttttcttgt   2520
ttgtcaaata gtaaatgata tttgcccttg cagtaattct actggtgaaa acatgcaaa    2580 gaagaggaag tcacagaaac atgtctcaat tcccatgtgc tgtgactgta gactgtctta   2640
ccatagactg tcttacccat cccctggata tgctcttgtt ttttccctct aatagctatg   2700
gaaagatgca tagaaagagt ataatgtttt aaaacataag gcattcgtct gccatttttc   2760
aattacatgc tgacttccct tacaattgag atttgcccat aggttaaaca tggttagaaa   2820
caactgaaag cataaaagaa aaatctaggc cgggtgcagt ggctcatgcc tatattccct   2880
gcactttggg aggccaaagc aggaggatcg cttgagccca ggagttcaag accaacctgg   2940 tgaaccccg tctctacaaa aaaacacaaa aaatagccag gcatggtggc gtgtacatgt     3000
ggtctcagat acttgggagg ctgaggtggg agggttgatc acttgaggct gagaggtcaa   3060
ggttgcagtg agccataatc gtgccactgc agtccagcct aggcaacaga gtgagacttt   3120
gtctcaaaaa aagagaaatt ttccttaata agaaagtaa ttttactct gatgtgcaat     3180 acatttgtta ttaaattat tatttaagat ggtagcacta gtcttaaatt gtataaaata    3240 tccctaaca tgtttaaatg tccatttta ttcattatgc tttgaaaaat aattatgggg     3300
aaatacatgt ttgttattaa atttattatt aaagatagta gcactagtct taaatttgat   3360
ataacatctc ctaacttgtt taaatgtcca tttttattct ttatgtttga aaataaatta   3420
tggggatcct atttagctct tagtaccact aatcaaaagt tcggcatgta gctcatgatc   3480
tatgctgttt ctatgtcgtg gaagcaccgg atgggggtag tgagcaaatc tgccctgctc   3540
agcagtcacc atagcagctg actgaaaatc agcactgcct gagtagtttt gatcagttta   3600
acttgaatca ctaactgact gaaaattgaa tgggcaaata agtgcttttg tctccagagt   3660
atgcgggaga cccttccacc tcaagatgga tatttcttcc ccaaggattt caagatgaat   3720 tgaaatttt aatcaagata gtgtgcttta ttctgttgta ttttttatta tttaatata    3780 ctgtaagcca aactgaaata acatttgctg ttttataggt ttgaagaaca taggaaaaac   3840
taagaggttt tgttttatt tttgctgatg aagagatatg tttaaatatg ttgtattgtt    3900
ttgtttagtt acaggacaat aatgaaatgg agttatatt tgttatttct attttgttat    3960
atttaataat agaattagat tgaaataaaa tataatggga aataatctgc agaatgtggg   4020
```

```
ttttcctggt gtttccctct gactctagtg cactgatgat ctctgataag gctcagctgc    4080
tttatagttc tctggctaat gcagcagata ctcttcctgc cagtggtaat acgatttttt    4140
aagaaggcag tttgtcaatt ttaatcttgt ggatacctt atactcttag ggtattattt    4200
tatacaaaag ccttgaggat tgcattctat tttctatatg accctcttga tatttaaaaa    4260
acactatgga taacaattct tcatttacct agtattatga agaatgaag gagttcaaac     4320 aaatgtgttt cccagttaac tagggtttac tgtttgagcc aatataaatg tttaactgtt    4380
tgtgatggca gtattcctaa agtacattgc atgttttcct aaatacagag tttaaataat    4440
ttcagtaatt cttagatgat tcagcttcat cattaagaat atcttttgtt ttatgttgag    4500
ttagaaatgc cttcatatag acatagtctt tcagacctct actgtcagtt ttcatttcta    4560
gctgctttca gggttttatg aattttcagg caaagcttta atttatacta agcttaggaa    4620
gtatggctaa tgccaacggc agttttttc ttcttaattc cacatgactg aggcatatat     4680
gatctctggg taggtgagtt gttgtgacaa ccacaagcac ttttttttt tttaaagaaa     4740 aaaaggtagt gaattttaa tcatctggac tttaagaagg attctggagt atacttaggc     4800
ctgaaattat atatatttgg cttggaaatg tgtttttctt caattacatc tacaagtaag    4860
tacagctgaa attcagagga cccataagag ttcacatgaa aaaaatcaat ttatttgaaa    4920
aggcaagatg caggagagag gaagccttgc aaacctgcag actgcttttt gcccaatata    4980
gattgggtaa ggctgcaaaa cataagctta attagctcac atgctctgct ctcacgtggc    5040
accagtggat agtgtgagag aattaggctg tagaacaaat ggccttctct ttcagcattc    5100
acaccactac aaaatcatct tttatatcaa cagaagaata agcataaact aagcaaaagg    5160
tcaataagta cctgaaacca agattggcta gagatatatc ttaatgcaat ccattttctg    5220
atggattgtt acgagttggc tatataatgt atgtatggta ttttgatttg tgtaaaagtt    5280
ttaaaaatca agctttaagt acatggacat ttttaaataa atatttaaa gacaatttag     5340 aaaattgcct taatatcatt gttggctaaa tagaataggg gacatgcata ttaaggaaaa    5400
ggtcatggag aaataatatt ggtatcaaac aaatacattg atttgtcatg atacacattg    5460
aatttgatcc aatagtttaa ggaataggta ggaaaatttg gtttctattt ttcgatttcc    5520
tgtaaatcag tgacataaat aattcttagc ttatttata tttccttgtc ttaaatactg     5580
agctcagtaa gttgtgttag gggattattt ctcagttgag actttcttat atgacatttt    5640
actatgtttt gacttcctga ctattaaaaa taaatagtag atacaatttt cataaagtga    5700
agaattatat aatcactgct ttataactga ctttattata tttatttcaa agttcattta    5760
aaggctacta ttcatcctct gtgatggaat ggtcaggaat tgttttctc atagtttaat     5820 tccaacaaca atattagtcg tatccaaaat aacctttaat gctaaacttt actgatgtat    5880
atccaaagct tctcatttc agacagatta tccagaagc agtcataaac agaagaatag      5940
gtggtatgtt cctaatgata ttatttctac taatggaata aactgtaata ttagaaatta    6000
tgctgctaat tatatcagct ctgaggtaat ttctgaaatg ttcagactca gtcggaacaa    6060
attggaaaat ttaaattttt attcttagct ataaagcaag aaagtaaaca cattaatttc    6120
ctcaacattt ttaagccaat taaaaatata aagatacac accaatatct tcttcaggct     6180
ctgacaggcc tcctggaaac ttccacatat ttttcaactg cagtataaag tcagaaaata    6240
aagttaacat aactttcact aacacacaca tatgtagatt tcacaaaatc cacctataat    6300
tggtcaaagt ggttgagaat atatttttta gtaattgcat gcaaaatttt tctagcttcc    6360
```

```
atcctttctc cctcgtttct tcttttttg ggggagctgg taactgatga aatcttttcc      6420 cacctttct cttcaggaaa tataagtggt tttgtttggt taacgtgata cattctgtat      6480
gaatgaaaca ttggagggaa acatctactg aatttctgta atttaaaata ttttgctgct    6540
agttaactat gaacagatag aagaatctta cagatgctgc tataaataag tagaaaatat    6600
aaatttcatc actaaaatat gctattttaa aatctatttc ctatattgta tttctaatca    6660
gatgtattac tcttattatt tctattgtat gtgttaatga ttttatgtaa aaatgtaatt    6720
gcttttcatg agtagtatga ataaaattga ttagtttgtg ttttcttgtc tccc          6774
```

<210> SEQ ID NO 9
<211> LENGTH: 98
<212> TYPE: DNA
<213> ORGANISM: Homo sapiens

<400> SEQUENCE: 9

```
cgaggggata cagcagcaat tcatgttttg aagtgttcta aatggttcaa aacgtgaggc    60
gctgctatac cccctcgtgg ggaaggtaga aggtgggg                            98
```

<210> SEQ ID NO 10
<211> LENGTH: 71
<212> TYPE: DNA
<213> ORGANISM: Homo sapiens

<400> SEQUENCE: 10

```
tgccctagca gcgggaacag ttctgcagtg agcgatcggt gctctggggt attgtttccg    60
ctgccagggt a                                                         71
```

<210> SEQ ID NO 11
<211> LENGTH: 37
<212> TYPE: DNA
<213> ORGANISM: Homo sapiens

<400> SEQUENCE: 11

```
taggcgatcg ctcgagcaga cagattaatc cagaagc                             37
```

<210> SEQ ID NO 12
<211> LENGTH: 37
<212> TYPE: DNA
<213> ORGANISM: Homo sapiens

<400> SEQUENCE: 12

```
ttgcggccag cggccgcggg agacaagaaa acacaaa                             37
```

<210> SEQ ID NO 13
<211> LENGTH: 35
<212> TYPE: DNA
<213> ORGANISM: Homo sapiens

<400> SEQUENCE: 13

```
taggcgatcg ctcgagattg aaggtgacct ctgcc                               35
```

<210> SEQ ID NO 14
<211> LENGTH: 37
<212> TYPE: DNA
<213> ORGANISM: Homo sapiens

<400> SEQUENCE: 14

```
ttgcggccag cggccgcctc tcccaaggac ttatgaa                             37
```

```
<210> SEQ ID NO 15
<211> LENGTH: 21
<212> TYPE: DNA
<213> ORGANISM: Homo sapiens

<400> SEQUENCE: 15
ggcttccttc agtcatccag t                                              21

<210> SEQ ID NO 16
<211> LENGTH: 20
<212> TYPE: DNA
<213> ORGANISM: Homo sapiens

<400> SEQUENCE: 16
accttctacc ttccccacga                                                20

<210> SEQ ID NO 17
<211> LENGTH: 20
<212> TYPE: DNA
<213> ORGANISM: Homo sapiens

<400> SEQUENCE: 17
ggaaggtaga aggtggggtc                                                20

<210> SEQ ID NO 18
<211> LENGTH: 20
<212> TYPE: DNA
<213> ORGANISM: Homo sapiens

<400> SEQUENCE: 18
ggaaacaata ccccagagca                                                20

<210> SEQ ID NO 19
<211> LENGTH: 21
<212> TYPE: DNA
<213> ORGANISM: Homo sapiens

<400> SEQUENCE: 19
ggcttccttc agtcatccag t                                              21

<210> SEQ ID NO 20
<211> LENGTH: 20
<212> TYPE: DNA
<213> ORGANISM: Homo sapiens

<400> SEQUENCE: 20
gcggaaacaa taccccagag                                                20

<210> SEQ ID NO 21
<211> LENGTH: 38
<212> TYPE: DNA
<213> ORGANISM: Homo sapiens

<400> SEQUENCE: 21
tttctctatc gataggtacc ccatttttcga gtggagcc                           38

<210> SEQ ID NO 22
<211> LENGTH: 35
<212> TYPE: DNA
<213> ORGANISM: Homo sapiens

<400> SEQUENCE: 22
ccggaatgcc aagcttgagt caatgaaggg ggatc                               35
```

```
<210> SEQ ID NO 23
<211> LENGTH: 22
<212> TYPE: RNA
<213> ORGANISM: Homo sapiens

<400> SEQUENCE: 23
cagcagcaau ucauguuuug aa                                              22

<210> SEQ ID NO 24
<211> LENGTH: 23
<212> TYPE: RNA
<213> ORGANISM: Homo sapiens

<400> SEQUENCE: 24
uagcagcggg aacaguucug cag                                             23

<210> SEQ ID NO 25
<211> LENGTH: 20
<212> TYPE: RNA
<213> ORGANISM: Homo sapiens

<400> SEQUENCE: 25
uauuagaaau uaugcugcua                                                 20

<210> SEQ ID NO 26
<211> LENGTH: 20
<212> TYPE: RNA
<213> ORGANISM: Homo sapiens

<400> SEQUENCE: 26
uuuaaaauau uuugcugcua                                                 20

<210> SEQ ID NO 27
<211> LENGTH: 23
<212> TYPE: RNA
<213> ORGANISM: Homo sapiens

<400> SEQUENCE: 27
gaagaaucuu acagaugcug cua                                             23

<210> SEQ ID NO 28
<211> LENGTH: 21
<212> TYPE: RNA
<213> ORGANISM: Homo sapiens

<400> SEQUENCE: 28
cccucaauaa aauugcugcu g                                               21

<210> SEQ ID NO 29
<211> LENGTH: 21
<212> TYPE: RNA
<213> ORGANISM: Homo sapiens

<400> SEQUENCE: 29
gggaaaaugg gauugcugcu u                                               21
```